US011977083B2

(12) United States Patent
Rhyne et al.

(10) Patent No.: US 11,977,083 B2
(45) Date of Patent: May 7, 2024

(54) DIAGNOSTIC METHODS FOR CARDIOVASCULAR DISEASES

(71) Applicant: PREVENCIO, INC., Kirkland, WA (US)

(72) Inventors: Rhonda Fay Rhyne, Kirkland, WA (US); Craig Agamemnon Magaret, Seattle, WA (US); John Edward Strobeck, Saddle Ridge, NJ (US); James Louis Januzzi, Jr., Wellesley, MA (US)

(73) Assignee: PREVENCIO, INC., Kirkland, WA (US)

( * ) Notice: Subject to any disclaimer, the term of this patent is extended or adjusted under 35 U.S.C. 154(b) by 141 days.

(21) Appl. No.: 17/081,776

(22) Filed: Oct. 27, 2020

(65) Prior Publication Data

US 2021/0072260 A1 Mar. 11, 2021

Related U.S. Application Data

(62) Division of application No. 16/073,754, filed as application No. PCT/US2017/016081 on Feb. 1, 2017, now Pat. No. 10,983,135.

(60) Provisional application No. 62/378,535, filed on Aug. 23, 2016, provisional application No. 62/289,513, filed on Feb. 1, 2016.

(51) Int. Cl.
| | |
|---|---|
| *G01N 33/68* | (2006.01) |
| *A61B 5/00* | (2006.01) |
| *A61B 6/00* | (2006.01) |
| *A61B 6/50* | (2024.01) |

(52) U.S. Cl.
CPC ....... *G01N 33/6893* (2013.01); *A61B 5/4836* (2013.01); *A61B 5/4884* (2013.01); *A61B 6/503* (2013.01); *G01N 2800/324* (2013.01); *G01N 2800/52* (2013.01)

(58) Field of Classification Search
CPC ..... A61B 5/4836; A61B 5/4884; A61B 6/503; G01N 2800/324
See application file for complete search history.

(56) References Cited

U.S. PATENT DOCUMENTS

| | | | |
|---|---|---|---|
| 4,816,567 A | 3/1989 | Cabilly et al. | |
| 8,241,861 B1 | 8/2012 | Heinecke et al. | |
| 9,134,320 B2 | 9/2015 | Biessen et al. | |
| 10,983,135 B2 | 4/2021 | Rhyne et al. | |
| 2008/0057590 A1 | 3/2008 | Urdea et al. | |
| 2008/0185295 A1 | 8/2008 | Briman et al. | |
| 2008/0202927 A1 | 8/2008 | Kayyem et al. | |
| 2008/0269346 A1* | 10/2008 | Johnson | G01N 33/9453 435/6.17 |
| 2008/0300798 A1 | 12/2008 | McDevitt et al. | |
| 2010/0047901 A1 | 2/2010 | Bradley et al. | |
| 2010/0231242 A1 | 9/2010 | Gabriel et al. | |
| 2010/0329929 A1 | 12/2010 | Goix et al. | |
| 2010/0331200 A1 | 12/2010 | Gordon et al. | |
| 2011/0144914 A1 | 6/2011 | Harrington et al. | |
| 2011/0154648 A1 | 6/2011 | Gabriel et al. | |
| 2013/0261009 A1 | 10/2013 | Goix et al. | |
| 2013/0306491 A1 | 11/2013 | Briman et al. | |
| 2014/0011811 A1* | 1/2014 | Dudley | G01N 33/6887 514/249 |
| 2014/0256573 A1 | 9/2014 | Durand et al. | |
| 2015/0160229 A1* | 6/2015 | Schaal | G01N 33/6893 424/718 |
| 2016/0153980 A1 | 6/2016 | Durand et al. | |
| 2019/0369120 A1 | 12/2019 | Rhyne et al. | |

FOREIGN PATENT DOCUMENTS

| | | |
|---|---|---|
| CN | 101454024 A | 6/2009 |
| CN | 101495862 A | 7/2009 |
| JP | 2012-528655 A | 11/2012 |
| JP | 2013-178249 A | 9/2013 |
| KR | 20110085436 A | 7/2011 |
| WO | WO 2007/146229 A2 | 12/2007 |
| WO | WO 2008/131039 A2 | 10/2008 |
| WO | WO 2008/131039 A3 | 10/2008 |
| WO | WO 2010/144358 A1 | 12/2010 |
| WO | WO 2011/022628 A1 | 2/2011 |
| WO | WO 2012/145037 A1 | 10/2012 |
| WO | WO2014078615 A1 | 5/2014 |
| WO | WO 2015006713 A | 1/2015 |
| WO | WO 2015/171989 A1 | 11/2015 |
| WO | WO 2016/001795 A1 | 1/2016 |
| WO | WO 2017/136464 A1 | 8/2017 |

OTHER PUBLICATIONS

Damman (Heart 2010 96:1297-1302) (Year: 2010).*
Wettersten (Radcliffe Cardiology 2015, p. 102-106) (Year: 2015).*
Kitahara (J. Cardiac Failure 2010 16: 308-313) (Year: 2010).*
Bjorkegren, "Accumulation of Apolipoprotein C-I-Rich and Cholesterol-Rich VLDL Remnants During Exaggerated Postprandial Triglyceridemia in Normolipidemic Patients With Coronary Artery Disease," Circulation 101(3):227-230 (2000).
Moore et al., "Isoforms of apolipoprotein C-I associated with individuals with coronary artery disease," Biochemical and Biophysical Research Communications 404:1034-1038 (2011).
Aebersold and Mann, "Mass spectrometry-based proteomics,"Nature, 422:198-207 (2003).

(Continued)

*Primary Examiner* — Changhwa J Cheu

(74) *Attorney, Agent, or Firm* — Mintz, Levin, Cohn, Ferris, Glovsky and Popeo, P.C.

(57) ABSTRACT

Compositions and methods are provided for diagnosis and/or prognosis of cardiovascular diseases or events in a subject. In some embodiments, the method includes measuring and comparing the level of particular proteins to other proteins. In other embodiments, the method includes comparison with clinical variable information.

20 Claims, 52 Drawing Sheets

(56) References Cited

OTHER PUBLICATIONS

Armenta et al., "Microfluidic chips for protein differential expression profiling," Electrophoresis 30(7): 1145-1156 (2009).
Ayman et al., "Decorin overexpression reduces atherosclerosist development in apolipoprotein E-deficient mice," Atherosclerosis Atherosclerosis 187:31-39 (2006).
Berg, "The Additive Contribution from Inflammatory Genetic Markers on the Severity of Cardiovascular Disease," Scandinavian Journal of Immunology 69:36-42 (2009).
Bing et al., "Levels of IL-8,IL-10 in patients with chronic periodontitis and coronary heart disease," Shanghai Journal of Stomatology, vol. 24, No. 5, pp. 598-600 (2015).
Carr and Anderson, "Protein quantitation through targeted mass spectrometry: the way out of biomarker purgatory?" Clinical Chemistry. 54(11):1749-1752 (2008).
Clackson et al., "Making antibody fragments using phage display libraries," Nature, 352: 624-628 (1991).
Cury et al., "Acute chest pain imaging in the emergency department with cardiac computed tomography angiography," J. Nucl. Cardiol. 15(4):564-575 (2008).
Ding et al., "Effects of matrix metalloproteinase-9 and interleukin-18 on coronary heart disease and vessel complication in diabetes mellitus," Journal of Xi' an Jiaotong University (Medical Sciences) 35(5):646-650 (Sep. 30, 2014).
Driver et al. Urinary Kidney Injury Molecule 1 (KIM-1) and Interleukin 18 (IL-18) as Risk Markers for Heart Failure in Older Adults: The Health, Aging, and Body Composition (Health ABC) Study, Am J Kidney Dis, pp. 1-8 (2014).
Eapen et al., "Aggregate Risk Score Based on Markers of Inflammation, Cell Stress, and Coagulation is an Independent Predictor of Adverse Cardiovascular Outcomes," Journal of the American College of Cardiology 62(4):329-37 (2013).
Elmariah et al., "Multiple biomarker panel to screen for severe aortic stenosis: results from the Casablanca study," Open Heart e000916:1-8 (2018).
Ethier et al., "The proteomic reactor: a microfluidic device for processing minute amounts of protein prior to mass spectrometry analysis," J. Proteome Res. 5(10):2754-2759 (2006).
Extended European Search Report issued by the European Patent Office for Application No. 17748086.0, dated Jul. 15, 2019, 11 pages.
Gupta et al., "Clinical Assessment of Cardiovascular Disorders by Cardiac Biomarkers," Int. J. Pharm. Sci. Rev. Res. Nov.-Dec. International Journal of Pharmaceutical Sciences Review and Research 29(1):87-94 (2014).
Hochholzer et al., "Novel Biomarkers in Cardiovascular Disease: Update 2010," American Heart Journal, Elsevier, Amsterdam, NL 160(4):583-594 (2010).
Ibrahim et al., "A Clinical and Biomarker Scoring System to Predict the Presence of Obstructive Coronary Artery Disease," Journal of American College of Cardiology 69(9):1147-56 (2017).
Ingkanisorn et al., "Prognosis of negative adenosine stress magnetic resonance in patients presenting to an emergency department with chest pain," J. Am. Coll. Cardiol. 47(7): 1427-1432 (2006).
International Search Report issued by the International Searching Authority for Application No. PCT/US2018/059080, dated Apr. 9, 2019, 6 pages.
International Search Report and Written Opinion issued by the International Searching Authority for Application No. PCTUS2017016081, dated May 18, 2017, 18 pages.
Kingsmore et al., "Multiplexed protein profiling on antibody-based microarrays by rolling circle amplification," Curr. Opin. Biotechnol. 14(1):74-81 (2003).
Kohler et al., "Continuous cultures of fused cells secreting antibody of predefined specificity," Nature, 256: 495-497 (1975).
Lekawanvijit et al., "Myocardial infarction impairs renal function, induces renal interstitial fibrosis, and increases renal KIM-1 expression: implications for cardiorenal syndrome," Am J Physiol Heart Circ Physiol. 302:H1884-H1893 (2012).

Li et al., "Application of microfluidic devices to proteomics research: identification of trace-level protein digests and affinity capture of target peptides," Mol. Cell. Proteomics 1.2:157 (2002).
Li et al., "Correlation between coronary atherosclerotic plaques and MMP2, MMP9 levels," Journal of Hainan Medical University 20(1):38-40 (2014), 5 pages including English abstract.
Li et al., "Integrated system for high-throughput protein identification using a microfabricated device coupled to capillary electrophoresis/ nanoelectrospray mass spectrometry," Proteomics I(8):975-986 (2001).
Li et al., "Serum soluble selectin and interleukin drug levels in patients with acute coronary syndrome," Chin J. Clinicians (Electronic Edition), vol. 6, No. 6, 2 pages and English Abstract (Mar. 31, 2012).
Liu et al., "Hypoadiponetinemia an Important marker Indicating the severity of coronary artery atheroselerosis," Chin J Entochrnol Metab vol. 21, No. 1, 4 pages (2005).
Lynch et al., "Functional protein nanoarrays for biomarker profiling," Proteomics4(6):1695-1702 (2004).
Marcucci et al., "Cardiovascular death and nonfatal myocardial infarction in acute coronary syndrome patients receiving coronary stenting are predicted by residual platelet reactivity to ADP detected by a point-of-care assay: a 12-month follow-up," 2009, Circulation 119(2):237-242 (originally published online Dec. 31, 2008).
Marks et al., "By-passing immunization. Human antibodies from V-gene libraries displayed on phage," J. Mol. Biol., 222(3): 581-597 (1991).
Martin-Ventura et al., "Biomarkers in cardiovascular medicine," Rev. Esp. Cardiol 62(6):677-688 (2009).
McCarthy et al., A clinical and proteomics approach to predict the presence of obstructive peripheral arterial disease: From the Catheter Sampled Blood Archive in Cardiovascular Diseases (Casablanca) Study, Clinical Cardiology 41:903-09 (2018).
McCarthy et al., "Derivation and External Validation of a High Sensitivity Troponin Based Proteomic Model to Predict the Presence of Obstructive Coronary Artery Disease: Value in the Troponin" Indeterminant Zone, HART CADhs Poster AHA, 1 page (2019).
McCarthy et al., "Usefulness of Multiple Biomarkers for Predicting Incident Major Adverse Cardiac Events in Patients Who Underwent Diagnostic Coronary Angiography (from the Catheter Sampled Blood Archive in Cardiovascular Diseases [Casablanca] Study)," Am J Cardiol 120:25-32 (2017).
McCarthy, et al., Abstract 18948: A Clinical and Biomarker Scoring System to Predict the Presence of Obstructive Peripheral Artery Disease: Results From the Catheter Sampled Blood Archive in Cardiovascular Diseases (Casablanca) Study, Circulation 136(1) (2018), 6 pages, retrieved online on Jan. 10, 2020 at https://ahajournals.org/doi/abs/10.1161/circ.136.suppl_1.18948.
Mor et al., "Serum Protein Markers for Early Detection of Ovarian Cancer," PNAS 102:7677-7682 (2005).
Morrison et al., "Chimeric human antibody molecules: mouse antigen-binding domains with human constant region domains," Proc. Natl. Acad. Sci. USA, 81: 6851-6855 (1984).
Murray and Lopez, "Mortality by cause for eight regions of the world: Global Burden of Disease Study," Lancet 349:(9061)1269-1276 (1997).
Pan, S., "Mass spectrometry based targeted protein guantification: methods and applications," J. Proteome Research, February; 8(2):787-97 (2009).
Ramsey et al., "High-efficiency, two-dimensional separations of protein digests on microfluidic devices," Anal. Chem. 75(15):3758-3764 (2003).
Schillinger et al., "Acute chest pain-identification of patients at low risk for coronary events. The impact of symptoms, medical history and risk factors," Wien Klin. Wochenschr. 116(3):83-89 (2004).
Selvaraj et al., "Point-of-care determination of baseline platelet function as a predictor of clinical outcomes in patients who present to the emergency department with chest pain," J. Throm. Thrombolysis 18(2):109-115 (2004).
Sharma et al., "Coronary computed tomographic angiography (CCTA) in community hospitals: current and emerging role," Vasc. Health Risk Manag. 6:307-316 (2010).

(56) References Cited

OTHER PUBLICATIONS

Sorger, "Microfluidics closes in on point-of-care assays," Nature Biotechnol. 26:1345-1346 (2008).
Tadros et al., "Clinical predictors of 30-day cardiac events in patients with acute coronary syndrome at a community hospital," South Med. J. 96(11):1113-1120 (2003).
Vaisar, HDL in humans with Cardiovascular disease exhibits a proteomic signature, Clinica Chimica Acta 411:972-979 (2010).
Van Kimmenade et al., "Emerging Biomarkers in Heart Failure," Clinical Chemistry 58(1):127-138 (2012).
Vaudel, M., et al., "Peptide and protein quantification: a map of the minefield," Proteomics, vol. 10(4):650-670 (2010).
Wang et al., "Clinical Values of IMA, cTnI, MYO and CK-MB in Early Diagnosis of Acute Coronary Syndrome," Dept of Clinical Laboratory, Shuguang Hospital 21(6):671-673 (2014).
Westermeier and Marouga, "Protein detection methods in proteomics research," Bioscience Reports 25(1-2):19-32 (2005).
Xiao et al.,"Coronary atherosclerotic Heart Disease Patient Serum and Work Level and Meeting," (The Second Department of Cardiology, The First Affiliated Hospital of Dalian Medical University, Dalian 116000, Liaoning), China Academic Journal Electronic Publishing House, pp. 6314-6315 (2014).
Yan et al., "The changes of circulating stem cells and stem cell factor in patients with acute myocardial infarction," Chin J. Geriatr Heart Brain Vessel Dis 9(2):82-85 (2007).
Yang et al., "The dynamic chane of extracellular matrix in human coronary atherogenesis," Zhonghua Bing Li Xue Za Zhi, Cardiovascular Institute and Fu Wai Hospital. Chinese Academy of medical Sciencesand Peking Union Medical College, Beijing 27(3):177-81 (1998).
Yang et al., "Serum Midkine Analysis of the correlation between Ji Hongqiao and coronary heart disease and its risk factors," Chin J Cardiol, vol. 39 Supplement, p. 113, 3 pages including English translation (May 31, 2011).
Yin et al., A member of the leucine-rich low-molecular-weight proteoglycan family Research progress on the relationship with atherosclerosis Chin J Cerebrovase, vol. 10, No. 3, pp. 158-161 and English Abstract (2013).
Yusuf et al., Effect of potentially modifiable risk factors associated with myocardial infarction in 52 countries (the INTERHEART study): case-control study, Lancet, 364:937-52 (2004).
Zhang et al., "Coronary Heart Yuezhuang Disease-Clinical Phenotypes Determination of Adiponectin," Chinese Journal of Clinical Laboratory Science, vol. 26, No. 6, p. 455 and English Abstract (Jun. 25, 2008).
Zhang et al., "Increased Expression of Stem Cell Factor Gene in Atherosclerotic Vascular Smooth Muscle Cells," Chinese Journal of Hypertension 7(4):363-365 (1999).
Zheng et al., "Quantification of proteins using lanthanide labeling and HPLC/ICP-MS detection," J. of Analytical Atomic Spectrometry, 26, 1233-1236 (2011).
Jungbauer et al. (2011) "Kidney Injury Molecule-1 and N-acetyl-β-dglucosaminidase in Chronic Heart Failure: Possible Biomarkers of Cardiorenal Syndrome", European journal of heart failure, 13(10):1104-1110.
Medic et al. (Nov. 30, 2015) "Kidney Injury Molecule-1 and Cardiovascular Diseases: From Basic Science to Clinical Practice", BioMed Research International 2015, Article ID 854070, 1-10.

\* cited by examiner

False positive rate
(AUC = 0.802)

False positive rate
(AUC = 0.783)

DIAGNOSTIC METHODS FOR CARDIOVASCULAR DISEASES

CROSS REFERENCED RELATED APPLICATIONS

This application is a divisional application of U.S. application Ser. No. 16/073,754, filed on Jul. 27, 2018, which is a 371 of international application number PCT/US2017/016081, filed Feb. 1, 2017, which claims priority to, and benefit of, U.S. Provisional Application No. 62/289,513 filed Feb. 1, 2016 and U.S. Provisional application No. 62/378,535 filed Aug. 23, 2016, the contents of which are incorporated herein by reference in their entireties.

FIELD OF THE INVENTION

The present disclosure relates biomarker panels, assays, and kits and methods for determining the diagnosis and/or prognosis of a cardiovascular disease or outcome in a patient.

BACKGROUND OF THE INVENTION

Atherosclerotic cardiovascular disease (ASCVD) and its associated cardiovascular events (CVE) including, for example, obstructive coronary artery disease (CAD), myocardial infarction (MI), stroke, and cardiovascular death (CVD) are predominantly caused by an underlying vascular endothelial process leading to deposition of lipid material and other proteins resulting in atherosclerotic plaque formation in multiple vascular beds in the human body. While this process is associated with identifiable and modifiable risk factors, the disease process and its related events noted above remain the leading cause of death and severe disability worldwide (Yusuf et al., Effect of potentially modifiable risk factors associated with myocardial infarction in 52 countries (the INTERHEART study): case-control study, Lancet, 364:937-52 (2004)).

In the Western world, cardiovascular disease, typically associated with underlying atherosclerosis, is the leading cause of death (Martin-Ventura et al., 2009, Rev. Esp. Cardiol 62(6):677-688, citing Murray and Lopez, 1997, Lancet 349:1269-1276). Risk factors for cardiac disease are well known, and include hypertension, diabetes, smoking, elevated cholesterol, obesity, and family history. However, despite the prevalence of obstructive coronary artery disease (CAD) and the appreciation of its risk factors, the link between the onset of symptoms and a cardiac event requiring intervention remains elusive. Symptoms can be non-specific, such as a feeling of heaviness in the chest, and can reflect CAD but could also be explained by gastric distress; pain in the left arm could be of cardiac origin or could be caused by arthritis. Even when pain is highly likely to be cardiac in origin, there can be questions regarding the type and intensity of treatment required; in some scenarios, medication may be sufficient, but in others, an interventional strategy is necessary to avoid CVE.

A number of technologies have been developed to identify patients at high risk for an adverse cardiac event. These include exercise and pharmacologic stress testing using evaluations of the ECG response, the cardiac wall motion response using ultrasound, and changes in myocardial perfusion using nuclear imaging techniques. Coronary angiography, the most invasive approach, has been considered the "gold standard" diagnostic tool to evaluate coronary artery anatomy, cardiac structure, and function, but it is invasive, costly, has defined complications, and is subject to operator-dependent variability (Sharma et al., 2010, Vasc. Health Risk Manag. 6:307-316). Other, newer and less-invasive options are being explored, including coronary computed tomographic angiography (Sharma et al., supra; Cury et al., 2008. J. Nucl. Cardiol. 15(4):564-575), biomarkers (e.g., Martin-Ventura et al., 2009, Rev. Esp. Cardiol 62(6'): 677-688), adenosine stress magnetic resonance perfusion imaging (Ingkanisorn et al., 2006, J. Am. Coll. Cardiol. 47(7): 1427-1432), the use of clinical predictors (Tadros et al., 2003. South Med. J. 96(11):1113-1120; Schillinger et al., 2004, Wien Klin. Wochenschr. 116(3):83-89), and indicators of platelet activity (Marcucci et al., 2009, Circulation 119: 237-242 (originally published online Dec. 31, 2008); Selvaraj et al., 2004, J. Throm. Thrombolysis 18(2):109-115).

A need therefore exists for a simple and reliable method to improve the diagnosis of cardiovascular pathologies and the prediction of CVE.

SUMMARY OF THE INVENTION

The present disclosure provides methods for determining the diagnosis and/or prognosis of a cardiovascular disease or outcome in a subject, comprising the steps: (i) determining the level of at least one, at least two, at least three, at least four or greater than four biomarkers in a biological sample obtained from the subject, wherein the biomarkers are selected from the group consisting of those set forth in Tables 1A, 1B, 2A, and 2B; (ii) optionally, determining the status of at least one clinical variable for the subject, wherein the clinical variable is selected from the group consisting of those set forth in Tables 3A, 3B, 4A and 4B; (iii) calculating a diagnostic and/or prognostic score for the subject based on the determined level of at least one biomarker and, optionally, the status of the clinical variable(s) determined in step (ii); (iv) classifying the diagnostic or prognostic score as a positive or negative result; and (v) determining a therapeutic or diagnostic intervention regimen based on the positive or negative result.

The diagnosis or prognosis provided by the methods of the present disclosure are particularly important in defining and determining a therapeutic path forward for a patient receiving a positive diagnosis of coronary artery disease and/or a positive prognosis of cardiovascular death, myocardial infarct (MI), stroke, all cause death, or a composite thereof. In this way, the determined diagnosis and/or prognosis of a cardiovascular disease or outcome in the subject facilitates a determination by a medical practitioner of a need for a therapeutic or diagnostic intervention in the subject.

In certain more specific embodiments, the biomarkers used in the methods are selected from the biomarkers listed in Tables 1A, 1B, 2A, and 2B, particularly those that have a p-value of less than 0.1, less than 0.05, less than 0.01 or less than 0.001.

In a particular embodiment, the method comprises determining the levels of at least one, at least two, at three, at least four, or greater than four biomarkers selected from the group consisting of adiponectin, apolipoprotein A-II, apolipoprotein C-I, decorin, interleukin-8, kidney injury molecule-1, matrix metalloproteinase 9 (MMP-9), midkine, myoglobin, N terminal prohormone of brain natriuretic protein (NT-proBNP), osteopontin, pulmonary surfactant associated protein D, stem cell factor, tissue inhibitor of metalloproteinases-1 (TIMP-1), troponin, and vascular cell adhesion molecule (VCAM).

In still other embodiments, in addition to determining biomarker levels in the biological sample, the method further comprises determining the status of at least one clinical variable, such as those listed in Tables 3A, 3B, 4A and 4B, particularly those having a p-value of less than 0.1, less than 0.05, less than 0.01, or less than 0.001.

In a more particular embodiment, the method comprises determining the status of at least one clinical variable selected from the group consisting of age, history of coronary artery bypass graft surgery (CABG), history of diabetes type 2, history of hemodialysis, history of myocardial infarct (MI), history of percutaneous coronary intervention (e.g., balloon angioplasty with or without stent placement), and sex.

In still other embodiments of the present disclosure, step (i) of the method comprises determining the level of at least one, at least two, at least three, at least four, or greater than four biomarkers selected the groups consisting of adiponectin, apolipoprotein A-II, apolipoprotein C-I, decorin, interleukin-8, kidney injury molecule-1, matrix metalloproteinase 9 (MMP-9), midkine, myoglobin, N terminal prohormone of brain natriuretic protein (NT-proBNP), osteopontin, pulmonary surfactant associated protein D, stem cell factor, tissue inhibitor of metalloproteinases-1 (TIMP-1), troponin, and vascular cell adhesion molecule (VCAM), and step (ii) comprises determining the status of at least one clinical variables selected from age, history of coronary artery bypass graft surgery (CABG), history of diabetes type 2, history of hemodialysis, history of myocardial infarct (MI), history of percutaneous coronary intervention (e.g. balloon angioplasty with or without stent placement), and sex.

The methods advantageously provide a diagnosis of obstructive coronary artery disease in the subject. In certain more specific embodiments, the diagnosis of obstructive coronary artery disease in the subject comprises a diagnosis of 70% or greater obstruction in a major epicardial vessel.

In still additional embodiments of the disclosure, step (i) of the method comprises determining the level of at least one, at least two, at least three, at least four, or greater than four biomarkers selected from the group consisting of adiponectin, apolipoprotein C-I, decorin, interleukin-8, kidney injury molecule-1, matrix metalloproteinase 9, midkine, myoglobin, pulmonary surfactant associated protein D, stem cell factor, and troponin.

In further particular embodiments, the methods provide a prognosis of the likelihood for a cardiac outcome, such as an outcome selected from cardiovascular death, myocardial infarct (MI), stroke, all cause death, or a composite thereof.

According to another aspect of the present provides methods for diagnosing the presence of obstructive coronary artery disease in a subject, comprising the steps: (i) determining the level of at least one, at least two, at least three, at least four, or greater than four biomarkers in a biological sample obtained from the subject, wherein the biomarkers are selected from the group consisting of the biomarkers listed in Tables 1A and 1B; (ii) optionally determining the status of at least one clinical variable for the subject, wherein the clinical variable is selected from the group consisting of the clinical variables listed in Tables 3A and 3B; (iii) calculating a diagnostic score for the subject based on the determined level of the at least one biomarker and optionally the status of the at least one clinical variable; (iv) classifying the score as a positive or negative diagnosis of obstructive coronary artery disease; and (iv) determining a therapeutic or diagnostic intervention regimen based on the positive or negative diagnosis.

In certain more specific embodiments, the biomarkers are selected from those listed in Tables 1A and 1B having p-values of less than 0.1, less than 0.05, less than 0.01 or less than 0.001.

In other more specific embodiments, step (i) of the method comprises determining the levels at least one, at least two, at least three, at least four, or greater than four biomarkers selected from the group consisting of adiponectin, apolipoprotein C-I, decorin, interleukin-8, kidney injury molecule-1, matrix metalloproteinase 9, midkine, myoglobin, pulmonary surfactant associated protein D, stem cell factor, and troponin.

In other embodiments, the clinical variable(s) assessed according to the method is selected from those listed in Tables 3A and 3B having p-values of less than 0.1, less than 0.05, less than 0.01 or less than 0.001.

In still other embodiments, step (ii) of the method comprises determining the status of at least one clinical variables selected from the group consisting of age, history of coronary artery bypass graft surgery (CABG), history of diabetes type 2, history of hemodialysis, history of myocardial infarct (MI), history of percutaneous coronary intervention (e.g., balloon angioplasty with or without stent placement), and sex.

In further embodiments, step (i) of the method comprises determining the levels at least one, at least two, at least three, at least four, or greater than four biomarkers selected the groups consisting of adiponectin, apolipoprotein C-I, decorin, interleukin-8, kidney injury molecule-1, matrix metalloproteinase 9, midkine, myoglobin, pulmonary surfactant associated protein D, stem cell factor, and troponin and step (ii) comprises determining the status of at least one clinical variables selected from age, history of coronary artery bypass graft surgery (CABG), history of diabetes type 2, history of hemodialysis, history of myocardial infarct (MI), history of percutaneous coronary intervention (e.g., balloon angioplasty with or without stent placement), and sex.

In other embodiments, a positive diagnosis for obstructive coronary artery disease in the subject facilitates a determination by a medical practitioner of the need for an intervention or further testing. An intervention or further testing may include but are not limited to one or more of a diagnostic cardiac catheterization (also referred to as "cath"), percutaneous coronary intervention (balloon angioplasty with or without stent placement), coronary artery bypass graft (CABG), and administration of pharmacologic agents, such as one selected from one or more of nitrates, beta blockers, ACE inhibitor and lipid-lowering agents.

In other embodiments, a negative diagnosis for obstructive coronary artery disease in the subject facilitates a determination by a medical practitioner of the need for an intervention or further testing. An intervention or further testing may include but are not limited to one or more of ongoing monitoring and management of coronary risk factors including hypertension, diabetes, and smoking, and lifestyle modifications selected from diet modification, exercise, and smoking cessation.

Another aspect of the present disclosure provides methods for the prognosis of a cardiac outcome in a subject, comprising the steps: (i) determining the level of at least one biomarker in a biological sample obtained from the subject, wherein the biomarkers are selected from the group consisting of the biomarkers listed in Tables 2A and 2B; (ii) optionally determining the status of at least one clinical variable for the subject, wherein the clinical variable is selected from the group consisting of the clinical variables listed in Tables 4A and 4B; (iii) calculating a prognostic score for the subject based on the determined levels of the at least one biomarker and, optionally, the status of the clinical variable(s) determined in step (ii); (iv) classifying the prognostic score as a positive or negative prognosis; and (v) determining a therapeutic or diagnostic intervention regimen based on the positive or negative prognosis.

In more specific embodiments, the biomarkers evaluated in the method are selected from those listed in Tables 2A and 2B having p-values of less than 0.1, less than 0.05, less than 0.01 or less than 0.001.

In other embodiments, the clinical variable(s) assessed according to the method is selected from those listed in Tables 4A and 4B having p-values of less than 0.1, less than 0.05, less than 0.01 or less than 0.001.

In other specific embodiments, step (i) of the method comprises determining the levels of at least one, at least two, at least three, at least four, or greater than four biomarkers selected from the group consisting of apolipoprotein A-II, kidney injury molecule-1, midkine, N terminal prohormone of brain natriuretic protein (NT-proBNP), osteopontin, tissue inhibitor of metalloproteinases-1 (TIMP-1), and vascular cell adhesion molecule (VCAM).

In still other embodiments, the prognosis of a cardiac outcome is a prognosis of cardiovascular death, myocardial infarct (MI), stroke, all cause death, or a composite thereof.

In additional embodiments, a positive prognosis of a cardiac outcome facilitates a determination by a medical practitioner of the need for an intervention or further testing. An intervention or further testing may include but are not limited to one or more of stress testing with ECG response or myocardial perfusion imaging, coronary computed tomography angiogram, diagnostic cardiac catheterization, percutaneous coronary intervention (e.g., balloon angioplasty with or without stent placement), coronary artery bypass graft (CABG), enrollment in a clinical trial, and administration or monitoring of effects of agents selected from, but not limited to, nitrates, beta blockers, ACE inhibitors, antiplatelet agents and lipid-lowering agents.

In other embodiments, a negative prognosis of a cardiac outcome facilitates a determination by a medical practitioner of the need for an intervention or further testing. An intervention or further testing may include but are not limited to one or more of ongoing monitoring and management of coronary risk factors including hypertension, diabetes, hyperlipidemia and smoking; and lifestyle modifications selected from diet modification, exercise and smoking cessation.

In other aspects, the present disclosure provides a diagnostic or prognostic kit comprising a panel of biomarkers and optionally clinical variables as described.

DETAILED DESCRIPTION OF THE INVENTION

Figure 1:
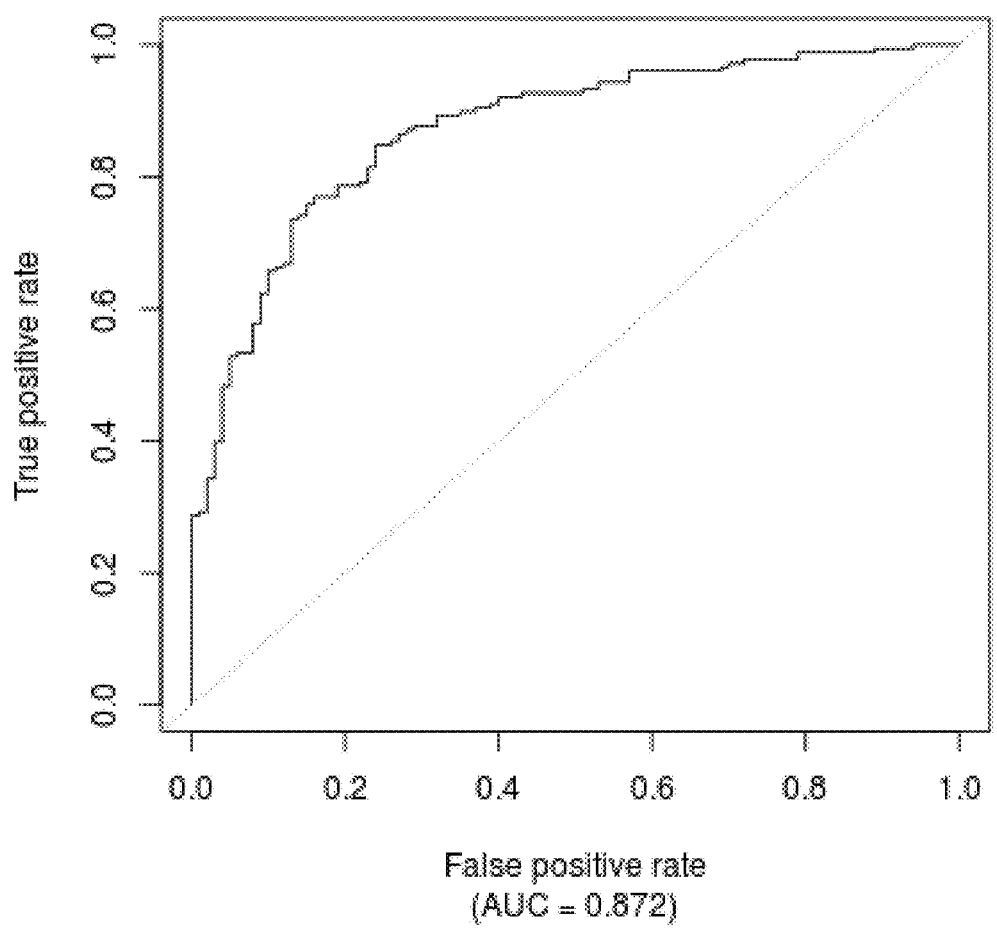
FIG. 1 shows a receiver operating characteristic curve for the Prevencio CAD panel FM139/685 (as described in Example 1), in the internal validation set (N=278) to diagnose the presence of severe CAD (≥70% stenosis in any vessel). The panel had a robust area under the curve (AUC) of 0.87.
Figure 2:
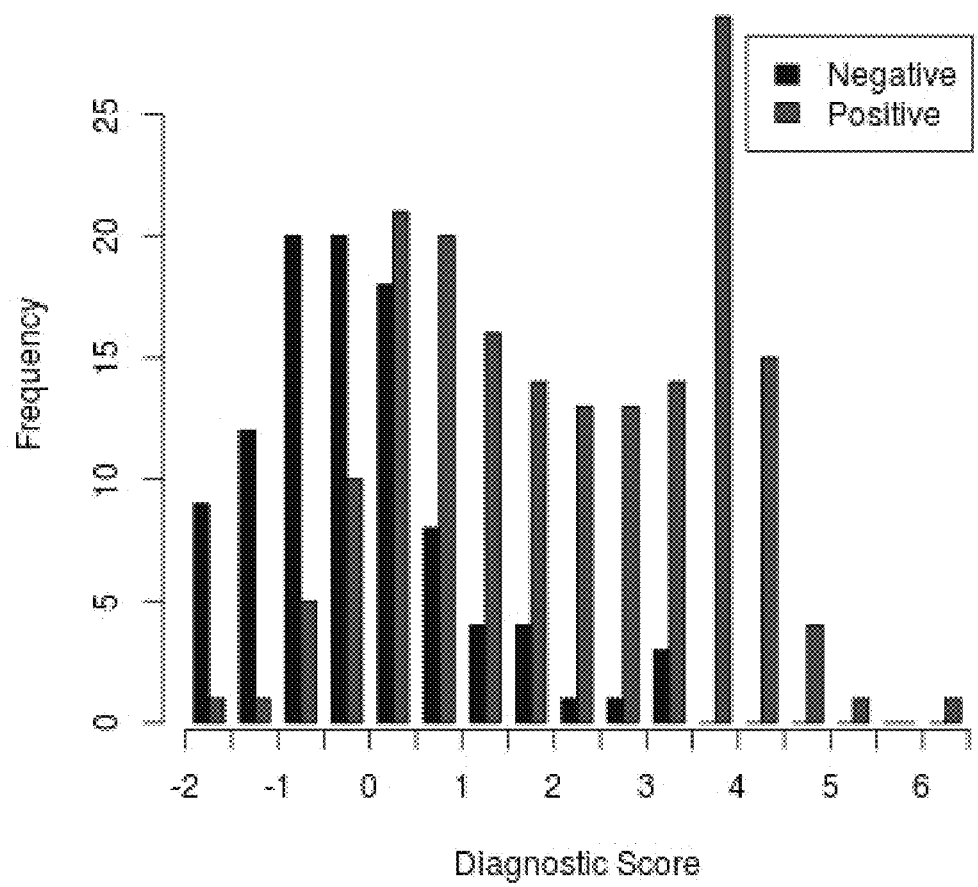
FIG. 2 shows a distribution of the CAD panel FM139/685 (as described in Example 1), in the internal validation set (N=278) to diagnose the presence of severe CAD (≥70% stenosis in any vessel). A bimodal distribution is noted, with preponderance of those with significant CAD distributed at higher scores. Positive=subjects with at least one coronary stenosis ≥70%, negative=subjects with no coronary stenoses ≥70%.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., Molecular Cloning: A Laboratory Manual (3rd Edition, 2001); Sambrook, et al., Molecular Cloning: A Laboratory Manual (2nd Edition, 1989); Maniatis et al., Molecular Cloning: A Laboratory Manual (1982); Ausubel et al., Current Protocols in Molecular Biology (John Wiley and Sons, updated July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); and Harlow and Lane, Antibodies, (Cold Spring Harbor Laboratory Press, Cold Spring Harbor, N. Y., 1998).

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art.

As used herein, the singular terms "a", "an", and "the" include the plural reference unless the context clearly indicates otherwise.

The term "invention" or "present invention" as used herein is a non-limiting term and is not intended to refer to any single embodiment of the particular invention but encompasses all possible embodiments as described in the specification and the claims.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2, or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Cardiovascular Diseases and Events

The present disclosure relates generally to the diagnosis and/or prognosis of cardiovascular disease and/or adverse cardiovascular events. As used herein, the term "diagnosis" refers to an identification or likelihood of the presence of a cardiovascular disease or event in a subject. As also used herein, the term "prognosis" refers to the likelihood or risk of a subject developing a particular outcome or particular event.

The term "cardiovascular disease" refers to a class of diseases that involve the heart or blood vessels. Cardiovascular disease includes coronary artery diseases (CAD), myocardial infarction (commonly known as a heart attack), stroke, hypertensive heart disease, rheumatic heart disease, cardiomyopathy, cardiac arrhythmias (i.e., atrial fibrillation, ventricular tachycardia, etc.), cerebrovascular disease, peripheral arterial disease, and arterial thrombosis.

The term "cardiovascular event" as used herein denotes a variety of adverse outcomes related to the cardiovascular system. These events include but are not limited to myocardial infarct, cardiovascular death, and stroke.

The term "coronary artery disease" or "CAD" refers to a particular type of cardiovascular disease. "Obstructive coronary artery disease" is characterized by atherosclerotic obstruction in the coronary arteries. Such obstruction may be clinically relevant at levels of 50% or greater, 60% or greater, 70% or greater, 80% or greater, 90% or greater, or 100%. Atherosclerotic plaque, the hallmark of atherosclerosis, progressively narrows the coronary artery lumen and impairs antegrade myocardial blood flow. The reduction in coronary artery flow may be symptomatic or asymptomatic. Symptoms of coronary obstruction typically occur with exertion, but can occur at rest, and may culminate in a myocardial infarction, stroke, and/or cardiovascular death depending on obstruction severity and the rapidity of development.

The term "cardiovascular death" or "CV death" or "CVD" as used herein refers to death resulting from an acute myocardial infarction (MI), sudden cardiac death, death due to heart failure (HF), death due to stroke, death due to cardiovascular (CV) procedures, death due to CV thrombosis or hemorrhage, death due to cardiac infection, and death due to other recognized CV causes within a specified period of time after the test sample is obtained.

The terms "myocardial infarction" or "MI" and "acute myocardial infarction" or "AMI" are commonly known as a heart attack and occurs when blood flow is limited to a part of the heart, causing damage to the heart muscle. The most common symptom is chest pain or discomfort which may travel into the shoulder, arm, back, neck, or jaw. Often, it is in the center or left side of the chest and lasts for more than a few minutes. The discomfort may occasionally feel like heartburn. Other symptoms may include shortness of breath, nausea, feeling faint, a cold sweat, or feeling tired. Most MIs occur due to obstructive coronary artery disease. Identified risk factors of obstructive coronary artery disease include high blood pressure, smoking, diabetes, lack of exercise, obesity, high blood cholesterol, poor diet, family history of early cardiovascular death or myocardial infarction, and excessive alcohol intake, among others. The mechanism of an MI often involves progression or rupture of the atherosclerotic plaque causing complete blockage of a coronary artery. MIs are less commonly caused by coronary artery spasms, which may be due to medications such as cocaine, significant emotional stress, and extreme cold, among others.

The term "stroke" also known as cerebrovascular accident (CVA), cerebrovascular insult (CVI), or brain attack, refers to a situation when poor blood flow to the brain results in brain cell death. There are two main types of stroke: ischemic, due to lack of blood flow caused by thrombosis or embolus, and hemorrhagic, due to bleeding. They typically result in significant dysfunction in the portions of the brain affected. Signs and symptoms of a stroke may include an inability to move or to experience sensations of touch, heat, cold, or pain on one side of the body, problems understanding or speaking, feeling like the world is spinning, or loss of vision to one side among others. Signs and symptoms often appear soon after the stroke has occurred.

The term "all-cause death" or "all-cause mortality" is defined as death from any non-trauma-related cause, including CV death, within a specified period of time after the test sample is obtained.

Biomarkers and Clinical Variables

As described herein, biomarkers of the present invention can be advantageously used in the diagnosis and prognosis of cardiovascular diseases and events. The terms "marker" and "biomarker" are used interchangeably throughout the disclosure. As used herein, a biomarker refers generally to a protein or polypeptide, the level or concentration of which is associated with a particular biological state, particularly a state associated with a cardiovascular disease, event or outcome. Panels, assays, kits and methods of the present invention may comprise antibodies, binding fragments thereof or other types of binding agents, which are specific for the biomarkers described herein.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. In various embodiments, detecting the levels of naturally occurring biomarker proteins in a biological sample is contemplated for use within diagnostic, prognostic, or monitoring methods disclosed herein. The term also includes fusion proteins, including, but not limited to, naturally occurring fusion proteins with a heterologous amino acid sequence, fusions with heterologous and homologous leader sequences, with or without N-terminal methionine residues; immunologically tagged proteins; and the like.

A "substantially isolated" or "isolated" substance is one that is substantially free of its associated surrounding materials in nature. By substantially free is meant at least 50%, preferably at least 70%, more preferably at least 80%, and even more preferably at least 90% free of the materials with which it is associated in nature. As used herein, "isolated" can refer to polynucleotides, polypeptides, antibodies, cells, samples, and the like.

Certain illustrative diagnostic biomarkers of the present invention can be found listed in Tables 1A and 1B, while certain illustrative prognostic biomarkers can be found listed in Tables 2A and 2B. Based on the information therein in Tables 1A, 1B, 2A, and 2B, the skilled artisan can readily identify, select and implement a biomarker or biomarker combination in accordance with the present disclosure.

In certain specific embodiments, the biomarkers used in accordance with the present invention include those listed in Tables 1A, 1B, 2A, and 2B, particularly those that are associated with a p-value of less than 0.1, less than 0.05, less than 0.01 or less than 0.001.

In other specific embodiments, the biomarkers used in accordance with the present disclosure are selected from the group consisting of adiponectin, apolipoprotein A-II, apolipoprotein C-I, decorin, interleukin-8, kidney injury molecule-1, matrix metalloproteinase 9, midkine, myoglobin, N terminal prohormone of brain natriuretic protein (NT-proBNP), osteopontin, pulmonary surfactant associated protein D, stem cell factor, tissue inhibitor of metalloproteinases-1 (TIMP-1), troponin, and vascular cell adhesion molecule (VCAM).

As used herein, "adiponectin" refers to a protein involved in regulating glucose as well as fatty acid breakdown. It is also referred to as GBP-28, apM1, AdipoQ, and Acrp30. Adiponectin is a 244-amino-acid peptide secreted by adipose tissue, whose roles include the regulation of glucose and fatty acid metabolism.

As used herein, "apolipoprotein A-II" refers to an apolipoprotein found in high density lipoprotein (HDL) cholesterol in plasma.

As used herein, "apolipoprotein C-I" is a protein component of lipoproteins normally found in the plasma and responsible for the activation of esterified lecithin cholesterol and in removal of cholesterol from tissues.

As used herein, "decorin", also known as PG40 and PGS2, is a protein, which belongs to the small leucine-rich proteoglycan family. It regulates assembly of the extracellular collagen matrix.

As used herein, "interleukin-8", also known as IL8, neutrophil chemotactic factor, chemokine ligand 8, and CXCL8, is a chemokine produced by macrophages and other cell types such as epithelial cells, airway smooth muscle cells, and endothelial cells. It induces chemotaxis in target cells, primarily neutrophils but also other granulocytes, causing them to migrate toward the site of infection. IL-8 also induces phagocytosis once they have arrived. IL-8 is also known to be a potent promoter of angiogenesis. In target cells, IL-8 induces a series of physiological responses required for migration and phagocytosis, such as increases in intracellular $Ca^{2+}$, exocytosis (e.g. histamine release), and the respiratory burst.

As used herein, "kidney injury molecule-1", also known as "KIM-1" is a type I cell membrane glycoprotein that serves as a receptor for oxidized lipoproteins and plays a functional role in the kidney. KIM-1 is a proximal renal tubular marker whose concentrations have been linked to acute kidney injury.

As used herein, "matrix metalloproteinase 9", also known as MMP-9, 92 kDA type IV collagenase, 92 kDa gelatinase, and gelatinase B or GELB, is a is a matrixin, a class of enzymes that belong to the zinc-metalloproteinases family involved in the degradation of the extracellular matrix. Proteins of the matrix metalloproteinase (MMP) family are involved in the breakdown of extracellular matrix in normal physiological processes, such as embryonic development, reproduction, angiogenesis, bone development, wound healing, cell migration, learning and memory, as well as in pathological processes, such as arthritis, intracerebral hemorrhage, and metastasis.

As used herein, "midkine", also known as "neurite growth-promoting factor 2" or "NEGF2", refers to a basic heparin-binding growth factor of low molecular weight and forms a family with pleiotrophin. Midkine is a heparin-binding cytokine/growth factor with a molecular weight of 13 kDa.

As used herein, "myoglobin", is an iron- and oxygen-binding protein found in the muscle tissue of vertebrates in general and in almost all mammals. Myoglobin is released from damaged muscle tissue (rhabdomyolysis), which has very high concentrations of myoglobin. The released myoglobin is filtered by the kidneys but is toxic to the renal tubular epithelium and so may cause acute kidney injury. It is not the myoglobin itself that is toxic (it is a protoxin) but the ferrihemate portion that is dissociated from myoglobin in acidic environments (e.g., acidic urine, lysosomes). Myoglobin is a sensitive marker for muscle injury, making it a potential marker for heart attack in patients with chest pain.

As used herein, "N-terminal prohormone of brain natriuretic peptide" or "NT-PBNP" is also known as "NT-proBNP" or "BNPT" and refers to an N-terminal inactive protein that is cleaved from proBNP to release brain natriuretic peptide.

As used herein, "osteopontin", also known as "bone sialoprotein I", "BSP-1", "BNSP", "early T-lymphocyte activation", "ETA-1", "secreted phosphoprotein 1", "SPP1", "2ar", "*Rickettsia* resistance", or "Ric", refers to a glycoprotein (small integrin binding ligand N-linked glycoprotein) first identified in osteoblasts. It includes all isoforms and post-translational modifications.

As used herein, "pulmonary surfactant associated protein D", also referred to as surfactant, pulmonary-associated protein D, or SP-D or SFTPD, is a protein that contributes to the lung's defense against inhaled microorganisms, organic antigens and toxins.

As used herein, "stem cell factor", also known as SCF, KIT-ligand, KL, and steel factor, is a cytokine that binds to the c-KIT receptor (CD117). SCF can exist both as a transmembrane protein and a soluble protein. This cytokine plays an important role in hematopoiesis (formation of blood cells), spermatogenesis, and melanogenesis.

As used herein, "tissue inhibitor of metalloproteinases-1", also known as "TIMP-1" or "TIMP metallopeptidase inhibitor 1", refers to a glycoprotein expressed in several tissues. It is a natural inhibitor of matrix metalloproteinases, a group of peptidases involved in the degradation of extracellular matrix. It is able to promote cell proliferation in a wide range of cell types.

As used herein, "troponin", also known as the troponin complex, is a complex of three regulatory proteins (troponin C, troponin I, and troponin T) that is integral to muscle contraction in skeletal muscle and cardiac muscle, but not smooth muscle. As used herein a troponin biomarker may identify each of these proteins individually or in combination. An increased level of the cardiac protein isoform of troponin circulating in the blood has been shown to be a biomarker of heart disorders, the most important of which is myocardial infarction. Raised troponin levels indicate cardiac muscle cell death as the molecule is released into the blood upon injury to the heart.

As used herein, "vascular cell adhesion molecule", also known as VCAM-1, VCAM, cluster of differentiation 106, and CD106, is a cell adhesion molecule. The VCAM-1 protein mediates the adhesion of lymphocytes, monocytes, eosinophils, and basophils to vascular endothelium. It also functions in leukocyte-endothelial cell signal transduction, and it may play a role in the development of atherosclerosis and rheumatoid arthritis.

It will be understood by one skilled in the art that these and other biomarkers disclosed herein (e.g., those set forth in Tables 1A, 1B, 2A, and 2B) can be readily identified, made and used in the context of the present disclosure in light of the information provided herein.

As used herein, the term "score" refers to a binary, multilevel, or continuous result as it relates diagnostic or prognostic determinations.

As used herein, the term "panel" refers to specific combination of biomarkers and clinical markers used to determine a diagnosis or prognosis of a cardiovascular disease or outcome in a subject. The term "panel" may also refer to an assay comprising a set of biomarkers used to determine a diagnosis or prognosis of a cardiovascular disease or outcome in a subject.

As further described herein, the "training set" is the set of patients or patient samples that are used in the process of training (i.e., developing, evaluating and building) the final diagnostic or prognostic model. The "validation set" is a set of patients or patient samples that are withheld from the training process, and are only used to validate the performance of the final diagnostic or prognostic model.

As further described herein, the biomarkers of the present invention can optionally be used in combination with certain clinical variables in order to provide for an improved diagnosis and/or prognosis of a cardiovascular disease or event in a subject. For example, illustrative clinical variables useful in the context of the present disclosure can be found listed in Tables 3A, 3B, 4A, and 4B.

Table 1A below shows biomarker concentrations and their diagnostic association that differ between those in the training set (N=649) with at least one coronary artery stenosis ≥70% (N=428) and those who did not in the cohort of subjects who received a coronary cath, with or without an optional peripheral cath.

TABLE 1A

Diagnostic Biomarkers (Received Coronary Cath; Peripheral Cath Optional) (Training Set)

| Biomarker | Concentration in Subjects with Coronary Stenosis (N = 428) | Concentration in Subjects without Coronary Stenosis (N = 221) | p-value |
|---|---|---|---|
| Adiponectin (ug/mL) | 3.4 (2.2, 5.1) | 4.5 (2.9, 7.2) | <0.001 |
| Alpha-1-Antitrypsin (AAT) (mg/mL) | 1.8 (1.5, 2.1) | 1.8 (1.5, 2.1) | 0.248 |
| Alpha-2-Macroglobulin (A2Macro) (mg/mL) | 1.9 (1.6, 2.3) | 1.9 (1.6, 2.3) | 0.816 |
| Angiopoietin-1 (ANG-1) (ng/mL) | 6.7 (5, 9.6) | 7.3 (5, 11) | 0.179 |
| Angiotensin-Converting Enzyme (ACE) (ng/mL) | 79 (60, 103.2) | 78 (59.8, 105) | 0.954 |
| Apolipoprotein(a) (Lp(a)) (ug/mL) | 193.5 (68, 457.2) | 152 (56, 446.5) | 0.295 |
| Apolipoprotein A-I (Apo A-I) (mg/mL) | 1.7 (1.4, 2.1) | 1.8 (1.6, 2.2) | <0.001 |
| Apolipoprotein A-II (Apo A-II) (ng/mL) | 309 (247, 371.2) | 308 (255, 376.2) | 0.662 |
| Apolipoprotein B (Apo B) (ug/mL) | 1350 (1040, 1790) | 1390 (1150, 1852) | 0.113 |
| Apolipoprotein C-I (Apo C-I) (ng/mL) | 307 (252, 367.8) | 336.5 (277.8, 391.2) | <0.001 |
| Apolipoprotein C-III (Apo C-III) (ug/mL) | 218 (164, 271.8) | 212 (155.8, 267.2) | 0.691 |
| Apolipoprotein H (Apo H) (ug/mL) | 331 (270, 390.5) | 343.5 (268, 384) | 0.987 |
| Beta-2-Microglobulin (B2M) (ug/mL) | 1.7 (1.4, 2.5) | 1.6 (1.4, 2.1) | 0.012 |
| Brain-Derived Neurotrophic Factor (BDNF) (ng/mL) | 2.15 (0.9, 4.325) | 2.75 (1.1, 4.725) | 0.017 |
| C-Reactive Protein (CRP) (ug/mL) | 3.75 (1.6, 11) | 3.05 (1.2, 7.575) | 0.014 |
| Carbonic anhydrase 9 (CA-9) (ng/mL) | 0.16 (0.091, 0.26) | 0.14 (0.085, 0.222) | 0.055 |
| Carcinoembryonic antigen-related cell adhesion molecule 1 (CEACAM1) (ng/mL) | 24 (20, 27) | 23 (21, 28.2) | 0.258 |
| CD5 Antigen-like (CD5L) (ng/mL) | 3760 (2898, 5275) | 3470 (2690, 4900) | 0.031 |
| Decorin (ng/mL) | 2.4 (2, 3.6) | 2.3 (1.9, 2.9) | 0.009 |
| E-Selectin (ng/mL) | 5.2 (3.6, 7.1) | 4.8 (3.6, 6.8) | 0.312 |
| EN-RAGE (ng/mL) | 28 (16, 50) | 24 (15.8, 49) | 0.243 |
| Eotaxin-1 (pg/mL) | 104 (42.5, 148) | 96 (42.5, 137.2) | 0.343 |
| Factor VII (ng/mL) | 465.5 (346, 587.2) | 451.5 (359.5, 577.8) | 0.894 |
| Ferritin (FRTN) (ng/mL) | 134 (69.8, 235) | 129.5 (67, 198.8) | 0.409 |
| Fetuin-A (ug/mL) | 698.5 (582.5, 828) | 675.5 (583.8, 810) | 0.627 |
| Fibrinogen (mg/mL) | 4.4 (3.6, 5.4) | 4.1 (3.4, 5.1) | 0.026 |

TABLE 1A-continued

Diagnostic Biomarkers (Received Coronary Cath; Peripheral Cath Optional) (Training Set)

| Biomarker | Concentration in Subjects with Coronary Stenosis (N = 428) | Concentration in Subjects without Coronary Stenosis (N = 221) | p-value |
|---|---|---|---|
| Follicle-Stimulating Hormone (FSH) (mIU/mL) | 6.2 (3.7, 17) | 8.7 (3.5, 42.2) | 0.011 |
| Growth Hormone (GH) (ng/mL) | 0.32 (0.07, 0.9) | 0.26 (0.07, 0.69) | 0.134 |
| Haptoglobin (mg/mL) | 1.3 (0.66, 2.1) | 0.88 (0.478, 1.7) | <0.001 |
| Immunoglobulin A (IgA) (mg/mL) | 2.4 (1.5, 3.425) | 2.25 (1.6, 3.125) | 0.536 |
| Immunoglobulin M (IgM) (mg/mL) | 1.4 (0.928, 2.2) | 1.4 (0.995, 2.225) | 0.348 |
| Insulin (uIU/mL) | 1 (0.11, 2.5) | 0.49 (0.11, 1.5) | <0.001 |
| Intercellular Adhesion Molecule 1 (ICAM-1) (ng/mL) | 107 (85, 133) | 102.5 (83, 125.2) | 0.102 |
| Interferon gamma Induced Protein 10 (IP-10) (pg/mL) | 307.5 (232.8, 399.2) | 288 (223.2, 402) | 0.207 |
| Interleukin-1 receptor antagonist (IL-1ra) (pg/mL) | 119 (90, 158) | 108.5 (83.8, 140.2) | 0.005 |
| Interleukin-6 receptor (IL-6r) (ng/mL) | 24 (19, 29) | 23 (18, 29) | 0.174 |
| Interleukin-8 (IL-8) (pg/mL) | 6.7 (4.6, 10) | 5.7 (4, 9) | 0.01 |
| Interleukin-12 Subunit p40 (IL-12p40) (ng/mL) | 0.595 (0.468, 0.73) | 0.57 (0.44, 0.71) | 0.132 |
| Interleukin-15 (IL-15) (ng/mL) | 0.57 (0.46, 0.7) | 0.54 (0.448, 0.66) | 0.071 |
| Interleukin-18 (IL-18) (pg/mL) | 203 (155.2, 272) | 188 (135.5, 255) | 0.009 |
| Interleukin-18-binding protein (IL-18bp) (ng/mL) | 9.6 (7.4, 13) | 8.8 (6.6, 11) | <0.001 |
| Interleukin-23 (IL-23) (ng/mL) | 2.6 (2, 3.2) | 2.4 (1.9, 3.1) | 0.146 |
| Kidney Injury Molecule-1 (KIM-1) (ng/mL) | 0.043 (0.014, 0.073) | 0.032 (0.014, 0.052) | <0.001 |
| Leptin (ng/mL) | 9.2 (4.5, 21) | 7.9 (4, 20) | 0.424 |
| Luteinizing Hormone (LH) (mIU/mL) | 4.7 (3.3, 7.9) | 5.3 (3.375, 13) | 0.014 |
| Macrophage Colony-Stimulating Factor 1 (M-CSF) (ng/mL) | 0.45 (0.16, 0.73) | 0.38 (0.16, 0.572) | 0.005 |
| Macrophage Inflammatory Protein-1 beta (MIP-1 beta) (pg/mL) | 258 (193.8, 355.2) | 264 (182.5, 351) | 0.539 |
| Matrix Metalloproteinase-2 (MMP-2) (ng/mL) | 1360 (1130, 1642) | 1320 (1120, 1600) | 0.314 |
| Matrix Metalloproteinase-3 (MMP-3) (ng/mL) | 7.2 (5.3, 11) | 6 (4.3, 9.2) | <0.001 |
| Matrix Metalloproteinase-7 (MMP-7) (ng/mL) | 0.37 (0.26, 0.58) | 0.3 (0.218, 0.46) | <0.001 |
| Matrix Metalloproteinase-9 (MMP-9) (ng/mL) | 128 (91.5, 183) | 119.5 (86.8, 167.2) | 0.197 |
| Matrix Metalloproteinase-9, total (MMP-9, total) (ng/mL) | 597.5 (435.5, 833.2) | 531 (379.5, 741) | 0.013 |
| Midkine (ng/mL) | 15 (10.8, 22) | 12 (9.9, 17) | <0.001 |
| Monocyte Chemotactic Protein 1 (MCP-1) (pg/mL) | 112 (79, 160.2) | 103 (77, 152) | 0.272 |
| Monocyte Chemotactic Protein 2 (MCP-2) (pg/mL) | 23 (17, 29) | 23 (17.8, 30) | 0.804 |
| Monocyte Chemotactic Protein 4 (MCP-4) (pg/mL) | 2300 (1720, 3382) | 2300 (1538, 3362) | 0.587 |
| Monokine Induced by Gamma Interferon (MIG) (pg/mL) | 990 (591.5, 1780) | 852 (551, 1462) | 0.033 |
| Myeloid Progenitor Inhibitory Factor 1 (MPIF-1) (ng/mL) | 1.3 (0.98, 1.6) | 1.1 (0.88, 1.4) | <0.001 |
| Myoglobin (ng/mL) | 33 (24, 52.2) | 28 (20, 43.2) | <0.001 |
| N-terminal prohormone of brain natriuretic peptide (NT proBNP) (pg/mL) | 1520 (552.5, 4270) | 1370 (449.8, 3650) | 0.144 |
| Osteopontin (ng/mL) | 28 (21, 43.5) | 26 (19, 37) | 0.022 |
| Pancreatic Polypeptide (PPP) (pg/mL) | 98 (54, 183) | 79 (43, 130) | 0.005 |
| Plasminogen Activator Inhibitor 1 (PAI-1) (ng/mL) | 43 (26, 69) | 46.5 (25, 75) | 0.465 |
| Platelet endothelial cell adhesion molecule (PECAM-1) (ng/mL) | 54 (46, 64.2) | 55 (45, 62.2) | 0.575 |

TABLE 1A-continued

Diagnostic Biomarkers (Received Coronary Cath; Peripheral Cath Optional) (Training Set)

| Biomarker | Concentration in Subjects with Coronary Stenosis (N = 428) | Concentration in Subjects without Coronary Stenosis (N = 221) | p-value |
|---|---|---|---|
| Prolactin (PRL) (ng/mL) | 8 (5.4, 12) | 8.4 (5.6, 13) | 0.188 |
| Pulmonary and Activation-Regulated Chemokine (PARC) (ng/mL) | 101 (75.8, 138.2) | 92 (65.8, 135.2) | 0.08 |
| Pulmonary surfactant-associated protein D (SP-D) (ng/mL) | 5.5 (3.4, 8.7) | 4.5 (3.1, 7.3) | 0.003 |
| Resistin (ng/mL) | 2.4 (1.8, 3.5) | 2.3 (1.7, 3.2) | 0.149 |
| Serotransferrin (Transferrin) (mg/dl) | 273.5 (235.8, 316.2) | 274.5 (233, 315) | 0.765 |
| Serum Amyloid P-Component (SAP) (ug/mL) | 13 (10, 16) | 12 (9.4, 15) | 0.016 |
| Stem Cell Factor (SCF) (pg/mL) | 376 (292, 478.2) | 340.5 (258, 423.2) | <0.001 |
| T-Cell-Specific Protein RANTES (RANTES) (ng/mL) | 8.1 (3.7, 16) | 9.3 (4.5, 19) | 0.07 |
| Tamm-Horsfall Urinary Glycoprotein (THP) (ug/mL) | 0.029 (0.02, 0.038) | 0.034 (0.024, 0.044) | <0.001 |
| Thrombomodulin (TM) (ng/mL) | 3.8 (3.1, 4.7) | 3.55 (3, 4.2) | 0.002 |
| Thrombospondin-1 (ng/mL) | 4090 (2020, 7100) | 5260 (2442, 7742) | 0.019 |
| Thyroid-Stimulating Hormone (TSH) (uIU/mL) | 1.2 (0.79, 1.8) | 1.2 (0.82, 1.8) | 0.385 |
| Thyroxine-Binding Globulin (TBG) (ug/mL) | 38 (32, 44) | 36 (29, 45) | 0.124 |
| Tissue Inhibitor of Metalloproteinases 1 (TIMP-1) (ng/mL) | 73 (60, 94) | 72.5 (58, 90.2) | 0.451 |
| Transthyretin (TTR) (mg/dl) | 26 (22, 30) | 25.5 (21, 31) | 0.854 |
| Troponin (pg/ml) | 9.6 (4, 35.7) | 5.8 (3, 13.6) | <0.001 |
| Tumor necrosis factor receptor 2 (TNFR2) (ng/mL) | 6.4 (4.8, 9.6) | 6 (4.5, 7.5) | 0.001 |
| Vascular Cell Adhesion Molecule-1 (VCAM-1) (ng/mL) | 586 (464.8, 730.2) | 528 (442, 669.2) | 0.004 |
| Vascular Endothelial Growth Factor (VEGF) (pg/mL) | 98.5 (70.8, 137.5) | 103.5 (73.8, 140) | 0.373 |
| Vitamin D-Binding Protein (VDBP) (ug/mL) | 249 (191.2, 310.5) | 249 (194.5, 306.2) | 0.927 |
| Vitamin K-Dependent Protein S (VKDPS) (ug/mL) | 14 (11, 17) | 13 (11, 16) | 0.078 |
| Vitronectin (ug/mL) | 465 (352, 593) | 444.5 (349.5, 552) | 0.148 |
| von Willebrand Factor (vWF) (ug/mL) | 134 (96, 181) | 124.5 (90, 175.2) | 0.147 |

Table 1B below shows biomarker concentrations and their diagnostic association that differ between those in the training set (N=566) with at least one coronary artery stenosis ≥70% (N=361) and those who did not in the cohort of subjects who received a coronary cath only.

TABLE 1B

Diagnostic Biomarkers (Received Coronary Cath Only) (Training Set)

| Biomarker | Concentration in Subjects with Coronary Stenosis (N = 361) | Concentration in Subjects without Coronary Stenosis (N = 205) | p-value |
|---|---|---|---|
| Adiponectin (ug/mL) | 3.5 (2.2, 5.4) | 4.6 (2.9, 7.3) | <0.001 |
| Alpha-1-Antitrypsin (AAT) (mg/mL) | 1.8 (1.5, 2.1) | 1.8 (1.5, 2.1) | 0.479 |
| Alpha-2-Macroglobulin (A2Macro) (mg/mL) | 1.9 (1.5, 2.3) | 1.9 (1.6, 2.3) | 0.989 |
| Angiopoietin-1 (ANG-1) (ng/mL) | 6.7 (5, 9.5) | 7.3 (5.1, 11) | 0.155 |
| Angiotensin-Converting Enzyme (ACE) (ng/mL) | 79 (60, 106) | 77.5 (59.8, 103.2) | 0.763 |
| Apolipoprotein(a) (Lp(a)) (ug/mL) | 199 (69, 455) | 156.5 (55.5, 446.5) | 0.313 |

TABLE 1B-continued

Diagnostic Biomarkers (Received Coronary Cath Only) (Training Set)

| Biomarker | Concentration in Subjects with Coronary Stenosis (N = 361) | Concentration in Subjects without Coronary Stenosis (N = 205) | p-value |
|---|---|---|---|
| Apolipoprotein A-I (Apo A-I) (mg/mL) | 1.7 (1.4, 2.1) | 1.9 (1.6, 2.225) | <0.001 |
| Apolipoprotein A-II (Apo A-II) (ng/mL) | 308 (247, 369) | 311.5 (255, 377.2) | 0.5 |
| Apolipoprotein B (Apo B) (ug/mL) | 1320 (1040, 1770) | 1395 (1150, 1875) | 0.048 |
| Apolipoprotein C-I (Apo C-I) (ng/mL) | 308 (251, 367) | 339 (287.8, 393.5) | <0.001 |
| Apolipoprotein C-III (Apo C-III) (ug/mL) | 218 (159, 274) | 214 (158, 267.2) | 0.977 |
| Apolipoprotein H (Apo H) (ug/mL) | 328 (270, 388) | 344.5 (277.2, 384.2) | 0.707 |
| Beta-2-Microglobulin (B2M) (ug/mL) | 1.7 (1.3, 2.4) | 1.6 (1.4, 2.1) | 0.096 |
| Brain-Derived Neurotrophic Factor (BDNF) (ng/mL) | 2.2 (0.89, 4.3) | 2.85 (1.175, 4.7) | 0.013 |
| C-Reactive Protein (CRP) (ug/mL) | 3.5 (1.5, 10) | 3.2 (1.3, 8) | 0.094 |
| Carbonic anhydrase 9 (CA-9) (ng/mL) | 0.16 (0.09, 0.26) | 0.14 (0.084, 0.22) | 0.04 |
| Carcinoembryonic antigen-related cell adhesion molecule 1 (CEACAM1) (ng/mL) | 23 (20, 27) | 23 (21, 28) | 0.271 |
| CD5 Antigen-like (CD5L) (ng/mL) | 3750 (2840, 5110) | 3470 (2690, 4845) | 0.101 |
| Decorin (ng/mL) | 2.4 (2, 3.7) | 2.3 (1.9, 2.925) | 0.014 |
| E-Selectin (ng/mL) | 5.2 (3.6, 7) | 4.8 (3.6, 6.8) | 0.33 |
| EN-RAGE (ng/mL) | 27 (16, 51) | 25 (15, 49) | 0.333 |
| Eotaxin-1 (pg/mL) | 102 (42.5, 144) | 96 (42.5, 137) | 0.664 |
| Factor VII (ng/mL) | 465 (340, 592) | 450 (357.8, 577) | 0.971 |
| Ferritin (FRTN) (ng/mL) | 137 (73, 241) | 130 (67, 197.2) | 0.303 |
| Fetuin-A (ug/mL) | 700 (584, 829) | 676.5 (583.8, 13.8) | 0.689 |
| Fibrinogen (mg/mL) | 4.4 (3.6, 5.3) | 4.1 (3.5, 5.1) | 0.133 |
| Follicle-Stimulating Hormone (FSH) (mIU/mL) | 6 (3.7, 17) | 8.8 (3.6, 43) | 0.007 |
| Growth Hormone (GH) (ng/mL) | 0.34 (0.07, 0.98) | 0.26 (0.07, 0.69) | 0.053 |
| Haptoglobin (mg/mL) | 1.3 (0.65, 2.1) | 0.825 (0.458, 1.6) | <0.001 |
| Immunoglobulin A (IgA) (mg/mL) | 2.4 (1.5, 3.4) | 2.2 (1.5, 3.125) | 0.445 |
| Immunoglobulin M (IgM) (mg/mL) | 1.4 (0.93, 2.2) | 1.4 (1, 2.3) | 0.34 |
| Insulin (uIU/mL) | 1 (0.22, 2.5) | 0.545 (0.11, 1.6) | <0.001 |
| Intercellular Adhesion Molecule 1 (ICAM-1) (ng/mL) | 106 (85, 133) | 102 (81.8, 125) | 0.098 |
| Interferon gamma Induced Protein 10 (IP-10) (pg/mL) | 304 (232, 396) | 291 (227.8, 406.2) | 0.631 |
| Interleukin-1 receptor antagonist (IL-1ra) (pg/mL) | 119 (90, 158) | 108.5 (84, 141) | 0.018 |
| Interleukin-6 receptor (IL-6r) (ng/mL) | 24 (19, 29) | 23 (18, 29) | 0.304 |
| Interleukin-8 (IL-8) (pg/mL) | 6.6 (4.6, 10) | 5.7 (4, 8.8) | 0.014 |
| Interleukin-12 Subunit p40 (IL-12p40) (ng/mL) | 0.58 (0.46, 0.73) | 0.57 (0.44, 0.71) | 0.346 |
| Interleukin-15 (IL-15) (ng/mL) | 0.57 (0.45, 0.7) | 0.54 (0.45, 0.67) | 0.231 |
| Interleukin-18 (IL-18) (pg/mL) | 204 (156, 272) | 188 (136, 256) | 0.021 |
| Interleukin-18-binding protein (IL-18bp) (ng/mL) | 9.4 (7.3, 13) | 8.9 (6.6, 11) | 0.002 |
| Interleukin-23 (IL-23) (ng/mL) | 2.6 (2, 3.3) | 2.4 (1.9, 3.1) | 0.253 |
| Kidney Injury Molecule-1 (KIM-1) (ng/mL) | 0.042 (0.014, 0.07) | 0.032 (0.014, 0.051) | <0.001 |
| Leptin (ng/mL) | 9.2 (4.3, 21) | 8.1 (4, 20.2) | 0.603 |
| Luteinizing Hormone (LH) (mIU/mL) | 4.7 (3.3, 7.8) | 5.35 (3.375, 13) | 0.01 |
| Macrophage Colony-Stimulating Factor 1 (M-CSF) (ng/mL) | 0.45 (0.16, 0.73) | 0.38 (0.16, 0.572) | 0.012 |
| Macrophage Inflammatory Protein-1 beta (MIP-1 beta) (pg/mL) | 256 (191, 345) | 269 (187.5, 350) | 0.964 |
| Matrix Metalloproteinase-2 (MMP-2) (ng/mL) | 1360 (1130, 1640) | 1320 (1120, 1615) | 0.35 |

TABLE 1B-continued

Diagnostic Biomarkers (Received Coronary Cath Only) (Training Set)

| Biomarker | Concentration in Subjects with Coronary Stenosis (N = 361) | Concentration in Subjects without Coronary Stenosis (N = 205) | p-value |
|---|---|---|---|
| Matrix Metalloproteinase-3 (MMP-3) (ng/mL) | 7 (5.1, 11) | 6 (4.3, 9.2) | 0.001 |
| Matrix Metalloproteinase-7 (MMP-7) (ng/mL) | 0.36 (0.25, 0.56) | 0.305 (0.21, 0.46) | 0.006 |
| Matrix Metalloproteinase-9 (MMP-9) (ng/mL) | 133 (94, 183) | 119.5 (89.2, 168.5) | 0.147 |
| Matrix Metalloproteinase-9, total (MMP-9, total) (ng/mL) | 605 (440, 859) | 531 (379.5, 741.5) | 0.007 |
| Midkine (ng/mL) | 14 (10, 21) | 12 (9.8, 17) | 0.004 |
| Monocyte Chemotactic Protein 1 (MCP-1) (pg/mL) | 110 (77, 158) | 103 (78, 150.5) | 0.567 |
| Monocyte Chemotactic Protein 2 (MCP-2) (pg/mL) | 23 (17, 29) | 23 (18, 30) | 0.297 |
| Monocyte Chemotactic Protein 4 (MCP-4) (pg/mL) | 2260 (1690, 3390) | 2305 (1562, 3360) | 0.85 |
| Monokine Induced by Gamma Interferon (MIG) (pg/mL) | 964 (578, 1750) | 877.5 (551, 1560) | 0.175 |
| Myeloid Progenitor Inhibitory Factor 1 (MPIF-1) (ng/mL) | 1.3 (0.97, 1.6) | 1.1 (0.88, 1.5) | 0.003 |
| Myoglobin (ng/mL) | 33 (24, 52) | 27 (20, 43.2) | <0.001 |
| N-terminal prohormone of brain natriuretic peptide (NT proBNP) (pg/mL) | 1500 (535, 4700) | 1380 (449.8, 3820) | 0.15 |
| Osteopontin (ng/mL) | 28 (20, 43.2) | 25 (18.5, 35.5) | 0.049 |
| Pancreatic Polypeptide (PPP) (pg/mL) | 93 (49, 181) | 76.5 (43, 131) | 0.02 |
| Plasminogen Activator Inhibitor 1 (PAI-1) (ng/mL) | 44 (26, 69) | 47 (25.8, 75) | 0.442 |
| Platelet endothelial cell adhesion molecule (PECAM-1) (ng/mL) | 54 (45, 64) | 55 (45, 62) | 0.702 |
| Prolactin (PRL) (ng/mL) | 8 (5.2, 12) | 8.4 (5.5, 13) | 0.195 |
| Pulmonary and Activation-Regulated Chemokine (PARC) (ng/mL) | 99 (74, 135) | 94 (66, 136.2) | 0.329 |
| Pulmonary surfactant-associated protein D (SP-D) (ng/mL) | 5.5 (3.5, 8.7) | 4.5 (3, 7.2) | 0.002 |
| Resistin (ng/mL) | 2.4 (1.8, 3.5) | 2.3 (1.7, 3.2) | 0.268 |
| Serotransferrin (Transferrin) (mg/dl) | 272 (235, 314) | 276.5 (233, 315) | 0.994 |
| Serum Amyloid P-Component (SAP) (ug/mL) | 13 (10, 16) | 12 (9.4, 15) | 0.052 |
| Stem Cell Factor (SCF) (pg/mL) | 374 (284, 478) | 341 (258, 423.2) | 0.006 |
| T-Cell-Specific Protein RANTES (RANTES) (ng/mL) | 8 (3.6, 16) | 9.5 (4.4, 18) | 0.061 |
| Tamm-Horsfall Urinary Glycoprotein (THP) (ug/mL) | 0.03 (0.02, 0.039) | 0.034 (0.024, 0.044) | 0.002 |
| Thrombomodulin (TM) (ng/mL) | 3.8 (3.1, 4.7) | 3.55 (3, 4.2) | 0.01 |
| Thrombospondin-1 (ng/mL) | 3940 (2020, 7080) | 5360 (2478, 7655) | 0.011 |
| Thyroid-Stimulating Hormone (TSH) (uIU/mL) | 1.1 (0.79, 1.7) | 1.2 (0.818, 1.8) | 0.218 |
| Thyroxine-Binding Globulin (TBG) (ug/mL) | 37 (32, 44) | 36 (29, 45) | 0.359 |
| Tissue Inhibitor of Metalloproteinases 1 (TIMP-1) (ng/mL) | 72 (58, 93) | 71.5 (58, 89.5) | 0.712 |
| Transthyretin (TTR) (mg/dl) | 26 (22, 30) | 26 (21, 31) | 0.928 |
| Troponin (pg/ml) | 9.6 (3.8, 40.7) | 5.8 (2.9, 14) | <0.001 |
| Tumor necrosis factor receptor 2 (TNFR2) (ng/mL) | 6.3 (4.8, 9.6) | 6 (4.6, 7.5) | 0.015 |
| Vascular Cell Adhesion Molecule-1 (VCAM-1) (ng/mL) | 588 (465, 733) | 533 (448.8, 682.2) | 0.022 |
| Vascular Endothelial Growth Factor (VEGF) (pg/mL) | 99 (68, 144) | 105.5 (73.8, 140) | 0.39 |
| Vitamin D-Binding Protein (VDBP) (ug/mL) | 248 (188, 313) | 250 (192.2, 310.2) | 0.984 |
| Vitamin K-Dependent Protein S (VKDPS) (ug/mL) | 14 (11, 17) | 13 (11, 16) | 0.099 |

TABLE 1B-continued

Diagnostic Biomarkers (Received Coronary Cath Only) (Training Set)

| Biomarker | Concentration in Subjects with Coronary Stenosis (N = 361) | Concentration in Subjects without Coronary Stenosis (N = 205) | p-value |
|---|---|---|---|
| Vitronectin (ug/mL) | 467 (352, 593) | 446 (350, 552) | 0.224 |
| von Willebrand Factor (vWF) (ug/mL) | 135 (95, 184) | 124.5 (90.8, 171.8) | 0.187 |

Table 2A shows biomarker concentrations and their prognostic association in patients with major adverse cardiac events (MACE) within 365 days of the blood draw (for the training set, N=649). The numbers in this table were calculated using the composite endpoint of one-year MACE with CV death, MI, or major stroke; these proteins produce similar results with the composite endpoint of one-year MACE with all-cause death, MI and/or major stroke.

TABLE 2A

Prognostic Biomarkers (Within 365 Days Post-Cath) (Training Set)

| Biomarker | Concentration in Subjects with one-year MACE (N = 82) | Concentration in Subjects without one-year MACE (N = 567) | p-value |
|---|---|---|---|
| Adiponectin (ug/mL) | 4.9 (2.85, 7.45) | 3.6 (2.325, 5.6) | 0.002 |
| Alpha-1-Antitrypsin (AAT) (mg/mL) | 2 (1.625, 2.4) | 1.8 (1.5, 2.1) | <0.001 |
| Alpha-2-Macroglobulin (A2Macro) (mg/mL) | 2.1 (1.7, 2.575) | 1.9 (1.6, 2.3) | 0.001 |
| Angiopoietin-1 (ANG-1) (ng/mL) | 7 (5, 10.8) | 6.8 (5, 9.8) | 0.715 |
| Angiotensin-Converting Enzyme (ACE) (ng/mL) | 75 (59, 106.5) | 79 (60, 104.8) | 0.629 |
| Apolipoprotein(a) (Lp(a)) (ug/mL) | 187 (77.8, 438.5) | 169.5 (60.2, 454.8) | 0.619 |
| Apolipoprotein A-I (Apo A-I) (mg/mL) | 1.75 (1.4, 2) | 1.8 (1.5, 2.1) | 0.117 |
| Apolipoprotein A-II (Apo A-II) (ng/mL) | 262 (214, 333.5) | 312.5 (255.5, 380) | <0.001 |
| Apolipoprotein B (Apo B) (ug/mL) | 1270 (964.5, 1668) | 1390 (1090, 1820) | 0.028 |
| Apolipoprotein C-I (Apo C-I) (ng/mL) | 309 (245.2, 357.2) | 314 (262, 381.5) | 0.089 |
| Apolipoprotein C-III (Apo C-III) (ug/mL) | 222 (170.5, 274) | 215.5 (158.2, 271) | 0.399 |
| Apolipoprotein H (Apo H) (ug/mL) | 328 (271.2, 388.5) | 333 (270, 387.8) | 0.965 |
| Beta-2-Microglobulin (B2M) (ug/mL) | 2.5 (1.8, 3.425) | 1.6 (1.3, 2.2) | <0.001 |
| Brain-Derived Neurotrophic Factor (BDNF) (ng/mL) | 2 (0.755, 4.325) | 2.35 (1, 4.6) | 0.238 |
| C-Reactive Protein (CRP) (ug/mL) | 6.55 (2.225, 18.75) | 3.3 (1.4, 8.3) | <0.001 |
| Carbonic anhydrase 9 (CA-9) (ng/mL) | 0.23 (0.15, 0.338) | 0.14 (0.085, 0.238) | <0.001 |
| Carcinoembryonic antigen-related cell adhesion molecule 1 (CEACAM1) (ng/mL) | 24 (21, 29) | 23 (20, 27.8) | 0.254 |
| CD5 Antigen-like (CD5L) (ng/mL) | 4200 (2798, 6418) | 3700 (2792, 4998) | 0.058 |
| Decorin (ng/mL) | 2.85 (2.1, 4.075) | 2.3 (1.9, 3.1) | <0.001 |
| E-Selectin (ng/mL) | 4.8 (3.5, 7) | 5.1 (3.7, 7) | 0.436 |
| EN-RAGE (ng/mL) | 34.5 (15, 56.8) | 26 (16, 49) | 0.378 |
| Eotaxin-1 (pg/mL) | 118.5 (42.5, 153) | 97 (42.5, 143.8) | 0.034 |
| Factor VII (ng/mL) | 404 (294.8, 544) | 468 (366, 586.5) | 0.009 |
| Ferritin (FRTN) (ng/mL) | 136 (81.2, 249.2) | 132 (68, 217.8) | 0.17 |
| Fetuin-A (ug/mL) | 644.5 (539.8, 766) | 696 (593, 828.5) | 0.005 |
| Fibrinogen (mg/mL) | 4.9 (4, 5.6) | 4.2 (3.5, 5.3) | 0.003 |
| Follicle-Stimulating Hormone (FSH) (mIU/mL) | 7.7 (4, 34.5) | 6.3 (3.6, 26.8) | 0.513 |
| Growth Hormone (GH) (ng/mL) | 0.55 (0.19, 1.075) | 0.28 (0.07, 0.798) | 0.009 |
| Haptoglobin (mg/mL) | 1.2 (0.68, 2.2) | 1.1 (0.54, 1.9) | 0.104 |
| Immunoglobulin A (IgA) (mg/mL) | 2.25 (1.6, 3.2) | 2.4 (1.5, 3.4) | 0.959 |

TABLE 2A-continued

Prognostic Biomarkers (Within 365 Days Post-Cath) (Training Set)

| Biomarker | Concentration in Subjects with one-year MACE (N = 82) | Concentration in Subjects without one-year MACE (N = 567) | p-value |
|---|---|---|---|
| Immunoglobulin M (IgM) (mg/mL) | 1.4 (1.1, 2) | 1.4 (0.942, 2.2) | 0.674 |
| Insulin (uIU/mL) | 0.89 (0.11, 1.8) | 0.815 (0.11, 2.175) | 0.837 |
| Intercellular Adhesion Molecule 1 (ICAM-1) (ng/mL) | 107 (86, 132.5) | 104 (84, 131) | 0.557 |
| Interferon gamma Induced Protein 10 (IP-10) (pg/mL) | 335 (242.5, 432.5) | 299.5 (228, 398) | 0.094 |
| Interleukin-1 receptor antagonist (IL-1ra) (pg/mL) | 122 (97.2, 160.5) | 114 (88, 148) | 0.1 |
| Interleukin-6 receptor (IL-6r) (ng/mL) | 23 (19, 29.8) | 24 (19, 29) | 0.988 |
| Interleukin-8 (IL-8) (pg/mL) | 10 (6.7, 15.8) | 6 (4.2, 9) | <0.001 |
| Interleukin-12 Subunit p40 (IL-12p40) (ng/mL) | 0.64 (0.48, 0.758) | 0.58 (0.45, 0.71) | 0.186 |
| Interleukin-15 (IL-15) (ng/mL) | 0.56 (0.46, 0.69) | 0.555 (0.45, 0.7) | 0.712 |
| Interleukin-18 (IL-18) (pg/mL) | 202 (154.8, 288.8) | 198 (144, 266) | 0.33 |
| Interleukin-18-binding protein (IL-18bp) (ng/mL) | 13 (9.3, 19) | 8.9 (7, 12) | <0.001 |
| Interleukin-23 (IL-23) (ng/mL) | 2.5 (1.725, 3.275) | 2.5 (2, 3.2) | 0.508 |
| Kidney Injury Molecule-1 (KIM-1) (ng/mL) | 0.062 (0.042, 0.14) | 0.034 (0.014, 0.058) | <0.001 |
| Leptin (ng/mL) | 7.8 (3.5, 18.8) | 9.1 (4.2, 21) | 0.252 |
| Luteinizing Hormone (LH) (mIU/mL) | 5.35 (3.5, 11.5) | 4.75 (3.3, 8.775) | 0.168 |
| Macrophage Colony-Stimulating Factor 1 (M-CSF) (ng/mL) | 0.74 (0.482, 1.4) | 0.385 (0.16, 0.6) | <0.001 |
| Macrophage Inflammatory Protein-1 beta (MIP-1 beta) (pg/mL) | 270 (196.2, 401.5) | 258 (188, 345) | 0.414 |
| Matrix Metalloproteinase-2 (MMP-2) (ng/mL) | 1440 (1255, 1888) | 1325 (1120, 1608) | <0.001 |
| Matrix Metalloproteinase-3 (MMP-3) (ng/mL) | 9.6 (7, 15.8) | 6.6 (4.7, 9.8) | <0.001 |
| Matrix Metalloproteinase-7 (MMP-7) (ng/mL) | 0.46 (0.33, 0.768) | 0.34 (0.232, 0.51) | <0.001 |
| Matrix Metalloproteinase-9 (MMP-9) (ng/mL) | 123.5 (76, 192.8) | 126.5 (91.2, 177.8) | 0.608 |
| Matrix Metalloproteinase-9, total (MMP-9, total) (ng/mL) | 554.5 (382.5, 931) | 580.5 (419.2, 795) | 0.921 |
| Midkine (ng/mL) | 21.5 (13.2, 36.5) | 13 (10, 19) | <0.001 |
| Monocyte Chemotactic Protein 1 (MCP-1) (pg/mL) | 113.5 (74, 161) | 108 (78, 158) | 0.811 |
| Monocyte Chemotactic Protein 2 (MCP-2) (pg/mL) | 24 (19, 29.8) | 23 (17, 30) | 0.268 |
| Monocyte Chemotactic Protein 4 (MCP-4) (pg/mL) | 2295 (1680, 3385) | 2300 (1662, 3360) | 0.867 |
| Monokine Induced by Gamma Interferon (MIG) (pg/mL) | 1555 (876.8, 2538) | 876 (554.5, 1588) | <0.001 |
| Myeloid Progenitor Inhibitory Factor 1 (MPIF-1) (ng/mL) | 1.5 (1.1, 2) | 1.2 (0.93, 1.5) | <0.001 |
| Myoglobin (ng/mL) | 47 (29, 78.5) | 30 (21, 45.8) | <0.001 |
| N-terminal prohormone of brain natriuretic peptide (NT proBNP) (pg/mL) | 5610 (2050, 15980) | 1310 (460.8, 3235) | <0.001 |
| Osteopontin (ng/mL) | 49 (26.2, 82.5) | 26 (19, 37) | <0.001 |
| Pancreatic Polypeptide (PPP) (pg/mL) | 147 (65, 317) | 87 (47.2, 148) | <0.001 |
| Plasminogen Activator Inhibitor 1 (PAI-1) (ng/mL) | 46 (26, 74.2) | 44 (26, 71.8) | 0.905 |
| Platelet endothelial cell adhesion molecule (PECAM-1) (ng/mL) | 55 (46, 67.5) | 54 (45, 63) | 0.344 |
| Prolactin (PRL) (ng/mL) | 9.8 (6.2, 15) | 7.9 (5.4, 12) | 0.019 |
| Pulmonary and Activation-Regulated Chemokine (PARC) (ng/mL) | 109 (84.2, 150.8) | 97 (71, 136) | 0.033 |
| Pulmonary surfactant-associated protein D (SP-D) (ng/mL) | 7 (4.1, 9.9) | 5 (3.1, 8.1) | <0.001 |
| Resistin (ng/mL) | 2.9 (2.1, 4.575) | 2.3 (1.8, 3.3) | <0.001 |
| Serotransferrin (Transferrin) (mg/dl) | 253.5 (210, 302) | 275.5 (239.2, 317) | 0.003 |

TABLE 2A-continued

Prognostic Biomarkers (Within 365 Days Post-Cath) (Training Set)

| Biomarker | Concentration in Subjects with one-year MACE (N = 82) | Concentration in Subjects without one-year MACE (N = 567) | p-value |
|---|---|---|---|
| Serum Amyloid P-Component (SAP) (ug/mL) | 11.5 (9.1, 14.8) | 13 (10, 16) | 0.015 |
| Stem Cell Factor (SCF) (pg/mL) | 432 (314.8, 621) | 348.5 (274, 443.2) | <0.001 |
| T-Cell-Specific Protein RANTES (RANTES) (ng/mL) | 8.1 (3.5, 18.8) | 8.5 (3.9, 17) | 0.866 |
| Tamm-Horsfall Urinary Glycoprotein (THP) (ug/mL) | 0.022 (0.013, 0.03) | 0.032 (0.022, 0.041) | <0.001 |
| Thrombomodulin (TM) (ng/mL) | 4.45 (3.6, 6.3) | 3.6 (3, 4.4) | <0.001 |
| Thrombospondin-1 (ng/mL) | 3670 (2010, 7210) | 4305 (2170, 7392) | 0.404 |
| Thyroid-Stimulating Hormone (TSH) (uIU/mL) | 1.3 (0.718, 1.9) | 1.2 (0.802, 1.7) | 0.709 |
| Thyroxine-Binding Globulin (TBG) (ug/mL) | 36 (31, 41.8) | 38 (31, 45) | 0.177 |
| Tissue Inhibitor of Metalloproteinases 1 (TIMP-1) (ng/mL) | 94.5 (77, 118.8) | 70 (58, 87) | <0.001 |
| Transthyretin (TTR) (mg/dl) | 23 (19, 28.8) | 26 (22, 30) | 0.001 |
| Troponin (pg/ml) | 39 (15.2, 184.3) | 6.5 (3.3, 18.1) | <0.001 |
| Tumor necrosis factor receptor 2 (TNFR2) (ng/mL) | 9.4 (6.3, 15) | 6 (4.7, 8.1) | <0.001 |
| Vascular Cell Adhesion Molecule-1 (VCAM-1) (ng/mL) | 705.5 (544, 982.2) | 545 (448.2, 681.8) | <0.001 |
| Vascular Endothelial Growth Factor (VEGF) (pg/mL) | 103.5 (69.5, 162.5) | 101 (72, 135) | 0.415 |
| Vitamin D-Binding Protein (VDBP) (ug/mL) | 233.5 (174.2, 306.8) | 250.5 (195.2, 309.2) | 0.189 |
| Vitamin K-Dependent Protein S (VKDPS) (ug/mL) | 13 (11, 16) | 14 (11, 16) | 0.454 |
| Vitronectin (ug/mL) | 426 (328.2, 534.5) | 463.5 (358, 591) | 0.043 |
| von Willebrand Factor (vWF) (ug/mL) | 182.5 (134.2, 233.5) | 123 (91, 171) | <0.001 |

Table 2B below shows biomarker concentrations and their prognostic association that differ between those in the training set (N=648) with a major adverse cardiac event (MACE) from 3-365 days of the blood draw and those who did not. The numbers in this table were calculated using the composite endpoint of one-year MACE with CV death, MI, or major stroke; these proteins produce similar results with the composite endpoint of one-year MACE with all-cause death, MI and/or major stroke.

TABLE 2B

Prognostic Biomarkers (3-365 Days Post-Cath) (Training Set)

| Biomarker | Concentration in Subjects with one-year MACE (N = 71) | Concentration in Subjects without one-year MACE (N = 577) | p-value |
|---|---|---|---|
| Adiponectin (ug/mL) | 5.1 (3.3, 7.95) | 3.6 (2.3, 5.6) | <0.001 |
| Alpha-1-Antitrypsin (AAT) (mg/mL) | 2 (1.7, 2.4) | 1.8 (1.5, 2.1) | <0.001 |
| Alpha-2-Macroglobulin (A2Macro) (mg/mL) | 2.1 (1.75, 2.5) | 1.9 (1.6, 2.3) | 0.002 |
| Angiopoietin-1 (ANG-1) (ng/mL) | 6.8 (4.9, 10) | 6.8 (5, 9.8) | 0.873 |
| Angiotensin-Converting Enzyme (ACE) (ng/mL) | 74 (59, 105) | 79 (60, 105) | 0.38 |
| Apolipoprotein(a) (Lp(a)) (ug/mL) | 199 (109, 420) | 166.5 (59, 455.5) | 0.271 |
| Apolipoprotein A-I (Apo A-I) (mg/mL) | 1.8 (1.4, 2) | 1.8 (1.5, 2.1) | 0.279 |
| Apolipoprotein A-II (Apo A-II) (ng/mL) | 263 (215, 331.5) | 312 (255, 380) | <0.001 |
| Apolipoprotein B (Apo B) (ug/mL) | 1280 (952.5, 1665) | 1390 (1090, 1820) | 0.063 |

TABLE 2B-continued

Prognostic Biomarkers (3-365 Days Post-Cath) (Training Set)

| Biomarker | Concentration in Subjects with one-year MACE (N = 71) | Concentration in Subjects without one-year MACE (N = 577) | p-value |
|---|---|---|---|
| Apolipoprotein C-I (Apo C-I) (ng/mL) | 308 (250.5, 356.5) | 314 (262, 380.2) | 0.166 |
| Apolipoprotein C-III (Apo C-III) (ug/mL) | 222 (168.5, 272) | 216 (158.8, 271) | 0.471 |
| Apolipoprotein H (Apo H) (ug/mL) | 337 (278.5, 397.5) | 332 (270, 387.2) | 0.54 |
| Beta-2-Microglobulin (B2M) (ug/mL) | 2.5 (1.8, 3.6) | 1.7 (1.3, 2.2) | <0.001 |
| Brain-Derived Neurotrophic Factor (BDNF) (ng/mL) | 1.9 (0.745, 4.05) | 2.35 (1, 4.6) | 0.192 |
| C-Reactive Protein (CRP) (ug/mL) | 7 (2.95, 19.5) | 3.3 (1.4, 8.325) | <0.001 |
| Carbonic anhydrase 9 (CA-9) (ng/mL) | 0.23 (0.16, 0.36) | 0.14 (0.085, 0.232) | <0.001 |
| Carcinoembryonic antigen-related cell adhesion molecule 1 (CEACAM1) (ng/mL) | 24 (21, 29) | 23 (20, 28) | 0.28 |
| CD5 Antigen-like (CD5L) (ng/mL) | 4090 (2770, 6630) | 3700 (2798, 5010) | 0.071 |
| Decorin (ng/mL) | 2.9 (2.15, 4.25) | 2.3 (1.9, 3.1) | <0.001 |
| E-Selectin (ng/mL) | 5.1 (3.5, 7) | 5.1 (3.7, 7) | 0.536 |
| EN-RAGE (ng/mL) | 35 (16, 58.5) | 26 (16, 49) | 0.219 |
| Eotaxin-1 (pg/mL) | 118 (42.5, 152) | 97 (42.5, 144.2) | 0.068 |
| Factor VII (ng/mL) | 395 (293, 539.5) | 468 (364, 587) | 0.009 |
| Ferritin (FRTN) (ng/mL) | 133 (84, 253) | 133 (68, 217.2) | 0.141 |
| Fetuin-A (ug/mL) | 651 (541.5, 766.5) | 692.5 (588.8, 827.2) | 0.021 |
| Fibrinogen (mg/mL) | 4.9 (4.1, 5.75) | 4.2 (3.5, 5.3) | <0.001 |
| Follicle-Stimulating Hormone (FSH) (mIU/mL) | 8 (4.7, 35) | 6.3 (3.6, 26.2) | 0.151 |
| Growth Hormone (GH) (ng/mL) | 0.56 (0.195, 0.98) | 0.28 (0.07, 0.802) | 0.009 |
| Haptoglobin (mg/mL) | 1.2 (0.67, 2.2) | 1.15 (0.54, 1.9) | 0.234 |
| Immunoglobulin A (IgA) (mg/mL) | 2.2 (1.6, 3.3) | 2.4 (1.5, 3.4) | 0.839 |
| Immunoglobulin M (IgM) (mg/mL) | 1.4 (1.1, 1.9) | 1.4 (0.94, 2.2) | 0.969 |
| Insulin (uIU/mL) | 1 (0.11, 1.9) | 0.815 (0.11, 2.1) | 0.806 |
| Intercellular Adhesion Molecule 1 (ICAM-1) (ng/mL) | 106 (83.5, 130.5) | 104 (84, 132.2) | 0.81 |
| Interferon gamma Induced Protein 10 (IP-10) (pg/mL) | 336 (246, 437) | 300 (228, 398) | 0.076 |
| Interleukin-1 receptor antagonist (IL-1ra) (pg/mL) | 121 (95.5, 158) | 114.5 (88, 148) | 0.224 |
| Interleukin-6 receptor (IL-6r) (ng/mL) | 23 (19, 30) | 24 (19, 29) | 0.782 |
| Interleukin-8 (IL-8) (pg/mL) | 11 (6.7, 16.5) | 6 (4.2, 9.1) | <0.001 |
| Interleukin-12 Subunit p40 (IL-12p40) (ng/mL) | 0.64 (0.48, 0.765) | 0.58 (0.458, 0.71) | 0.193 |
| Interleukin-15 (IL-15) (ng/mL) | 0.55 (0.46, 0.69) | 0.56 (0.45, 0.7) | 0.888 |
| Interleukin-18 (IL-18) (pg/mL) | 203 (160, 295.5) | 197 (143.5, 266) | 0.188 |
| Interleukin-18-binding protein (IL-18bp) (ng/mL) | 14 (9.3, 19) | 9 (7, 12) | <0.001 |
| Interleukin-23 (IL-23) (ng/mL) | 2.6 (1.8, 3.2) | 2.5 (2, 3.2) | 0.604 |
| Kidney Injury Molecule-1 (KIM-1) (ng/mL) | 0.066 (0.043, 0.14) | 0.034 (0.014, 0.059) | <0.001 |
| Leptin (ng/mL) | 8.4 (4.6, 19.5) | 8.9 (4.2, 21) | 0.743 |
| Luteinizing Hormone (LH) (mIU/mL) | 5.8 (3.65, 12) | 4.75 (3.3, 8.725) | 0.061 |
| Macrophage Colony-Stimulating Factor 1 (M-CSF) (ng/mL) | 0.79 (0.51, 1.55) | 0.39 (0.16, 0.6) | <0.001 |
| Macrophage Inflammatory Protein-1 beta (MIP-1 beta) (pg/mL) | 271 (198.5, 404.5) | 257 (187.5, 345) | 0.263 |
| Matrix Metalloproteinase-2 (MMP-2) (ng/mL) | 1500 (1320, 1900) | 1320 (1120, 1600) | <0.001 |
| Matrix Metalloproteinase-3 (MMP-3) (ng/mL) | 9.5 (7.1, 17) | 6.6 (4.7, 9.8) | <0.001 |
| Matrix Metalloproteinase-7 (MMP-7) (ng/mL) | 0.47 (0.315, 0.805) | 0.34 (0.24, 0.51) | <0.001 |
| Matrix Metalloproteinase-9 (MMP-9) (ng/mL) | 122 (74, 194) | 127 (91, 178) | 0.569 |

TABLE 2B-continued

Prognostic Biomarkers (3-365 Days Post-Cath) (Training Set)

| Biomarker | Concentration in Subjects with one-year MACE (N = 71) | Concentration in Subjects without one-year MACE (N = 577) | p-value |
|---|---|---|---|
| Matrix Metalloproteinase-9, total (MMP-9, total) (ng/mL) | 572 (366, 951) | 579.5 (418.5, 791) | 0.977 |
| Midkine (ng/mL) | 22 (14.5, 37) | 13 (10, 19) | <0.001 |
| Monocyte Chemotactic Protein 1 (MCP-1) (pg/mL) | 113 (73, 161.5) | 108 (78, 158) | 0.938 |
| Monocyte Chemotactic Protein 2 (MCP-2) (pg/mL) | 26 (19, 30) | 23 (17, 30) | 0.135 |
| Monocyte Chemotactic Protein 4 (MCP-4) (pg/mL) | 2370 (1635, 3320) | 2295 (1668, 3362) | 0.892 |
| Monokine Induced by Gamma Interferon (MIG) (pg/mL) | 1590 (915.5, 2690) | 879 (557.5, 1602) | <0.001 |
| Myeloid Progenitor Inhibitory Factor 1 (MPIF-1) (ng/mL) | 1.5 (1.1, 2) | 1.2 (0.93, 1.5) | <0.001 |
| Myoglobin (ng/mL) | 49 (30, 86) | 30 (21, 45.2) | <0.001 |
| N-terminal prohormone of brain natriuretic peptide (NT proBNP) (pg/mL) | 6470 (2220, 15980) | 1330 (461.5, 3302) | <0.001 |
| Osteopontin (ng/mL) | 53 (29.5, 83.5) | 26 (19, 37) | <0.001 |
| Pancreatic Polypeptide (PPP) (pg/mL) | 149 (68, 328) | 87 (46.5, 150.5) | <0.001 |
| Plasminogen Activator Inhibitor 1 (PAI-1) (ng/mL) | 46 (26, 66.5) | 44 (26, 73) | 0.766 |
| Platelet endothelial cell adhesion molecule (PECAM-1) (ng/mL) | 56 (46, 70) | 54 (45, 63) | 0.191 |
| Prolactin (PRL) (ng/mL) | 9.7 (6.3, 15) | 8 (5.5, 12) | 0.029 |
| Pulmonary and Activation-Regulated Chemokine (PARC) (ng/mL) | 108 (86, 141.5) | 97 (71, 137) | 0.056 |
| Pulmonary surfactant-associated protein D (SP-D) (ng/mL) | 7.2 (4.1, 9.8) | 5.1 (3.1, 8.1) | 0.002 |
| Resistin (ng/mL) | 3.1 (2.1, 4.65) | 2.3 (1.8, 3.3) | <0.001 |
| Serotransferrin (Transferrin) (mg/dl) | 253 (206.5, 303.5) | 274.5 (239, 317) | 0.007 |
| Serum Amyloid P-Component (SAP) (ug/mL) | 11 (9.2, 14.5) | 13 (10, 16) | 0.014 |
| Stem Cell Factor (SCF) (pg/mL) | 449 (317.5, 635) | 349 (274, 444) | <0.001 |
| T-Cell-Specific Protein RANTES (RANTES) (ng/mL) | 8.2 (3.7, 17) | 8.4 (3.9, 17) | 0.801 |
| Tamm-Horsfall Urinary Glycoprotein (THP) (ug/mL) | 0.022 (0.013, 0.03) | 0.032 (0.022, 0.041) | <0.001 |
| Thrombomodulin (TM) (ng/mL) | 4.7 (3.7, 6.95) | 3.6 (3, 4.4) | <0.001 |
| Thrombospondin-1 (ng/mL) | 3660 (1860, 6960) | 4305 (2170, 7445) | 0.359 |
| Thyroid-Stimulating Hormone (TSH) (uIU/mL) | 1.2 (0.625, 1.85) | 1.2 (0.808, 1.8) | 0.686 |
| Thyroxine-Binding Globulin (TBG) (ug/mL) | 36 (32, 41.5) | 37.5 (31, 45) | 0.46 |
| Tissue Inhibitor of Metalloproteinases 1 (TIMP-1) (ng/mL) | 96 (78, 126.5) | 71 (58, 87) | <0.001 |
| Transthyretin (TTR) (mg/dl) | 23 (18, 28.5) | 26 (22, 30) | <0.001 |
| Troponin (pg/ml) | 38.5 (15.2, 185.7) | 6.6 (3.3, 18.3) | <0.001 |
| Tumor necrosis factor receptor 2 (TNFR2) (ng/mL) | 10 (6.7, 15) | 6 (4.7, 8.1) | <0.001 |
| Vascular Cell Adhesion Molecule-1 (VCAM-1) (ng/mL) | 792 (582, 1015) | 543.5 (448.8, 680.2) | <0.001 |
| Vascular Endothelial Growth Factor (VEGF) (pg/mL) | 104 (67.5, 166) | 100 (72, 135) | 0.243 |
| Vitamin D-Binding Protein (VDBP) (ug/mL) | 231 (176.5, 309.5) | 250 (195.8, 307.8) | 0.316 |
| Vitamin K-Dependent Protein S (VKDPS) (ug/mL) | 13 (11, 16) | 14 (11, 16) | 0.493 |
| Vitronectin (ug/mL) | 424 (326.5, 542.5) | 463.5 (355.8, 591) | 0.062 |
| von Willebrand Factor (vWF) (ug/mL) | 190 (140.5, 238.5) | 123 (91, 171) | <0.001 |

Table 3A below shows baseline clinical variables and their diagnostic association that differ between those in the training set (N=649) with at least one coronary artery stenosis ≥70% (N=428) and those who did not in the cohort of subjects who received a coronary cath, with or without an optional peripheral cath.

TABLE 3A

Diagnostic Clinical Variables (Received Coronary Cath; Peripheral Cath Optional) (Training Set)

| Clinical Characteristics | Subjects with Coronary Stenosis ≥70% (N = 428) | Subjects w/o Coronary Stenosis ≥70% (N = 221) | p-value |
|---|---|---|---|
| Demographics | | | |
| Age (years) | 67.3 (11.5) | 64 (11.7) | <0.001 |
| Male sex | 337/428 (78.7%) | 129/221 (58.4%) | <0.001 |
| Caucasian | 408/428 (95.3%) | 204/221 (92.3%) | 0.152 |
| Vital Signs | | | |
| Heart rate (beat/min) | 69 (12.9) | 70.4 (14.5) | 0.246 |
| Systolic BP (mmHg) | 138.1 (23.8) | 135.1 (20.5) | 0.101 |
| Diastolic BP (mmHg) | 72.6 (11.7) | 73 (10.9) | 0.658 |
| Medical History | | | |
| Smoking | 60/424 (14.2%) | 32/219 (14.6%) | 0.906 |
| Atrial fibrillation/flutter | 79/428 (18.5%) | 49/221 (22.2%) | 0.298 |
| Hypertension | 338/428 (79%) | 147/221 (66.5%) | <0.001 |
| Coronary artery disease | 288/428 (67.3%) | 58/221 (26.2%) | <0.001 |
| Myocardial infarction | 138/428 (32.2%) | 26/221 (11.8%) | <0.001 |
| Heart failure | 94/428 (22%) | 54/221 (24.4%) | 0.491 |
| Peripheral artery disease | 102/428 (23.8%) | 29/221 (13.1%) | 0.001 |
| COPD | 74/428 (17.3%) | 45/221 (20.4%) | 0.338 |
| Diabetes, Type 1 | 9/428 (2.1%) | 3/221 (1.4%) | 0.76 |
| Diabetes, Type 2 | 125/428 (29.2%) | 30/221 (13.6%) | <0.001 |
| Any Diabetes | 134/428 (31.3%) | 33/221 (14.9%) | <0.001 |
| CVA/TIA | 46/428 (10.7%) | 22/221 (10%) | 0.789 |
| Chronic kidney disease | 68/428 (15.9%) | 10/221 (4.5%) | <0.001 |
| Hemodialysis | 12/426 (2.8%) | 3/221 (1.4%) | 0.285 |
| Angioplasty, peripheral and/or coronary | 64/428 (15%) | 12/221 (5.4%) | <0.001 |
| Stent, peripheral and/or coronary | 153/428 (35.7%) | 36/221 (16.3%) | <0.001 |
| CABG | 126/428 (29.4%) | 4/221 (1.8%) | <0.001 |
| Percutaneous coronary intervention | 183/428 (42.8%) | 6/221 (2.7%) | <0.001 |
| Medications | | | |
| ACE-I/ARB | 249/427 (58.3%) | 102/220 (46.4%) | 0.005 |
| Beta blocker | 342/427 (80.1%) | 133/220 (60.5%) | <0.001 |
| Aldosterone antagonist | 17/427 (4%) | 8/220 (3.6%) | 1 |
| Loop diuretics | 94/427 (22%) | 52/220 (23.6%) | 0.691 |
| Nitrates | 110/427 (25.8%) | 18/220 (8.2%) | <0.001 |
| CCB | 105/427 (24.6%) | 44/220 (20%) | 0.201 |
| Statin | 337/426 (79.1%) | 129/220 (58.6%) | <0.001 |
| Aspirin | 349/425 (82.1%) | 136/220 (61.8%) | <0.001 |
| Warfarin | 58/427 (13.6%) | 44/220 (20%) | 0.04 |
| Clopidogrel | 114/426 (26.8%) | 30/220 (13.6%) | <0.001 |
| Echocardiographic results | | | |
| LVEF (%) | 55.4 (15.3) | 57.3 (15.6) | 0.245 |
| RSVP (mmHg) | 40.9 (10.8) | 41.3 (11.8) | 0.817 |
| Stress test results | | | |
| Ischemia on Scan | 105/131 (80.2%) | 22/43 (51.2%) | <0.001 |
| Ischemia on ECG | 57/113 (50.4%) | 14/41 (34.1%) | 0.099 |
| Angiography results | | | |
| >=70% coronary stenosis in >=2 vessels | 274/428 (64%) | 0/221 (0%) | <0.001 |
| >=70% coronary stenosis in >=3 vessels | 152/428 (35.5%) | 0/221 (0%) | <0.001 |
| Lab Measures | | | |
| Sodium | 139.2 ± 3 | 140.1 ± 3.3 | 0.004 |
| Blood urea nitrogen (mg/dL) | 18 (15, 25) | 17 (14, 22) | 0.002 |
| Creatinine (mg/dL) | 1.1 (0.9, 1.4) | 1 (0.9, 1.2) | <0.001 |
| eGFR (median, CKDEPI) | 96.9 (69, 110.1) | 103.8 (84.6, 112.6) | <0.001 |
| Total cholesterol (mg/dL) | 141.4 (39.1) | 160.5 (49) | <0.001 |
| LDL cholesterol (mg/dL) | 75.4 (31.1) | 90.3 (37.8) | <0.001 |

TABLE 3A-continued

Diagnostic Clinical Variables (Received Coronary
Cath; Peripheral Cath Optional) (Training Set)

| Clinical Characteristics | Subjects with Coronary Stenosis ≥70% (N = 428) | Subjects w/o Coronary Stenosis ≥70% (N = 221) | p-value |
|---|---|---|---|
| Glycohemoglobin (%) | 6.4 (5.6, 7.1) | 5.7 (5.4, 6) | <0.001 |
| Glucose (mg/dL) | 104 (93, 129.5) | 99 (89, 108.5) | 0.001 |
| HGB (mg/dL) | 13.1 (1.8) | 13.4 (1.7) | 0.024 |

All continuous variables are displayed as mean ± standard deviation, unless otherwise specified. BP = blood pressure, MI = myocardial infarction, COPD = chronic obstructive pulmonary disease, CVA/TIA = cerebrovascular accident/transient ischemic attack, CKD = chronic kidney disease, CABG = coronary artery by-pass graft, ACE-I/ARB = angiotensin converting enzyme inhibitor/angiotensin receptor blocker, CCB = calcium channel blocker, LVEF = left ventricular ejection fraction, RVSP = right ventricular systolic pressure, eGFR = estimated glomerular filtration rate, LDL = low density lipoprotein, HGB = hemoglobin.

Table 3B below shows baseline clinical variables and their diagnostic association that differ between those in the training set (N=566) with at least one coronary artery stenosis ≥70% (N=361) and those who did not in the cohort of subjects who received a coronary cath only.

TABLE 3B

Diagnostic Clinical Variables (Received Coronary Cath Only) (Training Set)

| Clinical Characteristics | Subjects with Coronary Stenosis ≥70% (N = 361) | Subjects w/o Coronary Stenosis ≥70% (N = 205) | p-value |
|---|---|---|---|
| Demographics | | | |
| Age (years) | 67 (11.7) | 63.8 (11.7) | 0.002 |
| Male sex | 283/361 (78.4%) | 118/205 (57.6%) | <0.001 |
| Caucasian | 341/361 (94.5%) | 191/205 (93.2%) | 0.582 |
| Vital Signs | | | |
| Heart rate (beat/min) | 69.3 (13.2) | 70.7 (14.7) | 0.268 |
| Systolic BP (mmHg) | 136.4 (22.9) | 134.5 (19.9) | 0.311 |
| Diastolic BP (mmHg) | 72.6 (11.9) | 73.1 (11) | 0.604 |
| Medical History | | | |
| Smoking | 49/358 (13.7%) | 27/203 (13.3%) | 1 |
| Atrial fibrillation/flutter | 70/361 (19.4%) | 48/205 (23.4%) | 0.282 |
| Hypertension | 282/361 (78.1%) | 133/205 (64.9%) | <0.001 |
| Coronary artery disease | 235/361 (65.1%) | 46/205 (22.4%) | <0.001 |
| Myocardial infarction | 116/361 (32.1%) | 16/205 (7.8%) | <0.001 |
| Heart failure | 78/361 (21.6%) | 50/205 (24.4%) | 0.465 |
| Peripheral artery disease | 72/361 (19.9%) | 21/205 (10.2%) | 0.003 |
| COPD | 61/361 (16.9%) | 43/205 (21%) | 0.259 |
| Diabetes, Type 1 | 7/361 (1.9%) | 3/205 (1.5%) | 1 |
| Diabetes, Type 2 | 97/361 (26.9%) | 28/205 (13.7%) | <0.001 |
| Any Diabetes | 104/361 (28.8%) | 31/205 (15.1%) | <0.001 |
| CVA/TIA | 32/361 (8.9%) | 20/205 (9.8%) | 0.763 |
| Chronic kidney disease | 52/361 (14.4%) | 9/205 (4.4%) | <0.001 |
| Hemodialysis | 9/359 (2.5%) | 3/205 (1.5%) | 0.55 |
| Angioplasty, peripheral and/or coronary | 52/361 (14.4%) | 7/205 (3.4%) | <0.001 |
| Stent, peripheral and/or coronary | 124/361 (34.3%) | 26/205 (12.7%) | <0.001 |
| CABG | 94/361 (26%) | 1/205 (0.5%) | <0.001 |
| Percutaneous coronary intervention | 166/361 (46%) | 6/205 (2.9%) | <0.001 |
| Medications | | | |
| ACE-I/ARB | 209/361 (57.9%) | 92/204 (45.1%) | 0.004 |
| Beta blocker | 289/361 (80.1%) | 120/204 (58.8%) | <0.001 |
| Aldosterone antagonist | 12/361 (3.3%) | 8/204 (3.9%) | 0.813 |
| Loop diuretics | 76/361 (21.1%) | 48/204 (23.5%) | 0.526 |
| Nitrates | 89/361 (24.7%) | 14/204 (6.9%) | <0.001 |
| CCB | 86/361 (23.8%) | 40/204 (19.6%) | 0.293 |
| Statin | 280/360 (77.8%) | 117/204 (57.4%) | <0.001 |
| Aspirin | 292/359 (81.3%) | 124/204 (60.8%) | <0.001 |
| Warfarin | 51/361 (14.1%) | 43/204 (21.1%) | 0.035 |
| Clopidogrel | 96/361 (26.6%) | 23/204 (11.3%) | <0.001 |

TABLE 3B-continued

Diagnostic Clinical Variables (Received Coronary Cath Only) (Training Set)

| Clinical Characteristics | Subjects with Coronary Stenosis ≥70% (N = 361) | Subjects w/o Coronary Stenosis ≥70% (N = 205) | p-value |
|---|---|---|---|
| Echocardiographic results | | | |
| LVEF (%) | 55.2 (15.3) | 57.6 (15.9) | 0.18 |
| RSVP (mmHg) | 41.2 (11.2) | 41.5 (11.9) | 0.862 |
| Stress test results | | | |
| Ischemia on Scan | 89/112 (79.5%) | 20/37 (54.1%) | 0.005 |
| Ischemia on ECG | 48/97 (49.5%) | 14/36 (38.9%) | 0.33 |
| Angiography results | | | |
| >=70% coronary stenosis in >=2 vessels | 220/361 (60.9%) | 0/205 (0%) | <0.001 |
| >=70% coronary stenosis in >=3 vessels | 110/361 (30.5%) | 0/205 (0%) | <0.001 |
| Lab Measures | | | |
| Sodium | 139.2 (3.1) | 140.1 (3.3) | 0.005 |
| Blood urea nitrogen (mg/dL) | 18 (15, 25) | 17 (14, 22.2) | 0.012 |
| Creatinine (mg/dL) | 1.1 (0.9, 1.4) | 1 (0.9, 1.2) | <0.001 |
| eGFR (median, CKDEPI) | 99.4 (69.8, 111.1) | 103.8 (84.6, 112.5) | 0.012 |
| Total cholesterol (mg/dL) | 140.7 (37.1) | 164.6 (48.4) | <0.001 |
| LDL cholesterol (mg/dL) | 75.2 (29.4) | 93.3 (37.9) | <0.001 |
| Glycohemoglobin (%) | 6.3 (5.6, 7.1) | 5.7 (5.4, 6) | 0.001 |
| Glucose (mg/dL) | 103 (93, 125.2) | 99 (89, 107.8) | 0.006 |
| HGB (mg/dL) | 13.1 (1.7) | 13.5 (1.7) | 0.02 |

All continuous variables are displayed as mean ± standard deviation, unless otherwise specified. BP = blood pressure, MI = myocardial infarction, COPD = chronic obstructive pulmonary disease, CVA/TIA = cerebrovascular accident/transient ischemic attack, CKD = chronic kidney disease, CABG = coronary artery by-pass graft, ACE-I/ARB = angiotensin converting enzyme inhibitor/angiotensin receptor blocker, CCB = calcium channel blocker, LVEF = left ventricular ejection fraction, RVSP = right ventricular systolic pressure, eGFR = estimated glomerular filtration rate, LDL = low density lipoprotein, HGB = hemoglobin.

Table 4A below shows baseline clinical variables and their prognostic association that differ between those in the training set (N=649) in patients with major adverse cardiac events (MACE) within 365 days of the blood draw. The numbers in this table were calculated using the composite endpoint of one-year MACE with CV death, MI, or major stroke; these proteins produce similar results with the composite endpoint of one-year MACE with all-cause death, MI and/or major stroke.

TABLE 4A

Prognostic Clinical Variables (Within 365 Days Post-Cath) (Training Set)

| Clinical Characteristics | Concentration in Subjects with one-year MACE (N = 82) | Concentration in Subjects without one-year MACE (N = 567) | p-value |
|---|---|---|---|
| Demographics | | | |
| Age (years) | 71.9 (11.7) | 65.3 (11.4) | <0.001 |
| Male sex | 60/82 (73.2%) | 406/567 (71.6%) | 0.896 |
| Caucasian | 78/82 (95.1%) | 534/567 (94.2%) | 1 |
| Vital Signs | | | |
| Heart rate (beat/min) | 72.1 (14) | 69.1 (13.4) | 0.071 |
| Systolic BP (mmHg) | 133.4 (25.9) | 137.6 (22.2) | 0.173 |
| Diastolic BP (mmHg) | 69.9 (11.5) | 73.2 (11.4) | 0.02 |
| Medical History | | | |
| Smoking | 13/82 (15.9%) | 79/561 (14.1%) | 0.617 |
| Atrial fibrillation/flutter | 16/82 (19.5%) | 112/567 (19.8%) | 1 |
| Hypertension | 69/82 (84.1%) | 416/567 (73.4%) | 0.041 |
| Coronary artery disease | 51/82 (62.2%) | 295/567 (52%) | 0.097 |
| Prior MI | 28/82 (34.1%) | 136/567 (24%) | 0.057 |
| Heart failure | 35/82 (42.7%) | 113/567 (19.9%) | <0.001 |
| Peripheral artery disease | 22/82 (26.8%) | 109/567 (19.2%) | 0.14 |
| COPD | 26/82 (31.7%) | 93/567 (16.4%) | 0.002 |

TABLE 4A-continued

Prognostic Clinical Variables (Within 365 Days Post-Cath) (Training Set)

| Clinical Characteristics | Concentration in Subjects with one-year MACE (N = 82) | Concentration in Subjects without one-year MACE (N = 567) | p-value |
| --- | --- | --- | --- |
| Diabetes, Type 1 | 2/82 (2.4%) | 10/567 (1.8%) | 0.655 |
| Diabetes, Type 2 | 38/82 (46.3%) | 117/567 (20.6%) | <0.001 |
| Any Diabetes | 40/82 (48.8%) | 127/567 (22.4%) | <0.001 |
| CVA/TIA | 11/82 (13.4%) | 57/567 (10.1%) | 0.338 |
| Chronic kidney disease | 26/82 (31.7%) | 52/567 (9.2%) | <0.001 |
| Hemodialysis | 6/81 (7.4%) | 9/566 (1.6%) | 0.006 |
| Angioplasty, peripheral and/or coronary | 8/82 (9.8%) | 68/567 (12%) | 0.713 |
| Stent, peripheral and/or coronary | 31/82 (37.8%) | 158/567 (27.9%) | 0.069 |
| CABG | 21/82 (25.6%) | 109/567 (19.2%) | 0.185 |
| Percutaneous coronary intervention | 26/82 (31.7%) | 163/567 (28.7%) | 0.604 |
| Medications | | | |
| ACE-I/ARB | 50/82 (61%) | 301/565 (53.3%) | 0.195 |
| Beta blocker | 60/82 (73.2%) | 415/565 (73.5%) | 1 |
| Aldosterone antagonist | 3/82 (3.7%) | 22/565 (3.9%) | 1 |
| Loop diuretics | 32/82 (39%) | 114/565 (20.2%) | <0.001 |
| Nitrates | 23/82 (28%) | 105/565 (18.6%) | 0.053 |
| CCB | 21/82 (25.6%) | 128/565 (22.7%) | 0.575 |
| Statin | 61/82 (74.4%) | 405/564 (71.8%) | 0.694 |
| Aspirin | 61/82 (74.4%) | 424/563 (75.3%) | 0.891 |
| Warfarin | 12/82 (14.6%) | 90/565 (15.9%) | 0.872 |
| Clopidogrel | 24/82 (29.3%) | 120/564 (21.3%) | 0.118 |
| Echocardiographic results | | | |
| LVEF (%) | 49.3 (16.8) | 57.3 (14.8) | <0.001 |
| RSVP (mmHg) | 44.2 (11.3) | 40.4 (11.1) | 0.067 |
| Stress test results | | | |
| Ischemia on Scan | 17/20 (85%) | 110/154 (71.4%) | 0.286 |
| Ischemia on ECG | 6/15 (40%) | 65/139 (46.8%) | 0.787 |
| Angiography results | | | |
| >=70% coronary stenosis in >=2 vessels | 52/82 (63.4%) | 222/567 (39.2%) | <0.001 |
| >=70% coronary stenosis in >=3 vessels | 27/82 (32.9%) | 125/567 (22%) | 0.036 |
| Lab Measures | | | |
| Sodium | 138.6 (3.5) | 139.6 (3.1) | 0.026 |
| Blood urea nitrogen (mg/dL) | 25 (18.5, 37) | 17 (14, 22.5) | <0.001 |
| Creatinine (mg/dL) | 1.3 (1.1, 1.9) | 1.1 (0.9, 1.3) | <0.001 |
| eGFR (median, CKDEPI) | 67.7 (45.3, 89.3) | 102.3 (79.7, 112.3) | <0.001 |
| Total cholesterol (mg/dL) | 140.5 (51.3) | 147.2 (40.8) | 0.333 |
| LDL cholesterol (mg/dL) | 77.5 (42.9) | 79.4 (31.6) | 0.735 |
| Glycohemoglobin (%) | 6.5 (5.7, 7.7) | 6 (5.5, 6.9) | 0.077 |
| Glucose (mg/dL) | 114 (101, 145) | 100 (90, 120) | <0.001 |
| HGB (mg/dL) | 12.2 (1.9) | 13.3 (1.7) | <0.001 |

All continuous variables are displayed as mean ± standard deviation, unless otherwise specified. BP = blood pressure, MI = myocardial infarction, COPD = chronic obstructive pulmonary disease, CVA/TIA = cerebrovascular accident/transient ischemic attack, CKD = chronic kidney disease, CABG = coronary artery by-pass graft, ACE-I/ARB = angiotensin converting enzyme inhibitor/angiotensin receptor blocker, CCB = calcium channel blocker, LVEF = left ventricular ejection fraction, RVSP = right ventricular systolic pressure, eGFR = estimated glomerular filtration rate, LDL = low density lipoprotein, HGB = hemoglobin.

Table 4B below shows baseline clinical variables and their prognostic association that differ between those in the training set (N=648) with a major adverse cardiac event (MACE) from 3-365 days of the blood draw and those who did not. The numbers in this table were calculated using the composite endpoint of one-year MACE with CV death, MI, or major stroke; these proteins produce similar results with the composite endpoint of one-year MACE with all-cause death, MI and/or major stroke.

TABLE 4B

| Prognostic Clinical Variables (3-365 Days Post-Cath) (Training Set) | | | |
|---|---|---|---|
| Clinical Characteristics | Concentration in Subjects with one-year MACE (N = 71) | Concentration in Subjects without one-year MACE (N = 577) | p-value |
| Demographics | | | |
| Age (years) | 73 (11) | 65.3 (11.5) | <0.001 |
| Male sex | 50/71 (70.4%) | 415/577 (71.9%) | 0.781 |
| Caucasian | 67/71 (94.4%) | 544/577 (94.3%) | 1 |
| Vital Signs | | | |
| Heart rate (beat/min) | 72.4 (14.1) | 69.1 (13.4) | 0.068 |
| Systolic BP (mmHg) | 132.9 (26.5) | 137.5 (22.2) | 0.163 |
| Diastolic BP (mmHg) | 69.3 (11.8) | 73.2 (11.3) | 0.012 |
| Medical History | | | |
| Smoking | 10/71 (14.1%) | 82/571 (14.4%) | 1 |
| Atrial fibrillation/flutter | 15/71 (21.1%) | 113/577 (19.6%) | 0.753 |
| Hypertension | 62/71 (87.3%) | 423/577 (73.3%) | 0.009 |
| Coronary artery disease | 46/71 (64.8%) | 300/577 (52%) | 0.044 |
| Prior MI | 26/71 (36.6%) | 138/577 (23.9%) | 0.029 |
| Heart failure | 29/71 (40.8%) | 119/577 (20.6%) | <0.001 |
| Peripheral artery disease | 20/71 (28.2%) | 111/577 (19.2%) | 0.085 |
| COPD | 23/71 (32.4%) | 95/577 (16.5%) | 0.003 |
| Diabetes, Type 1 | 2/71 (2.8%) | 10/577 (1.7%) | 0.631 |
| Diabetes, Type 2 | 33/71 (46.5%) | 122/577 (21.1%) | <0.001 |
| Any Diabetes | 35/71 (49.3%) | 132/577 (22.9%) | <0.001 |
| CVA/TIA | 10/71 (14.1%) | 58/577 (10.1%) | 0.304 |
| Chronic kidney disease | 23/71 (32.4%) | 55/577 (9.5%) | <0.001 |
| Hemodialysis | 6/71 (8.5%) | 9/575 (1.6%) | 0.003 |
| Angioplasty, peripheral and/or coronary | 7/71 (9.9%) | 69/577 (12%) | 0.7 |
| Stent, peripheral and/or coronary | 28/71 (39.4%) | 161/577 (27.9%) | 0.052 |
| CABG | 20/71 (28.2%) | 110/577 (19.1%) | 0.083 |
| Percutaneous coronary intervention | 20/71 (28.2%) | 168/577 (29.1%) | 1 |
| Medications | | | |
| ACE-I/ARB | 41/71 (57.7%) | 310/575 (53.9%) | 0.614 |
| Beta blocker | 54/71 (76.1%) | 421/575 (73.2%) | 0.671 |
| Aldosterone antagonist | 2/71 (2.8%) | 23/575 (4%) | 1 |
| Loop diuretics | 30/71 (42.3%) | 116/575 (20.2%) | <0.001 |
| Nitrates | 22/71 (31%) | 106/575 (18.4%) | 0.017 |
| CCB | 19/71 (26.8%) | 130/575 (22.6%) | 0.456 |
| Statin | 53/71 (74.6%) | 412/574 (71.8%) | 0.675 |
| Aspirin | 51/71 (71.8%) | 433/573 (75.6%) | 0.471 |
| Warfarin | 12/71 (16.9%) | 90/575 (15.7%) | 0.733 |
| Clopidogrel | 21/71 (29.6%) | 122/574 (21.3%) | 0.129 |
| Echocardiographic results | | | |
| LVEF (%) | 50.3 (16.9) | 57 (15) | 0.008 |
| RSVP (mmHg) | 44.2 (11.6) | 40.5 (11) | 0.098 |
| Stress test results | | | |
| Ischemia on Scan | 14/16 (87.5%) | 113/158 (71.5%) | 0.241 |
| Ischemia on ECG | 4/12 (33.3%) | 67/142 (47.2%) | 0.387 |
| Angiography results | | | |
| >=70% coronary stenosis in >=2 vessels | 44/71 (62%) | 229/577 (39.7%) | <0.001 |
| >=70% coronary stenosis in >=3 vessels | 25/71 (35.2%) | 127/577 (22%) | 0.017 |
| Lab Measures | | | |
| Sodium | 138.7 (3.6) | 139.6 (3.1) | 0.058 |
| Blood urea nitrogen (mg/dL) | 25.5 (18.8, 36.5) | 17 (14, 23) | <0.001 |
| Creatinine (mg/dL) | 1.3 (1.1, 1.9) | 1.1 (0.9, 1.3) | <0.001 |
| eGFR (median, CKDEPI) | 65.7 (42.9, 86) | 102.2 (79.1, 112.4) | <0.001 |
| Total cholesterol (mg/dL) | 135.6 (44.2) | 147.8 (42.2) | 0.062 |

TABLE 4B-continued

Prognostic Clinical Variables (3-365 Days Post-Cath) (Training Set)

| Clinical Characteristics | Concentration in Subjects with one-year MACE (N = 71) | Concentration in Subjects without one-year MACE (N = 577) | p-value |
|---|---|---|---|
| LDL cholesterol (mg/dL) | 73.6 (36.2) | 80 (33.1) | 0.221 |
| Glycohemoglobin (%) | 6.5 (5.7, 7.2) | 6 (5.5, 6.9) | 0.117 |
| Glucose (mg/dL) | 114 (101, 144) | 101 (91, 120) | <0.001 |
| HGB (mg/dL) | 12 (1.8) | 13.4 (1.7) | <0.001 |

All continuous variables are displayed as mean ± standard deviation, unless otherwise specified. BP = blood pressure, MI = myocardial infarction, COPD = chronic obstructive pulmonary disease, CVA/TIA = cerebrovascular accident/transient ischemic attack, CKD = chronic kidney disease, CABG = coronary artery by-pass graft, ACE-I/ARB = angiotensin converting enzyme inhibitor/angiotensin receptor blocker, CCB = calcium channel blocker, LVEF = left ventricular ejection fraction, RVSP = right ventricular systolic pressure, eGFR = estimated glomerular filtration rate, LDL = low density lipoprotein, HGB = hemoglobin.

Diagnostic and Prognostic Methods

The methods of the invention relate generally to providing a diagnosis and/or prognosis of a cardiovascular disease or outcome in a subject, comprising the steps of: (i) determining the level of at least one biomarker in a biological sample obtained from the subject, particularly where the biomarkers are selected from the group consisting of those set forth in Tables 1A, 1B, 2A and 2B; (ii) optionally, determining the status of at least one clinical variable for the subject, where the clinical variable is selected from the group consisting of those set forth in Tables 3A, 3B, 4A and 4B; (iii) calculating a diagnostic or prognostic score based on the levels of the biomarkers determined in step (i) and, optionally, the status of the clinical variable(s) determined in step (ii); (iv) classifying the diagnostic or prognostic score as a positive or negative result; and (v) determining a therapeutic or diagnostic intervention regimen based on the positive or negative result.

Embodiments of the present invention provide methods for evaluating cardiovascular status in a subject, comprising: (i) obtaining a sample from a subject selected for evaluation; (ii) performing one or more assays configured to detect a biomarker selected from the group consisting of those set forth in Tables 1A, 1B, 2A, and 2B by introducing the sample obtained from the subject into an assay instrument which (a) contacts the sample with one or more antibodies which specifically bind for the detection of the biomarker(s) which are assayed, and (b) generates one or more assay results indicative of binding of each biomarker which is assayed to a respective antibody to provide one or more assay results; (iii) optionally, determining the status of at least one clinical variable for the subject, wherein the clinical variable is selected from the group consisting of those set forth in Tables 3A, 3B, 4A, and 4B; (iv) correlating the assay result(s) generated by the assay instrument and optionally the clinical variable status to the cardiovascular status of the subject, wherein said correlation step comprises correlating the assay result(s) to one or more of risk stratification, prognosis, diagnosis, classifying and monitoring of the cardiovascular status of the subject, wherein said correlating step comprises assigning a likelihood of a positive or negative diagnosis, or one or more future changes in cardiovascular status to the subject based on the assay result(s); and (v) treating the patient based on the predetermined subpopulation of individuals to which the patient is assigned, wherein the treatment comprises a therapeutic or diagnostic intervention regimen.

Embodiments of the present invention provide a method for diagnosing obstructive coronary artery disease in a subject comprising: (i) obtaining a sample from a subject selected for evaluation; (ii) performing one or more assays configured to detect a biomarker selected from the group consisting of those set forth in Tables 1A and 1B by introducing the sample obtained from the subject into an assay instrument which (a) contacts the sample with one or more antibodies which specifically bind for the detection of the biomarker(s) which are assayed, and (b) generates one or more assay results indicative of binding of each biomarker which is assayed to a respective antibody to provide one or more assay results; (iii) optionally, determining the status of at least one clinical variable for the subject, wherein the clinical variable is selected from the group consisting of those set forth in Tables 3A and 3B; (iv) correlating the assay result(s) generated by the assay instrument and optionally the clinical variable status to obstructive coronary artery disease, wherein said correlation step comprises correlating the assay result(s) and optionally the clinical variable(s) to a diagnostic score, wherein said correlating step comprises assigning the score to a positive or negative result; and (v) treating the patient based on the positive or negative result, wherein the treatment comprises a therapeutic or diagnostic intervention regimen.

In still other embodiments, the present disclosure provides methods for the prognosis of a cardiac outcome in a subject within time endpoints, comprising: (i) obtaining a sample from a subject selected for evaluation; (ii) performing one or more assays configured to detect a biomarker selected from the group consisting of those set forth in Tables 2A and 2B by introducing the sample obtained from the subject into an assay instrument which (a) contacts the sample with one or more antibodies which specifically bind for detection of the biomarker(s) which are assayed, and (b) generates one or more assay results indicative of binding of each biomarker which is assayed to a respective antibody to provide one or more assay results; (iii) optionally, determining the status of at least one clinical variable for the subject, wherein the clinical variable is selected from the group consisting of those set forth in Tables 4A and 4B; (iv) correlating the assay result(s) generated by the assay instrument and optionally the clinical variable status to the likelihood of a cardiac outcome in the subject, wherein said correlation step comprises correlating the assay result(s) and optionally the clinical variable(s) to a prognostic score, wherein said correlating step comprises assigning the score to a positive or negative result; and (v) treating the patient based on the positive or negative result, wherein the treatment comprises a therapeutic or diagnostic intervention regimen.

In certain specific embodiments, biomarkers, optionally used in conjunction with clinical variables, can be used in the methods of the present invention for the diagnosis of obstructive coronary artery disease. In other embodiments, biomarkers, optionally used in conjunction with clinical variables, can be used in the prognosis of cardiovascular outcomes, including but not limited to cardiovascular death, myocardial infarct, and stroke. The methods can also be used, for example, to predict the risk of a composite endpoint, which is a combination of various clinical events that might happen, such as cardiovascular death, myocardial infarct, or stroke where any one of those events would count as part of the composite endpoint. The composite may include all-cause death, which is inclusive of cardiovascular death.

In certain specific embodiments, the biomarkers and/or clinical variables used in accordance with the methods of the present invention include those listed in Tables 1A, 1B, 2A, 2B, 3A, 3B, 4A and 4B, particularly those which are associated with a p-value of less than 0.1, less than 0.05, less than 0.01 or less than 0.001.

In some embodiments, at least 1, at least 2, at least 3 or at least 4 biomarkers are used in the methods described herein. In other embodiments, the number of biomarkers employed can vary, and may include at least 5, 6, 7, 8, 9, 10, or more. In still other embodiments, the number of biomarkers can include at least 15, 20, 25 or 50, or more.

In more specific embodiments, the biomarkers used in the diagnostic methods of the invention are selected from adiponectin, apolipoprotein C-I, decorin, interleukin-8, kidney injury molecule-1, matrix metalloproteinase 9, midkine, myoglobin, pulmonary surfactant associated protein D, stem cell factor, and troponin.

In other specific embodiments, the biomarkers used in the prognostic methods of the invention are selected from apolipoprotein A-II, kidney injury molecule-1, midkine, N terminal prohormone of brain natriuretic protein (NT-proBNP), osteopontin, tissue inhibitor of metalloproteinases-1 (TIMP-1), and vascular cell adhesion molecule.

In some embodiments, the diagnostic or prognostic model will result in a numeric or categorical score that relates the patient's level of likelihood of CAD, e.g. including but not limited to positive predictive value (PPV), negative predictive value (NPV), sensitivity (Sn), or specificity (Sp) or the risk of a cardiovascular event occurring within the specified period of time. The number of levels used by the diagnostic model may be as few as two ("positive" vs. "negative") or as many as deemed clinically relevant, e.g., a diagnostic model for CAD may result a five-level score, where a higher score indicates a higher likelihood of disease. Specifically, a score of 1 indicates a strong degree of confidence in a low likelihood of CAD (determined by the test's NPV), a score of 5 indicates a strong degree of confidence in a high likelihood of CAD (determined by the test's PPV), and a score of 3 indicates a moderate likelihood for CAD.

Furthermore, in certain embodiments, upon making a positive diagnosis for obstructive coronary artery disease in the subject according to the methods disclosed herein, a medical practitioner can advantageously use the diagnosis to identify the need for a therapeutic, diagnostic or other intervention in the subject, particularly an intervention selected from one or more of a diagnostic cardiac catheterization, percutaneous coronary intervention (balloon angioplasty with or without stent placement), coronary artery bypass graft (CABG), and administration of pharmacologic agents selected from nitrates, beta blockers, ACE inhibitor and lipid-lowering agents.

Further still, in certain related embodiments, upon making a negative diagnosis for obstructive coronary artery disease in the subject according to the methods disclosed herein, a medical practitioner can advantageously use the information thereby obtained to identify the need for an intervention in the subject, such as an intervention selected from one or more of ongoing monitoring and management of coronary risk factors including hypertension, diabetes, and smoking, and lifestyle modifications selected from diet modification, exercise and smoking cessation.

In still other embodiments, upon making a positive prognosis of a cardiac outcome (e.g., a prognosis of cardiovascular death, myocardial infarct (MI), stroke, all cause death, or a composite thereof) according to the methods disclosed herein, a medical practitioner can advantageously use the prognostic information thereby obtained to identify the need for an intervention in the subject, such as an intervention selected from one or more of stress testing with ECG response or myocardial perfusion imaging, coronary computed tomography angiogram, diagnostic cardiac catheterization, percutaneous coronary (e.g., balloon angioplasty with or without stent placement), coronary artery bypass graft (CABG), enrollment in a clinical trial, and administration or monitoring of effects of agents selected from, but not limited to, of agents selected from nitrates, beta blockers, ACE inhibitors, antiplatelet agents and lipid-lowering agents.

In further related embodiments, upon making a negative prognosis of a cardiac outcome according to the methods described herein, a medical practitioner can advantageously use the information thereby obtained to identify the need for an intervention, particularly an intervention selected from one or more of ongoing monitoring and management of coronary risk factors including hypertension, diabetes, hyperlipidemia and smoking; and lifestyle modifications selected from diet modification, exercise and smoking cessation.

As used herein, a "biological sample" encompasses essentially any sample type obtained from a subject that can be used in a diagnostic or prognostic method described herein. The biological sample may be any bodily fluid, tissue or any other sample from which clinically relevant biomarker levels may be determined. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, but also, in some instances, includes cells in culture, cell supernatants, cell lysates, blood, serum, plasma, urine, cerebral spinal fluid, biological fluid, and tissue samples. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used. Biological samples can be derived from patients using well known techniques such as venipuncture, lumbar puncture, fluid sample such as saliva or urine, or tissue biopsy and the like.

In certain specific embodiments, the biological sample used in the methods of the present disclosure include but are not limited to, whole blood, plasma, serum, or urine. In some embodiments, the sample is whole blood. In some embodiments, the sample is plasma. In other embodiments, the sample is serum or urine.

Determining biomarker levels in a sample taken from a subject can be accomplished according to standard techniques known and available to the skilled artisan. In many instances, this will involve carrying out protein detection methods, which provide a quantitative measure of protein biomarkers present in a biological sample.

Many embodiments of the present disclosure are based, in part, on the use of binding agents that specifically bind to the biomarkers described herein and thereby allow for a determination of the levels of the biomarkers in a biological sample. Any of a variety of binding agents may be used including, for example, antibodies, polypeptides, sugars and nucleic acids.

In a specific embodiment of the present disclosure, the binding agent is an antibody or a fragment thereof that specifically binds to a biomarker of the present disclosure, and that is effective to determine the level of the biomarker to which it binds in a biological sample.

The term "specifically binds" or "binds specifically," in the context of binding interactions between two molecules, refers to high avidity and/or high affinity binding of an antibody (or other binding agent) to a specific polypeptide subsequence or epitope of a biomarker. Antibody binding to an epitope on a specific biomarker sequence (also referred to herein as "an epitope") is preferably stronger than binding of the same antibody to any other epitope, particularly those which may be present in molecules in association with, or in the same sample, as the specific biomarker of interest. Antibodies which bind specifically to a biomarker of interest may be capable of binding other polypeptides at a weak, yet detectable, level (e.g., 10% or less, 5% or less, 1% or less of the binding shown to the polypeptide of interest). Such weak binding, or background binding, is readily discernible from the specific antibody binding to the compound or polypeptide of interest, e.g. by use of appropriate controls. In general, antibodies used in compositions and methods of the invention which bind to a specific biomarker protein with a binding affinity of $10^7$ moles/L or more, preferably $10^8$ moles/L or more are said to bind specifically to the specific biomarker protein.

In one embodiment, the affinity of specific binding of an antibody or other binding agent to a biomarker is about 2 times greater than background binding, about 5 times greater than background binding, about 10 times greater than background binding, about 20 times greater than background binding, about 50 times greater than background binding, about 100 times greater than background binding, or about 1000 times greater than background binding, or more.

In another embodiment, the affinity of specific binding of an antibody or other binding agent to a biomarker is between about 2 to about 1000 times greater than background binding, between about 2 to 500 times greater than background binding, between about 2 to about 100 times greater than background binding, between about 2 to about 50 times greater than background binding, between about 2 to about 20 times greater than background binding, between about 2 to about 10 times greater than background binding, or any intervening range of affinity.

The term "antibody" herein is used in the broadest sense and specifically covers, but is not limited to, monoclonal antibodies, polyclonal antibodies, multispecific antibodies (e.g., bispecific antibodies) formed from at least two intact antibodies, single chain antibodies (e.g., scFv), and antibody fragments or other derivatives, so long as they exhibit the desired biological specificity.

The term "monoclonal antibody" as used herein refers to an antibody obtained from a population of substantially homogeneous antibodies, i.e., the individual antibodies comprising the population are identical except for possible naturally occurring mutations that can be present in minor amounts. In certain specific embodiments, the monoclonal antibody is an antibody specific for a biomarker described herein.

Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567), or any other suitable methodology known and available in the art. The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity and/or specificity (e.g., U.S. Pat. No. 4,816,567; Morrison et al., Proc. Natl. Acad. Sci. USA, 81: 6851-6855 (1984)). Methods of making chimeric antibodies are known in the art.

"Functional fragments" of antibodies can also be used and include those fragments that retain sufficient binding affinity and specificity for a biomarker so as to permit a determination of the level of the biomarker in a biological sample. In some cases, a functional fragment will bind to a biomarker with substantially the same affinity and/or specificity as an intact full chain molecule from which it may have been derived.

An "isolated" antibody is one which has been identified and separated and/or recovered from a component of its natural environment. Contaminant components of its natural environment are materials that would interfere with diagnostic or prognostic uses for the antibody, and may include enzymes, hormones, and other proteinaceous or non-proteinaceous solutes. In specific embodiments, the antibody will be purified to greater than 95% by weight of antibody, e.g., as determined by the Lowry method, and most preferably more than 99% by weight.

The terms "detectably labeled antibody" refers to an antibody (or antibody fragment) which retains binding specificity for a biomarker described herein, and which has an attached detectable label. The detectable label can be attached by any suitable means, e.g., by chemical conjugation or genetic engineering techniques. Methods for production of detectably labeled proteins are well known in the art. Detectable labels may be selected from a variety of such labels known in the art, including, but not limited to, haptens, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)).

In certain particular embodiments, the level of a protein biomarker of the present disclosure is determined using an assay or format including, but not limited to, e.g., immunoassays, ELISA sandwich assays, lateral flow assays, flow cytometry, mass spectrometric detection, calorimetric assays, binding to a protein array (e.g., antibody array), single molecule detection methods, nanotechnology-based detection methods, or fluorescent activated cell sorting (FACS). In some embodiments, an approach involves the use of labeled affinity reagents (e.g., antibodies, small molecules, etc.) that recognize epitopes of one or more biomarker proteins in an ELISA, antibody-labelled fluorescent bead array, antibody array, or FACS screen. As noted, any of a number of illustrative methods for producing, evaluating and/or using antibodies for detecting and quantifying the biomarkers herein are well known and available in the art. It will also be understood that the protein detection and quantification in accordance with the methods described herein can be carried out in single assay format, multiplex format, or other known formats.

A number of suitable high-throughput multiplex formats exist for evaluating the disclosed biomarkers. Typically, the term "high-throughput" refers to a format that performs a large number of assays per day, such as at least 100 assays, 1000 assays, up to as many as 10,000 assays or more per day. When enumerating assays, either the number of samples or the number of markers assayed can be considered.

In some embodiments of the present invention, the samples are analyzed on an assay instrument. For example, the assay instrument may be a multiplex analyzer that simultaneously measures multiple analytes, e.g. proteins, in a single microplate well. The assay format may be receptor-ligand assays, immunoassays, and enzymatic assays. An example of such an analyzer is the Luminex® 100/200 system which is a combination of three xMAP® Technologies. The first is xMAP microspheres, a family of fluorescently dyed micron-sized polystyrene microspheres that act as both the identifier and the solid surface to build the assay. The second is a flow cytometry-based instrument, the Luminex® 100/200 analyzer, which integrates key xMAP® detection components, such as lasers, optics, fluidics, and high-speed digital signal processors. The third component is the xPONENT® software, which is designed for protocol-based data acquisition with robust data regression analysis.

By determining biomarker levels and optionally clinical variable status for a subject, a dataset may be generated and used (as further described herein) to classify the biological sample to one or more of risk stratification, prognosis, diagnosis, and monitoring of the cardiovascular status of the subject, and further assigning a likelihood of a positive or negative diagnosis, outcome, or one or more future changes in cardiovascular status to the subject to thereby establish a diagnosis and/or prognosis of cardiovascular disease and/or outcome, as described herein. Of course, the dataset may be obtained via automation or manual methods.

Statistical Analysis

By analyzing combinations of biomarkers and optionally clinical variables as described herein, the methods of the invention are capable of discriminating between different endpoints. The endpoints may include, for example, obstructive coronary artery disease (CAD), cardiovascular death (CVD), myocardial infarction (MI), stroke, composites thereof, and composites further of all cause death. The identity of the markers and their corresponding features (e.g., concentration, quantitative levels) are used in developing and implementing an analytical process, or plurality of analytical processes, that discriminate between clinically relevant classes of patients.

A biomarker and clinical variable dataset may be used in an analytic process for correlating the assay result(s) generated by the assay instrument and optionally the clinical variable status to the cardiovascular status of the subject, wherein said correlation step comprises correlating the assay result(s) to one or more of risk stratification, prognosis, diagnosis, classifying and monitoring of the cardiovascular status of the subject, wherein said correlating step comprises assigning a likelihood of a positive or negative diagnosis, or one or more future changes in cardiovascular status to the subject based on the assay result(s).

A biomarker and clinical variable dataset may be used in an analytic process for generating a diagnostic and/or prognostic result or score. For example, an illustrative analytic process can comprise a linear model with one term for each component (protein level or clinical factor). The result of the model is a number that generates a diagnosis and/or prognosis. The result may also provide a multi-level or continuous score with a higher number representing a higher likelihood of disease or risk of event.

The examples below illustrate how data analysis algorithms can be used to construct a number of such analytical processes. Each of the data analysis algorithms described in the examples use features (e.g., quantitative protein levels and/or clinical factors) of a subset of the markers identified herein across a training population. Specific data analysis algorithms for building an analytical process or plurality of analytical processes, that discriminate between subjects disclosed herein will be described in the subsections below. Once an analytical process has been built using these exemplary data analysis algorithms or other techniques known in the art, the analytical process can be used to classify a test subject into one of the two or more phenotypic classes and/or predict survival/mortality or a severe medical event within a specified period of time after the blood test is obtained. This is accomplished by applying one or more analytical processes to one or more marker profile(s) obtained from the test subject. Such analytical processes, therefore, have enormous value as diagnostic or prognostic indicators.

The present invention therefore further provides for an algorithm that may be used to transform the levels of a panel of biomarkers, as described above, into a score that may be used to determine whether a patient is diagnosed with obstructive coronary artery disease or has a prognosis of risk for developing an adverse cardiovascular event.

The data are processed prior to the analytical process. The data in each dataset are collected by measuring the values for each marker, usually in duplicate or triplicate or in multiple replicates. The data may be manipulated; for example, raw data may be transformed using standard curves, and the average of replicate measurements used to calculate the average and standard deviation for each patient. These values may be transformed before being used in the models, e.g., log-transformed, normalized to a standard scale, Winsorized, etc. The data is transformed via computer software. This data can then be input into the analytical process with defined parameters.

The direct levels of the proteins (after log-transformation and normalization), the presence/absence of clinical factors represented in binary form (e.g. sex), and/or clinical factors in quantitative form (e.g., BMI, age) provide values that are plugged into the diagnostic model provided by the software, and the result is evaluated against one or more cutoffs to determine the diagnosis or prognosis.

The following are examples of the types of statistical analysis methods that are available to one of skill in the art to aid in the practice of the disclosed methods, panels, assays, and kits. The statistical analysis may be applied for one or both of two tasks. First, these and other statistical methods may be used to identify preferred subsets of markers and other indices that will form a preferred dataset. In addition, these and other statistical methods may be used to generate the analytical process that will be used with the dataset to generate the result. Several statistical methods presented herein or otherwise available in the art will perform both of these tasks and yield a model that is suitable for use as an analytical process for the practice of the methods disclosed herein.

Prior to analysis, the data is partitioned into a training set and a validation set. The training set is used to train, evaluate and build the final diagnostic or prognostic model. The validation set is not used at all during the training process, and is only used to validate final diagnostic or prognostic models. All processes below, except when explicitly mentioned, involve the use of only the training set.

The creation of training and validation sets is done through random selection. After these sets are determined, the balance of various outcomes (e.g., presence of 70% or greater obstruction, the occurrence of MI within one year, etc.) is considered to confirm that the outcomes of interest are properly represented in each data set.

The features (e.g., proteins and/or clinical factors) of the diagnostic and/or prognostic models are selected for each outcome using a combination of analytic processes, including least angle regression (LARS; a procedure based on stepwise forward selection), shrinkage in statistical learning methods such as least absolute shrinkage and selection operator (LASSO), significance testing, and expert opinion.

The statistical learning method used to generate a result (classification, survival/mortality within a specified time, etc.) may be any type of process capable of providing a result useful for classifying a sample (e.g., a linear model, a probabilistic model, a decision tree algorithm, or a comparison of the obtained dataset with a reference dataset).

The diagnostic or prognostic signal in the features is evaluated with these statistical learning methods using a cross-validation procedure. For each cross-validation fold, the training set is further split into training and validation sets (hereby called CV-training and CV-validation data sets).

For each fold of cross validation, the diagnostic or prognostic model is built using the CV-training data, and evaluated with the CV-validation data.

Models during the cross-validation process are evaluated with standard metrics of classification accuracy, e.g. the area under the ROC curve (AUC), sensitivity (Sn), specificity (Sp), positive predictive values (PPV), and negative predictive values (NPV).

Once a set of features (e.g. quantitative protein levels and optionally clinical factors) are selected to compose a final diagnostic or prognostic panel, a final predictive model is built using all of the training data.

Applying the patient data (e.g., quantitative protein levels and/or clinical factors) into the final predictive model yields a classification result. These results can be compared against a threshold for classifying a sample within a certain class (e.g., positive or negative diagnosis and/or prognosis, or a severity/likelihood score).

Final models are evaluated with the validation data set. To respect the authority of the validation data set, it is not used in an iterative way, to feed information back into the training process. It is only used as the full stop of the analytic pipeline.

Models are evaluated with the validation data set using metrics of accuracy, including the AUC, sensitivity, specificity, positive predictive value and/or negative predictive value. Other metrics of accuracy, such as hazard ratio, relative risk, and net reclassification index are considered separately for models of interest.

This final model or a model optimized for a particular biomarker platform, when used in a clinical setting, may be implemented as a software system, either running directly on the assay hardware platform or an independent system. The model may receive protein level or concentration data directly from the assay platform or other means of data transfer, and patient clinical data may be received via electronic, manual, or other query of patient medical records or through interactive input with the operator. This patient data may be processed and run through the final model, which will provide a result to clinicians and medical staff for purposes of decision support.

Panels, Assays, and Kits

The present invention further provides panels, assays, and kits comprising at least 1, at least 2, at least 3, at least 4 or greater than 4 biomarkers and/or clinical variable(s), in order to aid or facilitate a diagnostic or prognostic finding according to the present disclosure. For example, in some embodiments, a diagnostic or prognostic panel or kit comprises one or a plurality of biomarkers set out in Tables 1A, 1B, 2A, and 2B and optionally one or a plurality of applicable clinical variables set out in Tables 3A, 3B, 4A, and 4B.

It will be understood that, in many embodiments, the panels, assays, and kits described herein comprise antibodies, binding fragments thereof and/or other types of binding agents which are specific for the biomarkers of Tables 1A, 1B, 2A, and 2B, and which are useful for determining the levels of the corresponding biomarker in a biological sample according to the methods describe herein. Accordingly, in each description herein of a panel, assay, or kit comprising one or a plurality of biomarkers, it will be understood that the very same panel, assay, or kit can advantageously comprise, in addition or instead, one or a plurality of antibodies, binding fragments thereof or other types of binding agents, which are specific for the biomarkers of Tables 1A, 1B, 2A, and 2B. Of course, the panels, assays, and kits can further comprise, include or recommend a determination of one or a plurality of applicable clinical variables as set out in Tables 3A, 3B, 4A, and 4B.

In certain specific embodiments, the biomarkers and/or clinical variables used in in conjunction with a panel, assay, or kit include those listed in Tables 1A, 1B, 2A, 2B and Tables 3A, 3B, 4A and 4B, respectively, particularly those which are associated with a p-value of less than 0.1, less than 0.05, less than 0.01 or less than 0.001.

In some embodiments, panels, assays, and kits may comprise at least 1, at least 2, at least 3 or at least 4 biomarkers as described herein. In other embodiments, the number of biomarkers employed can include at least 5, 6, 7, 8, 9 or 10 or more. In still other embodiments, the number of biomarkers employed can include at least 15, 20, 25 or 50, or more.

In addition to the biomarkers disclosed in Tables 1A, 1B, 2A, and 2B, a panel, assay, or kit may include additional biomarkers (or binding agents thereto) not specifically described herein, particularly where the biomarkers in the panel themselves provide statistically significant information regarding a diagnosis or prognosis of interest, e.g., whether a patient has coronary artery disease or would be at increased risk for cardiovascular disease and/or an adverse cardiovascular event within one year, at one year, or beyond one year.

As described herein, panels, assays, and kits of the present disclosure can be used for identifying the presence of cardiovascular disease in a subject, particularly the presence of obstructive coronary artery disease and/or for predicting cardiac events. In some embodiments, a diagnostic panel, assay, or kit identifies in a subject the presence of 70% or greater obstruction in any major epicardial vessels.

In other embodiments, a prognostic panel, assay, or kit is used to predict the risk of a cardiovascular disease or event within one year, about 1 year, about 2 years, about 3 years, about 4 years, about 5 years, or more from the date on which the sample is drawn. Time endpoints are defined as from sample draw and include less than one year, one year, and greater than one year. Less than or within one year may be any time from time of sample draw up to and including 365 days. For example, the panel results may predict the risk of a cardiovascular disease or event from time of sample draw to 30 days, to 60 days, to 90 days, to 120 days, to 150 days, to 180 days, to 210 days, to 240 days, to 270 days, to 300 days, to 330 days, to 360 days, to 365 days. In yet other embodiments, time endpoints are defined as 3 days post sample draw to 30 days, to 60 days, to 90 days, to 120 days, to 150 days, to 180 days, to 210 days, to 240 days, to 270 days, to 300 days, to 330 days, to 360 days, to 365 days.

In specific embodiments, panels, assays, and kits for the diagnosis of obstructive CAD comprise at least 1, at least 2, at least 3, at least 4 or greater than four biomarkers, or antibodies, binding fragments thereof or other types of binding agents, which are specific for the biomarkers, where the biomarkers are selected from the group consisting of adiponectin, apolipoprotein C-I, decorin, interleukin-8, kidney injury molecule-1, matrix metalloproteinase 9, midkine, myoglobin, pulmonary surfactant associated protein D, stem cell factor, and troponin. In some embodiments, at least one clinical variable described herein is used in conjunction with the biomarker levels determined. In other embodiments, the clinical variable is selected from the group consisting of age, history of coronary artery bypass graft surgery (CABG), history of diabetes type 2, history of hemodialysis, history of myocardial infarct (MI), history of percutaneous coronary intervention (e.g., balloon angioplasty with or without stent placement), and sex.

In specific embodiments, a panel, assay, or kit for the diagnosis of 70% or greater obstruction in any major epicardial vessel comprises biomarkers for adiponectin, apolipoprotein C-1, kidney injury molecule-1, and midkine and clinical variables of history of percutaneous coronary intervention (e.g., balloon angioplasty with or without stent placement), and sex. This combination of biomarkers and clinical variables is represented by panel FM139/685 in Table 25, Example 1, and FIGS. 1-4.

Figure 5:
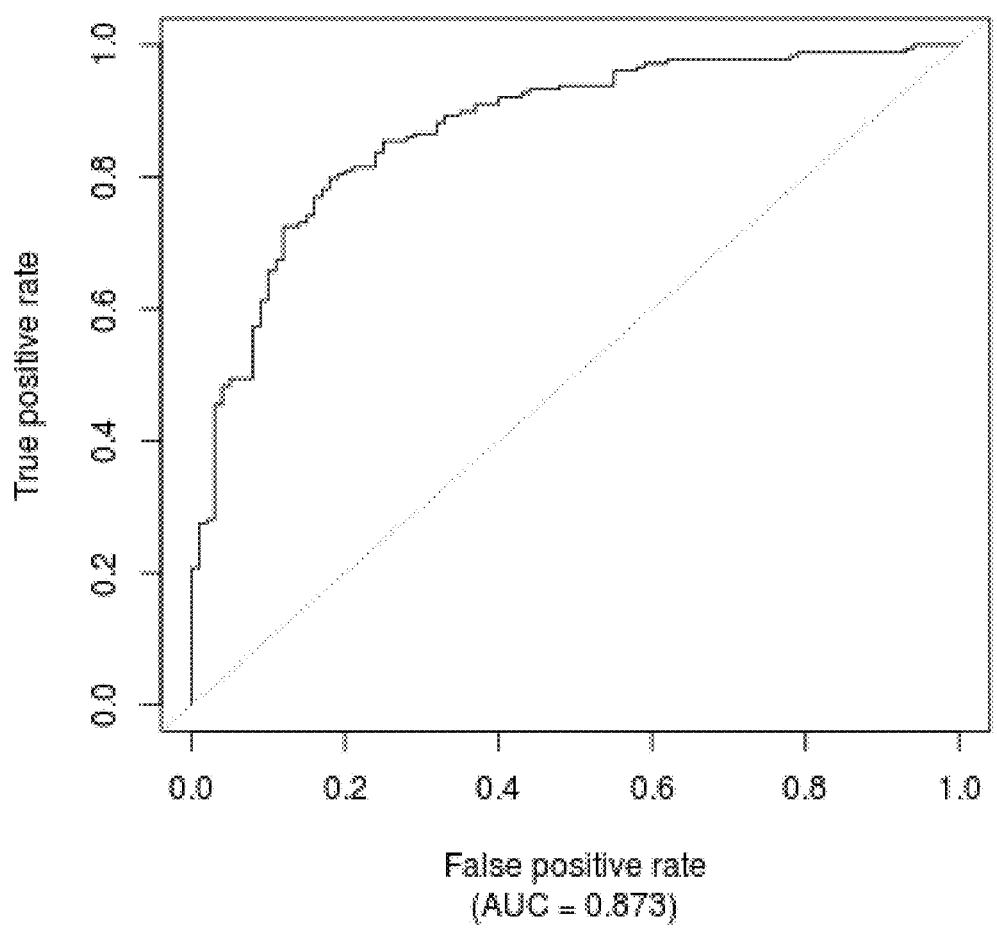
FIG. 5 shows a receiver operating characteristic curve for the Prevencio CAD panel FM144/696 in the internal validation set (N=278) to diagnose the presence of severe CAD (≥70% stenosis in any vessel). The panel had a robust area under the curve (AUC) of 0.87.

In specific embodiments, a panel, assay, or kit for the diagnosis of 70% or greater obstruction in any major epicardial vessel comprises biomarkers for adiponectin, apolipoprotein C-1, kidney injury molecule-1, and midkine and clinical variables of history of percutaneous coronary intervention (e.g., balloon angioplasty with or without stent placement), sex, and age. This combination of biomarkers and clinical variables is represented by panel FM144/696 in Table 25 and FIG. 5.

Figure 6:
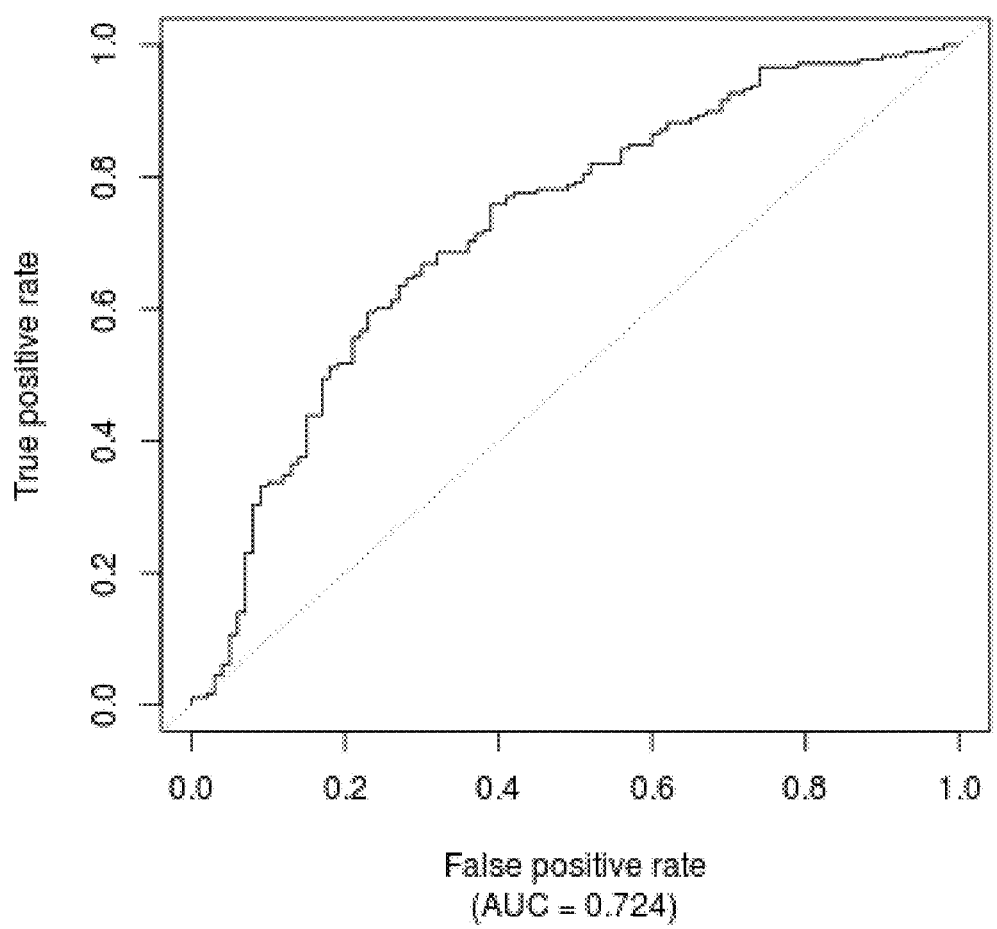
FIG. 6 shows a receiver operating characteristic curve for the Prevencio CAD panel FM145/701 in the internal validation set (N=278) to diagnose the presence of severe CAD (≥70% stenosis in any vessel). The panel had an area under the curve (AUC) of 0.72.

In another embodiment, a panel, assay, or kit for the diagnosis of 70% or greater obstruction in any major epicardial vessel comprises biomarkers for adiponectin, apolipoprotein C-I, kidney injury molecule-1, and midkine and clinical variables of sex and age. This combination of biomarkers and clinical variables is represented by panel FM145/701 in Table 25 and FIG. 6.

Figure 7:
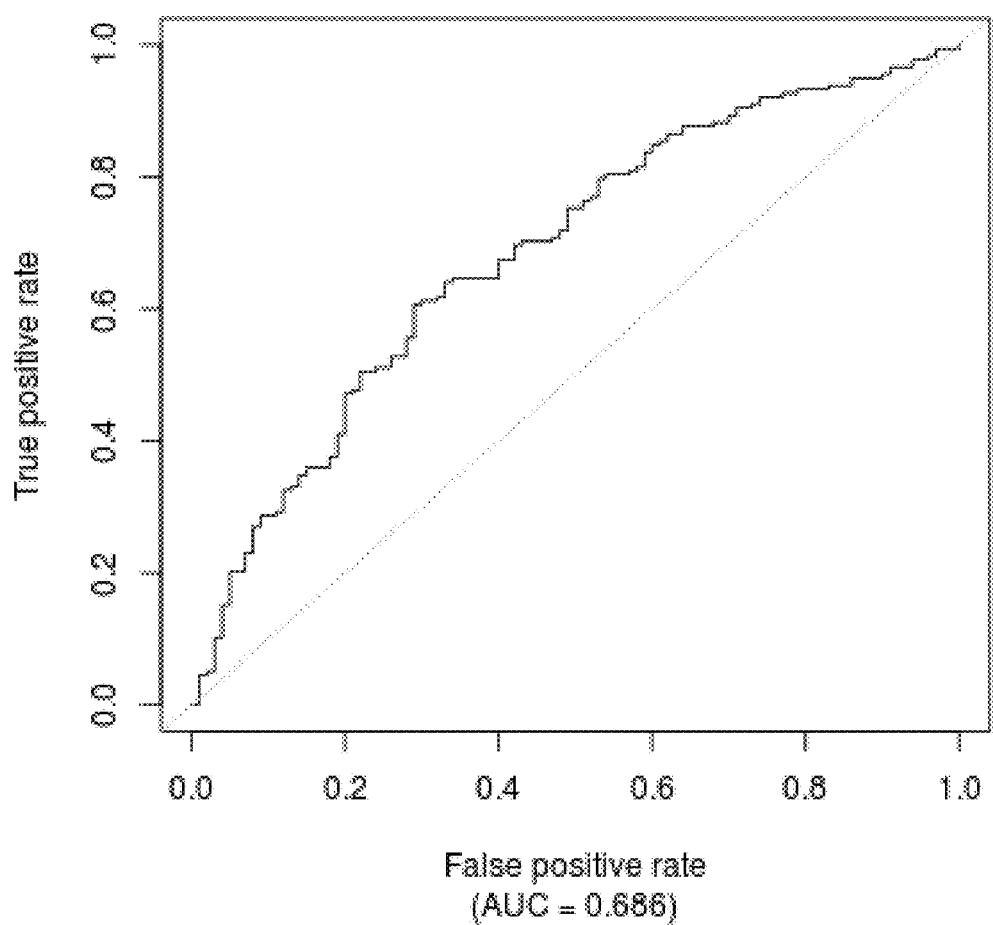
FIG. 7 shows a receiver operating characteristic curve for the Prevencio CAD panel FM146/690 in the internal validation set (N=278) to diagnose the presence of severe CAD (≥70% stenosis in any vessel). The panel had an area under the curve (AUC) of 0.69.

In another embodiment, a panel, assay, or kit for the diagnosis of 70% or greater obstruction in any major epicardial vessel comprises biomarkers for adiponectin, apolipoprotein C-I, kidney injury molecule-1, and midkine. This combination of biomarkers is represented by panel FM146/690 in Table 25 and FIG. 7.

Figure 8:
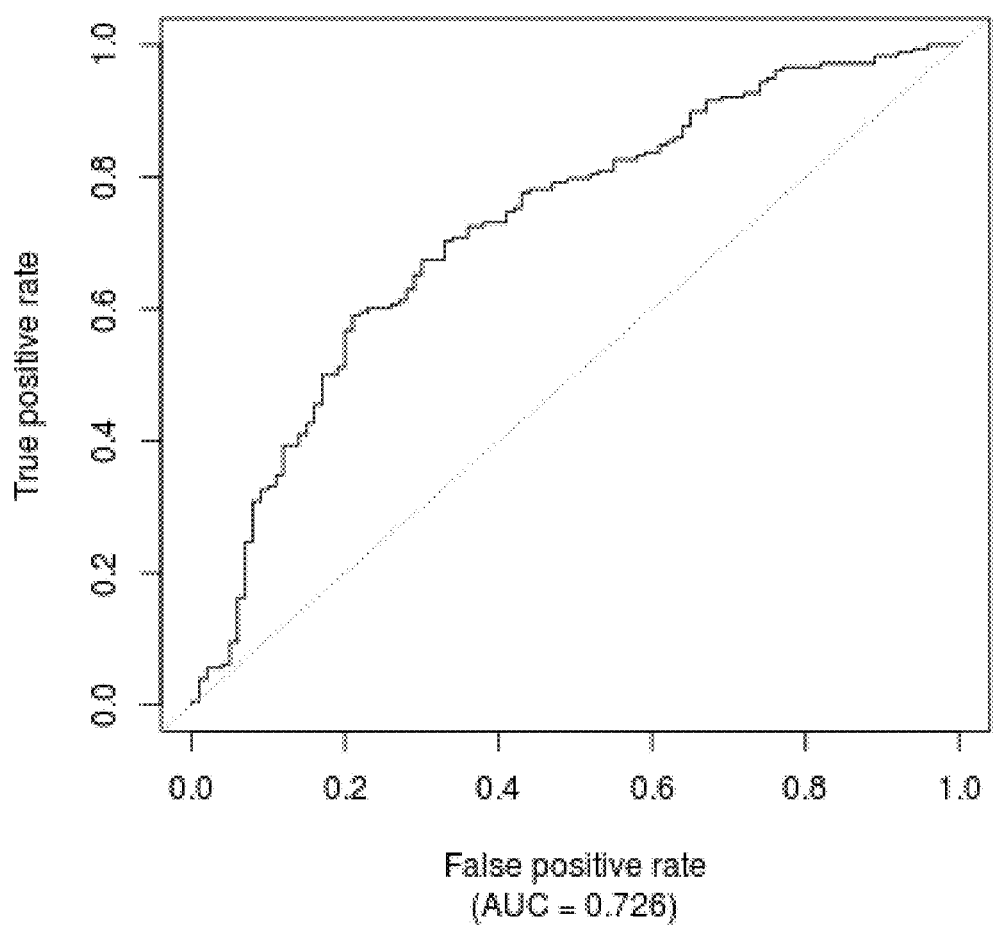
FIG. 8 shows a receiver operating characteristic curve for the Prevencio CAD panel FM152/757 in the internal validation set (N=278) to diagnose the presence of severe CAD (≥70% stenosis in any vessel). The panel had an area under the curve (AUC) of 0.73.

In another embodiment, a panel, assay, or kit for the diagnosis of 70% or greater obstruction in any major epicardial vessel comprises biomarkers for adiponectin, kidney injury molecule-1, and midkine and clinical variables of history of diabetes mellitus type 2, sex, and age. This combination of biomarkers and clinical variables is represented by panel FM152/757 in Table 25 and FIG. 8.

Embodiments of the present invention comprise a panels, assays, and kits for the diagnosis of 70% or greater obstruction in any major epicardial vessel comprising at least one biomarker and one or more clinical variables.

Figure 9:
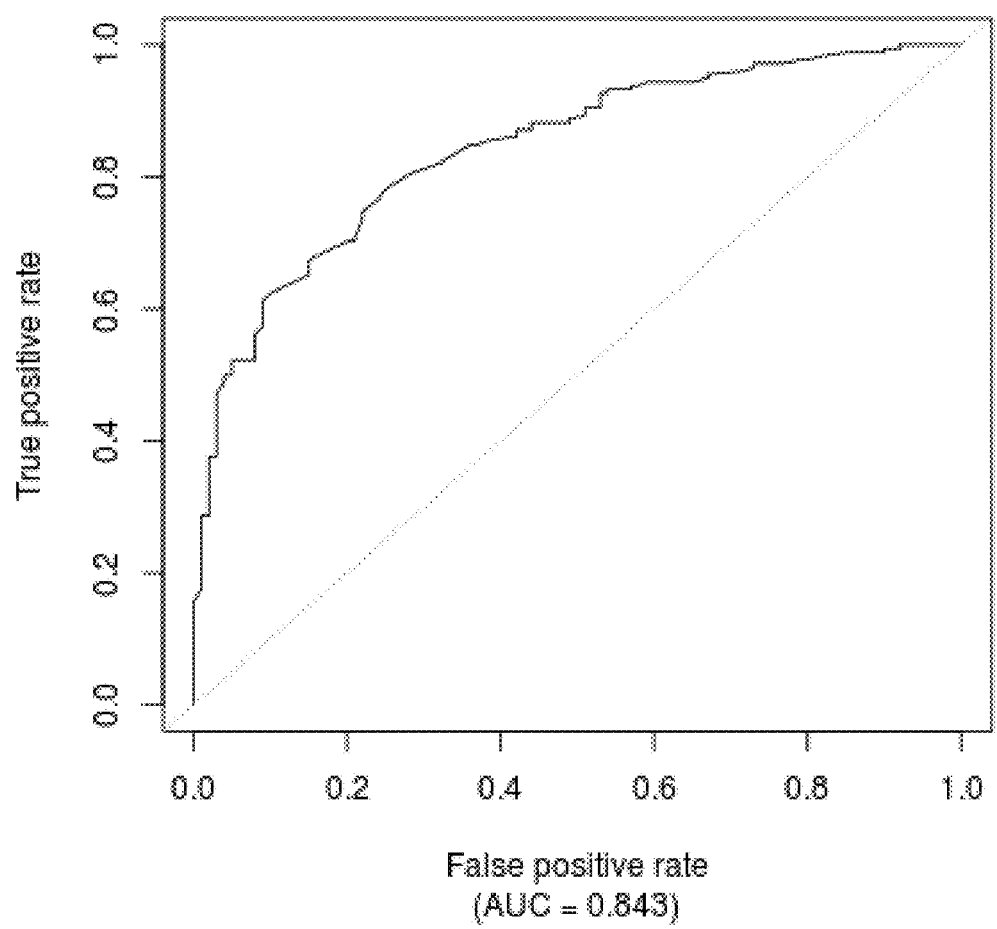
FIG. 9 shows a receiver operating characteristic curve for the Prevencio CAD panel FM117a/657 in the internal validation set (N=278) to diagnose the presence of severe CAD (≥70% stenosis in any vessel). The panel had a robust area under the curve (AUC) of 0.84.

In a specific embodiment, a panel, assay, or kit for the diagnosis of 70% or greater obstruction in any major epicardial vessel comprises a biomarker for midkine and clinical variables of history of percutaneous coronary intervention (e.g., balloon angioplasty with or without stent placement) and sex. This combination of biomarkers and clinical variables is represented by panel FM117a/657 in Table 25 and FIG. 9.

Figure 10:
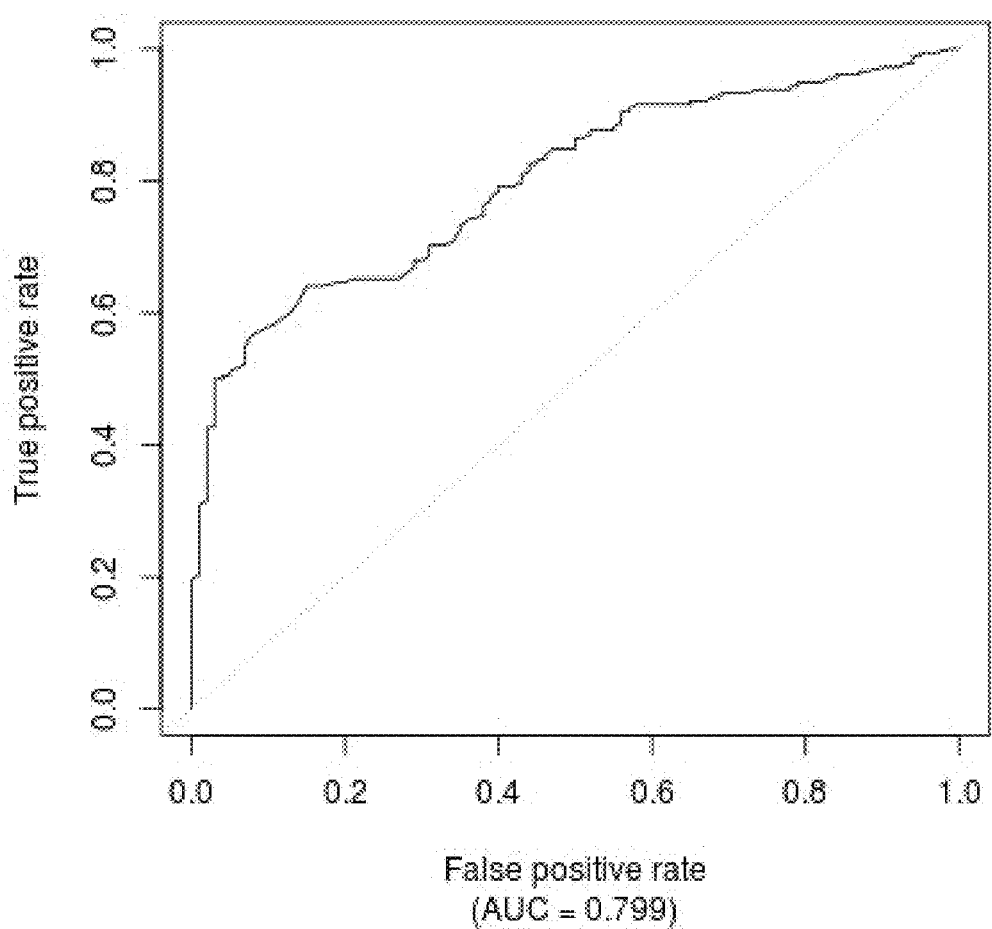
FIG. 10 shows a receiver operating characteristic curve for the Prevencio CAD panel FM139CLa/658 in the internal validation set (N=278) to diagnose the presence of severe CAD (≥70% stenosis in any vessel). The panel had a robust area under the curve (AUC) of 0.80.

In a specific embodiment, a panel, assay, or kit for the diagnosis of 70% or greater obstruction in any major epicardial vessel comprises a biomarker for adiponectin and clinical variables of history of percutaneous coronary intervention (e.g., balloon angioplasty with or without stent placement) and sex. This combination of biomarkers and clinical variables is represented by panel FM139CLa/658 in Table 25 and FIG. 10.

Figure 11:
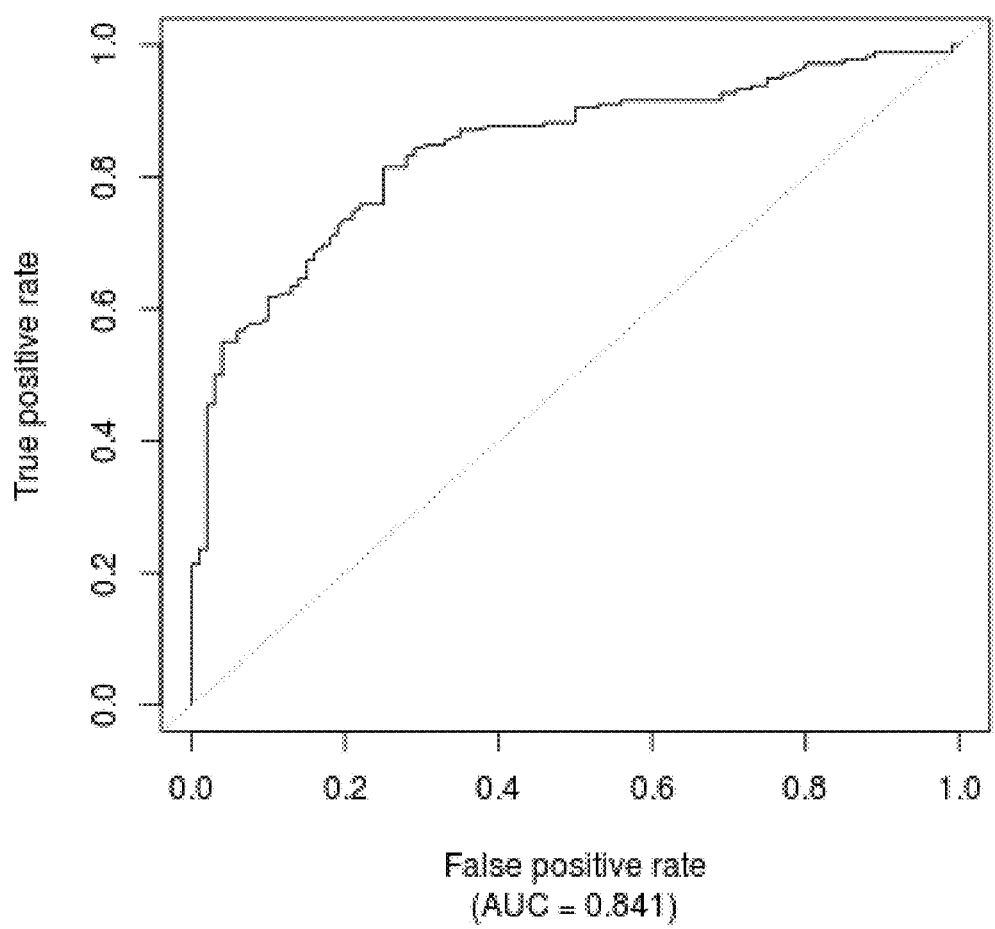
FIG. 11 shows a receiver operating characteristic curve for the Prevencio CAD panel FM139CLb/750 in the internal validation set (N=278) to diagnose the presence of severe CAD (≥70% stenosis in any vessel). The panel had a robust area under the curve (AUC) of 0.84.

In a specific embodiment, a panel, assay, or kit for the diagnosis of 70% or greater obstruction in any major epicardial vessel comprises a biomarker for apolipoprotein C-1 and clinical variables of history of percutaneous coronary intervention (e.g., balloon angioplasty with or without stent placement) and sex. This combination of biomarkers and clinical variables is represented by panel FM139CLb/750 in Table 25 and FIG. 11.

Figure 12:
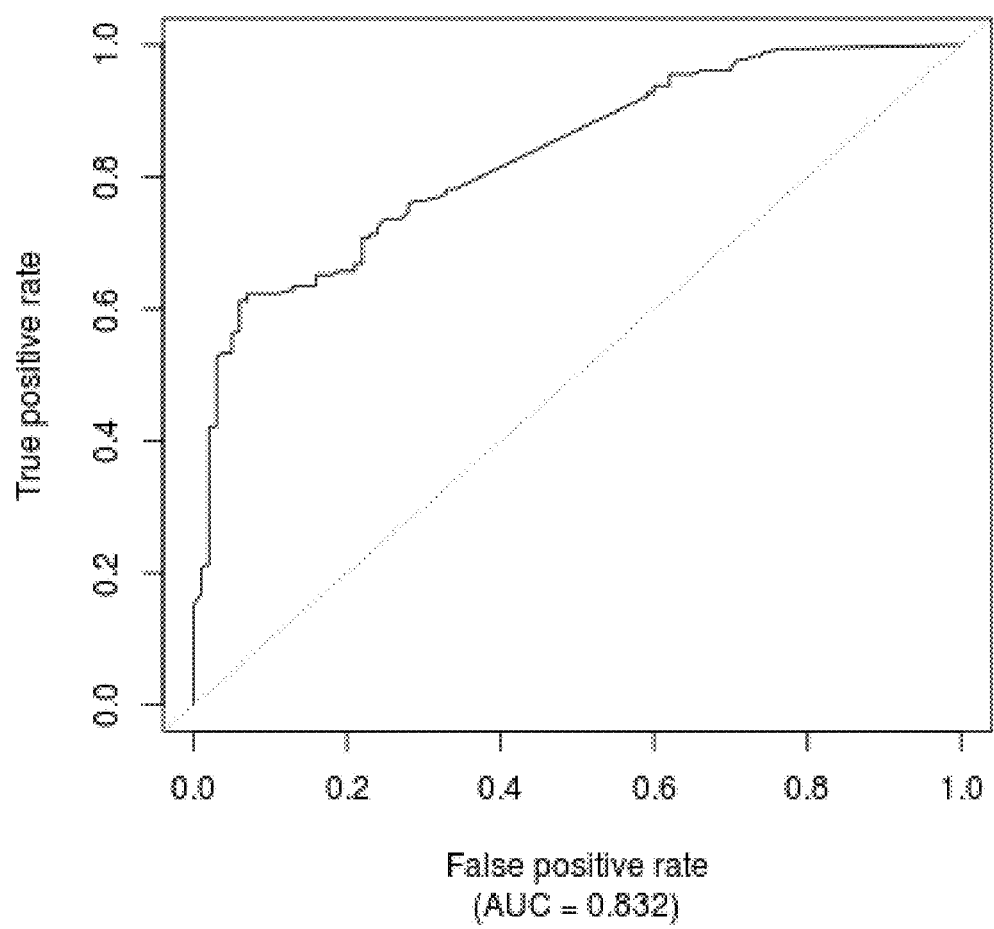
FIG. 12 shows a receiver operating characteristic curve for the Prevencio CAD panel FM139CLc/751 in the internal validation set (N=278) to diagnose the presence of severe CAD (≥70% stenosis in any vessel). The panel had a robust area under the curve (AUC) of 0.83.

In a specific embodiment, a panel, assay, or kit for the diagnosis of 70% or greater obstruction in any major epicardial vessel comprises a biomarker for kidney injury molecule-1 and clinical variables of history of percutaneous coronary intervention (e.g., balloon angioplasty with or without stent placement) and sex. This combination of biomarkers and clinical variables is represented by panel FM139CLc/751 in Table 25 and FIG. 12.

Figure 13:
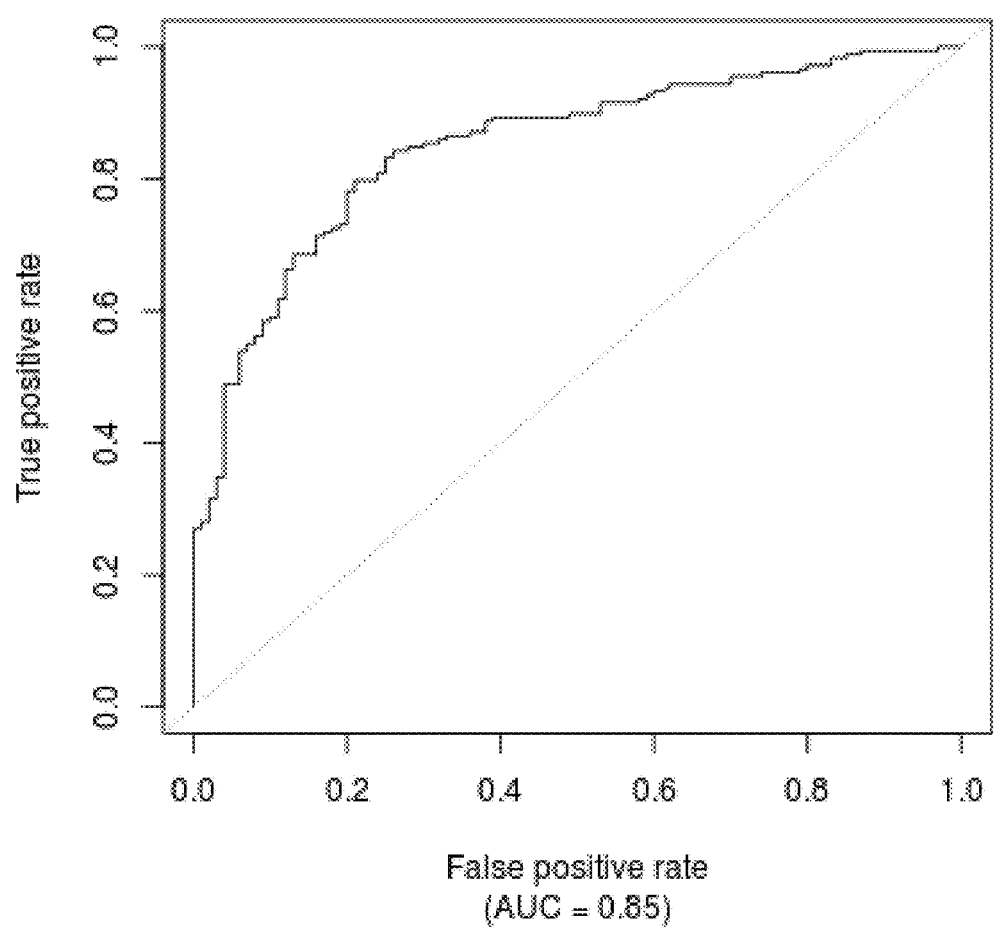
FIG. 13 shows a receiver operating characteristic curve for the Prevencio CAD panel FM117b/663 in the internal validation set (N=278) to diagnose the presence of severe CAD (≥70% stenosis in any vessel). The panel had a robust area under the curve (AUC) of 0.85.

In yet other embodiments, a panel, assay, or kit for the diagnosis of 70% or greater obstruction in any major epicardial vessel comprises biomarkers for adiponectin and midkine and clinical variables of history of percutaneous coronary intervention (e.g., balloon angioplasty with or without stent placement) and sex. This combination of biomarkers and clinical variables is represented by panel FM117b/663 in Table 25 and FIG. 13.

Figure 14:
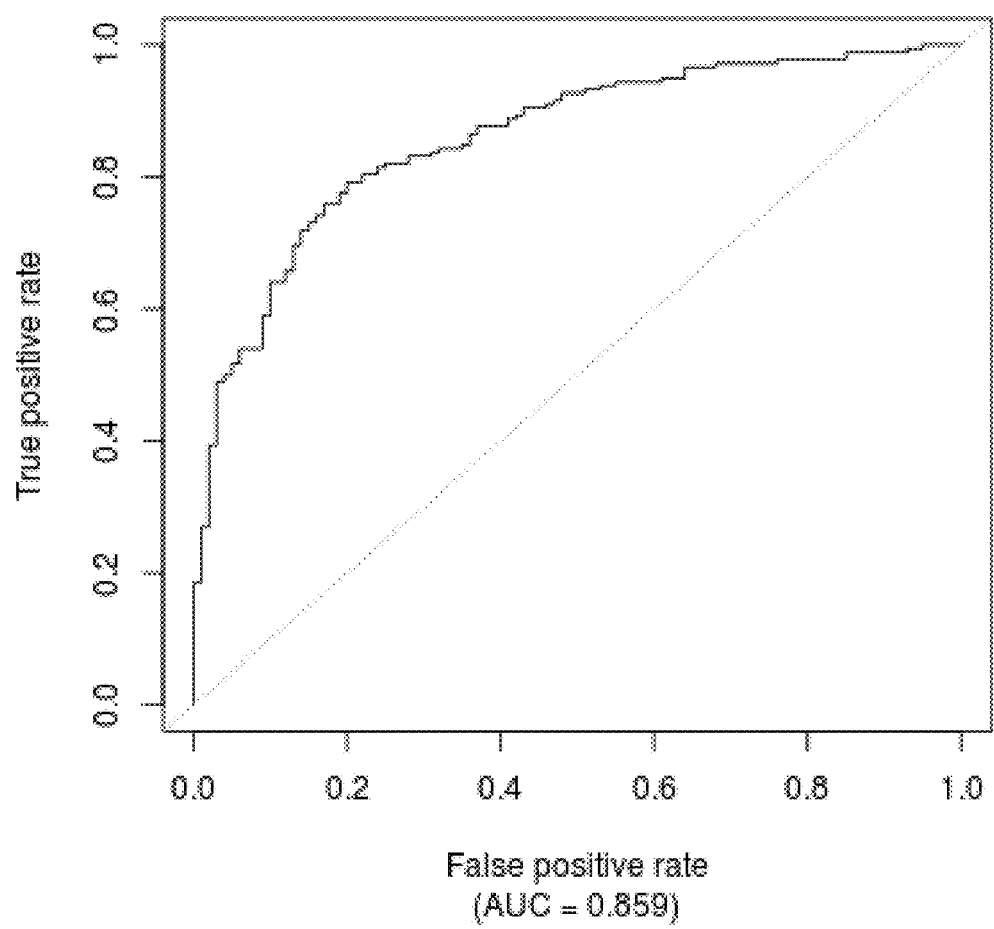
FIG. 14 shows receiver operating characteristic curve for the Prevencio CAD panel FM139CLd/752 in the internal validation set (N=278) to diagnose the presence of severe CAD (≥70% stenosis in any vessel). The panel had a robust area under the curve (AUC) of 0.86.

In another embodiment, a panel, assay, or kit for the diagnosis of 70% or greater obstruction in any major epicardial vessel comprises biomarkers for apolipoprotein C-I and midkine and clinical variables of history of percutaneous coronary intervention (e.g., balloon angioplasty with or without stent placement) and sex. This combination of biomarkers and clinical variables is represented by panel FM139CLd/752 in Table 25 and FIG. 14.

Figure 15:
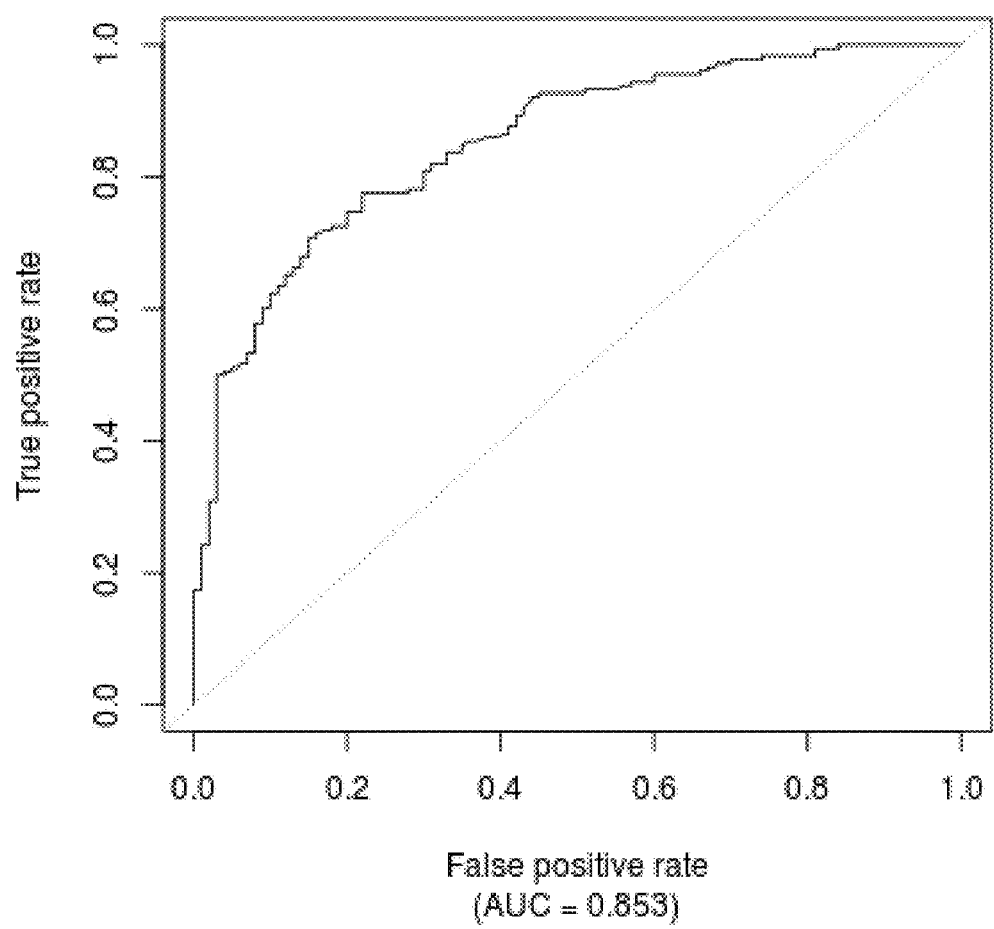
FIG. 15 shows receiver operating characteristic curve for the Prevencio CAD panel FM139CLe/753 in the internal validation set (N=278) to diagnose the presence of severe CAD (≥70% stenosis in any vessel). The panel had a robust area under the curve (AUC) of 0.85.

In another embodiment, a panel, assay, or kit for the diagnosis of 70% or greater obstruction in any major epicardial vessel comprises biomarkers for kidney injury molecule-1 and midkine and clinical variables of history of percutaneous coronary intervention (e.g., balloon angioplasty with or without stent placement), and sex. This combination of biomarkers and clinical variables is represented by panel FM139Cle/753 in Table 25 and FIG. 15.

Figure 16:
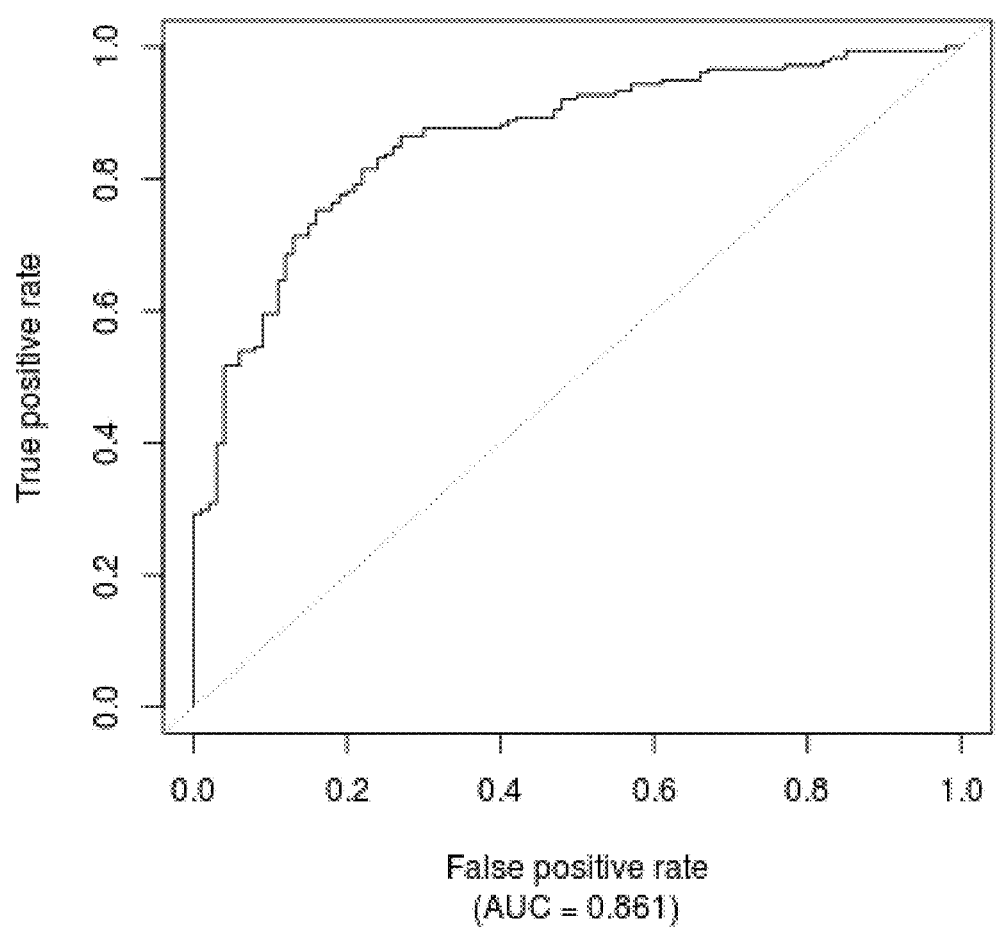
FIG. 16 shows receiver operating characteristic curve for the Prevencio CAD panel FM139CLf/754 in the internal validation set (N=278) to diagnose the presence of severe CAD (≥70% stenosis in any vessel). The panel had a robust area under the curve (AUC) of 0.86.

In a further embodiment, a panel, assay, or kit for the diagnosis of 70% or greater obstruction in any major epicardial vessel comprises biomarkers for adiponectin, apolipoprotein C-I, and midkine and clinical variables of history of percutaneous coronary intervention (e.g., balloon angioplasty with or without stent placement) and sex. This combination of biomarkers and clinical variables is represented by panel FM139CLf/754 in Table 25 and FIG. 16.

Figure 17:
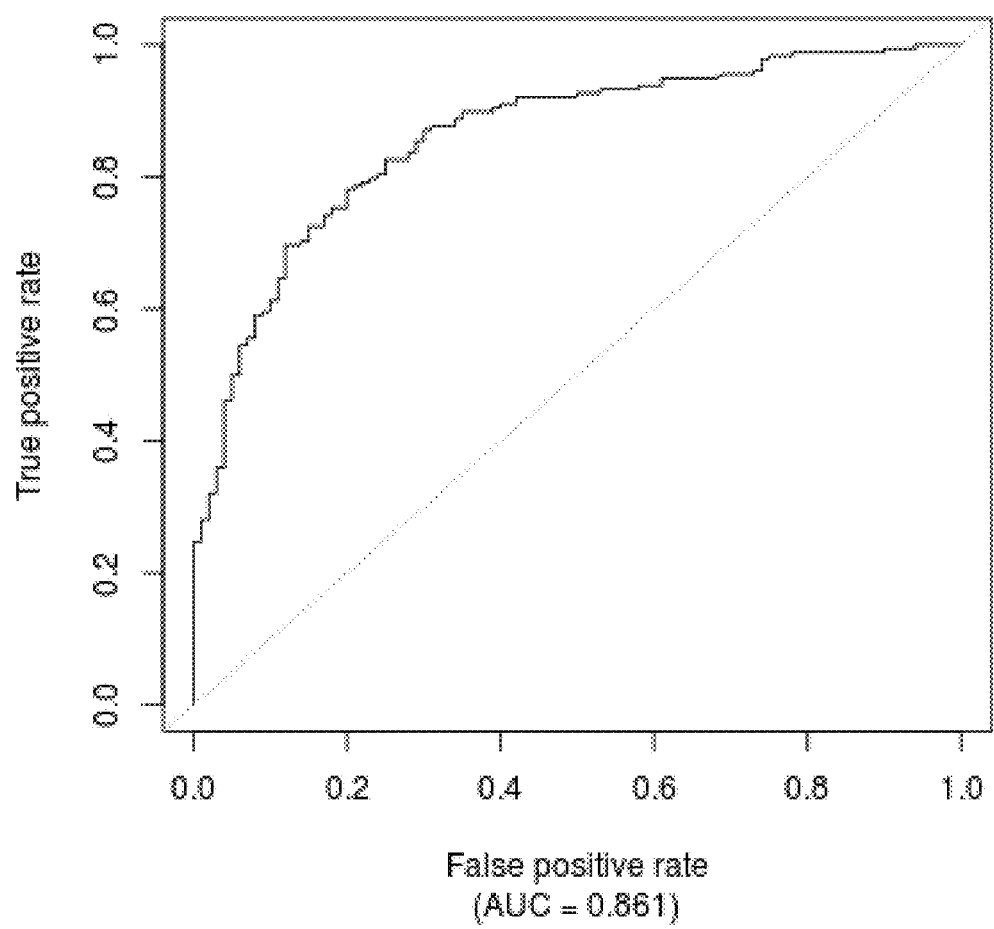
FIG. 17 shows receiver operating characteristic curve for the Prevencio CAD panel FM139CLg/755 in the internal validation set (N=278) to diagnose the presence of severe CAD (≥70% stenosis in any vessel). The panel had a robust area under the curve (AUC) of 0.86.

In yet another embodiment, a panel, assay, or kit for the diagnosis of 70% or greater obstruction in any major epicardial vessel comprises biomarkers for adiponectin, kidney injury molecule-1, and midkine and clinical variables of history of percutaneous coronary intervention (e.g., balloon angioplasty with or without stent placement), and sex. This combination of biomarkers and clinical variables is represented by panel FM139CLg/755 in Table 25 and FIG. 17.

In yet another embodiment, a panel, assay, or kit for the diagnosis of 70% or greater obstruction in any major epicardial vessel comprises biomarkers for adiponectin, decorin, and midkine and clinical variables of history of myocardial infarct (MI), history of percutaneous coronary intervention (e.g., balloon angioplasty with or without stent placement), and sex. This combination of biomarkers and clinical variables is represented by panel FM46/572 in Table 25, Example 2, and FIGS. 18-20.

Figure 21:
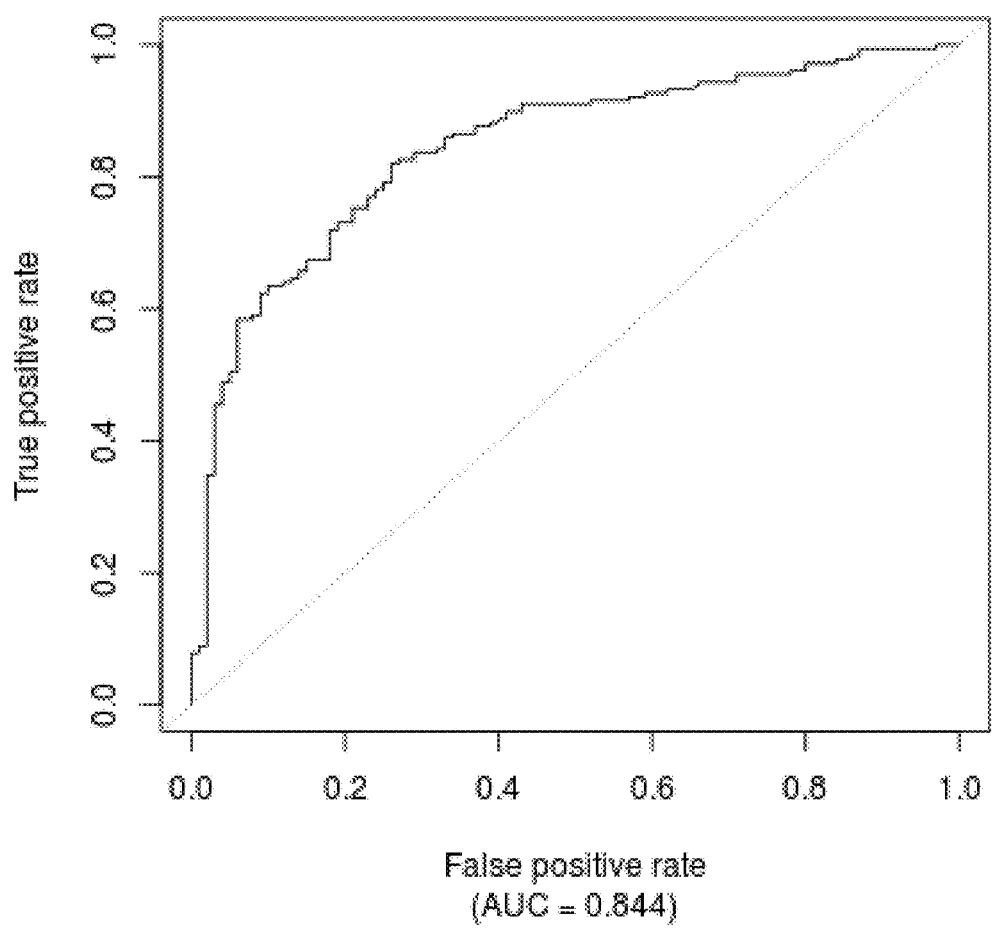
FIG. 21 shows receiver operating characteristic curve for the Prevencio CAD panel FM46Fd/586 in the internal validation set (N=278) to diagnose the presence of severe CAD (≥70% stenosis in any vessel). The panel had a robust area under the curve (AUC) of 0.84.

In yet another embodiment, a panel, assay, or kit for the diagnosis of 70% or greater obstruction in any major epicardial vessel comprises biomarkers for adiponectin and midkine and clinical variables of history of myocardial infarct (MI), history of percutaneous coronary intervention (e.g. balloon angioplasty with or without stent placement), and sex. This combination of biomarkers and clinical variables is represented by panel FM46Fd/586 in Table 25 and FIG. 21.

Figure 22:
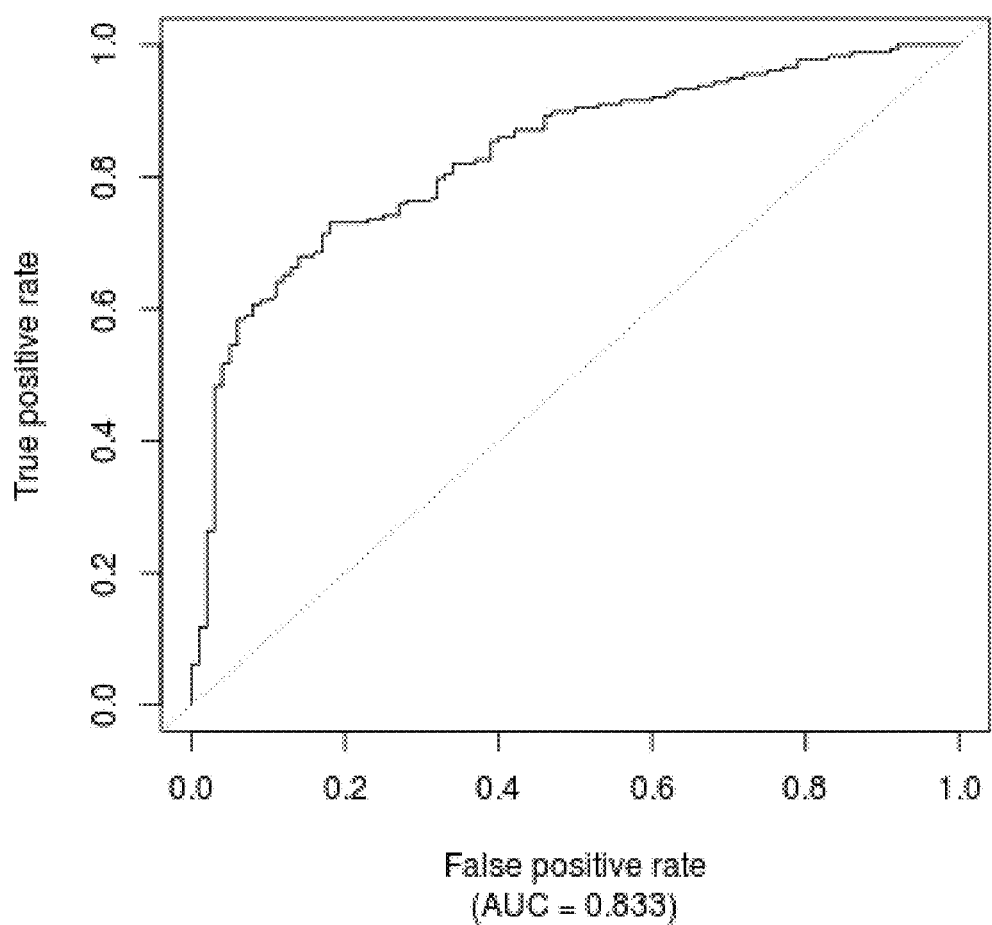
FIG. 22 shows receiver operating characteristic curve for the Prevencio CAD panel FM46Fe/587 in the internal validation set (N=278) to diagnose the presence of severe CAD (≥70% stenosis in any vessel). The panel had a robust area under the curve (AUC) of 0.83.

In yet another embodiment, a panel, assay, or kit for the diagnosis of 70% or greater obstruction in any major epicardial vessel comprises biomarkers for decorin and midkine and clinical variables of history of myocardial infarct (MI), history of percutaneous coronary intervention (e.g., balloon angioplasty with or without stent placement), and sex. This combination of biomarkers and clinical variables is represented by panel FM46Fe/587 in Table 25 and FIG. 22.

Figure 23:
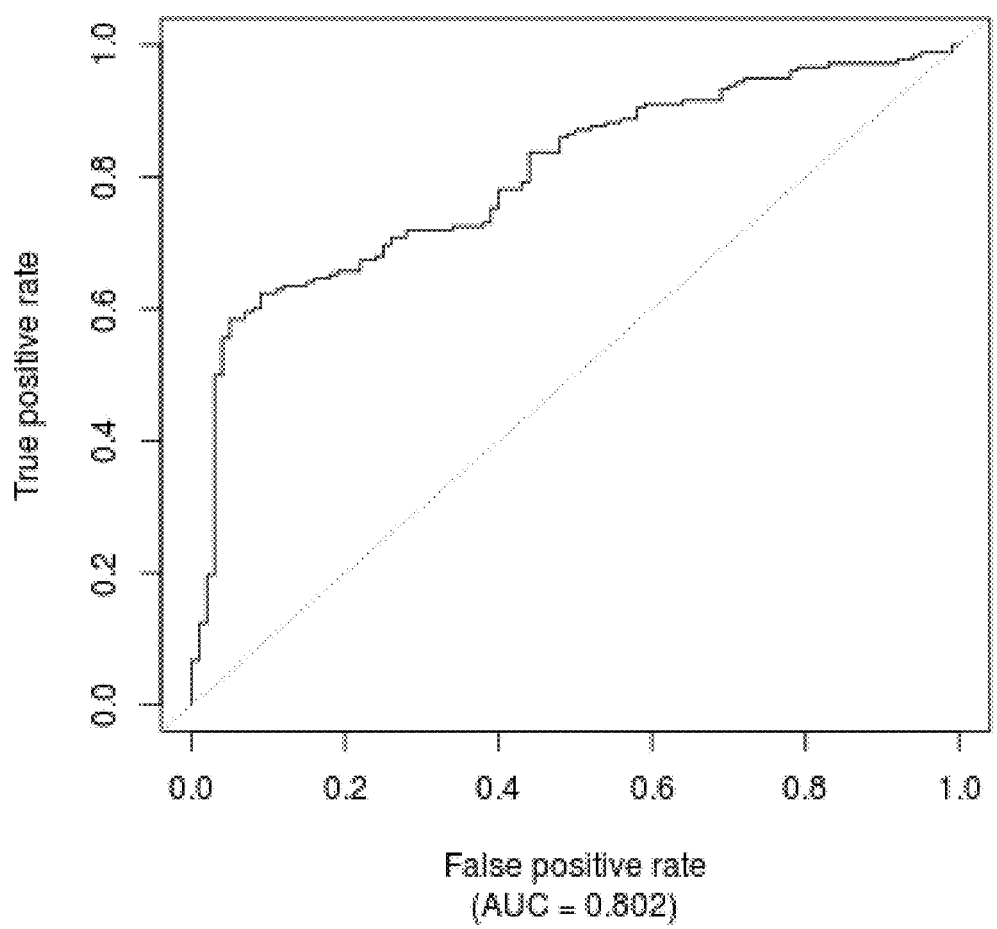
FIG. 23 shows receiver operating characteristic curve for the Prevencio CAD panel FM46Ff/588 in the internal validation set (N=278) to diagnose the presence of severe CAD (≥70% stenosis in any vessel). The panel had a robust area under the curve (AUC) of 0.80.

In yet another embodiment, a panel, assay, or kit for the diagnosis of 70% or greater obstruction in any major epicardial vessel comprises biomarkers for adiponectin and decorin and clinical variables of history of myocardial infarct (MI), history of percutaneous coronary intervention (e.g., balloon angioplasty with or without stent placement), and sex. This combination of biomarkers and clinical variables is represented by panel FM46Ff/588 in Table 25 and FIG. 23.

Figure 24:
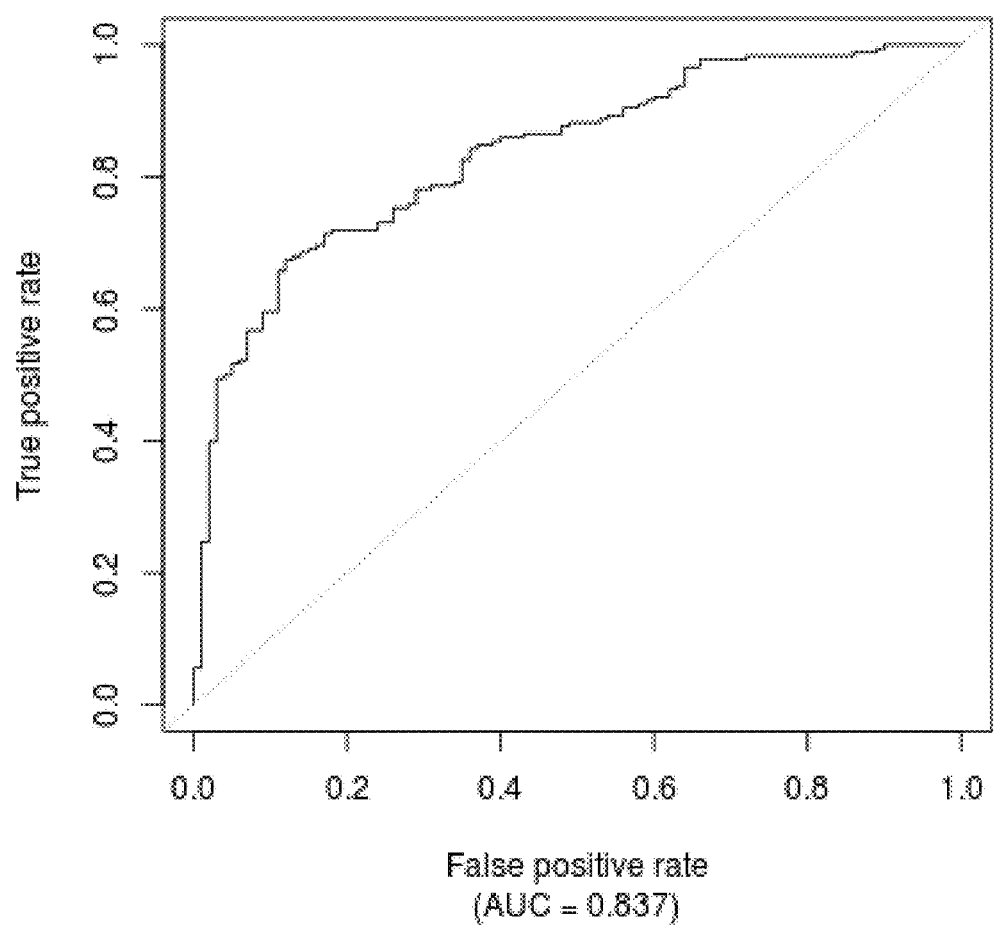
FIG. 24 shows receiver operating characteristic curve for the Prevencio CAD panel FM186/796 in the internal validation set (N=278) to diagnose the presence of severe CAD (≥70% stenosis in any vessel). The panel had a robust area under the curve (AUC) of 0.84.

In still another embodiment, a panel, assay, or kit for the diagnosis of 70% or greater obstruction in any major epicardial vessel comprises biomarkers for adiponectin, interleukin-8, kidney injury molecule-1, and stem cell factor and clinical variables of history of percutaneous coronary intervention (e.g., balloon angioplasty with or without stent placement), sex, and age. This combination of biomarkers and clinical variables is represented by panel FM186/796 in Table 25 and FIG. 24.

Figure 25:
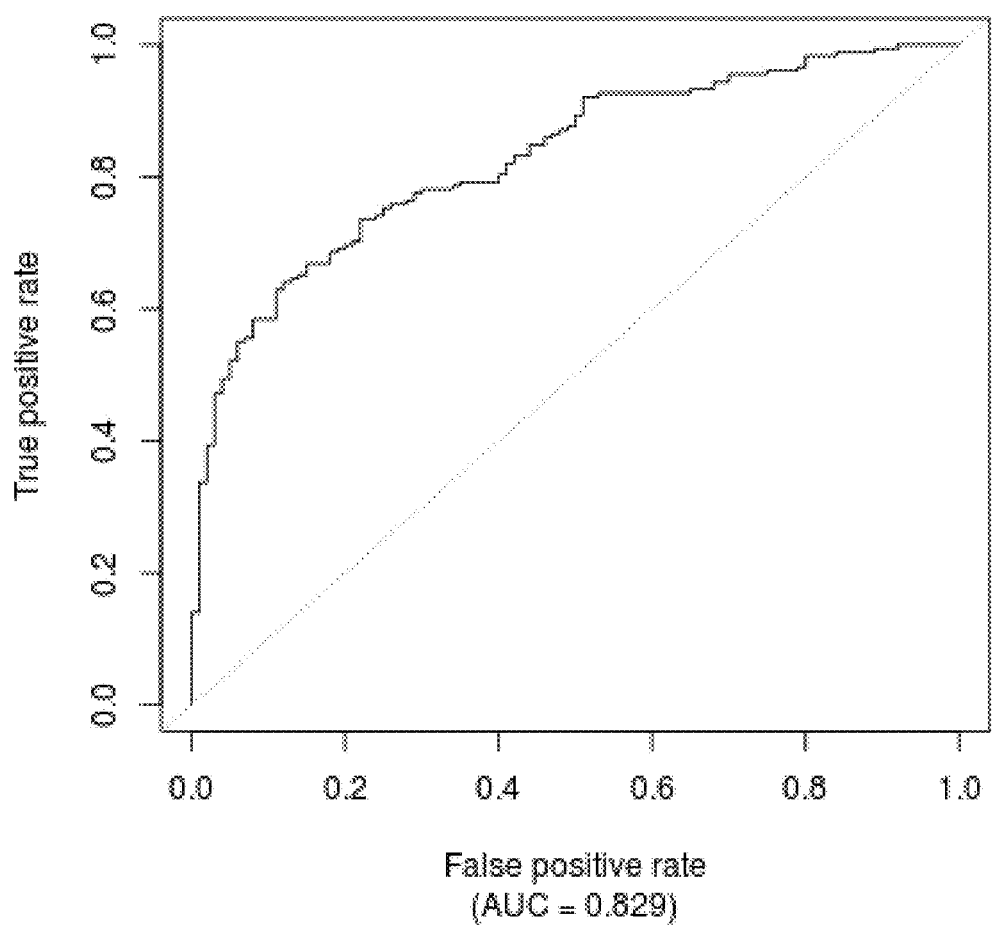
FIG. 25 shows receiver operating characteristic curve for the Prevencio CAD panel FM189/798 in the internal validation set (N=278) to diagnose the presence of severe CAD (≥70% stenosis in any vessel). The panel had a robust area under the curve (AUC) of 0.83.

In still another embodiment, a panel, assay, or kit for the diagnosis of 70% or greater obstruction in any major epicardial vessel comprises biomarkers for adiponectin, interleukin-8, kidney injury molecule-1, and stem cell factor and clinical variables of history of percutaneous coronary intervention (e.g., balloon angioplasty with or without stent placement) and sex. This combination of biomarkers and clinical variables is represented by panel FM189/798 in Table 25 and FIG. 25.

Figure 26:
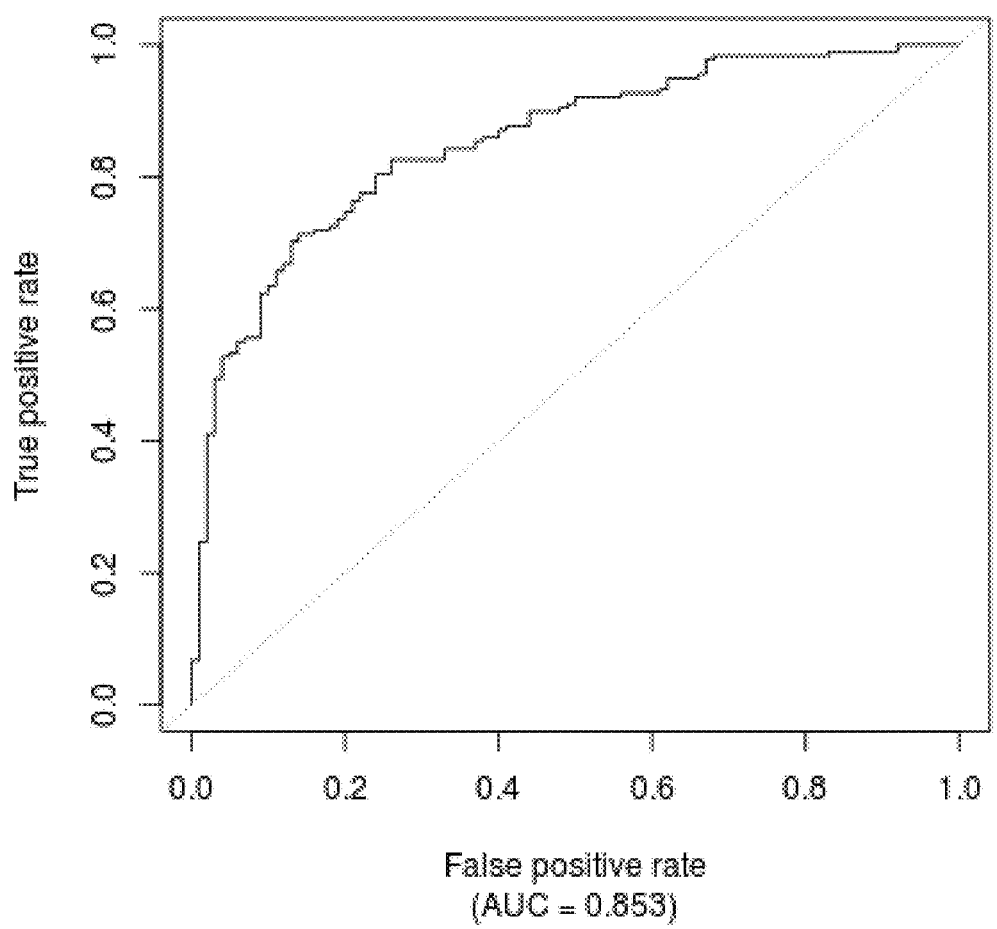
FIG. 26 shows receiver operating characteristic curve for the Prevencio CAD panel FM187/792 in the internal validation set (N=278) to diagnose the presence of severe CAD (≥70% stenosis in any vessel). The panel had a robust area under the curve (AUC) of 0.85.

In still another embodiment, a panel, assay, or kit for the diagnosis of 70% or greater obstruction in any major epicardial vessel comprises biomarkers for adiponectin, apolipoprotein C-1, interleukin-8, kidney injury molecule-1, and stem cell factor and clinical variables of history of percutaneous coronary intervention (e.g., balloon angioplasty with or without stent placement), sex, and age. This combination of biomarkers and clinical variable sis represented by panel FM187/792 in Table 25 and FIG. 26.

Figure 27:
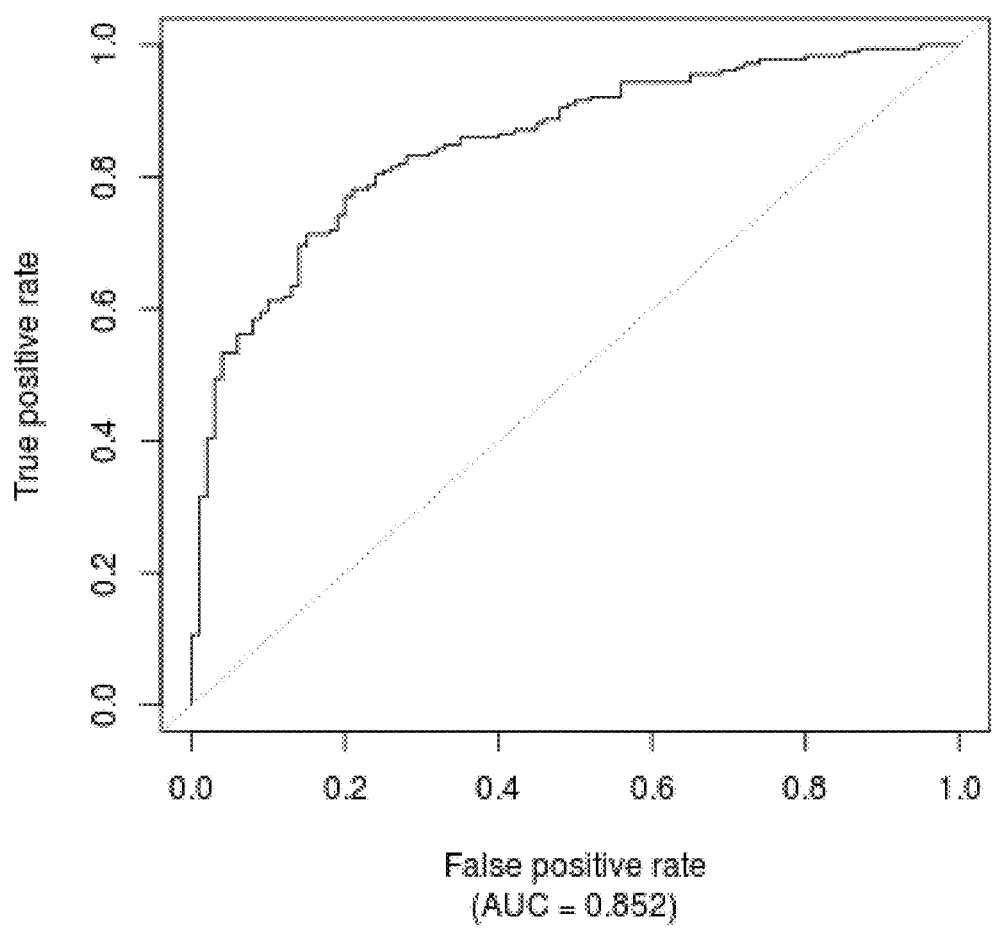
FIG. 27 shows receiver operating characteristic curve for the Prevencio CAD panel FM188/794 in the internal validation set (N=278) to diagnose the presence of severe CAD (≥70% stenosis in any vessel). The panel had a robust area under the curve (AUC) of 0.85.

In still another embodiment, a panel, assay, or kit for the diagnosis of 70% or greater obstruction in any major epicardial vessel comprises biomarkers for adiponectin, apolipoprotein C-1, interleukin-8, kidney injury molecule-1, and stem cell factor and clinical variables of history of percutaneous coronary intervention (e.g., balloon angioplasty with or without stent placement), and sex. This combination of biomarkers and clinical variables is represented by panel FM188/794 in Table 25 and FIG. 27.

Figure 28:
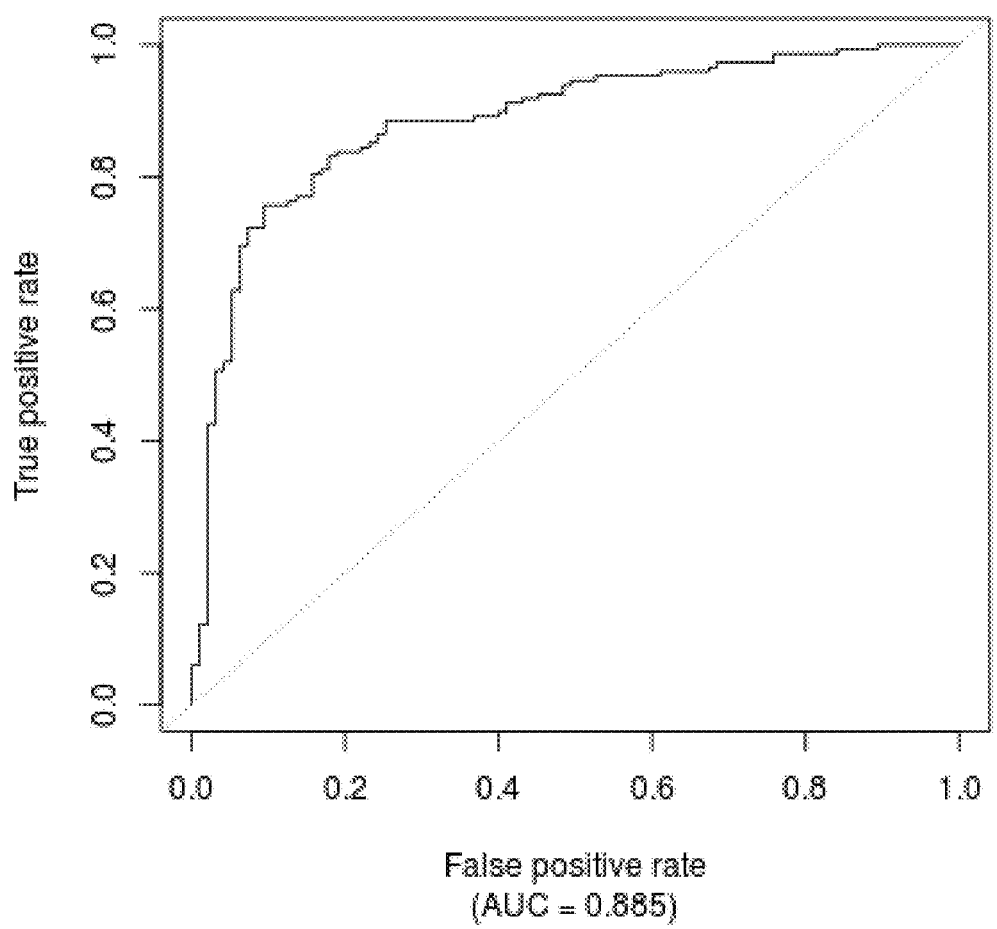
FIG. 28 shows receiver operating characteristic curve for the Prevencio CAD panel FM02/410 (as described Example 3), in the internal validation set (N=243) to diagnose the presence of severe CAD (≥70% stenosis in any vessel). The panel had a robust area under the curve (AUC) of 0.89.

In still another embodiment, a panel, assay, or kit for the diagnosis of 70% or greater obstruction in any major epicardial vessel comprises biomarkers for adiponectin, apolipoprotein C-1, matrix metalloproteinase 9, midkine, myoglobin, and pulmonary surfactant associated protein D and clinical variables of history of coronary artery bypass graft surgery (CABG), history of percutaneous coronary intervention (e.g., balloon angioplasty with or without stent placement), and sex. This combination of biomarkers and clinical variables is represented by panel FM02/410 in Table 25, Example 3, and FIG. 28.

Figure 29:
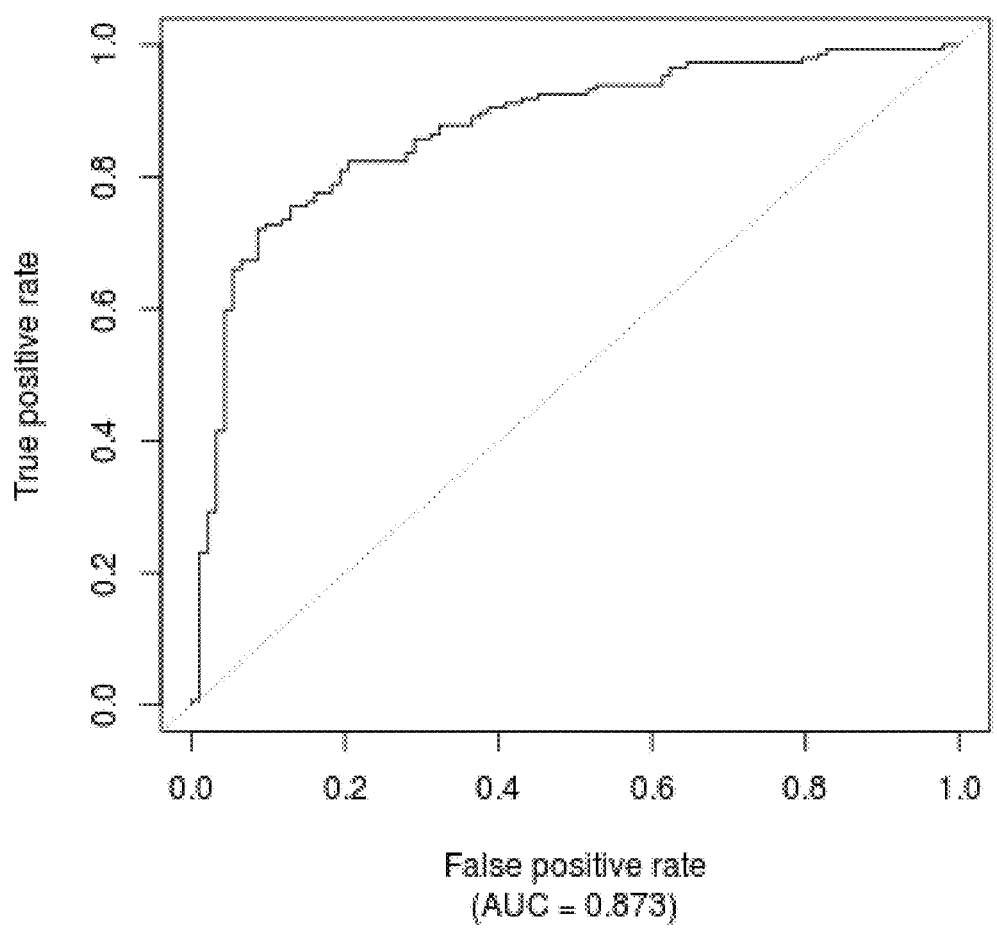
FIG. 29 shows receiver operating characteristic curve for the Prevencio CAD panel FM01/390 in the internal validation set (N=243) to diagnose the presence of severe CAD (≥70% stenosis in any vessel). The panel had a robust area under the curve (AUC) of 0.87.

In still another embodiment, a panel, assay, or kit for the diagnosis of 70% or greater obstruction in any major epicardial vessel comprises biomarkers for adiponectin, midkine, pulmonary surfactant associated protein D, and troponin and clinical variables of history of coronary artery bypass graft surgery (CABG), history of hemodialysis, history of myocardial infarct, and sex. This combination of biomarkers and clinical variables is represented by panel FM01/390 in Table 25 and FIG. 29.

Embodiments of the present invention also provide panels, assays, and kits for the prognosis of composite cardiovascular death, myocardial infarction or stroke, where the panels comprise one or more biomarkers or antibodies, binding fragments thereof or other types of binding agents, which are specific for the biomarkers disclosed herein. Such panels, assays, and kits can be used, for example, for determining a prognosis of the risk of a composite cardiovascular death, myocardial infarction or stroke within a specified time in the subject, such as within one year, or within three years. In some embodiments, the time endpoint is defined as starting from sample draw. In other embodiments, the time endpoint is defined as starting from three (3) days post sample draw.

Figure 30:
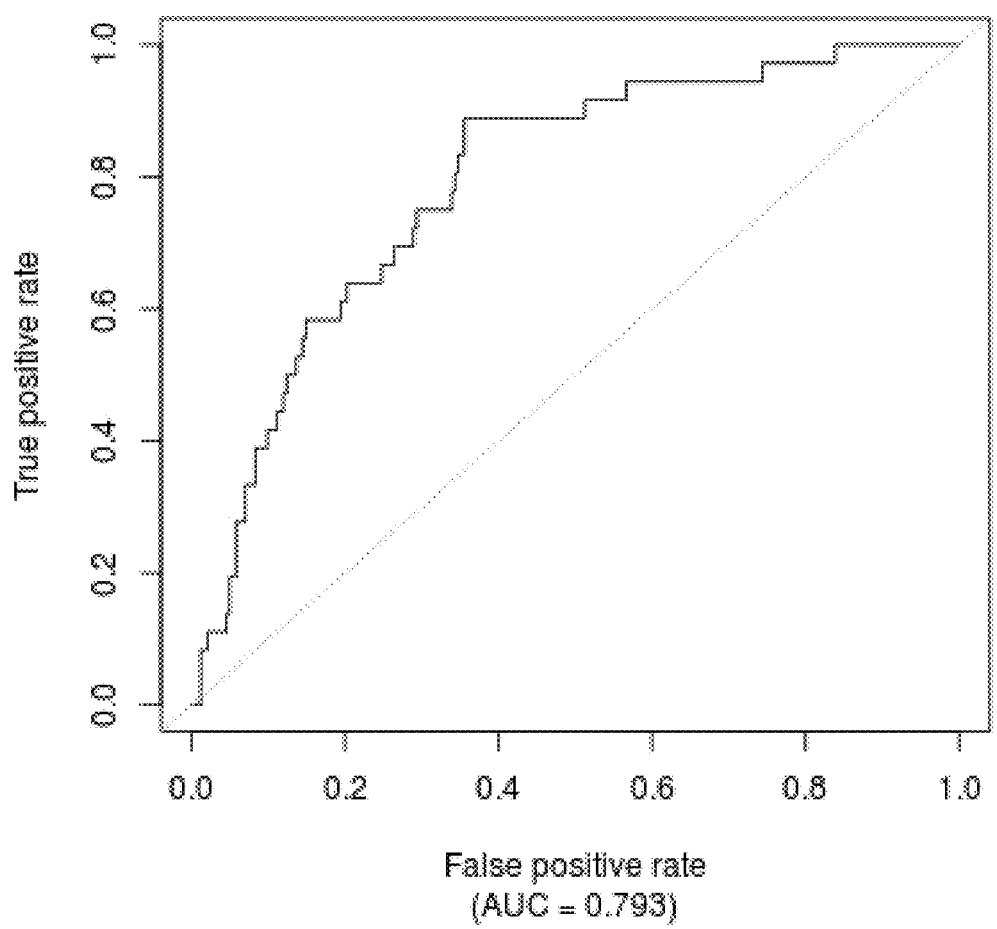
FIG. 30 shows receiver operating characteristic curve for the Prevencio prognostic panel FM160/02 (as described in Example 4), in the internal validation set (N=278) for prognosis of one year (3-365 day) composite cardiovascular death, myocardial infarct or stroke. The panel had an area under the curve (AUC) of 0.79.

In certain specific embodiments, a panel, assay, or kit for the prognosis of a composite cardiovascular death, myocardial infarction or stroke comprises the biomarkers kidney injurymolecule-1, N terminal prohormone of brain natriuretic protein (NT-proBNP), osteopontin, and tissue inhibitor of metalloproteinases-1 (TIMP-1). In some embodiments, the time endpoint is defined as starting from three (3) days post sample draw. This combination of biomarkers is represented by panel FM160/02 in Table 25, Example 4, and FIG. 30.

Figure 31:
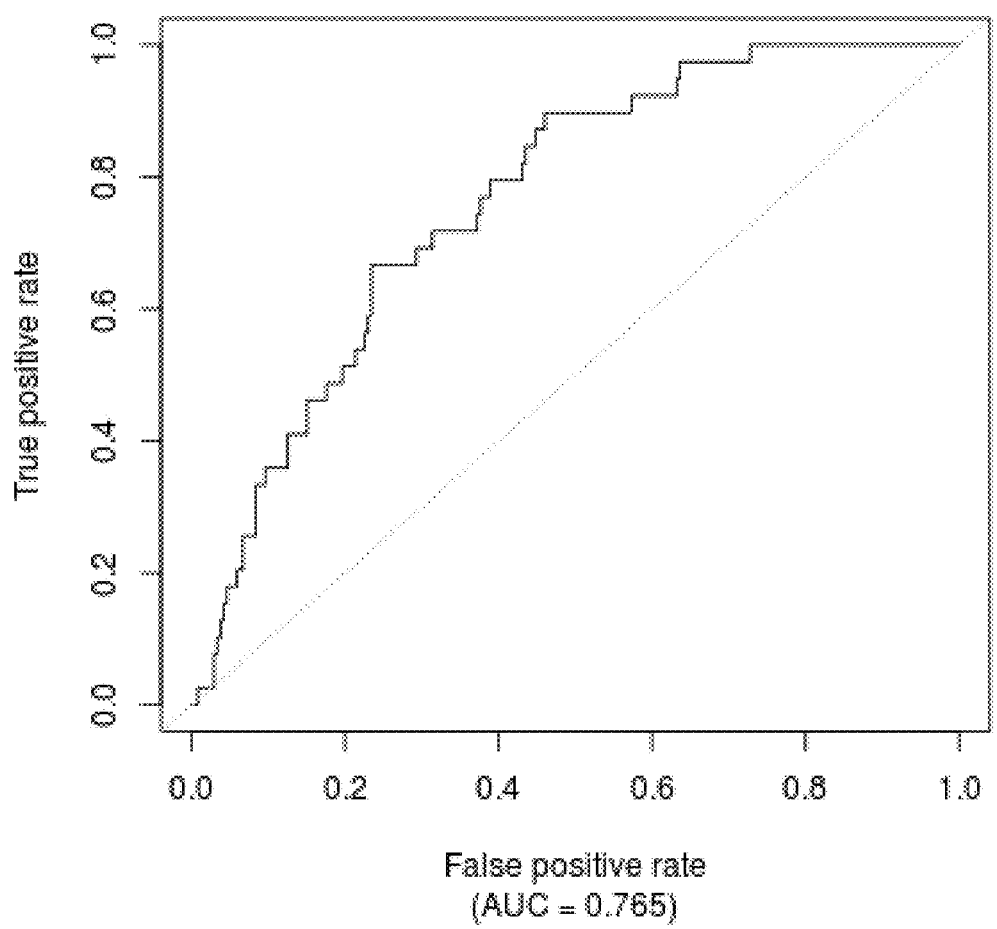
FIG. 31 shows receiver operating characteristic curve for the Prevencio prognostic panel FM96/04 (as described in Example 5) in the internal validation set (N=278) for prognosis of one year (0-365 day) composite cardiovascular death, myocardial infarct or stroke. The panel had an area under the curve (AUC) of 0.77.
Figure 32:
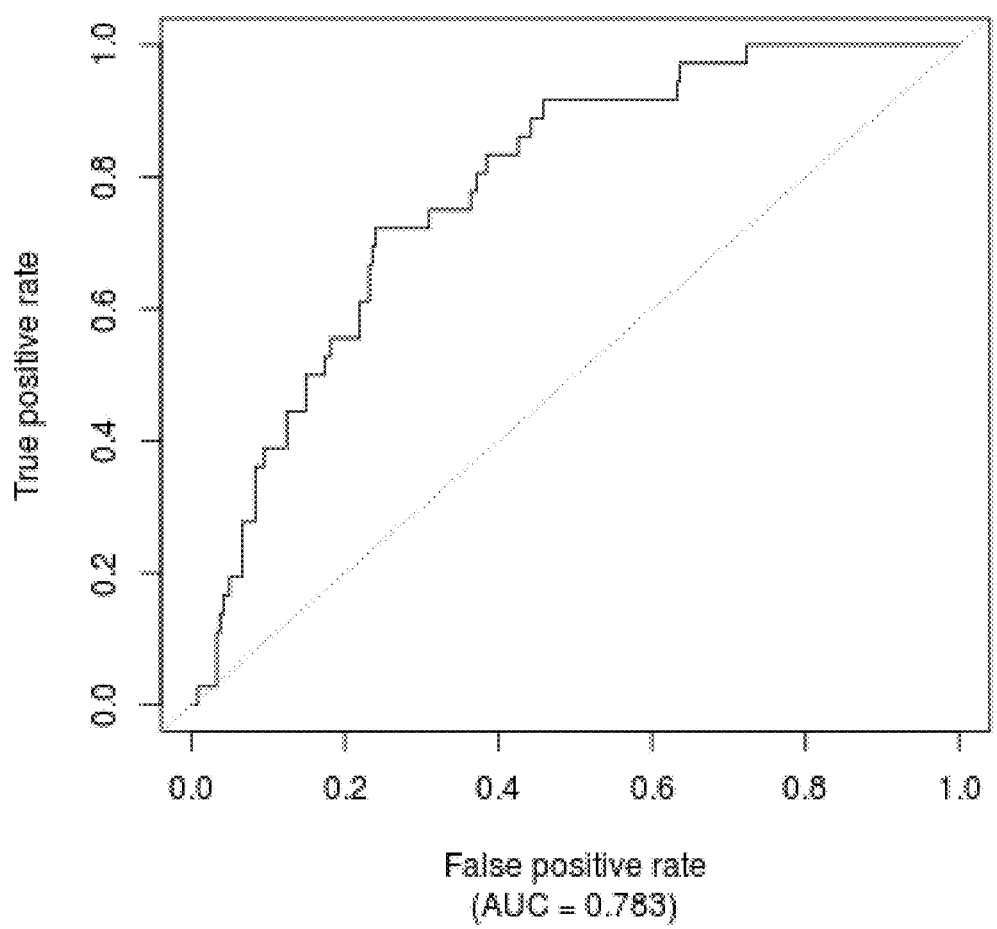
FIG. 32 shows receiver operating characteristic curve for the Prevencio prognostic panel FM190/33 in the internal validation set (N=278) for prognosis of one year (3-365 day) composite cardiovascular death, myocardial infarct or stroke. The panel had an area under the curve (AUC) of 0.78.

In certain specific embodiments, a panel, assay, or kit for the prognosis of a composite cardiovascular death, myocardial infarction or stroke comprises the biomarkers N terminal prohormone of brain natriuretic protein (NT-proBNP), osteopontin, and tissue inhibitor of metalloproteinases-1 (TIMP-1). In some embodiments, the time endpoint is defined as starting from sample draw (as described by panel FM96/04 in Table 25, Example 5, and FIG. 31). In other embodiments the time endpoint is defined as starting from three (3) days post sample draw. This combination of biomarkers is represented by panel FM 190/33 in Table 25 and FIG. 32.

Figure 33:
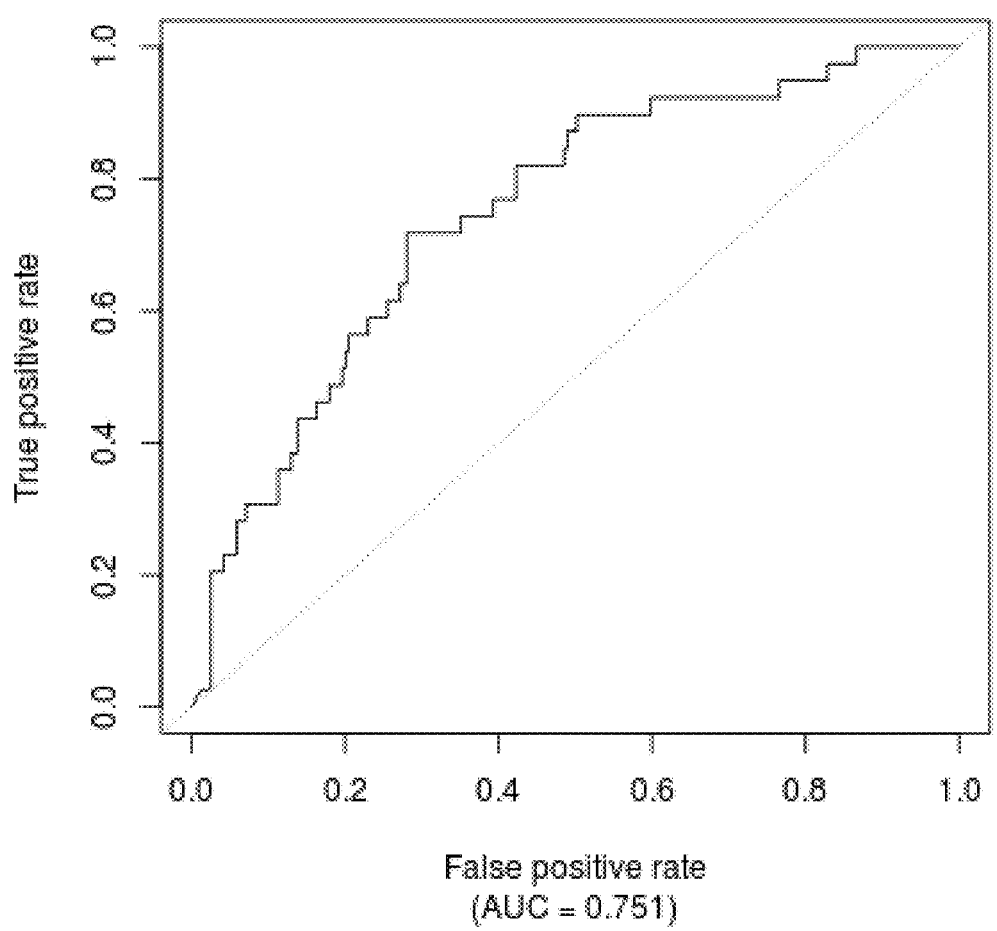
FIG. 33 shows receiver operating characteristic curve for the Prevencio prognostic panel FM98/03 in the internal validation set (N=278) for prognosis of one year (0-365 day) composite cardiovascular death, myocardial infarct or stroke. The panel had an area under the curve (AUC) of 0.75.

In another specific embodiment, a panel, assay, or kit for the prognosis of a composite cardiovascular death, myocardial infarction or stroke comprises at least NT-proBNP and osteopontin. In some embodiments, the time endpoint is defined as starting from sample draw. This combination of biomarkers is represented by panel FM98/03 in Table 25 and FIG. 33.

Embodiments of the present invention also provide panels, assays, and kits for the prognosis of a composite endpoint of all-cause death, myocardial infarction or stroke, where the panels comprise one or more biomarkers or antibodies, binding fragments thereof or other types of binding agents, which are specific for the biomarkers disclosed herein. Such panels, assays, and kits can be used, for example, for determining a prognosis of the risk of a composite endpoint of all-cause death, myocardial infarction or stroke, within a specified time in the subject, such as within one year, or within three years. In some embodiments, the time endpoint is defined as starting from sample draw. In other embodiments, the time endpoint is defined as starting from three (3) days post sample draw.

Figure 34:
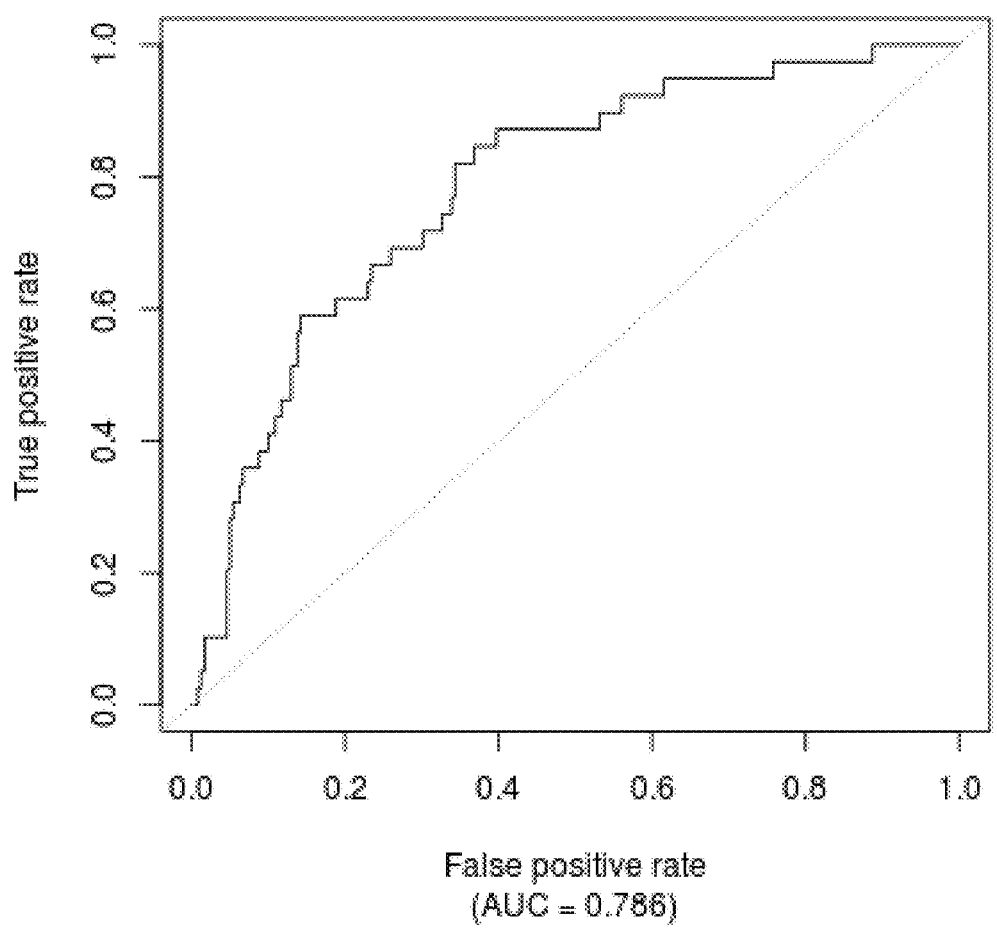
FIG. 34 shows receiver operating characteristic curve for the Prevencio prognostic panel FM209/02 in the internal validation set (N=278) for prognosis of one year (3-365 day) composite all-cause death, myocardial infarct or stroke. The panel had an area under the curve (AUC) of 0.79.

In certain specific embodiments, a panel, assay, or kit for the prognosis of a composite endpoint of all-cause death, myocardial infarction or stroke comprises biomarkers for kidney injury molecule-1, N terminal prohormone of brain natriuretic protein (NT-proBNP), osteopontin, and tissue inhibitor of metalloproteinases-1 (TIMP-1). In some embodiments, the time endpoint is defined as starting from three (3) days post sample draw. This combination of biomarkers is represented by panel FM209/02 in Table 25 and FIG. 34.

Figure 35:
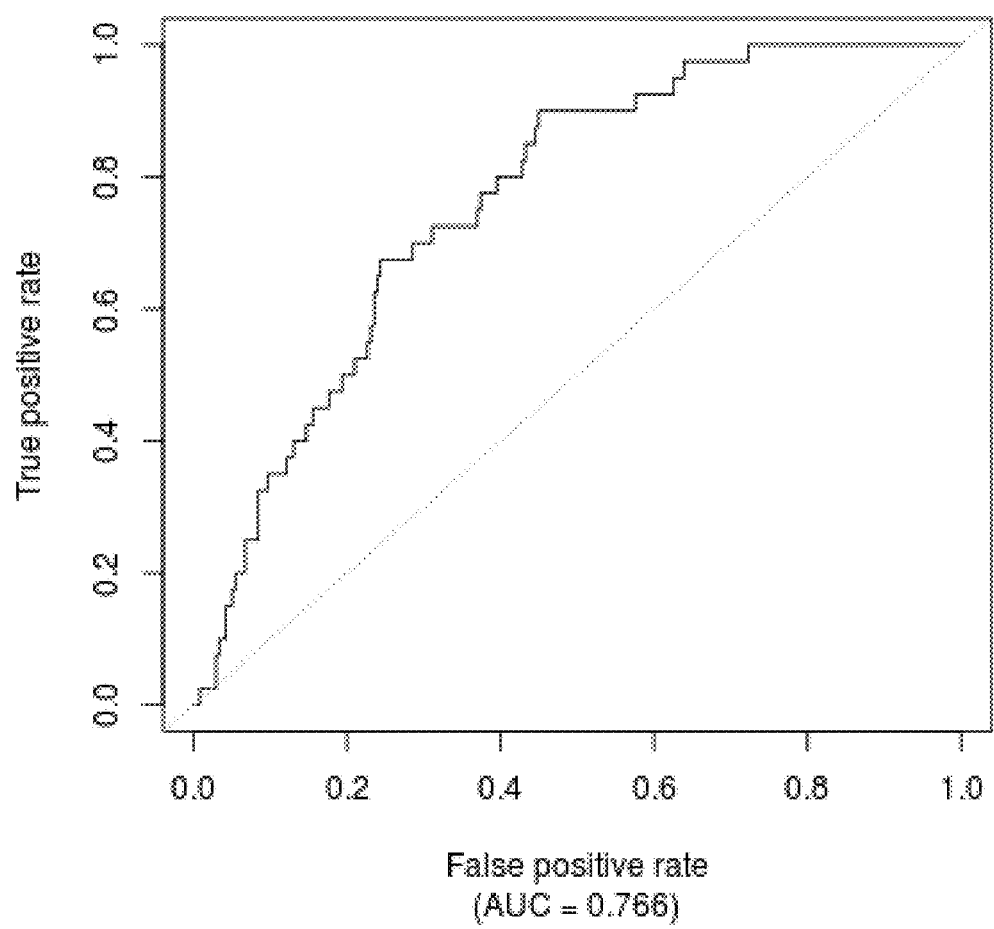
FIG. 35 shows receiver operating characteristic curve for the Prevencio prognostic panel FM111/05 in the internal validation set (N=278) for prognosis of one year (0-365 day) composite all-cause death, myocardial infarct or stroke. The panel had an area under the curve (AUC) of 0.77.
Figure 36:
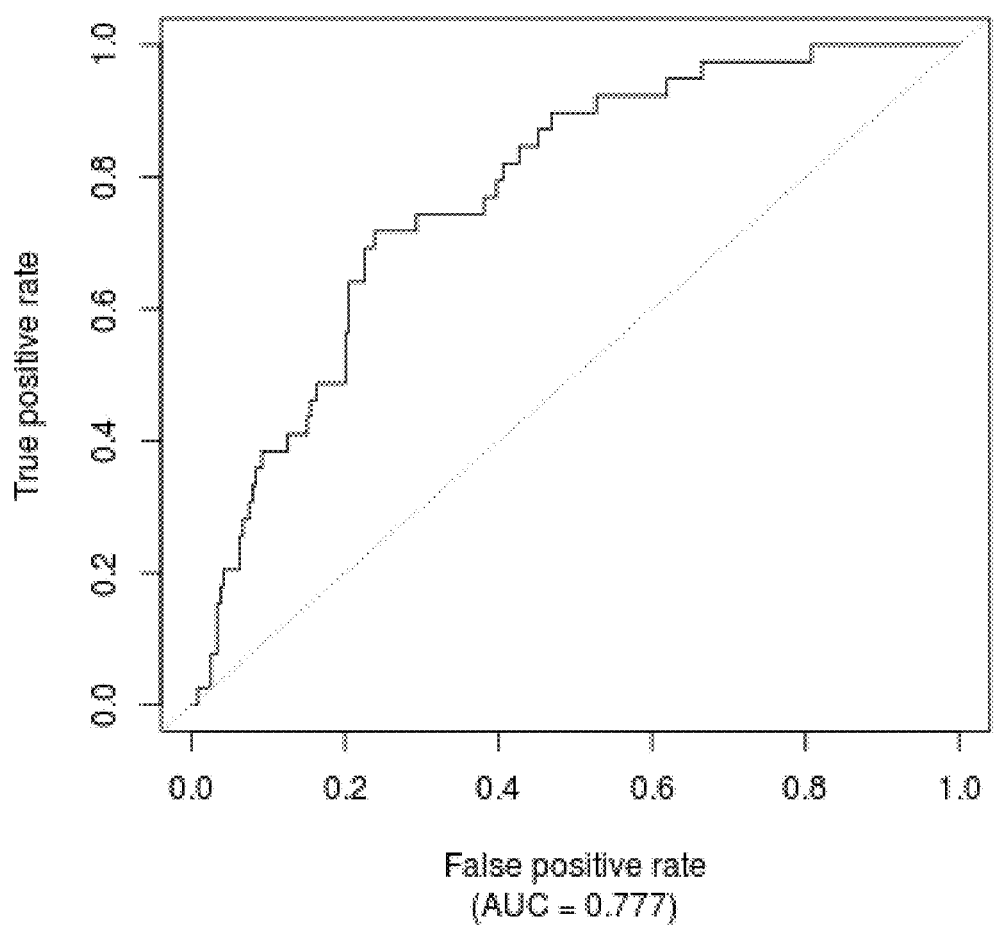
FIG. 36 shows receiver operating characteristic curve for the Prevencio prognostic panel FM210/03 in the internal validation set (N=278) for prognosis of one year (3-365 day) composite all-cause death, myocardial infarct or stroke. The panel had an area under the curve (AUC) of 0.78.

In one specific embodiment, a panel, assay, or kit for the prognosis of a composite endpoint of all-cause death, myocardial infarction or stroke comprises N terminal prohormone of brain natriuretic protein (NT-proBNP), osteopontin, and tissue inhibitor of metalloproteinases-1 (TIMP-1). In some embodiments, the time endpoint is defined as starting from sample draw. (As described by panel FM111/05 in Table 25 and FIG. 35). In other embodiments, the time endpoint is defined as starting from three (3) days post sample draw. This combination of biomarkers is represented by panel FM210/03 in Table 25 and FIG. 36.

Figure 37:
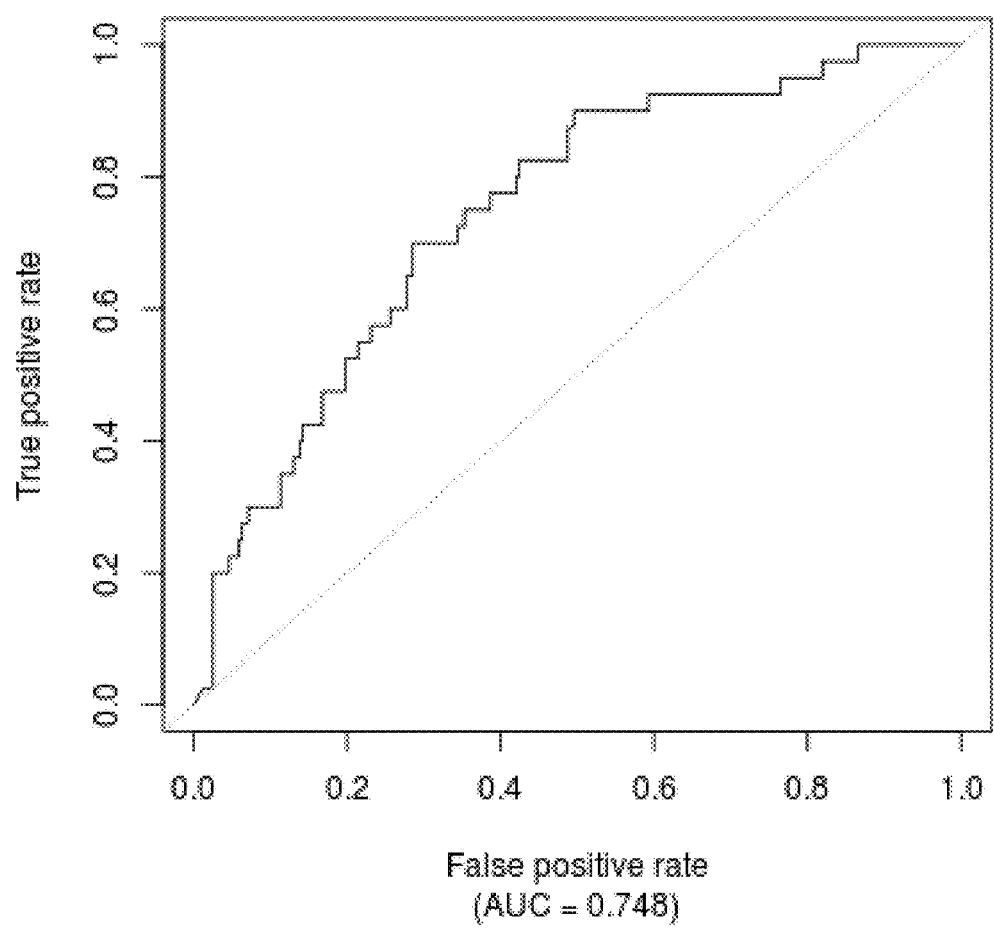
FIG. 37 shows receiver operating characteristic curve for the Prevencio prognostic panel FM110/04 in the internal validation set (N=278) for prognosis of one year (0-365 day) composite all-cause death, myocardial infarct or stroke. The panel had an area under the curve (AUC) of 0.75.

In another specific embodiment, a panel, assay, or kit for the prognosis of a composite endpoint of all-cause death, myocardial infarction or stroke comprises NT-proBNP and osteopontin. In some embodiments, the time endpoint is defined as starting from sample draw. This combination of biomarkers and clinical variables is represented by panel FM110/04 in Table 25 and FIG. 37.

Embodiments of the present invention also provide panels, assays, and kits for the prognosis of a composite endpoint of cardiovascular death or myocardial infarction, wherein the panels, assays, and kits comprise one or more biomarkers or antibodies, binding fragments thereof or other types of binding agents, which are specific for the biomarkers disclosed herein. Such panels, assays, and kits can be used, for example, for determining a prognosis of cardiovascular death or myocardial infarction within a specified time in the subject, such as within one year, or within three years. In some embodiments, the time endpoint is defined as starting from sample draw. In other embodiments, the time endpoint is defined as starting from three (3) days post sample draw.

Figure 38:
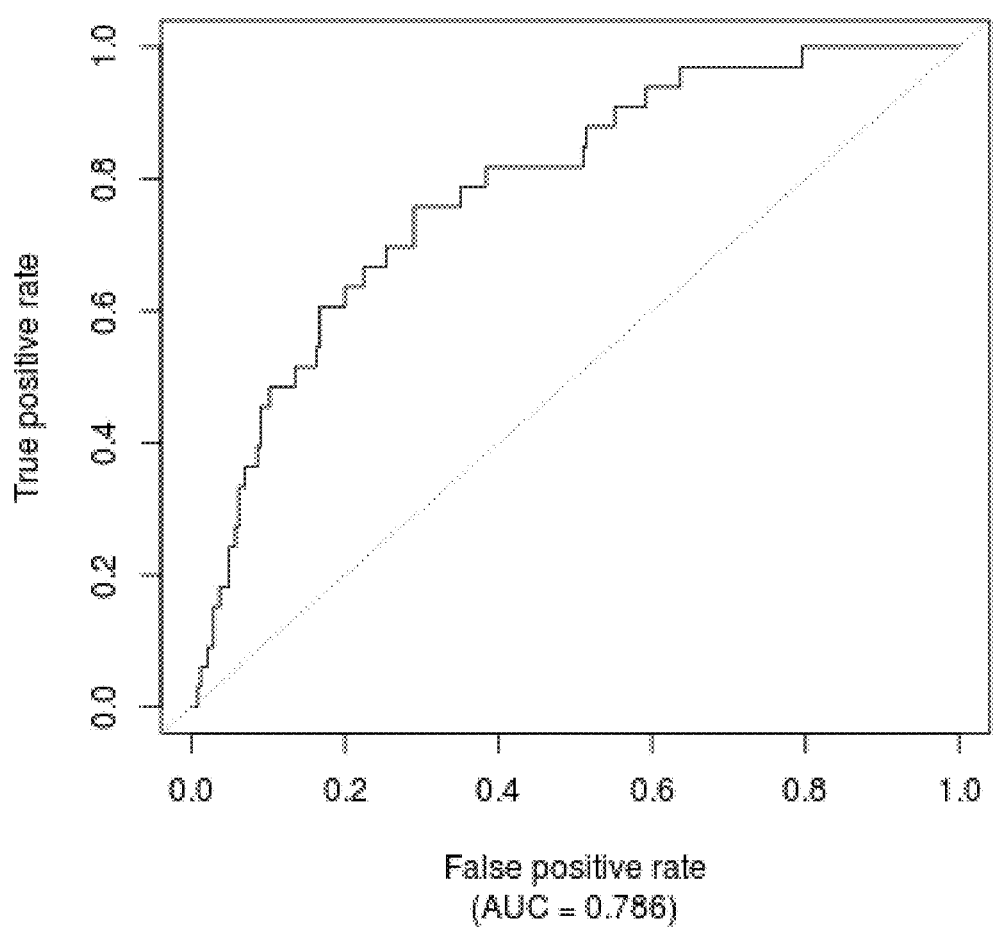
FIG. 38 shows receiver operating characteristic curve for the Prevencio prognostic panel FM211/03 in the internal validation set (N=278) for prognosis of one year (3-365 day) composite cardiovascular death or myocardial infarct. The panel had an area under the curve (AUC) of 0.79.

In certain specific embodiments, a panel, assay, or kit for the prognosis of a composite endpoint of cardiovascular death or myocardial infarction comprises biomarkers for apolipoprotein A-II, N terminal prohormone of brain natriuretic protein (NT-proBNP), and osteopontin. In some embodiments, the time endpoint is defined as starting from three (3) days post sample draw. This combination of biomarkers is represented by panel FM211/03 in Table 25 and FIG. 38.

Figure 39:
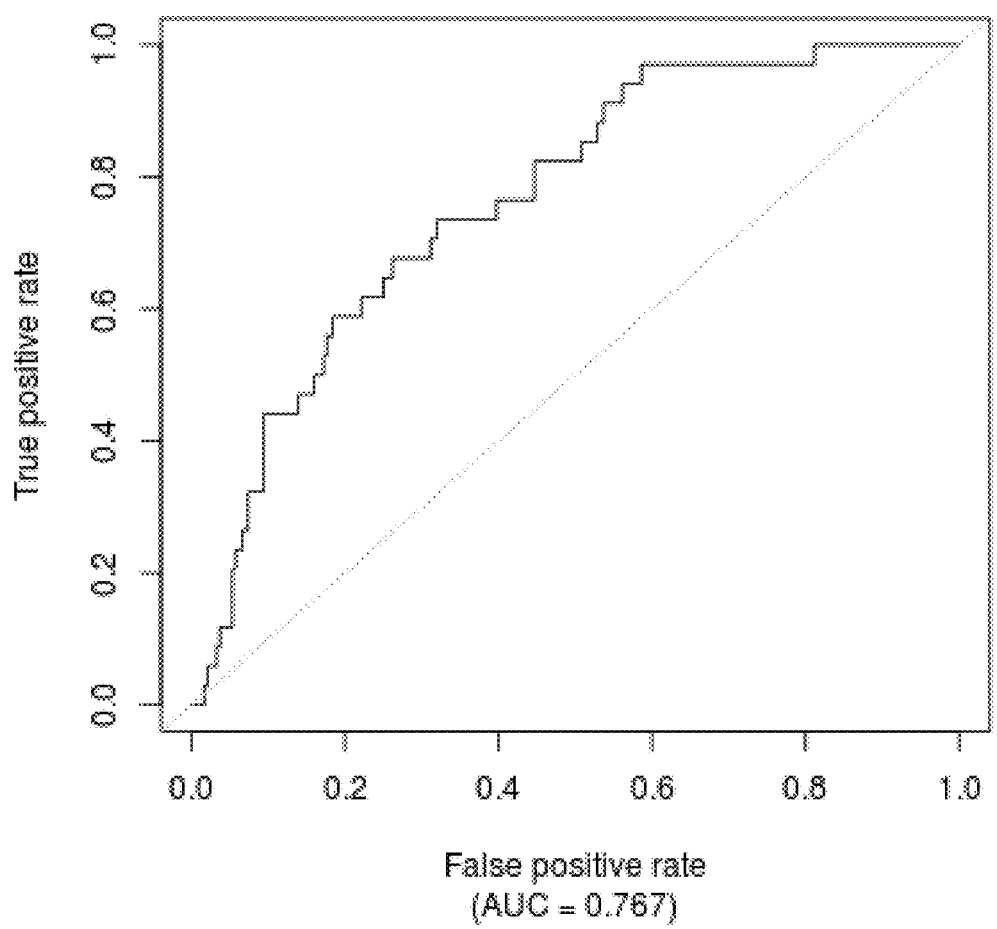
FIG. 39 shows receiver operating characteristic curve for the Prevencio prognostic panel FM77/26 in the internal validation set (N=278) for prognosis of one year (0-365 day) composite cardiovascular death or myocardial infarct. The panel had an area under the curve (AUC) of 0.77.
Figure 40:
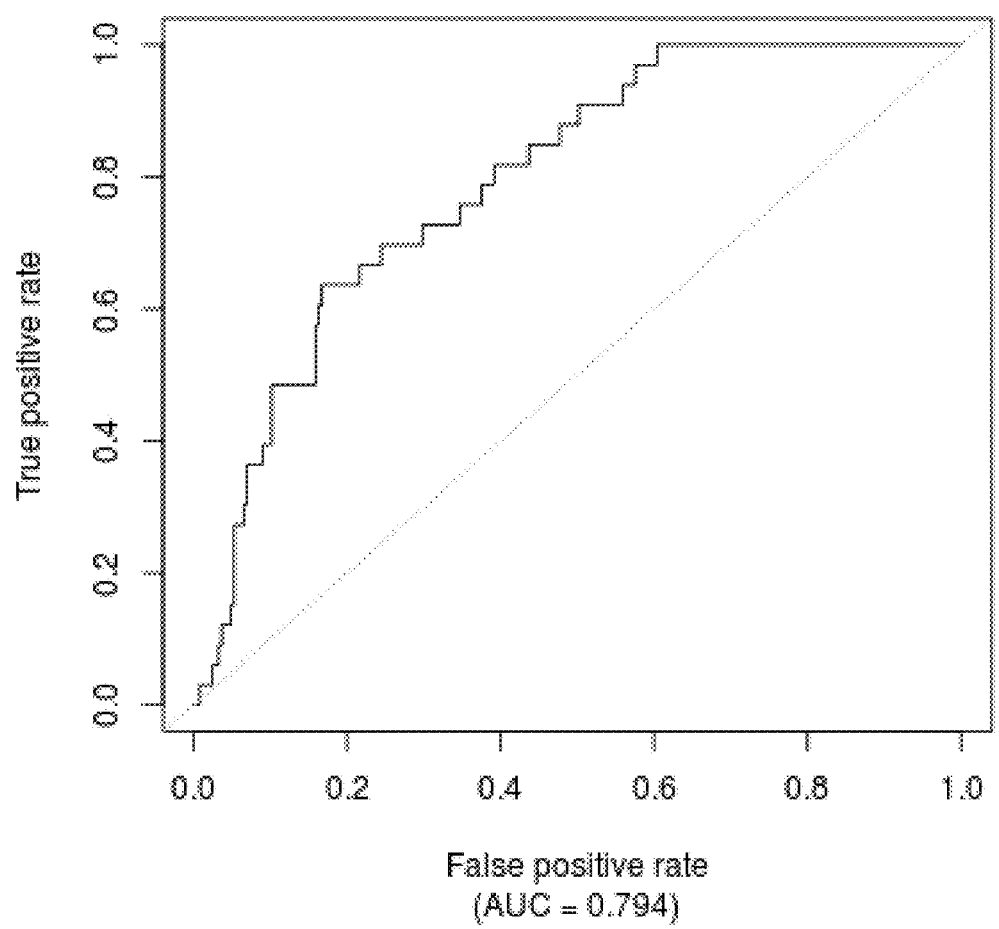
FIG. 40 shows receiver operating characteristic curve for the Prevencio prognostic panel FM212/02 in the internal validation set (N=278) for prognosis of one year (3-365 day) composite cardiovascular death or myocardial infarct. The panel had an area under the curve (AUC) of 0.79.

In other specific embodiments, a panel, assay, or kit for the prognosis of a composite endpoint of cardiovascular death or myocardial infarction comprises biomarkers for apolipoprotein A-II, midkine, N terminal prohormone of brain natriuretic protein (NT-proBNP), and osteopontin. In some embodiments, the time endpoint is defined as starting from sample draw (as described by panel FM77/26 in Table 25 and FIG. 39). In other embodiments, the time endpoint is defined as starting from three (3) days post sample draw. This combination of biomarkers is represented by panel FM212/02 in Table 25 and FIG. 40.

Embodiments of the present invention also provide panels, assays, and kits for the prognosis of myocardial infarct (MI), wherein the panels comprise one or more biomarkers or antibodies, binding fragments thereof or other types of binding agents, which are specific for the biomarkers disclosed herein. These can be used, for example, for determining a prognosis of risk of myocardial infarction within a specified time in the subject, such as within one year, or within three years. In some embodiments, the time endpoint is defined as starting from sample draw. In other embodiments, the time endpoint is defined as starting from three (3) days post sample draw.

Figure 41:
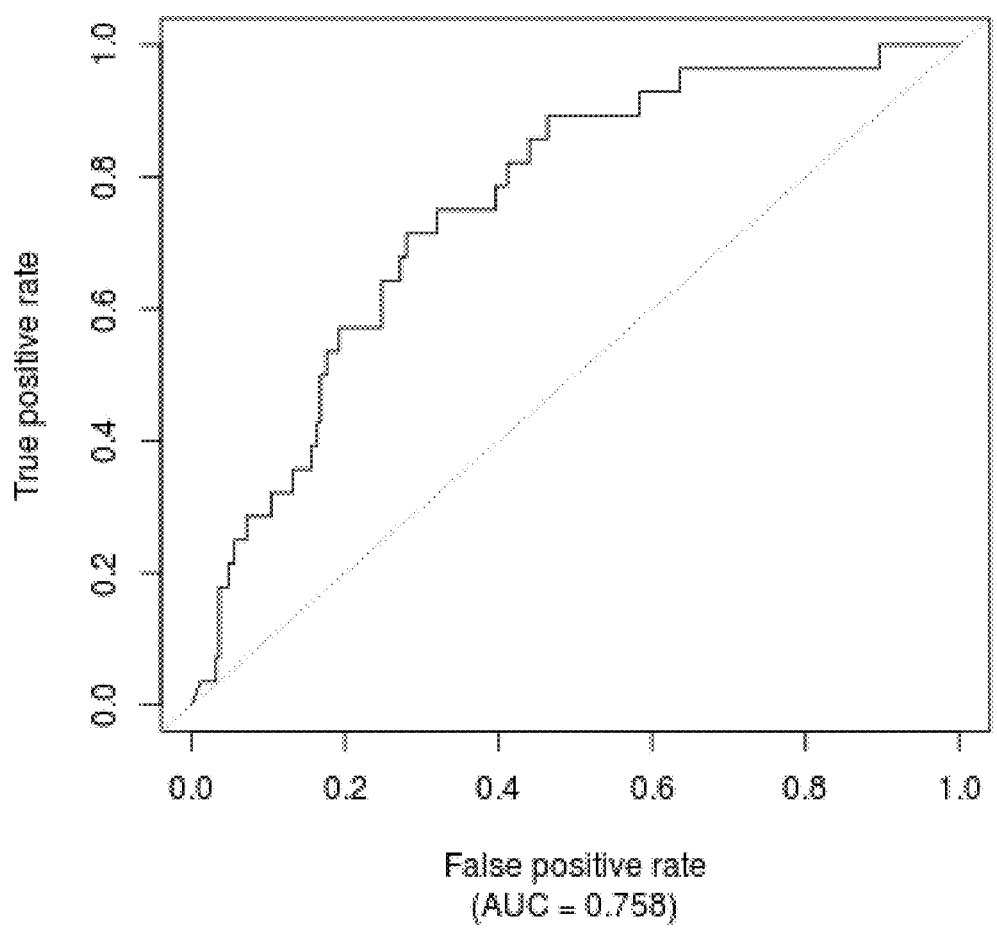
FIG. 41 shows receiver operating characteristic curve for the Prevencio prognostic panel FM201/MI002 in the internal validation set (N=278) for prognosis of one year (3-365 day) myocardial infarct. The panel had an area under the curve (AUC) of 0.76.

In certain specific embodiments, a panel, assay, or kit for the prognosis of myocardial infarct comprises biomarkers for N terminal prohormone of brain natriuretic protein (NT-proBNP) and osteopontin. In some embodiments, the time endpoint is defined as starting from three (3) days post sample draw. This combination of biomarkers is represented by panel FM201/MI002 in Table 25 and FIG. 41.

Figure 42:
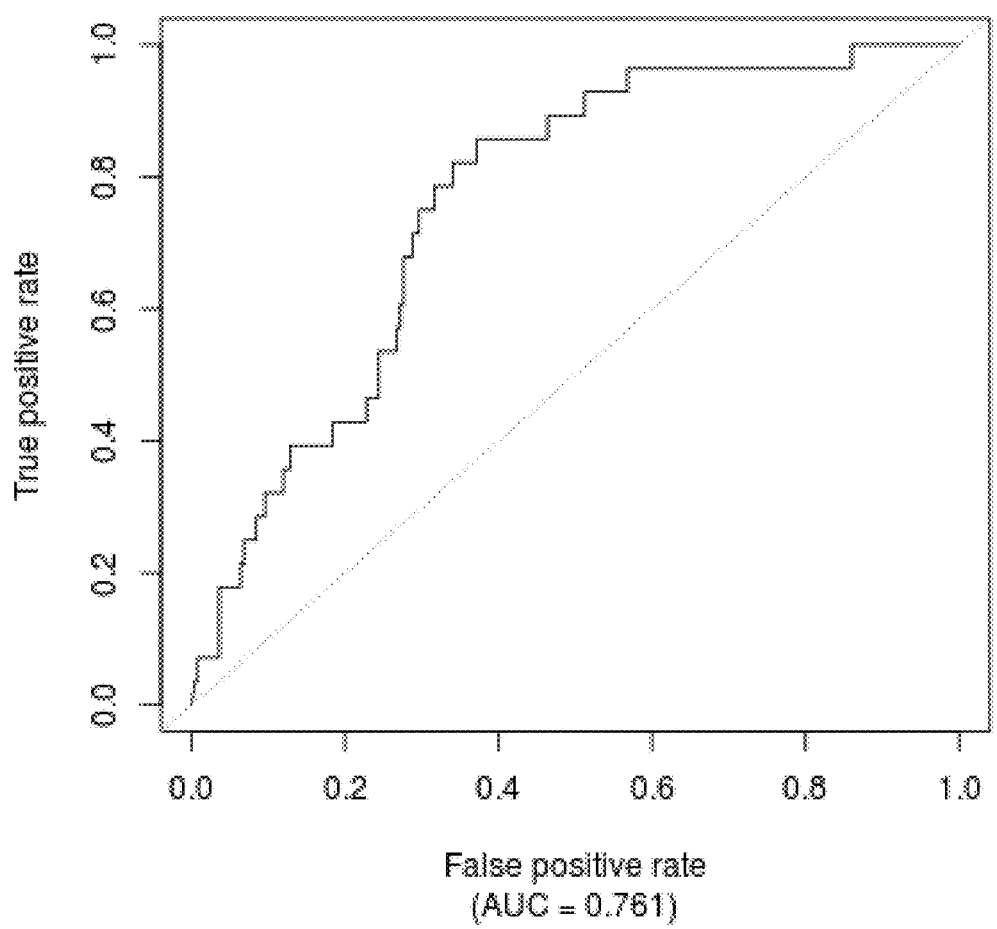
FIG. 42 shows receiver operating characteristic curve for the Prevencio prognostic panel FM204/MI003 in the internal validation set (N=278) for prognosis of one year (3-365 day) myocardial infarct. The panel had an area under the curve (AUC) of 0.76.

In certain specific embodiments, a panel, assay, or kit for the prognosis of myocardial infarct comprises biomarkers for N terminal prohormone of brain natriuretic protein (NT-proBNP), osteopontin, and vascular cell adhesion molecule. In some embodiments, the time endpoint is defined as starting from three (3) days post sample draw. This combination of biomarkers is represented by panel FM204/MI003 in Table 25 and FIG. 42.

Figure 43:
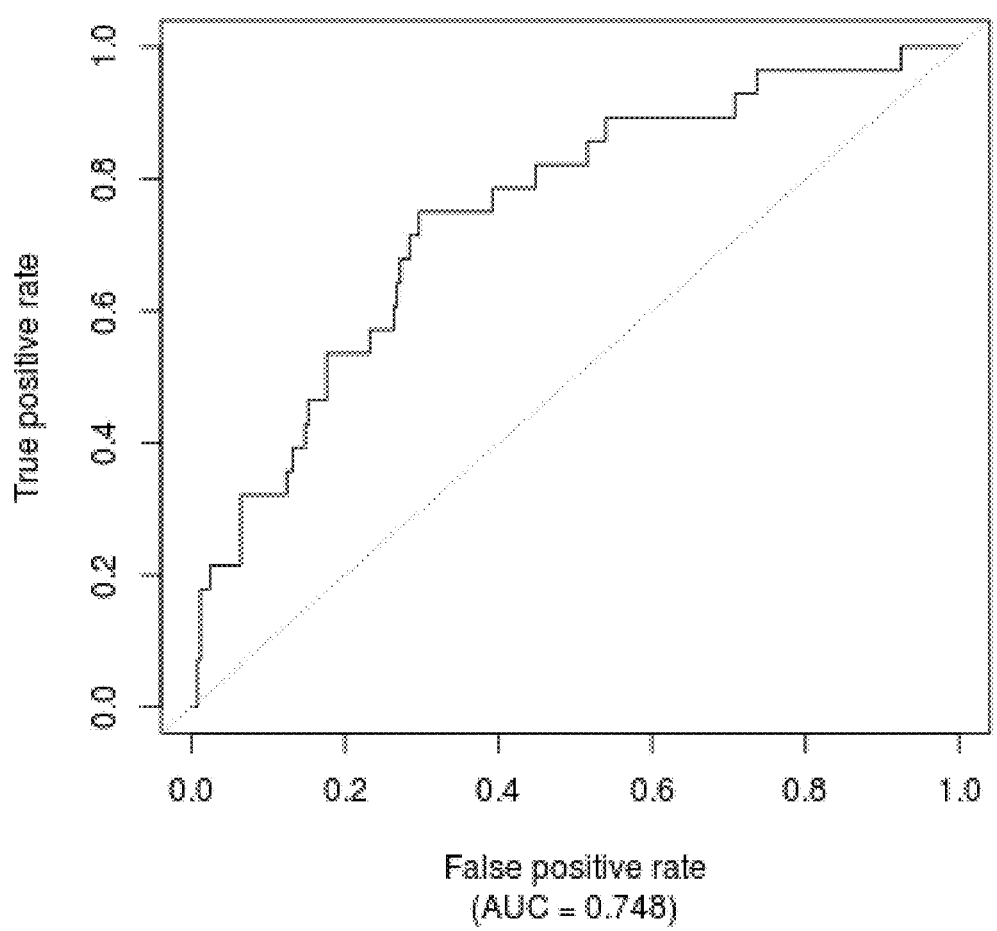
FIG. 43 shows receiver operating characteristic curve for the Prevencio prognostic panel FM202/MI005 in the internal validation set (N=278) for prognosis of one year (3-365 day) myocardial infarct. The panel had an area under the curve (AUC) of 0.75.

In certain specific embodiments, a panel, assay, or kit for the prognosis of myocardial infarct comprises biomarkers for kidney injury molecule-1, N terminal prohormone of brain natriuretic protein (NT-proBNP), and vascular cell adhesion molecule. In some embodiments, the time endpoint is defined as starting from three (3) days post sample draw. This combination of biomarkers is represented by panel FM202/MI005 in Table 25 and FIG. 43.

Figure 44:
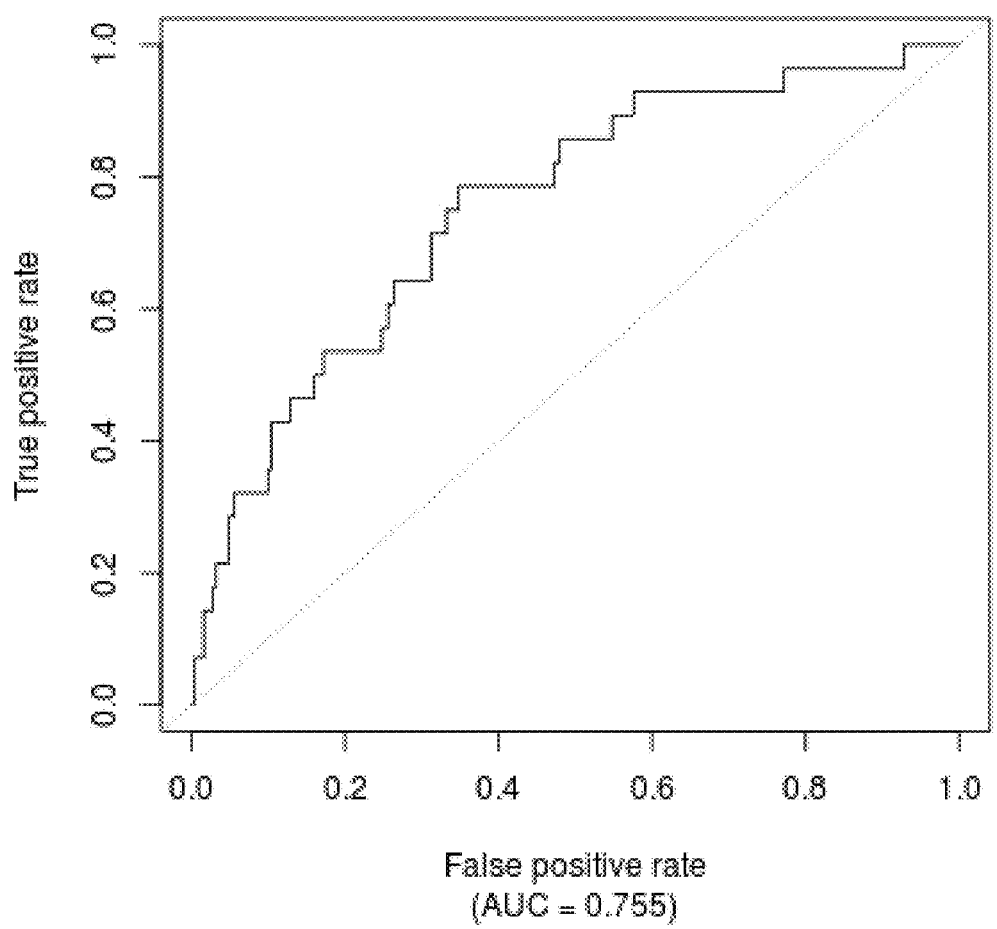
FIG. 44 shows receiver operating characteristic curve for the Prevencio prognostic panel FM205/MI007 in the internal validation set (N=278) for prognosis of one year (3-365 day) myocardial infarct. The panel had an area under the curve (AUC) of 0.75.

In certain specific embodiments, a panel, assay, or kit for the prognosis of myocardial infarct comprises biomarkers for kidney injury molecule-1, N terminal prohormone of brain natriuretic protein (NT-proBNP), and osteopontin. In some embodiments, the time endpoint is defined as starting from three (3) days post sample draw. This combination of biomarkers is represented by panel FM205/MI007 in Table 25 and FIG. 44.

Figure 45:
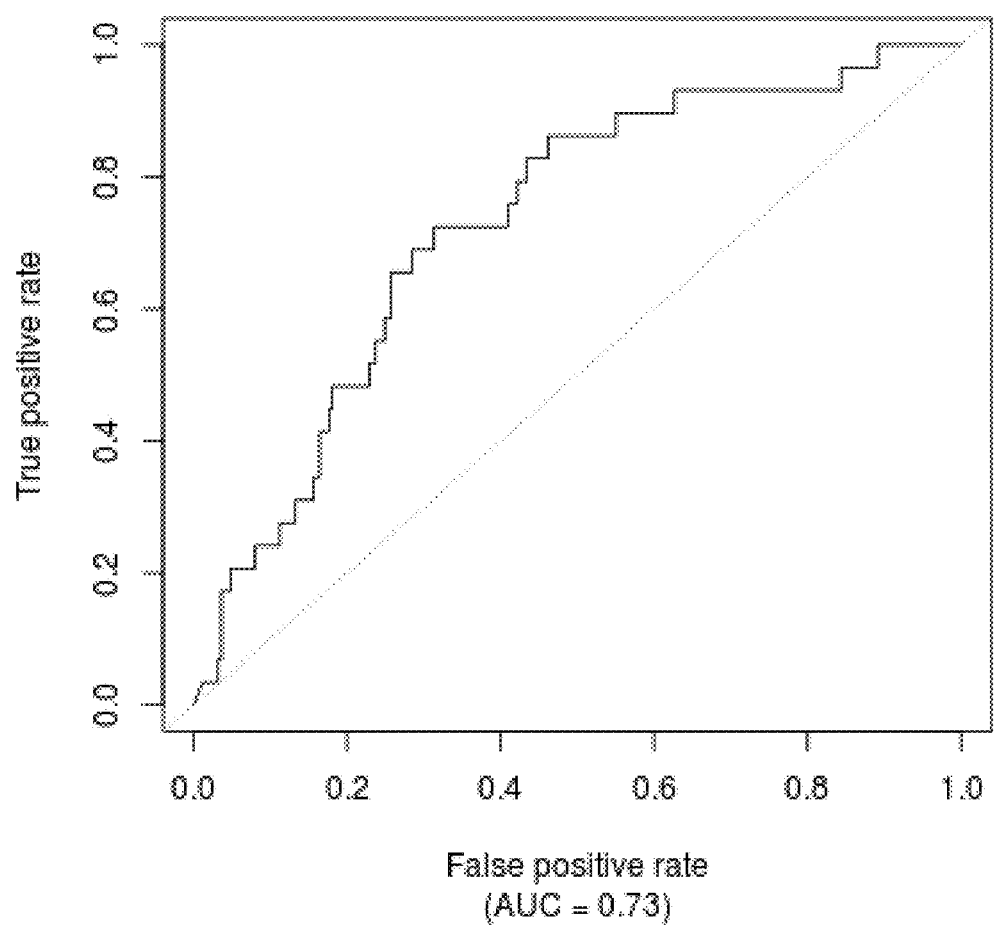
FIG. 45 shows receiver operating characteristic curve for the Prevencio prognostic panel FM63/64 in the internal validation set (N=278) for prognosis of one year (0-365 day) myocardial infarct. The panel had an area under the curve (AUC) of 0.73.

In certain specific embodiments, a panel, assay, or kit for the prognosis of myocardial infarct comprises biomarkers for N terminal prohormone of brain natriuretic protein (NT-proBNP), and. In some embodiments, the time endpoint is defined as starting from sample draw. This combination of biomarkers is represented by panel FM63/64 in Table 25 and FIG. 45.

Embodiments of the present invention further provide panels, assays, and kits for prognosis of cardiovascular death, wherein the panels comprise one or more biomarkers, or antibodies, binding fragments thereof or other types of binding agents, which are specific for the biomarkers disclosed herein. Such panels, assays, and kits can be used, for example, for determining a prognosis of cardiovascular death within a specified time in the subject, such as within one year, or within three years. In some embodiments, the time endpoint is defined as starting from sample draw. In other embodiments, the time endpoint is defined as starting from three (3) days post sample draw. In some embodiments, at least one clinical variable described herein is used in conjunction with the biomarker levels determined. In a specific embodiment, the clinical variable is history of diabetes mellitus type 2.

Figure 46:
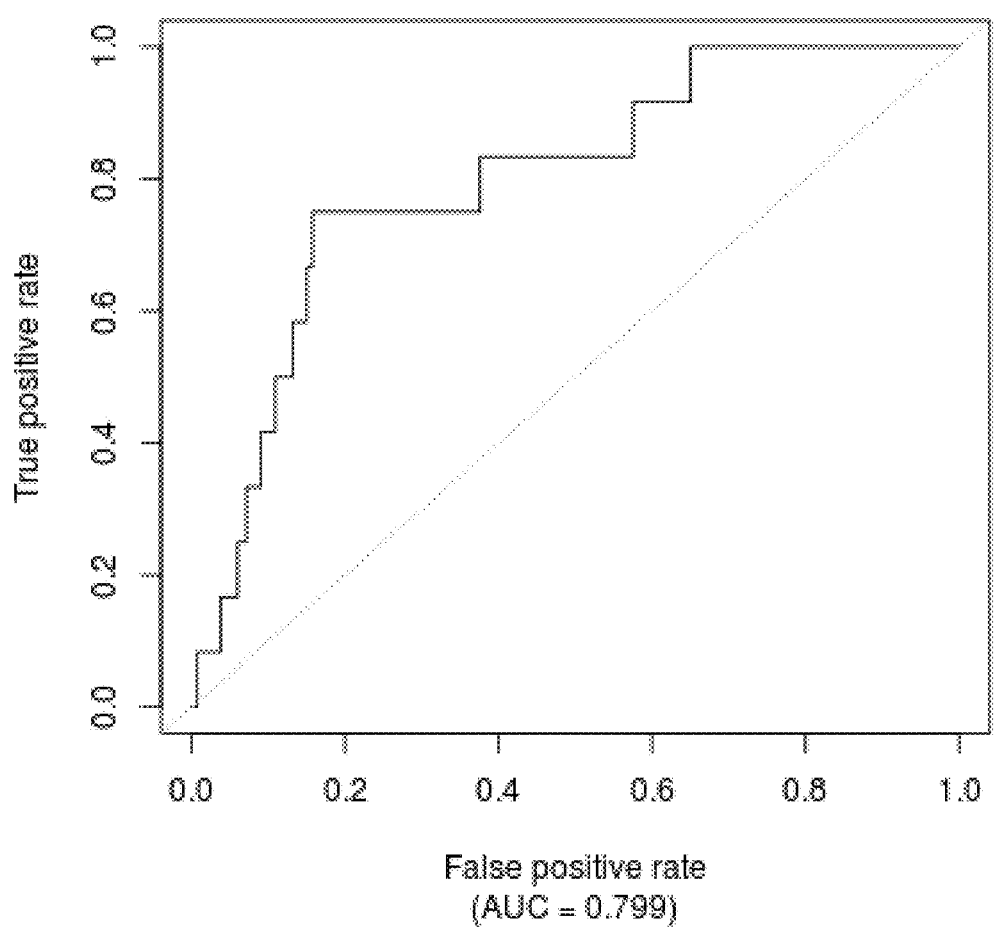
FIG. 46 shows receiver operating characteristic curve for the Prevencio prognostic panel FM52/244 in the internal validation set (N=278) for prognosis of one year (0-365 day) cardiovascular death. The panel had a robust area under the curve (AUC) of 0.80.
Figure 47:
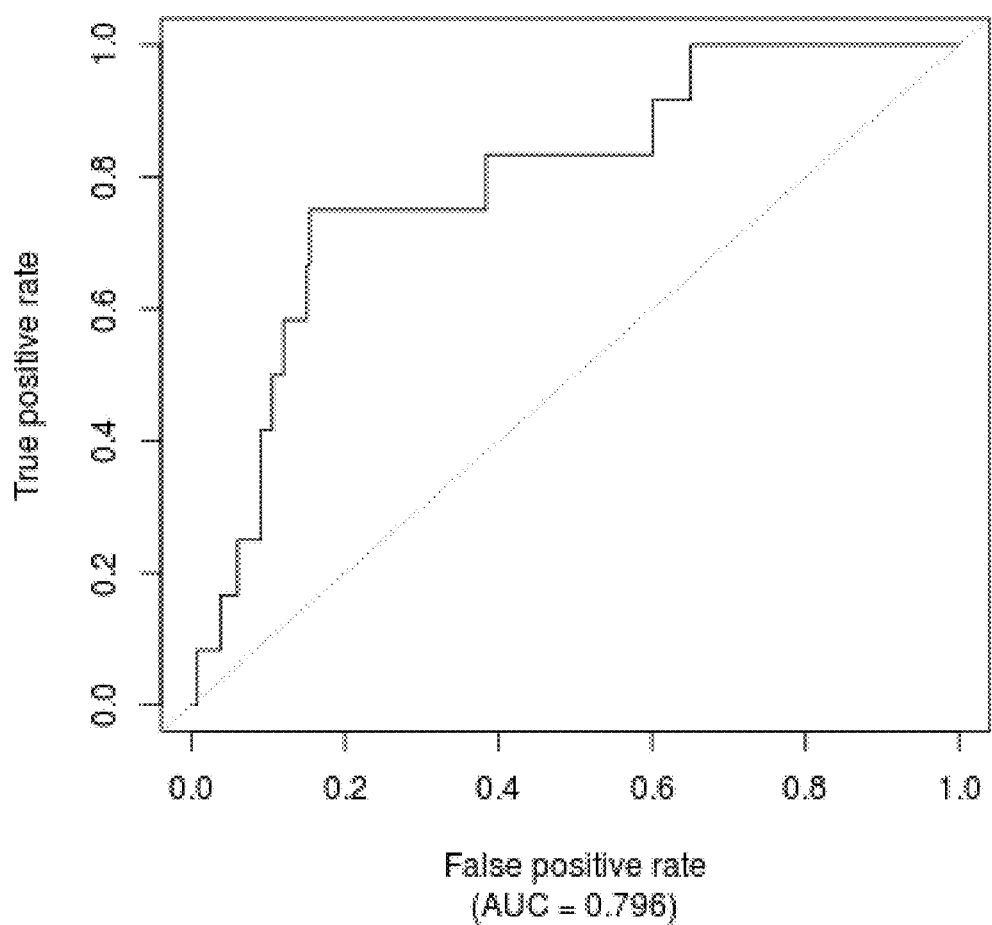
FIG. 47 shows receiver operating characteristic curve for the Prevencio prognostic panel FM194/CVD001 in the internal validation set (N=278) for prognosis of one year (3-365 day) cardiovascular death. The panel had a robust area under the curve (AUC) of 0.80.
Figure 48:
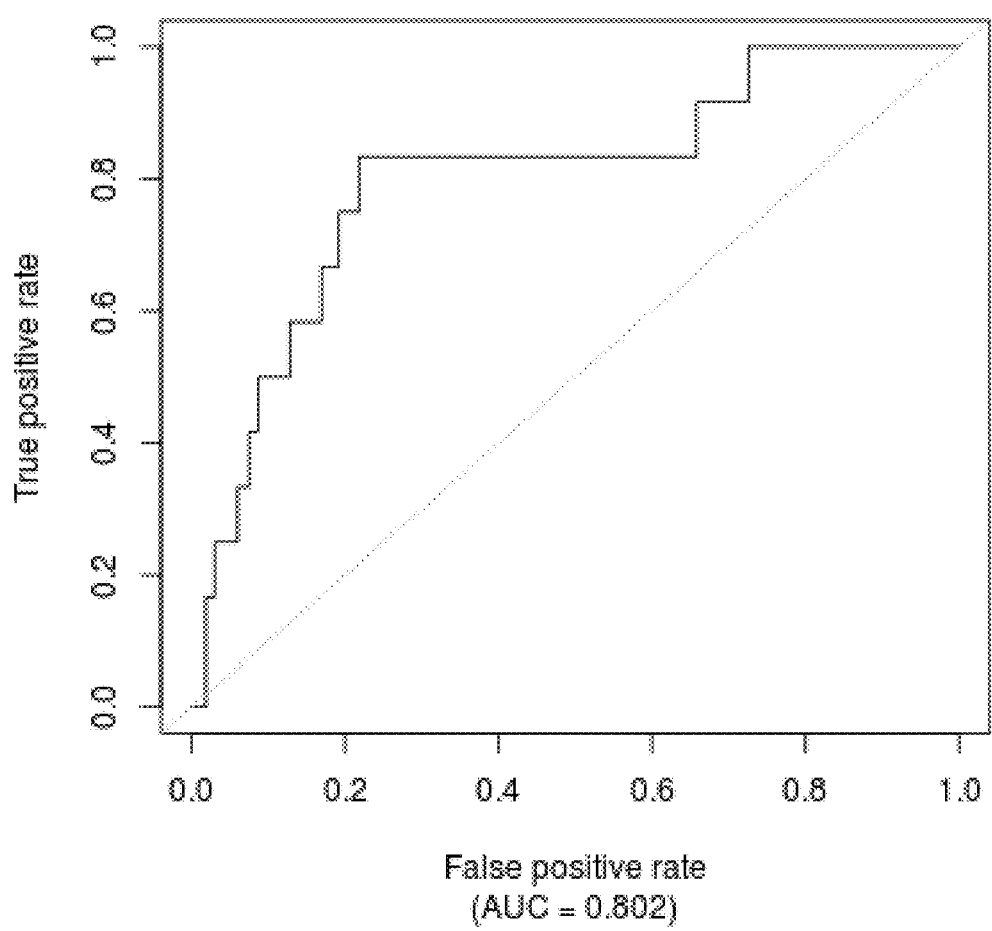
FIG. 48 shows receiver operating characteristic curve for the Prevencio prognostic panel FM193/R08 in the internal validation set (N=278) for prognosis of one year (3-365 day) cardiovascular death. The panel had a robust area under the curve (AUC) of 0.80.

In certain specific embodiments, a panel, assay, or kit for the prognosis of cardiovascular death comprises biomarkers for apolipoprotein A-II and osteopontin. In some embodiments, the time endpoint is defined as starting from sample draw. In some embodiments, the time endpoint is defined as starting from sample draw (as described by panel FM52/244 in Table 25 and FIG. 46). In some embodiments, the time endpoint is defined as starting from three (3) days post sample draw. This combination of biomarkers is represented by panel FM194/CVD001 in Table 25 and FIG. 47. In a specific embodiment, the time endpoint is defined as starting from three (3) days post sample draw and further comprises at clinical variable is history of diabetes mellitus type 2. This combination of biomarkers and clinical variables is represented by panel FM193/R08 in Table 25 and FIG. 48.

Figure 49:
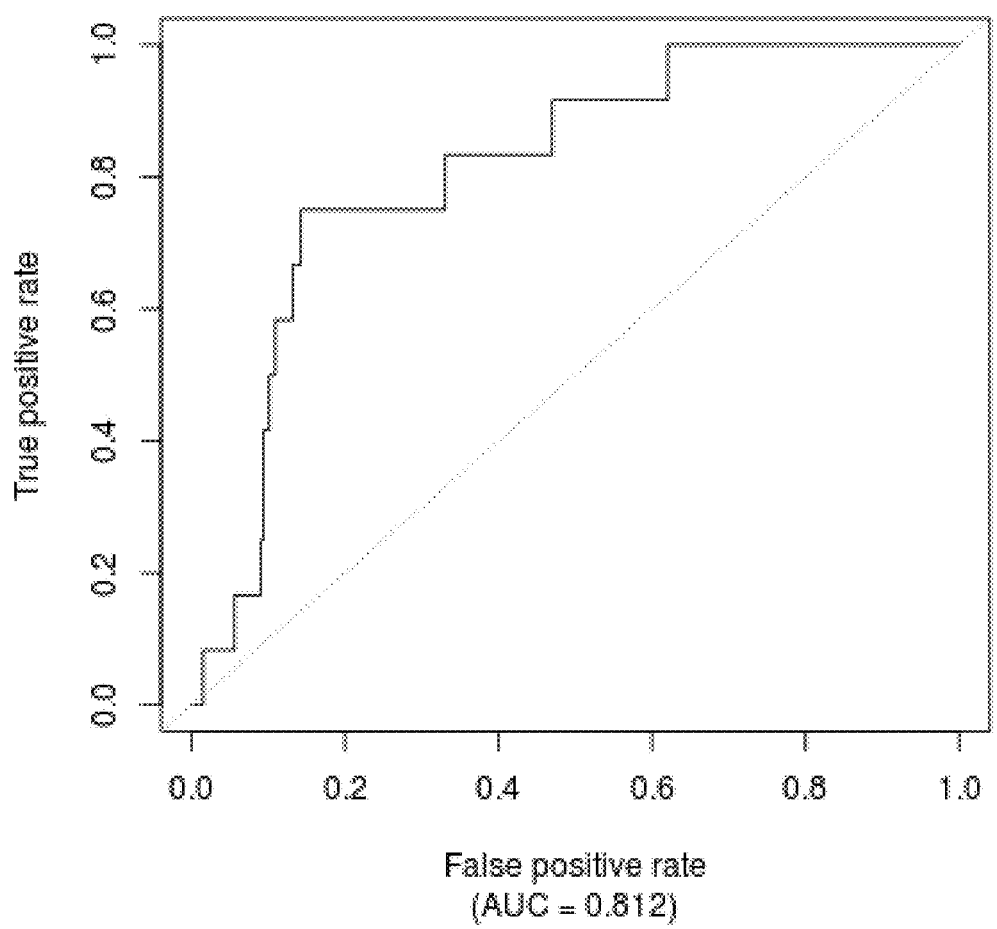
FIG. 49 shows receiver operating characteristic curve for the Prevencio prognostic panel FM53/237 in the internal validation set (N=278) for prognosis of one year (0-365 day) cardiovascular death. The panel had a robust area under the curve (AUC) of 0.81.
Figure 50:
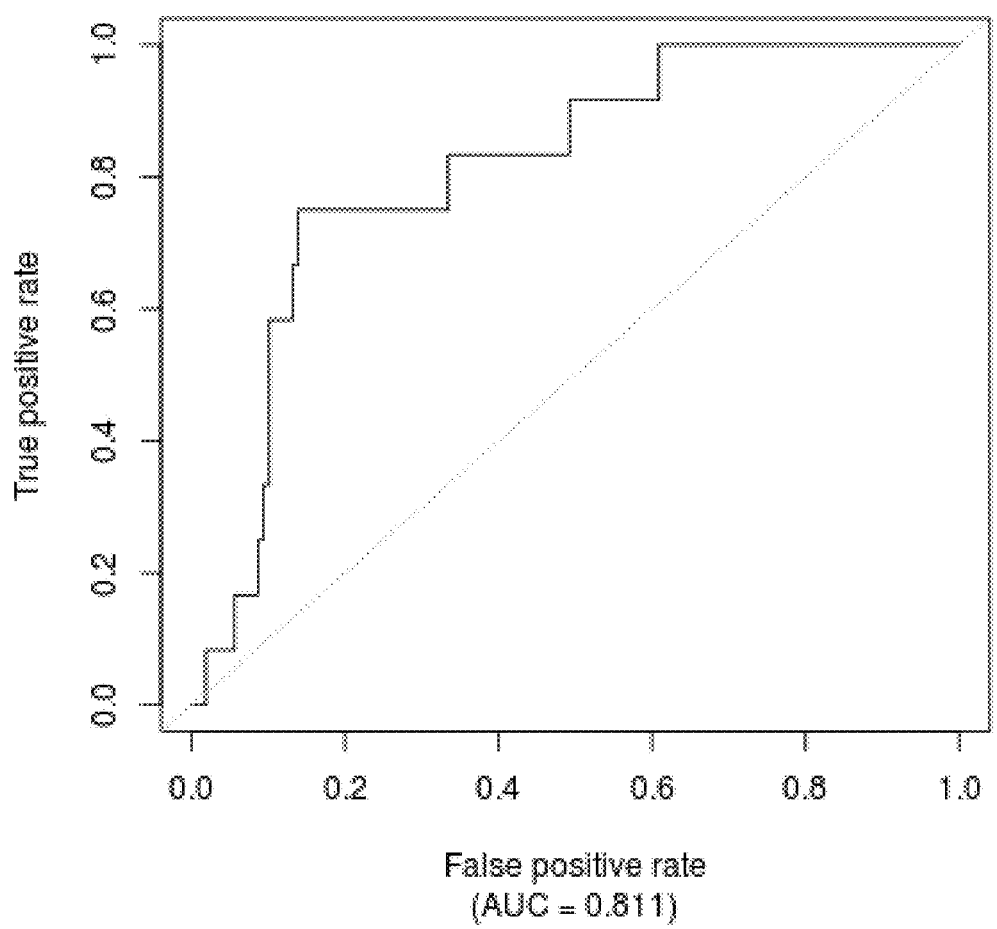
FIG. 50 shows receiver operating characteristic curve for the Prevencio prognostic panel FM195/CVD002 in the internal validation set (N=278) for prognosis of one year (3-365 day) cardiovascular death. The panel had a robust area under the curve (AUC) of 0.81.

In certain specific embodiments, a panel, assay, or kit for the prognosis of cardiovascular death comprises biomarkers for apolipoprotein A-II, midkine, and osteopontin. In some embodiments, the time endpoint is defined as starting from sample draw. This combination of biomarkers is represented by panel FM53/237 in Table 25 and FIG. 49. In some embodiments, the time endpoint is defined as starting from three (3) days post sample draw. This is represented by panel FM195/CVD002 in Table 25 and FIG. 50.

Figure 51:
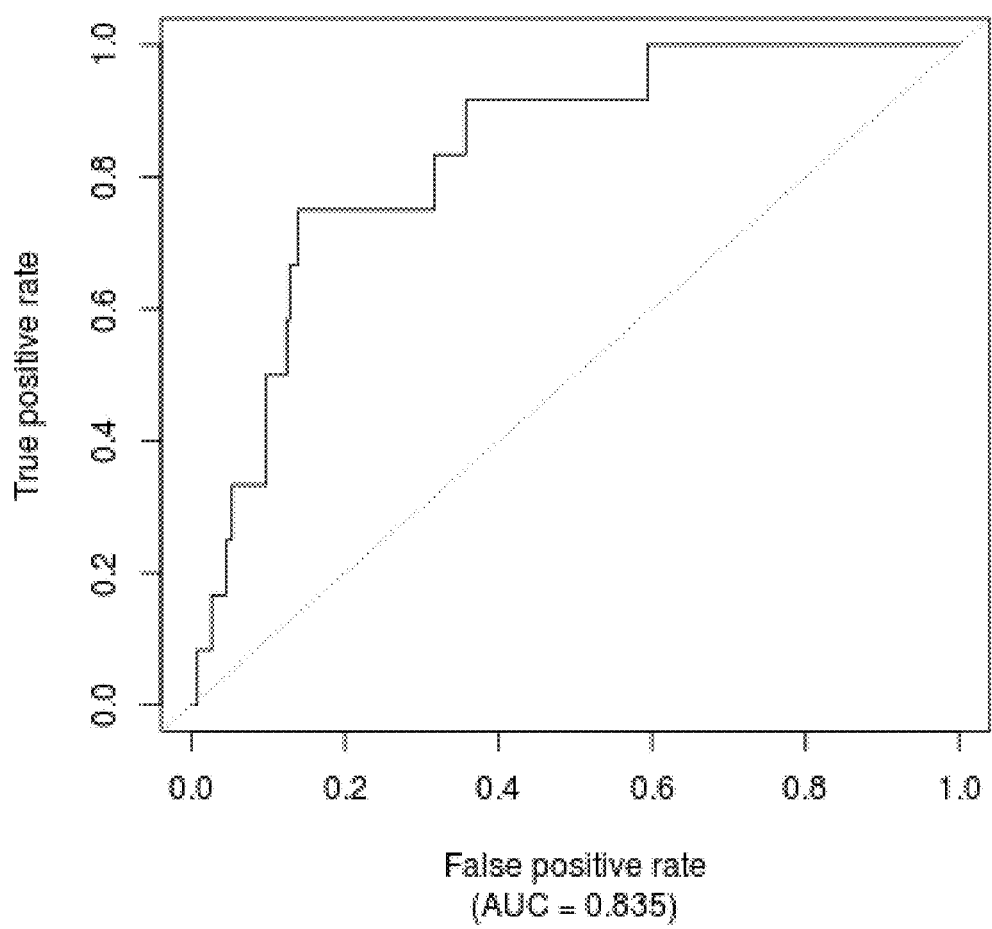
FIG. 51 shows receiver operating characteristic curve for the Prevencio prognostic panel FM207/04 in the internal validation set (N=278) for prognosis of one year (3-365 day) cardiovascular death. The panel had a robust area under the curve (AUC) of 0.83.

In certain specific embodiments, a panel, assay, or kit for the prognosis of cardiovascular death comprises biomarkers for apolipoprotein A-II, N terminal prohormone of brain natriuretic protein (NT-proBNP), osteopontin, and tissue inhibitor of metalloproteinases-1. In some embodiments, the time endpoint is defined as starting from three (3) days post sample draw. This combination of biomarkers is represented by panel FM207/R04 in Table 25 and FIG. 51.

Figure 52:
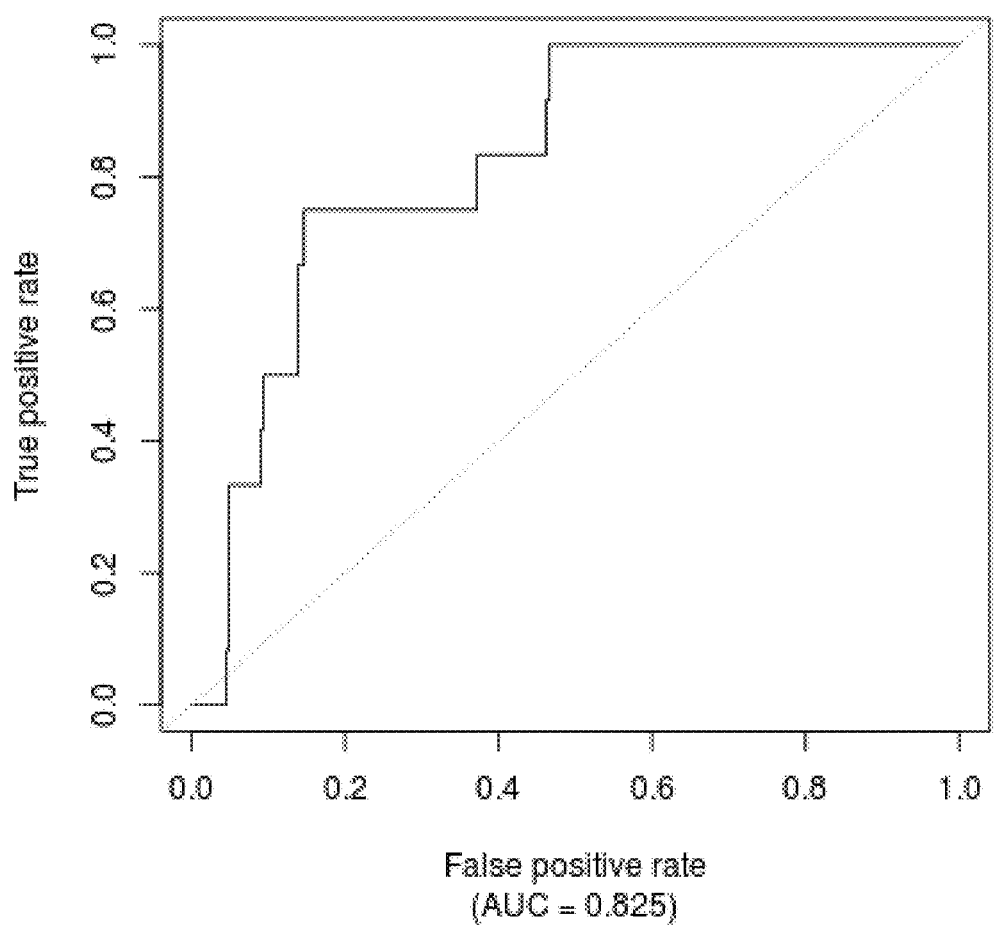
FIG. 52 shows receiver operating characteristic curve for the Prevencio prognostic panel FM208/R05 in the internal validation set (N=278) for prognosis of one year (3-365 day) cardiovascular death. The panel had a robust area under the curve (AUC) of 0.82.

In certain specific embodiments, a panel, assay, or kit for the prognosis of cardiovascular death comprises biomarkers for N terminal prohormone of brain natriuretic protein (NT-proBNP), osteopontin, and tissue inhibitor of metalloproteinases-1. In some embodiments, the time endpoint is defined as starting from three (3) days post sample draw. This combination of biomarkers is represented by panel FM208/R05 in Table 25 and FIG. 52.

In certain embodiments, a panel, assay, or kit comprises at least 1, at least 2, at least 3, at least 4 or greater than 4 antibodies or binding fragments thereof, or other types of binding agents, where the antibodies, binding fragments or other binding agents are specific for a biomarker of Table 1A, 1B, 2A, and 2B.

It will be understood that the panels, assays, and kits of the present disclosure may further comprise virtually any other compounds, compositions, components, instructions, or the like, that may be necessary or desired in facilitating a determination of a diagnosis or prognosis according to the present disclosure. These may include instructions for using the panel, assay, or kit, instructions for making a diagnostic or prognostic determination (e.g., by calculating a diagnostic or prognostic score), instructions or other recommendations for a medical practitioner in relation to preferred or desired modes of therapeutic or diagnostic intervention in the subject in light of the diagnostic or prognostic determination, and the like.

In some embodiments, the panels, assays, and kits of the invention will facilitate detection of the biomarkers discussed herein. Means for measuring such blood, plasma and/or serum levels are known in the art, and include, for example, the use of an immunoassay. Standard techniques that may be used, for example, include enzyme-linked immunosorbent assay ("ELISA") or Western blot.

In addition to the methods described above, any method known in the art for quantitatively measuring levels of protein in a sample, e.g., non-antibody-based methods, can be used in the methods and kits of the invention. For example, mass spectrometry-based (such as, for example, Multiple Reaction Monitoring (MRM) mass spectrometry) or HPLC-based methods can be used. Methods of protein quantification are described in, for example, Ling-Na Zheng et al., 2011, J. of Analytical Atomic Spectrometry, 26, 1233-1236; Vaudel, M., et al., 2010, Proteomics, Vol. 10: 4; Pan, S., 2009 J. Proteome Research, February; 8(2):787-97; Westermeier and Marouga, 2005, Bioscience Reports, Vol. 25, Nos. 1/2; Carr and Anderson, 2008, Clinical Chemistry. 54:1749-1752; and Aebersold and Mann, 2003, Nature, Vol. 422.

Additionally, technologies such as those used in the field of proteomics and other areas may also be embodied in methods, kits and other aspects of the invention. Such technologies include, for example, the use of micro- and nano-fluidic chips, biosensors and other technologies as described, for example, in United States Patent Application Nos. US2008/0202927; US2014/0256573; US2016/0153980; WO2016/001795; US2008/0185295; US2010/0047901; US2010/0231242; US2011/0154648; US2013/0306491; US2010/0329929; US2013/0261009; Sorger, 2008, Nature Biotechnol. 26:1345-1346; Li et al., 2002, Mol. Cell. Proteomics 1.2:157; Hou et al., 2006, J. Proteome Res. 5(10):2754-2759; Li et al., 2001, Proteomics 1(8):975-986; Ramsey et al., 2003, Anal. Chem. 75(15):3758-3764; Armenta et al., 2009, Electrophoresis 30(7): 1145-1156; Lynch et al., 2004, Proteomics 4(6):1695-1702; Kingsmore et al., 2003, Curr. Opin. Biotechnol. 14(1):74-81).

EXAMPLES

Example 1: A Clinical and Biomarker Scoring System to Diagnose Obstructive Coronary Artery Disease (CAD), Panel FM139/685

A convenience sample of 1251 patients undergoing coronary and/or peripheral angiography with or without intervention between 2008 and 2011 were prospectively enrolled. Patients who received only a peripheral angiography or no catherization procedure at all were excluded from this analysis (N=244). Additionally, a chronological subset of the final 153 patients who had received either a coronary or peripheral cath were withheld from this analysis, for their potential use in further validation of these models. Patients were referred for these procedures for numerous reasons; this includes angiography following acute processes such as myocardial infarction (MI), unstable angina pectoris, and heart failure (HF), but also for non-acute processes, such as for diagnostic evaluation of stable chest pain, failed stress testing, or pre-operatively prior to heart valve surgery.

After informed consent was obtained, detailed clinical and historical variables and reason for referral for angiography were recorded at the time of the procedure. Results of coronary angiography were also recorded with highest percent stenosis within each major coronary arteries or their branches. For the purposes of this analysis, significant coronary stenosis was characterized as ≥70% luminal obstruction.

Medical record review from time of enrollment to end of follow up was undertaken. For identification of clinical end points, review of medical records as well as phone follow up with patients and/or managing physicians was performed. The Social Security Death Index and/or postings of death announcements were used to confirm vital status. The following clinical end events were identified, adjudicated, and recorded by study investigators: death, non-fatal MI, HF, stroke, transient ischemic attack, peripheral arterial complication and cardiac arrhythmia. For any recurring events, each discrete event was recorded. Additionally, deaths were adjudicated for presence/absence of a cardiovascular cause.

Fifteen (15) mL of blood was obtained immediately before and immediately after the angiographic procedure through a centrally-placed vascular access sheath. The blood was immediately centrifuged for 15 minutes, serum and plasma aliquoted on ice and frozen at −80° C. until biomarker measurement. Only the blood obtained immediately before the procedure was used for this analysis.

After a single freeze-thaw cycle, 200 ul of plasma was analyzed for more than 100 protein biomarkers on a Luminex 100/200 xMAP technology platform. This technology utilizes multiplexed, microsphere-based assays in a single reaction vessel. It combines optical classification schemes, biochemical assays, flow cytometry and advanced digital signal processing hardware and software. Multiplexing is accomplished by assigning each protein-specific assay a microsphere set labeled with a unique fluorescence signature. An assay-specific capture antibody is conjugated covalently to each unique set of microspheres. The assay-specific capture antibody on each microsphere binds the protein of interest. A cocktail of assay-specific, biotinylated detecting antibodies is reacted with the microsphere mixture, followed by a streptavidin-labeled fluorescent "reporter" molecule. Similar to a flow cytometer, as each individual microsphere passes through a series of excitation beams, it is analyzed for size, encoded fluorescence signature and the amount of fluorescence generated is proportionate to the protein level. A minimum of 100 individual microspheres from each unique set are analyzed and the median value of the protein-specific fluorescence is logged. Using internal controls of known quantity, sensitive and quantitative results are achieved with precision enhanced by the analysis of 100 microspheres per data point.

The patients selected for analysis consisted of the chronologically initial 927 patients who received a coronary angiogram. These include patients who may have also received a peripheral angiogram concomitantly.

The 927 patients selected for analysis were randomly split into a training set (70%, or N=649) and a holdout validation set (30%, or N=278). Baseline clinical characteristics and protein concentrations between those with and without ≥70% coronary stenosis in at least one major epicardial coronary artery were compared (Tables 1A, 3A, 5, and 6); dichotomous variables were compared using two-sided Fishers exact test, while continuous variables were compared using two-sided two-sample T test. The biomarkers compared were tested with the Wilcoxon Rank Sum test, as their concentrations were not normally distributed. For any marker result that was unmeasurable, we utilized a standard approach of imputing concentrations 50% below the limit of detection.

All work for biomarker selection and the development of a diagnostic model was done exclusively on the training set. The level or concentration values for all proteins underwent the following transformation to facilitate the predictive analysis: (a) they were log-transformed to achieve a normal distribution; (b) outliers were clipped at the value of three times the median absolute deviation; and (c) the values were re-scaled to distribution with a zero mean and unit variance. Candidate panels of proteins and clinical features were selected via least angle regression (LARS), and models were generated using least absolute shrinkage and selection operator (LASSO) with logistic regression, using Monte Carlo cross-validation with 400 iterations. Candidates were subjected to further assessment of discrimination via iterative model building, assessing change in area under the curve (AUC) with the addition of biomarkers to the base model, along with assessment of improvement in calibration from their addition through minimization of the Akaike or Bayesian Information Criteria (AIC, BIC) and goodness of fit in Hosmer-Lemeshow testing.

Figure 3:
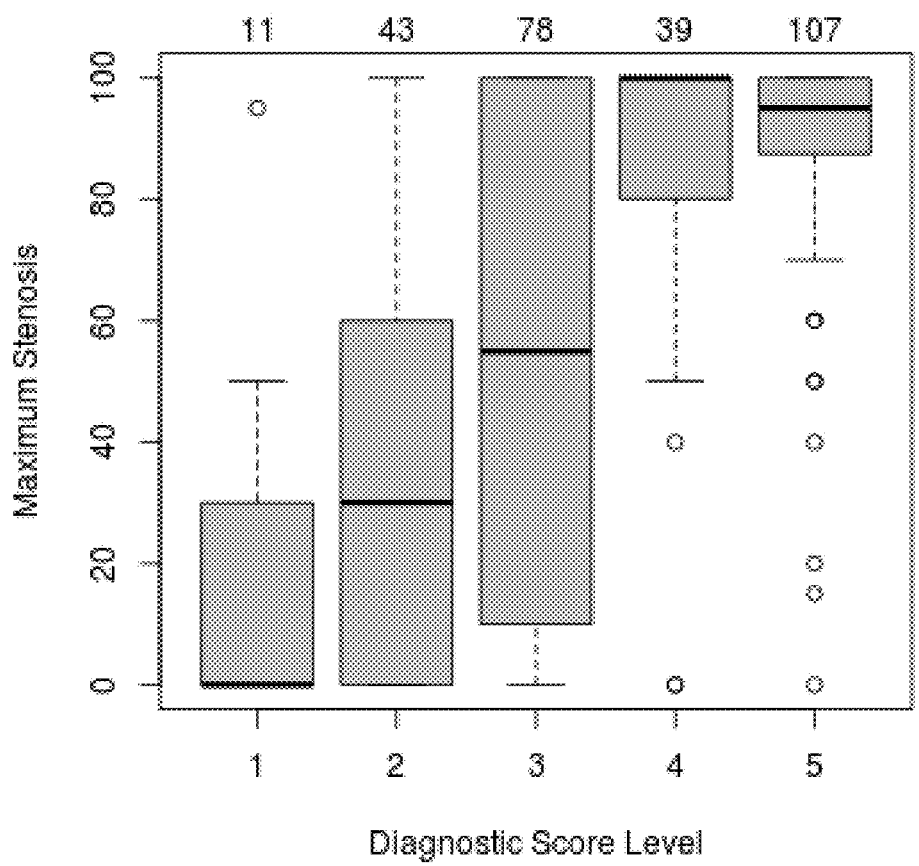
FIG. 3 shows results from dividing the CAD panel FM139/685 (as described in Example 1), in the internal validation set (N=278) into 5 categories of predicted likelihood of CAD (≥70% stenosis in any vessel). In doing so, 42% of subjects could be "ruled in" or "ruled out" for severe CAD with a PPV of 93% and a NPV of 91%, respectively.
Figure 4:
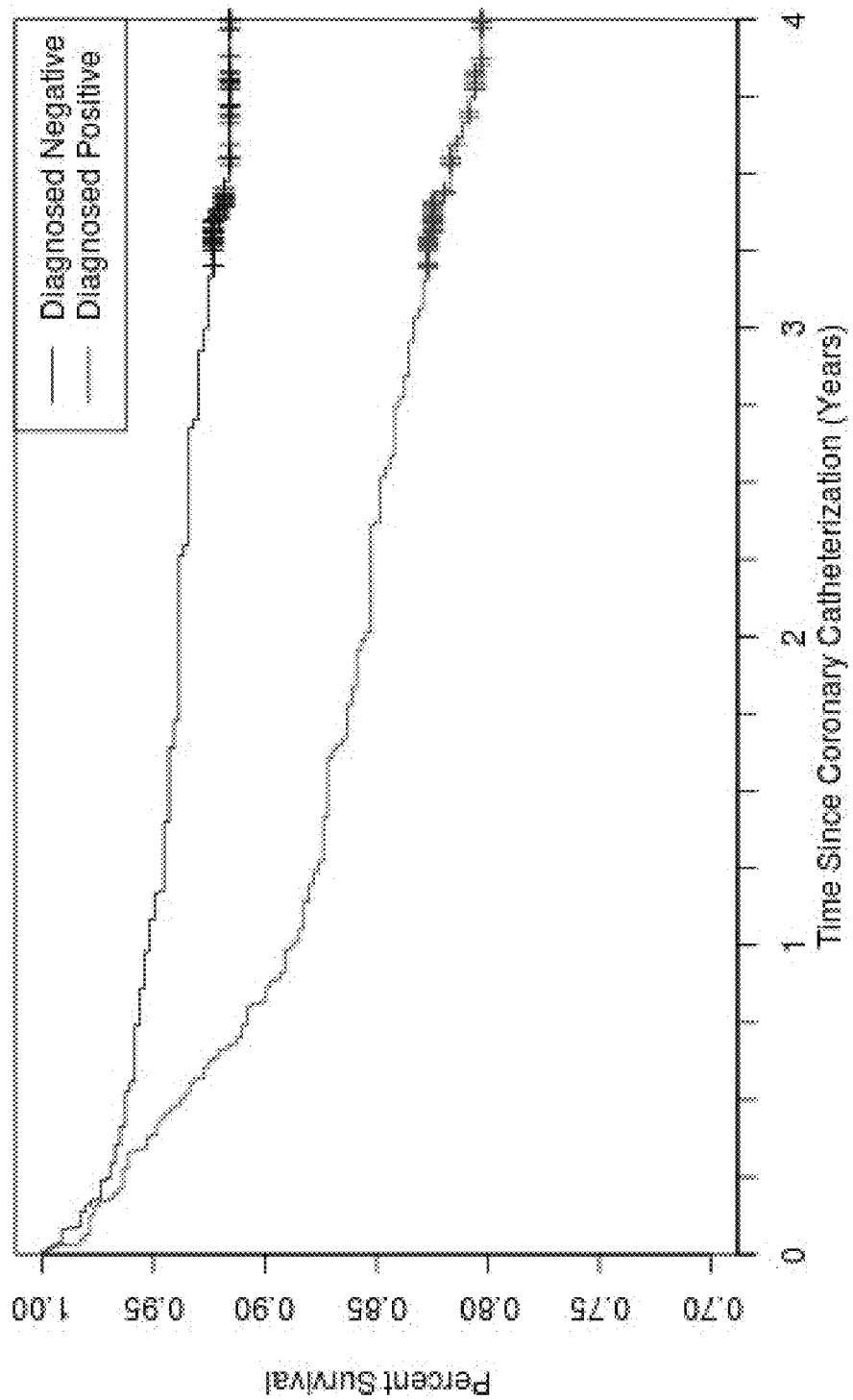
FIG. 4 shows Kaplan-Meier survival curves depicting time to incident acute MI as a function of CAD Score in panel FM139/685 (as described in Example 1). Though developed as a diagnostic tool for CAD, the score also presaged incident acute MI during follow-up.

Once the final panel was selected, a final model was built with all of the training data. Multivariable logistic regression evaluated the performance of the model in the training set as a whole as well as in several relevant subgroups, to determine how well the model performed in men vs. women, in those who had a history of CAD vs. those who did not have a history of CAD, and in those presenting with and without a myocardial infarct. Diagnostic odds ratios (OR) with 95% confidence intervals (CI) were generated. Subsequently, the final model was evaluated with the validation set: to do so, we generated a score distribution within the validation cohort, followed by receiver operator characteristic (ROC) testing with valor of the score as a function of the AUC. Operating characteristics of the score were calculated, with sensitivity (Sn), specificity (Sp), positive and negative predictive value (PPV, NPV) generated. We also looked at methods for transforming the single diagnostic score into levels of likelihood (e.g., a five-level score, where a score of 1 means that the patient is extremely unlikely to have CAD, and a score of 5 means that the patient is extremely likely to have CAD), and evaluated each of these levels with the above operating characteristics (FIG. 3 and Table 9). To evaluate prognostic meaning of the CAD score, we performed age- and CAD-score-adjusted Cox proportional hazards analyses to evaluate whether a score above the optimal threshold for CAD diagnosis also predicted future acute MI; hazard ratios (HR) for an elevated CAD score as well as per unit score increase with 95% CI were estimated. Lastly, time to first acute MI event as a function of elevated CAD score was calculated, displayed as Kaplan-Meier survival curves, and compared using log-rank testing (FIG. 4).

All statistics were performed using R software, version 3.3 (R Foundation for Statistical Computing, Vienna, AT); p-values are two-sided, with a value <0.05 considered significant.

Table 1A shows biomarker concentrations and their diagnostic association that differ between those in the training set (N=649) with at least one coronary artery stenosis ≥70% (N=428) and those who did not in the cohort of subjects who received a coronary cath, with or without an optional peripheral cath.

Notably, of all the protein biomarkers (Table 1A) measured in the training set, those with severe CAD had lower concentrations of adiponectin and apolipoprotein C-I (apo C-I), and higher concentrations of kidney injury molecule-1 and midkine.

Baseline clinical variables of subjects in the validation set (N=278) were similar to those in the training set, and are included in Table 5 (for diagnostic protein biomarkers) and Table 6 (for clinical variables). Table 5 below shows protein biomarker concentrations and their diagnostic association that differ between those in the validation set (N=278) with at least one coronary artery stenosis ≥70% (N=178) and those who did not in the cohort of subjects who received a coronary cath, with or without an optional peripheral cath.

TABLE 5

Diagnostic Biomarkers (Received Coronary Cath; Peripheral Cath Optional) (Validation Set)

| Biomarker | Concentration in Subjects with Coronary Stenosis (N = 178) | Concentration in Subjects without Coronary Stenosis (N = 100) | p-value |
|---|---|---|---|
| Adiponectin (ug/mL) | 3.85 (2.225, 5.825) | 4.3 (2.9, 7.35) | 0.03 |
| Alpha-1-Antitrypsin (AAT) (mg/mL) | 1.8 (1.5, 2.175) | 1.8 (1.5, 2.1) | 0.63 |
| Alpha-2-Macroglobulin (A2Macro) (mg/mL) | 1.8 (1.5, 2.3) | 1.8 (1.5, 2.2) | 0.602 |
| Angiopoietin-1 (ANG-1) (ng/mL) | 6.4 (4.9, 9.6) | 7.2 (5.1, 11) | 0.171 |
| Angiotensin-Converting Enzyme (ACE) (ng/mL) | 81 (62.2, 106) | 77 (63.5, 104.8) | 0.934 |
| Apolipoprotein(a) (Lp(a)) (ug/mL) | 210 (73, 600.2) | 250.5 (68, 544) | 0.929 |
| Apolipoprotein A-I (Apo A-I) (mg/mL) | 1.7 (1.4, 2.1) | 1.9 (1.6, 2.325) | 0.007 |
| Apolipoprotein A-II (Apo A-II) (ng/mL) | 306.5 (251.2, 383.8) | 345 (276, 395.8) | 0.058 |
| Apolipoprotein B (Apo B) (ug/mL) | 1395 (1082, 1830) | 1495 (1210, 1818) | 0.116 |
| Apolipoprotein C-I (Apo C-I) (ng/mL) | 304 (244.5, 362.5) | 357.5 (303.5, 411) | <0.001 |
| Apolipoprotein C-III (Apo C-III) (ug/mL) | 208 (158.2, 271.8) | 215.5 (171.5, 256.2) | 0.844 |
| Apolipoprotein H (Apo H) (ug/mL) | 336.5 (278.2, 402) | 329.5 (271.2, 391.5) | 0.457 |
| Beta-2-Microglobulin (B2M) (ug/mL) | 1.8 (1.4, 2.5) | 1.75 (1.3, 2.3) | 0.355 |
| Brain-Derived Neurotrophic Factor (BDNF) (ng/mL) | 2.2 (1.1, 4.275) | 2.65 (1.35, 5.7) | 0.181 |
| C-Reactive Protein (CRP) (ug/mL) | 4 (1.4, 11) | 4.55 (1.575, 10.25) | 0.845 |
| Carbonic anhydrase 9 (CA-9) (ng/mL) | 0.14 (0.089, 0.25) | 0.12 (0.072, 0.2) | 0.084 |
| Carcinoembryonic antigen-related cell adhesion molecule 1 (CEACAM1) (ng/mL) | 24 (20, 29) | 23.5 (20, 29) | 0.924 |
| CD5 Antigen-like (CD5L) (ng/mL) | 3715 (2880, 4905) | 3960 (2782, 5170) | 0.69 |
| Decorin (ng/mL) | 2.4 (1.925, 3.4) | 2.3 (1.9, 3.2) | 0.339 |
| E-Selectin (ng/mL) | 5.2 (3.6, 6.7) | 5.8 (4.5, 7.1) | 0.066 |
| EN-RAGE (ng/mL) | 34 (19, 61.5) | 23.5 (15.8, 48.2) | 0.006 |
| Eotaxin-1 (pg/mL) | 98 (42.5, 156) | 97 (42.5, 131) | 0.273 |

TABLE 5-continued

Diagnostic Biomarkers (Received Coronary Cath; Peripheral Cath Optional) (Validation Set)

| Biomarker | Concentration in Subjects with Coronary Stenosis (N = 178) | Concentration in Subjects without Coronary Stenosis (N = 100) | p-value |
|---|---|---|---|
| Factor VII (ng/mL) | 455.5 (351.8, 581.2) | 491.5 (369.2, 605.8) | 0.387 |
| Ferritin (FRTN) (ng/mL) | 145.5 (70.2, 266.5) | 135.5 (67.8, 223.2) | 0.625 |
| Fetuin-A (ug/mL) | 677 (550.5, 826.2) | 732 (581.2, 825.8) | 0.098 |
| Fibrinogen (mg/mL) | 4.5 (3.7, 5.575) | 4.45 (3.5, 5.5) | 0.443 |
| Follicle-Stimulating Hormone (FSH) (mIU/mL) | 6.2 (1.8, 13) | 13.5 (5.8, 40.2) | <0.001 |
| Growth Hormone (GH) (ng/mL) | 0.38 (0.162, 1.3) | 0.32 (0.13, 0.935) | 0.244 |
| Haptoglobin (mg/mL) | 1.1 (0.565, 1.9) | 1 (0.372, 1.9) | 0.423 |
| Immunoglobulin A (IgA) (mg/mL) | 2.3 (1.625, 3.175) | 2.3 (1.575, 3.325) | 0.839 |
| Immunoglobulin M (IgM) (mg/mL) | 1.3 (0.872, 1.975) | 1.4 (0.988, 2.025) | 0.188 |
| Insulin (uIU/mL) | 0.86 (0.11, 2.4) | 0.495 (0.11, 1.35) | 0.007 |
| Intercellular Adhesion Molecule 1 (ICAM-1) (ng/mL) | 100 (86.2, 126) | 107.5 (85, 134.2) | 0.426 |
| Interferon gamma Induced Protein 10 (IP-10) (pg/mL) | 291 (221.5, 403) | 304.5 (225.2, 421.2) | 0.691 |
| Interleukin-1 receptor antagonist (IL-1ra) (pg/mL) | 121 (88, 157.8) | 106.5 (79.5, 134.8) | 0.046 |
| Interleukin-6 receptor (IL-6r) (ng/mL) | 25 (20, 30) | 23 (18, 29) | 0.142 |
| Interleukin-8 (IL-8) (pg/mL) | 6.8 (4.5, 9.3) | 6.2 (4.4, 9.1) | 0.21 |
| Interleukin-12 Subunit p40 (IL-12p40) (ng/mL) | 0.58 (0.49, 0.72) | 0.575 (0.448, 0.702) | 0.272 |
| Interleukin-15 (IL-15) (ng/mL) | 0.595 (0.46, 0.69) | 0.555 (0.45, 0.67) | 0.271 |
| Interleukin-18 (IL-18) (pg/mL) | 213 (156.5, 289.8) | 180.5 (135.8, 234) | 0.003 |
| Interleukin-18-binding protein (IL-18bp) (ng/mL) | 9.9 (7.7, 14) | 8.7 (6.7, 12) | 0.027 |
| Interleukin-23 (IL-23) (ng/mL) | 2.7 (2, 3.2) | 2.5 (1.875, 3.2) | 0.116 |
| Kidney Injury Molecule-1 (KIM-1) (ng/mL) | 0.042 (0.014, 0.084) | 0.031 (0.014, 0.052) | 0.005 |
| Leptin (ng/mL) | 8 (4.2, 16.8) | 10 (4.7, 21.2) | 0.278 |
| Luteinizing Hormone (LH) (mIU/mL) | 4.7 (3, 7.8) | 7 (3.9, 13) | <0.001 |
| Macrophage Colony-Stimulating Factor 1 (M-CSF) (ng/mL) | 0.45 (0.16, 0.72) | 0.39 (0.16, 0.62) | 0.051 |
| Macrophage Inflammatory Protein-1 beta (MIP-1 beta) (pg/mL) | 273 (204.8, 366.8) | 259 (208, 345.5) | 0.693 |
| Matrix Metalloproteinase-2 (MMP-2) (ng/mL) | 1330 (1070, 1618) | 1275 (1050, 1602) | 0.938 |
| Matrix Metalloproteinase-3 (MMP-3) (ng/mL) | 7.2 (5.3, 11) | 5.6 (3.9, 7.8) | <0.001 |
| Matrix Metalloproteinase-7 (MMP-7) (ng/mL) | 0.345 (0.23, 0.55) | 0.315 (0.22, 0.5) | 0.255 |
| Matrix Metalloproteinase-9 (MMP-9) (ng/mL) | 133.5 (97, 192) | 111.5 (81.8, 169.2) | 0.028 |
| Matrix Metalloproteinase-9, total (MMP-9, total) (ng/mL) | 641.5 (463.5, 879.5) | 526.5 (395, 799.2) | 0.022 |
| Midkine (ng/mL) | 15 (10, 22.8) | 13 (9.3, 19) | 0.066 |
| Monocyte Chemotactic Protein 1 (MCP-1) (pg/mL) | 104.5 (77, 152) | 113.5 (73, 152.8) | 0.666 |
| Monocyte Chemotactic Protein 2 (MCP-2) (pg/mL) | 23.5 (17.2, 30.8) | 25 (19, 30.2) | 0.339 |
| Monocyte Chemotactic Protein 4 (MCP-4) (pg/mL) | 2140 (1530, 3200) | 2415 (1575, 3262) | 0.517 |
| Monokine Induced by Gamma Interferon (MIG) (pg/mL) | 1000 (575, 1748) | 868 (536.8, 1462) | 0.342 |
| Myeloid Progenitor Inhibitory Factor 1 (MPIF-1) (ng/mL) | 1.3 (1, 1.7) | 1.2 (0.992, 1.6) | 0.553 |
| Myoglobin (ng/mL) | 35 (24, 47) | 27 (21, 42.2) | 0.007 |
| N-terminal prohormone of brain natriuretic peptide (NT proBNP) | 1415 (531, 4288) | 1815 (604.8, 4655) | 0.424 |
| Osteopontin (ng/mL) | 31 (21, 47.8) | 25.5 (19.8, 38.2) | 0.026 |
| Pancreatic Polypeptide (PPP) (pg/mL) | 86 (54, 161) | 79.5 (44.8, 152.2) | 0.145 |
| Plasminogen Activator Inhibitor 1 (PAI-1) (ng/mL) | 45.5 (28, 67.8) | 44.5 (27, 77.2) | 0.613 |

TABLE 5-continued

Diagnostic Biomarkers (Received Coronary Cath; Peripheral Cath Optional) (Validation Set)

| Biomarker | Concentration in Subjects with Coronary Stenosis (N = 178) | Concentration in Subjects without Coronary Stenosis (N = 100) | p-value |
|---|---|---|---|
| Platelet endothelial cell adhesion molecule (PECAM-1) (ng/mL) | 53 (45.2, 65.8) | 58 (47.5, 69) | 0.096 |
| Prolactin (PRL) (ng/mL) | 7 (4.9, 11.8) | 9 (5.7, 13) | 0.042 |
| Pulmonary and Activation-Regulated Chemokine (PARC) (ng/mL) | 102.5 (76.5, 134) | 96 (72.5, 142.2) | 0.368 |
| Pulmonary surfactant-associated protein D (SP-D) (ng/mL) | 5.5 (3.6, 8.7) | 5.3 (3.2, 8.4) | 0.54 |
| Resistin (ng/mL) | 2.7 (2, 3.875) | 2.3 (1.675, 3.3) | 0.002 |
| Serotransferrin (Transferrin) (mg/dl) | 269 (224.5, 303.8) | 264.5 (239.2, 319.5) | 0.859 |
| Serum Amyloid P-Component (SAP) (ug/mL) | 13 (10, 17) | 13 (9.5, 17) | 0.472 |
| Stem Cell Factor (SCF) (pg/mL) | 383 (293, 493.8) | 345.5 (290.8, 427.2) | 0.025 |
| T-Cell-Specific Protein RANTES (RANTES) (ng/mL) | 7.8 (4.1, 13.8) | 11 (4.1, 20.2) | 0.121 |
| Tamm-Horsfall Urinary Glycoprotein (THP) (ug/mL) | 0.03 (0.021, 0.041) | 0.032 (0.022, 0.041) | 0.382 |
| Thrombomodulin (TM) (ng/mL) | 4 (3.3, 4.975) | 3.6 (3, 4.425) | 0.015 |
| Thrombospondin-1 (ng/mL) | 4415 (2248, 7315) | 4610 (2285, 7835) | 0.599 |
| Thyroid-Stimulating Hormone (TSH) (uIU/mL) | 1.2 (0.782, 1.875) | 1.2 (0.728, 1.9) | 0.931 |
| Thyroxine-Binding Globulin (TBG) (ug/mL) | 37 (31, 43) | 38 (32, 45.2) | 0.246 |
| Tissue Inhibitor of Metalloproteinases 1 (TIMP-1) (ng/mL) | 72 (62, 92) | 76 (58, 93.5) | 0.921 |
| Transthyretin (TTR) (mg/dl) | 26 (21, 31) | 26 (21, 30.2) | 0.962 |
| Troponin (pg/ml) | 10.3 (4, 110.6) | 6.2 (3.1, 20.8) | 0.002 |
| Tumor necrosis factor receptor 2 (TNFR2) (ng/mL) | 6.7 (5, 9.7) | 6.3 (4.5, 8.7) | 0.097 |
| Vascular Cell Adhesion Molecule-1 (VCAM-1) (ng/mL) | 581.5 (460, 752.8) | 533 (416.8, 693.5) | 0.081 |
| Vascular Endothelial Growth Factor (VEGF) (pg/mL) | 99.5 (71.2, 135) | 93 (63, 145.5) | 0.618 |
| Vitamin D-Binding Protein (VDBP) (ug/mL) | 246.5 (190.5, 315.5) | 250.5 (158.8, 314.2) | 0.902 |
| Vitamin K-Dependent Protein S (VKDPS) (ug/mL) | 14 (11, 17) | 14 (11, 17) | 0.559 |
| Vitronectin (ug/mL) | 445.5 (350, 560) | 463.5 (358.8, 581) | 0.584 |
| von Willebrand Factor (vWF) (ug/mL) | 139.5 (100, 188.8) | 123 (87, 166.8) | 0.038 |

Table 6 below shows baseline clinical variables and their diagnostic association that differ between those in the validation set (N=278) with at least one coronary artery stenosis ≥70% (N=178) and those who did not in the cohort of subjects who received a coronary cath, with or without an optional peripheral cath.

TABLE 6

Diagnostic Clinical Variables (Received Coronary Cath; Peripheral Cath Optional) (Validation Set)

| Clinical Characteristics | Subjects with Coronary Stenosis ≥70% (N = 178) | Subjects w/o Coronary Stenosis ≥70% (N = 100) | p-value |
|---|---|---|---|
| Demographics | | | |
| Age (years) | 67.8 (11.6) | 65.5 (11.8) | 0.109 |
| Male sex | 144/178 (80.9%) | 55/100 (55%) | <0.001 |
| Caucasian | 167/178 (93.8%) | 95/100 (95%) | 0.793 |
| Vital Signs | | | |
| Heart rate (beat/min) | 67.6 (14.1) | 70.8 (13.4) | 0.071 |
| Systolic BP (mmHg) | 136.4 (22.2) | 132.6 (22.2) | 0.182 |
| Diastolic BP (mmHg) | 73 (11.3) | 70.5 (11.5) | 0.099 |

TABLE 6-continued

Diagnostic Clinical Variables (Received Coronary
Cath; Peripheral Cath Optional) (Validation Set)

| Clinical Characteristics | Subjects with Coronary Stenosis ≥70% (N = 178) | Subjects w/o Coronary Stenosis ≥70% (N = 100) | p-value |
|---|---|---|---|
| Medical History | | | |
| Smoking | 29/176 (16.5%) | 12/99 (12.1%) | 0.381 |
| Atrial fibrillation/flutter | 30/178 (16.9%) | 28/100 (28%) | 0.032 |
| Hypertension | 130/178 (73%) | 70/100 (70%) | 0.677 |
| Coronary artery disease | 106/178 (59.6%) | 29/100 (29%) | <0.001 |
| Myocardial infarction | 47/178 (26.4%) | 15/100 (15%) | 0.035 |
| Heart failure | 34/178 (19.1%) | 21/100 (21%) | 0.754 |
| Peripheral artery disease | 38/178 (21.3%) | 9/100 (9%) | 0.008 |
| COPD | 25/178 (14%) | 18/100 (18%) | 0.392 |
| Diabetes, Type 1 | 1/178 (0.6%) | 2/100 (2%) | 0.294 |
| Diabetes, Type 2 | 54/178 (30.3%) | 14/100 (14%) | 0.002 |
| Any Diabetes | 54/178 (30.3%) | 16/100 (16%) | 0.009 |
| CVA/TIA | 24/178 (13.5%) | 5/100 (5%) | 0.026 |
| Chronic kidney disease | 27/178 (15.2%) | 7/100 (7%) | 0.056 |
| Hemodialysis | 3/178 (1.7%) | 3/100 (3%) | 0.67 |
| Angioplasty, peripheral and/or coronary | 19/178 (10.7%) | 4/100 (4%) | 0.068 |
| Stent, peripheral and/or coronary | 51/178 (28.7%) | 14/100 (14%) | 0.005 |
| CABG | 46/178 (25.8%) | 3/100 (3%) | <0.001 |
| Percutaneous coronary intervention | 87/178 (48.9%) | 3/100 (3%) | <0.001 |
| Medications | | | |
| ACE-I/ARB | 94/177 (53.1%) | 51/99 (51.5%) | 0.803 |
| Beta blocker | 120/177 (67.8%) | 64/100 (64%) | 0.596 |
| Aldosterone antagonist | 8/177 (4.5%) | 5/100 (5%) | 1 |
| Loop diuretics | 35/177 (19.8%) | 22/100 (22%) | 0.757 |
| Nitrates | 40/176 (22.7%) | 14/100 (14%) | 0.085 |
| CCB | 48/178 (27%) | 25/100 (25%) | 0.777 |
| Statin | 136/177 (76.8%) | 62/100 (62%) | 0.012 |
| Aspirin | 149/178 (83.7%) | 59/100 (59%) | <0.001 |
| Warfarin | 26/177 (14.7%) | 24/100 (24%) | 0.073 |
| Clopidogrel | 55/177 (31.1%) | 10/100 (10%) | <0.001 |
| Echocardiographic results | | | |
| LVEF (%) | 55.8 (15) | 55.5 (15.8) | 0.904 |
| RSVP (mmHg) | 41.7 (11.6) | 42 (12.7) | 0.905 |
| Stress test results | | | |
| Ischemia on Scan | 38/49 (77.6%) | 10/12 (83.3%) | 1 |
| Ischemia on ECG | 19/36 (52.8%) | 6/11 (54.5%) | 1 |
| Angiography results | | | |
| >=70% coronary stenosis in >=2 vessels | 104/178 (58.4%) | 0/100 (0%) | <0.001 |
| >=70% coronary stenosis in >=3 vessels | 57/178 (32%) | 0/100 (0%) | <0.001 |
| Lab Measures | | | |
| Sodium | 139 (3.5) | 139.7 (3.1) | 0.116 |
| Blood urea nitrogen (mg/dL) | 19 (15, 25.2) | 17 (14, 22.2) | 0.048 |
| Creatinine (mg/dL) | 1.1 (0.9, 1.3) | 1.1 (0.9, 1.2) | 0.077 |
| eGFR (median, CKDEPI) | 96.8 (73.5, 110.4) | 98.5 (80.8, 110.5) | 0.788 |
| Total cholesterol (mg/dL) | 154.6 (45.8) | 163.9 (41.9) | 0.175 |
| LDL cholesterol (mg/dL) | 89.2 (40.2) | 90 (29.4) | 0.889 |
| Glycohemoglobin (%) | 6.2 (5.7, 6.6) | 6.2 (5.9, 6.9) | 0.412 |
| Glucose (mg/dL) | 102 (95, 124) | 104 (89.8, 123.2) | 0.936 |
| HGB (mg/dL) | 13.2 (1.7) | 13.2 (1.5) | 0.974 |

Following the described methods, from the training cohort (N=649), independent predictors of CAD ≥70% in any one vessel included four biomarkers (adiponectin, apolipoprotein C-I, kidney injury molecule-1, and midkine) and clinical variables (history of percutaneous coronary intervention e.g., balloon angioplasty with or without stent placement, and sex). This combination of protein biomarkers and clinical variables is represented by panel FM139/685 as shown in Table 25 and FIGS. 1-4.

Model fitting is displayed in Table 7, which shows that the addition of each individual biomarker to clinical variables improved discrimination, while simultaneously improving calibration for coronary stenosis of ≥70%, as evidenced by minimization of the AIC or BIC, and with concomitant goodness of fit through Hosmer-Lemeshow testing. With respect to the biomarkers, candidates were retained if they strengthened the model and/or improved calibration.

TABLE 7

Model Fitting for Diagnostic CAD Panel FM139/685, Example 1 (Received Coronary Cath; Peripheral Cath Optional) (Validation Set)

| Model | AUC | AIC | BIC | Hosmer-Lemeshow p-value |
|---|---|---|---|---|
| Model 1: Clinical factors alone | 0.79 | 671.7 | 685.1 | 1.0 |
| Model 2: Clinical factors + midkine | 0.84 | 639.4 | 657.3 | 0.35 |
| Model 3: Clinical factors + adiponectin | 0.80 | 667.9 | 685.8 | 0.83 |
| Model 4: Clinical factors + apolipoprotein C-I | 0.84 | 662.4 | 680.3 | 0.99 |
| Model 5: Clinical factors + kidney injury molecule-1 | 0.83 | 648.2 | 666.1 | 0.77 |
| Model 6: Clinical factors + midkine, adiponectin, apolipoprotein C-I, and kidney injury molecule-1 | 0.87 | 612.1 | 643.4 | 0.40 |

AUC = area under the curve,
AIC = Akaike information criterion,
BIC = Bayesian information criterion In multivariable logistic regression, among those in the training cohort, our score was strongly predictive of severe CAD in all subjects (OR=9.74, 95% CI 6.05-16.1; P<0.001). To better understand performance of the score in various subgroups, we then examined score performance in men (OR=7.88, 95% CI=4.31-14.9; P<0.001), women (OR=24.8, 95% CI=7.11-111.6; P<0.001), as well as those without prior history of CAD (OR=8.67, 95% CI=4.38-17.9; P<0.001).

For the validation cohort, we calculated individual scores and expressed results as a function of CAD presence. In doing so, a bimodal score distribution was revealed (FIG. 2), with higher prevalence of severe CAD in those with higher scores, and lower prevalence among those with lower scores. In ROC testing, for the gold standard diagnosis of ≥70% stenosis of any major epicardial coronary artery, the scores generated had an AUC of 0.87 (FIG. 1; P<0.001).

Table 8 shows the operating characteristics of the FM139/685 CAD algorithm across various scores. For sensitivity and specificity, the 95% confidence interval is listed in parentheses. At the optimal score cut-point, we found 77% sensitivity, 84% specificity, PPV of 90% and NPV of 67% for severe CAD. In subjects with a history of CAD the score had a sensitivity of 84%, specificity of 66%, PPV of 90%, and NPV of 53% for prediction of CAD. In subjects without a history of CAD the score had a sensitivity of 78%, specificity of 80%, PPV of 80%, and NPV of 78% for prediction of CAD. The CAD score was also tested for performance in patients presenting with and without an MI. The AUC of the score for predicting severe CAD in subjects presenting without an acute MI was 0.87 (P<0.001).

TABLE 8

Performance of Diagnostic Panel FM139/685, Example 1 (Received Coronary Cath; Peripheral Cath Optional) (Validation Set)

| Cutoff | Sensitivity | Specificity | PPV | NPV |
|---|---|---|---|---|
| 6.5 | 0 (0, 0) | 1 (1, 1) | — | 0.36 |
| 6 | 0.006 (0, 0.017) | 1 (1, 1) | 1 | 0.361 |
| 5.5 | 0.011 (0, 0.027) | 1 (1, 1) | 1 | 0.362 |
| 5 | 0.034 (0.007, 0.06) | 1 (1, 1) | 1 | 0.368 |
| 4.5 | 0.034 (0.007, 0.06) | 1 (1, 1) | 1 | 0.368 |
| 4 | 0.118 (0.071, 0.165) | 1 (1, 1) | 1 | 0.389 |
| 3.5 | 0.281 (0.215, 0.347) | 1 (1, 1) | 1 | 0.439 |
| 3 | 0.36 (0.289, 0.43) | 0.97 (0.937, 1) | 0.955 | 0.46 |
| 2.5 | 0.433 (0.36, 0.505) | 0.96 (0.922, 0.998) | 0.951 | 0.487 |
| 2 | 0.506 (0.432, 0.579) | 0.95 (0.907, 0.993) | 0.947 | 0.519 |
| 1.5 | 0.584 (0.512, 0.657) | 0.91 (0.854, 0.966) | 0.92 | 0.552 |
| 1 | 0.674 (0.605, 0.743) | 0.87 (0.804, 0.936) | 0.902 | 0.6 |
| 0.5 | 0.787 (0.726, 0.847) | 0.79 (0.71, 0.87) | 0.87 | 0.675 |
| 0 | 0.904 (0.861, 0.948) | 0.61 (0.514, 0.706) | 0.805 | 0.782 |
| −0.5 | 0.961 (0.932, 0.989) | 0.41 (0.314, 0.506) | 0.743 | 0.854 |
| −1 | 0.989 (0.973, 1) | 0.21 (0.13, 0.29) | 0.69 | 0.913 |
| −1.5 | 0.994 (0.983, 1) | 0.09 (0.034, 0.146) | 0.66 | 0.9 |
| −2 | 1 (1, 1) | 0 (0, 0) | 0.64 | — |

Table 9 below shows a scoring model using a five-level scoring system, and illustrates the performance of the model when the raw diagnostic value is partitioned into a five-level score, each optimized for different operating characteristics and diagnostic confidence, with a higher score indicating an increased risk for the presence of CAD. Scores 1-2 indicate a negative diagnosis, scores 4-5 indicates a positive diagnosis, and a score of 3 indicates a diagnosis of moderate risk. The cutoffs for score levels 1 and 2 were optimized for NPV (0.9 and 0.8 respectively), and tested in the validation set with NPV values of 0.91 and 0.76 respectively. The cutoffs for score levels 4 and 5 were optimized for PPV (0.9 and 0.95 respectively), and tested in the validation set with PPV values of 0.85 and 0.93 respectively. This is also depicted in FIG. 3.

TABLE 9

Performance of 5-Level Score for Diagnostic Panel FM139/685, Example 1 (Received Coronary Cath; Peripheral Cath Optional) (Validation Set)

| | | Optimized For | | Observed in Validation Set | |
|---|---|---|---|---|---|
| Score | # Patients | PPV | NPV | PPV | NPV |
| 5 | 107 | 0.95 | — | 0.925 | — |
| 4 | 39 | 0.9 | — | 0.846 | — |
| 3 | 78 | NA | NA | 0.462 | 0.538 |
| 2 | 43 | — | 0.8 | — | 0.791 |
| 1 | 11 | — | 0.9 | — | 0.909 |

Notably, among those with available data to calculate the Framingham Risk Score (N=577), we found the CAD algorithm to have consistent and superior AUC over the Framingham Risk Score's ability to predict the presence of CAD (0.87 versus 0.52; P<0.001). Of the 649 in the training set, 154 had exercise stress tests without imaging and 174 had nuclear stress tests; of the 278 patients in the validation set, 47 had exercise stress tests without imaging and 61 had nuclear stress tests. Among patients undergoing cardiac stress testing per standard of care, the CAD score was substantially more accurate for predicting angiographically severe CAD (again, 0.87 vs. 0.52; P<0.001 for difference in AUC).

During a mean follow up of 3.6 years, in the entire cohort of subjects, the CAD diagnostic scoring system independently predicted subsequent incident of acute MI in age- and score-adjusted models (HR=2.39; 95% CI=1.65-3.47; P<0.001). When modeled as a continuous variable, the score was similarly predictive, with higher scores predictive of higher risk for incident acute MI (HR=1.19 per unit score increase; 95% CI=1.09-1.31; P<0.001). Those with a dichotomously elevated score had a shorter time to first event than those with a lower CAD score, as evidenced by rapid and sustained divergence of the Kaplan-Meier survival curves (FIG. 4; log rank p-value <0.001).

Using patients referred for coronary angiography for a broad range of indications, we describe a novel scoring system to predict the presence of severe epicardial CAD (≥70% stenosis in at least one major vessel). This score consisted of a combination of clinical variables and concentrations of 4 biologically relevant biomarkers. For the diagnosis of ≥70% stenosis of any major epicardial coronary artery, the score generated had an area under the ROC curve of 0.87 in the validation set, and at the optimal cut-point, the score was both highly sensitive (77%) and specific (84%) for the diagnosis of CAD, with a PPV of 90%. Importantly, the CAD score performed particularly well in women, and while one element of the score was history of percutaneous coronary intervention (also referred to as PCI), the score performance was similar in subjects without a history of CAD or in those without an MI at presentation. Among those with available data to calculate a Framingham Risk Score, the CAD score had significantly higher AUC when predicting the presence of CAD than did the Framingham Risk Score; such data are similar to Pen and colleagues, who found the Framingham score to be less accurate for determining prevalent coronary plaque burden detected with CT angiography. The score also performed significantly better for the diagnosis of CAD than stress testing.

The clinical and biomarker scoring strategy disclosed herein can reliably diagnose the presence of severe epicardial CAD. Advantages of a reliable clinical and biomarker score for diagnosing CAD presence include the fact such a technology can be widely disseminated in a cost-effective manner, easily interpreted, and are associated with a well-defined sequence of therapeutic steps.

Example 2: A Clinical and Biomarker Scoring System to Diagnose Obstructive Coronary Artery Disease (CAD), Panel FM46/572

Figure 18:
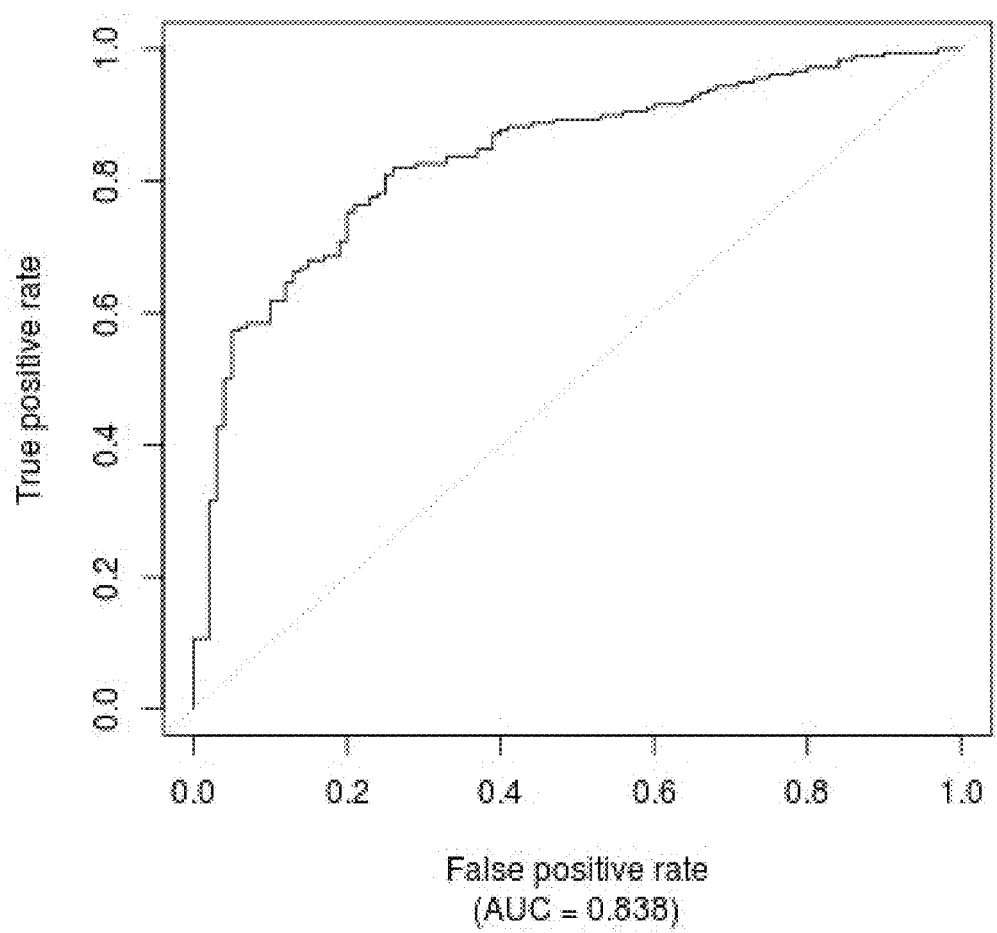
FIG. 18 shows a receiver operating characteristic curve for the Prevencio CAD panel FM46/572 (as described in Example 2), in the internal validation set (N=278) to diagnose the presence of severe CAD (≥70% stenosis in any vessel). The panel had a robust area under the curve (AUC) of 0.84.
Figure 19:
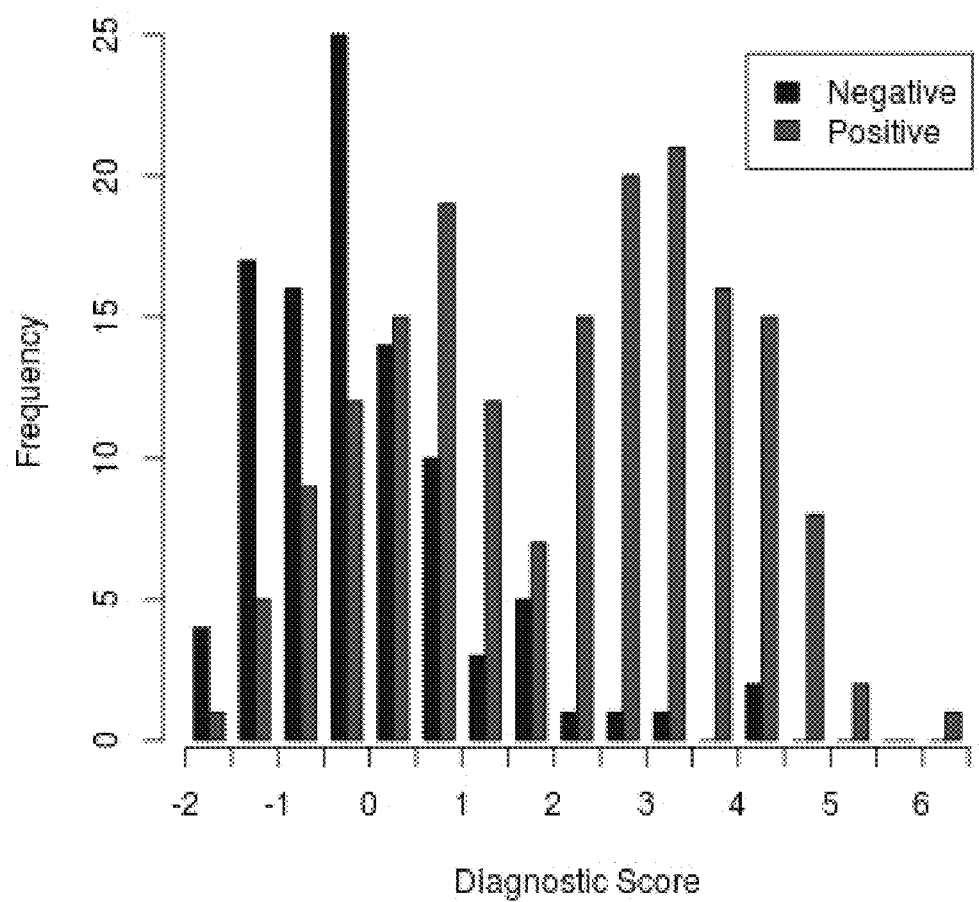
FIG. 19 shows a distribution of the CAD panel FM46/572 (as described in Example 2) in the internal validation set (N=278) to diagnose the presence of severe CAD (≥70% stenosis in any vessel). A bimodal distribution is noted, with preponderance of those with significant CAD distributed at higher scores. Positive=subjects with at least one coronary stenosis ≥70%, negative=subjects with no coronary stenoses ≥70%.
Figure 20:
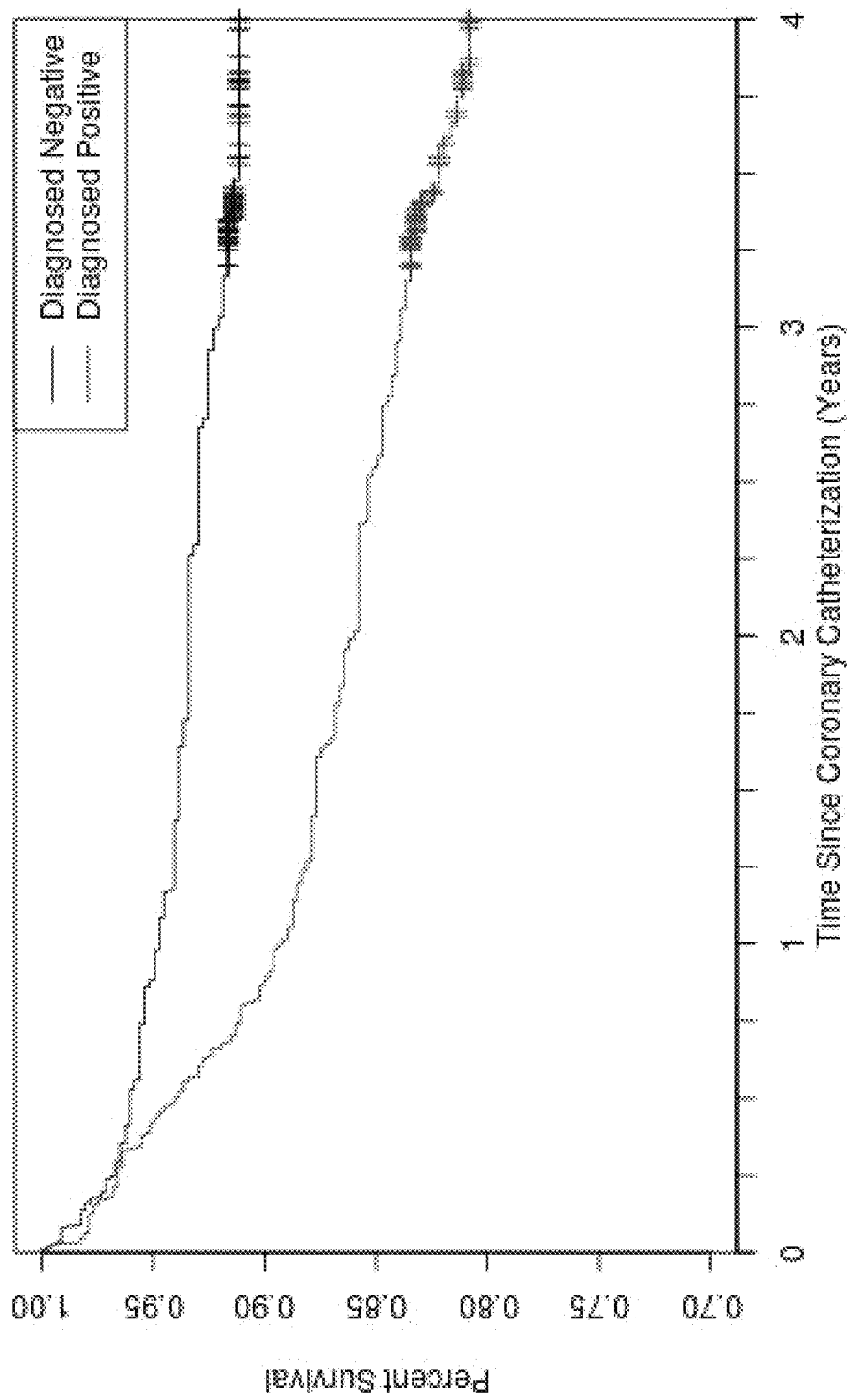
FIG. 20 shows Kaplan-Meier survival curves depicting time to incident acute MI as a function of CAD Score panel FM 46/572 (as described in Example 2). Though developed as a diagnostic tool for CAD, the score also presaged incident acute MI during follow-up.

This example demonstrates yet another non-invasive method employing a clinical and biomarker scoring system that offers, among other things, high accuracy in diagnosing the presence of anatomically significant CAD, and in providing a prognosis of cardiovascular events. This example utilized the same described methods (study design and participants, data acquisition, follow up, biomarker testing, statistics and results (Tables 1A, 3A, 5, and 6; FIGS. 18-20) as Example 1. The primary differences between Example 1 and Example 2 are the clinical variables and proteins that were utilized.

Following the described methods, from the training cohort (N=649), independent predictors of CAD ≥70% in any one vessel included three biomarkers (adiponectin, decorin, and midkine) and three clinical variables (history of myocardial infarct, history of percutaneous coronary intervention and sex). This combination of biomarkers and clinical variables are represented in panel FM46/572 as shown in Table 25 and FIGS. 18-20.

Model fitting is displayed in Table 10, which shows that the addition of each individual biomarker to clinical variables improved discrimination, while simultaneously improving calibration for coronary stenosis of ≥70%, as evidenced by minimization of the AIC or BIC, and with concomitant goodness of fit through Hosmer-Lemeshow testing. With respect to the biomarkers, candidates were retained if they strengthened the model and/or improved calibration.

TABLE 10

Model Fitting for Diagnostic CAD Panel FM46/572, Example 2 (Received Coronary Cath; Peripheral Cath Optional) (Validation Set)

| Model | AUC | AIC | BIC | Hosmer-Lemeshow p-value |
|---|---|---|---|---|
| Model 1: Clinical factors alone | 0.80 | 639.3 | 657.2 | 0.999 |
| Model 2: Clinical factors + midkine | 0.84 | 610.7 | 633.1 | 0.806 |
| Model 3: Clinical factors + adiponectin | 0.81 | 637.8 | 660.2 | 0.956 |
| Model 4: Clinical factors + decorin | 0.80 | 636.9 | 659.2 | 0.564 |
| Model 5: Clinical factors + adiponectin, midkine | 0.84 | 600.0 | 626.8 | 0.386 |
| Model 6: Clinical factors + adiponectin, decorin, midkine | 0.84 | 595.1 | 626.4 | 0.987 |

Notably, those with severe CAD had lower concentrations of adiponectin and higher concentrations of midkine and decorin. Biomarkers and their concentrations in subjects in the training set with and without coronary stenosis are shown in Table 1A, and the baseline clinical variable values in the training set are found in Table 3A. Baseline biomarker and clinical variables of subjects in the validation set (N=278) are included in Tables 5 and 6, respectively.

For the validation cohort, in ROC testing, for the gold standard diagnosis of ≥70% stenosis of any major epicardial coronary artery, the scores generated had an AUC of 0.84 (FIG. 18; P<0.001). For the validation cohort, individual scores were calculated and expressed results as a function of CAD presence. In doing so, a bimodal score distribution was revealed (FIG. 19), with higher prevalence of severe CAD in those with higher scores, and lower prevalence among those with lower scores.

Table 11 below shows the operating characteristics of the FM46/572 CAD algorithm across various scores. For sensitivity and specificity, the 95% confidence interval is listed in parentheses. At the optimal score cut-point, we found 69.7% sensitivity, 81.0% specificity, PPV of 86.7% and NPV of 60.0% for severe CAD.

TABLE 11

Performance of Diagnostic Panel FM46/572, Example 2 (Received Coronary Cath; Peripheral Cath Optional) (Validation Set)

| Cutoff | Sensitivity | Specificity | PPV | NPV |
|---|---|---|---|---|
| 6.5 | 0 (0, 0) | 1 (1, 1) | NA | 0.36 |
| 6 | 0.006 (−0.005, 0.017) | 1 (1, 1) | 1 | 0.361 |
| 5.5 | 0.006 (−0.005, 0.017) | 1 (1, 1) | 1 | 0.361 |
| 5 | 0.017 (−0.002, 0.036) | 1 (1, 1) | 1 | 0.364 |

TABLE 11-continued

Performance of Diagnostic Panel FM46/572, Example 2 (Received Coronary Cath; Peripheral Cath Optional) (Validation Set)

| Cutoff | Sensitivity | Specificity | PPV | NPV |
|---|---|---|---|---|
| 4.5 | 0.062 (0.026, 0.097) | 1 (1, 1) | 1 | 0.375 |
| 4 | 0.146 (0.094, 0.198) | 0.98 (0.953, 1.007) | 0.929 | 0.392 |
| 3.5 | 0.236 (0.174, 0.298) | 0.98 (0.953, 1.007) | 0.955 | 0.419 |
| 3 | 0.354 (0.284, 0.424) | 0.97 (0.937, 1.003) | 0.955 | 0.458 |
| 2.5 | 0.466 (0.393, 0.54) | 0.96 (0.922, 0.998) | 0.954 | 0.503 |
| 2 | 0.551 (0.477, 0.624) | 0.95 (0.907, 0.993) | 0.951 | 0.543 |
| 1.5 | 0.59 (0.518, 0.662) | 0.9 (0.841, 0.959) | 0.913 | 0.552 |
| 1 | 0.657 (0.588, 0.727) | 0.87 (0.804, 0.936) | 0.9 | 0.588 |
| 0.5 | 0.764 (0.702, 0.826) | 0.77 (0.688, 0.852) | 0.855 | 0.647 |
| 0 | 0.848 (0.796, 0.901) | 0.63 (0.535, 0.725) | 0.803 | 0.7 |
| −0.5 | 0.916 (0.875, 0.957) | 0.38 (0.285, 0.475) | 0.724 | 0.717 |
| −1 | 0.966 (0.94, 0.993) | 0.22 (0.139, 0.301) | 0.688 | 0.786 |
| −1.5 | 0.994 (0.983, 1.005) | 0.05 (0.007, 0.093) | 0.651 | 0.833 |
| −2 | 1 (1, 1) | 0.01 (−0.01, 0.03) | 0.643 | 1 |
| −2.5 | 1 (1, 1) | 0 (0, 0) | 0.64 | NA |

Table 12 below shows the scoring model using a three-level scoring system, and illustrates the performance of the model when the raw diagnostic value is partitioned into a three-level score, each optimized for different operating characteristics and diagnostic confidence, with a higher score indicating an increased risk for the presence of CAD. In a three-level score, a score of 1 indicates a negative or low likelihood of CAD diagnosis, a score of 3 indicates a positive or high likelihood of CAD diagnosis, and a score of two indicates a diagnosis of moderate likelihood of CAD diagnosis. The cutoff for score level 1 was optimized for NPV of 0.8 in the training set, and the cutoff for score level of 3 was optimized for a PPV of 0.95 in the training set.

TABLE 12

Performance of 3-Level Score for Diagnostic Panel FM46/572, Example 2 (Received Coronary Cath; Peripheral Cath Optional) (Validation Set)

| | | Optimized For | | Observed in Validation Set | |
|---|---|---|---|---|---|
| Score | # Patients | PPV | NPV | PPV | NPV |
| 3 | 103 | 0.95 | — | 0.951 | — |
| 2 | 85 | NA | NA | 0.624 | 0.376 |
| 1 | 90 | — | 0.8 | — | 0.700 |

Notably, among those with available data to calculate the Framingham Risk Score (N=577), we found the CAD algorithm to have consistent and superior AUC over the Framingham Risk Score's ability to predict the presence of CAD (0.84 versus 0.52; P<0.001). Of the 649 in the training set, 154 had exercise stress tests without imaging and 174 had nuclear stress tests; of the 278 patients in the validation set, 47 had exercise stress tests without imaging and 61 had nuclear stress tests. Among patients undergoing cardiac stress testing per standard of care, the CAD score was substantially more accurate for predicting angiographically severe CAD (again, 0.84 vs. 0.52; P<0.001 for difference in AUC).

During a mean follow up of 3.6 years, in the entire cohort of subjects, the CAD scoring system independently predicted subsequent incident acute MI in age- and score-adjusted models (HR=1.85; 95% CI=1.28-2.67; P<0.001). When modeled as a continuous variable, the score was similarly predictive, with higher scores predictive of higher risk for incident acute MI (HR=1.19 per unit score increase; 95% CI=1.08-1.30; P<0.001). Those with a dichotomously elevated score had a shorter time to first event than those with a lower CAD score, as evidenced by rapid and sustained divergence of the Kaplan-Meier survival curves (FIG. 20; log rank p-value <0.001).

Example 3: A Clinical and Biomarker Scoring System to Diagnose Obstructive Coronary Artery Disease (CAD), Panel FM02/410

This example demonstrates yet another non-invasive method employing a clinical and biomarker scoring system that offers, among other things, high accuracy in diagnosing the presence of anatomically significant CAD, and in providing a prognosis of cardiovascular events.

This example utilized the same described methods as Example 1 and 2 (study design, data acquisition, follow up, biomarker testing, statistics and results), with the exception of the subjects. This example included those subjects that only had a coronary catheterization, N=809, (vs. subjects with a coronary catheterization and optionally a peripheral catheterization (Tables 1B, 3B, 13, 14, 15 and 16 and FIG. 28).

The patients selected for analysis consisted of the chronologically initial 809 patients who received only a coronary angiogram. Patients who may have also received a peripheral angiogram concomitantly were excluded.

The 809 patients selected for analysis were randomly split into a training set (70%, or N=566, Tables 1B and 3B) and a holdout validation set (30%, or N=243, Tables 13 and 14). Baseline protein and clinical characteristics between those with and without ≥70% coronary stenosis in at least one major epicardial coronary artery were compared; dichotomous variables were compared using two-sided Fishers exact test, while continuous variables were compared using two-sided two-sample T test. The biomarkers compared were tested with the Wilcoxon Rank Sum test, as their concentrations were not normally distributed. For any marker result that was unmeasurable, we utilized a standard approach of imputing concentrations 50% below the limit of detection.

Table 13 below shows biomarker concentrations and their diagnostic association that differ between those in the validation set (N=243) with at least one coronary artery stenosis ≥70% (N=148) and those who did not in the cohort of subjects who received a coronary cath only.

TABLE 13

Diagnostic Biomarkers for Diagnostic Panel FM02/410, Example 3 (Received Coronary Cath Only) (Validation Set)

| Biomarker | Concentration in Subjects with Coronary Stenosis (N = 148) | Concentration in Subjects without Coronary Stenosis (N = 95) | p-value |
|---|---|---|---|
| Adiponectin (ug/mL) | 3.85 (2.2, 5.925) | 4.3 (2.85, 7.2) | 0.067 |
| Alpha-1-Antitrypsin (AAT) (mg/mL) | 1.8 (1.5, 2.225) | 1.8 (1.5, 2.05) | 0.439 |

TABLE 13-continued

Diagnostic Biomarkers for Diagnostic Panel FM02/410, Example 3 (Received Coronary Cath Only) (Validation Set)

| Biomarker | Concentration in Subjects with Coronary Stenosis (N = 148) | Concentration in Subjects without Coronary Stenosis (N = 95) | p-value |
|---|---|---|---|
| Alpha-2-Macroglobulin (A2Macro) (mg/mL) | 1.8 (1.5, 2.2) | 1.8 (1.5, 2.2) | 0.893 |
| Angiopoietin-1 (ANG-1) (ng/mL) | 6.4 (4.9, 9) | 7.2 (5, 11) | 0.18 |
| Angiotensin-Converting Enzyme (ACE) (ng/mL) | 79 (59.8, 105.2) | 80 (64, 108) | 0.55 |
| Apolipoprotein(a) (Lp(a)) (ug/mL) | 195 (71, 557.8) | 238 (76.5, 549) | 0.688 |
| Apolipoprotein A-I (Apo A-I) (mg/mL) | 1.7 (1.4, 2.1) | 1.9 (1.6, 2.35) | 0.008 |
| Apolipoprotein A-II (Apo A-II) (ng/mL) | 303.5 (250.8, 381.5) | 344 (277.5, 394) | 0.045 |
| Apolipoprotein B (Apo B) (ug/mL) | 1395 (1080, 1830) | 1490 (1210, 1905) | 0.082 |
| Apolipoprotein C-I (Apo C-I) (ng/mL) | 304 (243, 363.8) | 357 (298.5, 410) | <0.001 |
| Apolipoprotein C-III (Apo C-III) (ug/mL) | 208 (153.8, 274.8) | 214 (171, 260.5) | 0.823 |
| Apolipoprotein H (Apo H) (ug/mL) | 330 (273.8, 398.5) | 331 (270.5, 388.5) | 0.751 |
| Beta-2-Microglobulin (B2M) (ug/mL) | 1.8 (1.375, 2.325) | 1.7 (1.3, 2.35) | 0.672 |
| Brain-Derived Neurotrophic Factor (BDNF) (ng/mL) | 2.15 (1.1, 4.2) | 2.6 (1.09, 5.4) | 0.292 |
| C-Reactive Protein (CRP) (ug/mL) | 4.15 (1.55, 11.25) | 4.4 (1.55, 9.8) | 0.85 |
| Carbonic anhydrase 9 (CA-9) (ng/mL) | 0.14 (0.089, 0.26) | 0.13 (0.074, 0.2) | 0.117 |
| Carcinoembryonic antigen-related cell adhesion molecule 1 (CEACAM1) (ng/mL) | 24 (20, 29) | 23 (20, 29) | 0.926 |
| CD5 Antigen-like (CD5L) (ng/mL) | 3680 (2780, 4882) | 4030 (2865, 5330) | 0.288 |
| Decorin (ng/mL) | 2.35 (1.975, 3.7) | 2.3 (1.9, 3.2) | 0.352 |
| E-Selectin (ng/mL) | 5.2 (3.7, 6.7) | 5.8 (4.5, 7.1) | 0.056 |
| EN-RAGE (ng/mL) | 31.5 (19, 56.5) | 23 (15.5, 48.5) | 0.012 |
| Eotaxin-1 (pg/mL) | 103 (42.5, 160.5) | 97 (42.5, 130) | 0.123 |
| Factor VII (ng/mL) | 458.5 (353.2, 578.2) | 479 (367.5, 601.5) | 0.466 |
| Ferritin (FRTN) (ng/mL) | 147.5 (72.5, 258.5) | 135 (72, 234) | 0.677 |
| Fetuin-A (ug/mL) | 662.5 (546.8, 822.8) | 735 (588.5, 819) | 0.07 |
| Fibrinogen (mg/mL) | 4.5 (3.6, 5.525) | 4.4 (3.5, 5.45) | 0.434 |
| Follicle-Stimulating Hormone (FSH) (mIU/mL) | 6.4 (3.1, 13.2) | 10 (5.7, 40.5) | <0.001 |
| Growth Hormone (GH) (ng/mL) | 0.375 (0.16, 1.2) | 0.31 (0.07, 0.94) | 0.363 |
| Haptoglobin (mg/mL) | 1.2 (0.588, 1.9) | 1 (0.34, 1.8) | 0.173 |
| Immunoglobulin A (IgA) (mg/mL) | 2.3 (1.7, 3.2) | 2.3 (1.65, 3.25) | 0.995 |
| Immunoglobulin M (IgM) (mg/mL) | 1.35 (0.868, 2) | 1.4 (0.985, 2.05) | 0.21 |
| Insulin (uIU/mL) | 0.725 (0.11, 2.3) | 0.5 (0.11, 1.4) | 0.037 |
| Intercellular Adhesion Molecule 1 (ICAM-1) (ng/mL) | 101 (82, 126) | 108 (85, 134.5) | 0.413 |
| Interferon gamma Induced Protein 10 (IP-10) (pg/mL) | 295 (221, 432.5) | 309 (230.5, 440.5) | 0.828 |
| Interleukin-1 receptor antagonist (IL-1ra) (pg/mL) | 122 (87.8, 160.2) | 106 (79, 135.5) | 0.042 |
| Interleukin-6 receptor (IL-6r) (ng/mL) | 25 (19, 30) | 23 (18, 29) | 0.27 |
| Interleukin-8 (IL-8) (pg/mL) | 6.7 (4.2, 9.3) | 6.1 (4.3, 8.8) | 0.239 |
| Interleukin-12 Subunit p40 (IL-12p40) (ng/mL) | 0.575 (0.49, 0.72) | 0.57 (0.445, 0.715) | 0.297 |
| Interleukin-15 (IL-15) (ng/mL) | 0.585 (0.46, 0.69) | 0.56 (0.45, 0.68) | 0.363 |
| Interleukin-18 (IL-18) (pg/mL) | 216 (155.5, 292.5) | 181 (136, 234) | 0.004 |
| Interleukin-18-binding protein (IL-18bp) (ng/mL) | 9.9 (7.3, 14) | 8.7 (6.8, 12) | 0.082 |
| Interleukin-23 (IL-23) (ng/mL) | 2.65 (2, 3.2) | 2.5 (1.85, 3.2) | 0.099 |
| Kidney Injury Molecule-1 (KIM-1) (ng/mL) | 0.04 (0.014, 0.08) | 0.031 (0.014, 0.053) | 0.012 |
| Leptin (ng/mL) | 7.9 (4.2, 15) | 10 (4.7, 21.5) | 0.162 |
| Luteinizing Hormone (LH) (mIU/mL) | 4.6 (3, 7.85) | 6.8 (3.9, 13) | 0.002 |

TABLE 13-continued

Diagnostic Biomarkers for Diagnostic Panel FM02/410, Example 3 (Received Coronary Cath Only) (Validation Set)

| Biomarker | Concentration in Subjects with Coronary Stenosis (N = 148) | Concentration in Subjects without Coronary Stenosis (N = 95) | p-value |
|---|---|---|---|
| Macrophage Colony-Stimulating Factor 1 (M-CSF) (ng/mL) | 0.435 (0.16, 0.672) | 0.38 (0.16, 0.615) | 0.084 |
| Macrophage Inflammatory Protein-1 beta (MIP-1 beta) (pg/mL) | 271.5 (201, 363.5) | 262 (209.5, 350) | 0.915 |
| Matrix Metalloproteinase-2 (MMP-2) (ng/mL) | 1325 (1068, 1605) | 1270 (1050, 1620) | 0.905 |
| Matrix Metalloproteinase-3 (MMP-3) (ng/mL) | 7 (5.1, 11) | 5.7 (4, 7.8) | 0.002 |
| Matrix Metalloproteinase-7 (MMP-7) (ng/mL) | 0.34 (0.23, 0.535) | 0.3 (0.22, 0.495) | 0.31 |
| Matrix Metalloproteinase-9 (MMP-9) (ng/mL) | 131.5 (93, 192) | 111 (81.5, 169.5) | 0.068 |
| Matrix Metalloproteinase-9, total (MMP-9, total) (ng/mL) | 625 (450.2, 877.8) | 526 (393, 806) | 0.081 |
| Midkine (ng/mL) | 15 (9.9, 21.2) | 13 (9.3, 19) | 0.225 |
| Monocyte Chemotactic Protein 1 (MCP-1) (pg/mL) | 104.5 (77.8, 158) | 115 (74.5, 151) | 0.782 |
| Monocyte Chemotactic Protein 2 (MCP-2) (pg/mL) | 23.5 (18, 31) | 25 (19.5, 30.5) | 0.349 |
| Monocyte Chemotactic Protein 4 (MCP-4) (pg/mL) | 2125 (1538, 3050) | 2440 (1570, 3220) | 0.396 |
| Monokine Induced by Gamma Interferon (MIG) (pg/mL) | 1040 (559.5, 1992) | 962 (547, 1480) | 0.484 |
| Myeloid Progenitor Inhibitory Factor 1 (MPIF-1) (ng/mL) | 1.3 (1, 1.6) | 1.2 (0.95, 1.6) | 0.475 |
| Myoglobin (ng/mL) | 34 (22.8, 45) | 27 (21, 40.5) | 0.038 |
| N-terminal prohormone of brain natriuretic peptide (NT proBNP) (pg/mL) | 1290 (475.5, 3675) | 1710 (575, 4750) | 0.366 |
| Osteopontin (ng/mL) | 30 (20, 46.2) | 25 (18.5, 38) | 0.046 |
| Pancreatic Polypeptide (PPP) (pg/mL) | 86.5 (51.8, 155.8) | 80 (40.5, 158.5) | 0.308 |
| Plasminogen Activator Inhibitor 1 (PAI-1) (ng/mL) | 45.5 (27.8, 69.5) | 44 (27, 76.5) | 0.736 |
| Platelet endothelial cell adhesion molecule (PECAM-1) (ng/mL) | 53 (45, 65.2) | 58 (48, 68.5) | 0.075 |
| Prolactin (PRL) (ng/mL) | 7 (4.7, 11.2) | 8.9 (5.8, 13) | 0.033 |
| Pulmonary and Activation-Regulated Chemokine (PARC) (ng/mL) | 98.5 (75.8, 134) | 96 (72, 142.5) | 0.47 |
| Pulmonary surfactant-associated protein D (SP-D) (ng/mL) | 5.1 (3.6, 8.2) | 5.3 (3.2, 8.4) | 0.683 |
| Resistin (ng/mL) | 2.6 (1.9, 3.625) | 2.3 (1.7, 3.3) | 0.042 |
| Serotransferrin (Transferrin) (mg/dl) | 270.5 (224, 301.5) | 265 (240, 323.5) | 0.704 |
| Serum Amyloid P-Component (SAP) (ug/mL) | 13 (10, 17.2) | 13 (9.4, 17) | 0.299 |
| Stem Cell Factor (SCF) (pg/mL) | 384 (295, 496.5) | 345 (287.5, 431.5) | 0.037 |
| T-Cell-Specific Protein RANTES (RANTES) (ng/mL) | 7.8 (4, 14) | 11 (4, 19.5) | 0.249 |
| Tamm-Horsfall Urinary Glycoprotein (THP) (ug/mL) | 0.03 (0.022, 0.042) | 0.032 (0.021, 0.042) | 0.804 |
| Thrombomodulin (TM) (ng/mL) | 4 (3.3, 4.825) | 3.6 (3, 4.4) | 0.025 |
| Thrombospondin-1 (ng/mL) | 4415 (2175, 7255) | 4500 (2225, 7615) | 0.725 |
| Thyroid-Stimulating Hormone (TSH) (uIU/mL) | 1.25 (0.822, 1.825) | 1.3 (0.735, 1.9) | 0.963 |
| Thyroxine-Binding Globulin (TBG) (ug/mL) | 37 (30.8, 43) | 38 (32, 46) | 0.234 |
| Tissue Inhibitor of Metalloproteinases 1 (TIMP-1) (ng/mL) | 70 (59.8, 89) | 76 (58, 92.5) | 0.766 |
| Transthyretin (TTR) (mg/dl) | 25.5 (21, 31) | 26 (22, 30.5) | 0.691 |
| Troponin (pg/ml) | 10.2 (3.8, 111.2) | 6 (2.8, 20.8) | 0.003 |
| Tumor necrosis factor receptor 2 (TNFR2) (ng/mL) | 6.7 (5, 9.5) | 6.3 (4.5, 9) | 0.208 |
| Vascular Cell Adhesion Molecule-1 (VCAM-1) (ng/mL) | 570.5 (459, 725.5) | 536 (420.5, 697) | 0.232 |

TABLE 13-continued

Diagnostic Biomarkers for Diagnostic Panel FM02/410, Example 3 (Received Coronary Cath Only) (Validation Set)

| Biomarker | Concentration in Subjects with Coronary Stenosis (N = 148) | Concentration in Subjects without Coronary Stenosis (N = 95) | p-value |
|---|---|---|---|
| Vascular Endothelial Growth Factor (VEGF) (pg/mL) | 100 (73, 136.2) | 93 (63, 147.5) | 0.628 |
| Vitamin D-Binding Protein (VDBP) (ug/mL) | 246.5 (189.2, 314.5) | 250 (140.5, 311.5) | 0.881 |
| Vitamin K-Dependent Protein S (VKDPS) (ug/mL) | 13 (11, 17) | 14 (11, 17) | 0.477 |
| Vitronectin (ug/mL) | 445.5 (341, 556.2) | 465 (356.5, 584) | 0.466 |
| von Willebrand Factor (vWF) (ug/mL) | 138 (99, 189) | 125 (88, 166) | 0.086 |

Table 14 below shows baseline clinical variables and their diagnostic association that differ between those in the validation set (N=243) with at least one coronary artery stenosis ≥70% (N=148) and those who did not in the cohort of subjects who received a coronary cath only.

TABLE 14

Diagnostic Clinical Variables for Diagnostic Panel FM02/410, Example 3 (Received Coronary Cath Only) (Validation Set)

| Clinical Characteristics | Subjects with Coronary Stenosis ≥70% (N = 148) | Subjects w/o Coronary Stenosis ≥70% (N = 95) | p-value |
|---|---|---|---|
| Demographics | | | |
| Age (years) | 67.5 (12.2) | 65.4 (12) | 0.176 |
| Male sex | 120/148 (81.1%) | 53/95 (55.8%) | <0.001 |
| Caucasian | 140/148 (94.6%) | 90/95 (94.7%) | 1 |
| Vital Signs | | | |
| Heart rate (beat/min) | 68.2 (14.4) | 70.4 (12.9) | 0.212 |
| Systolic BP (mmHg) | 136.1 (22.1) | 133.6 (22.2) | 0.411 |
| Diastolic BP (mmHg) | 73.7 (11.7) | 71.3 (11.1) | 0.121 |
| Medical History | | | |
| Smoking | 25/146 (17.1%) | 9/94 (9.6%) | 0.129 |
| Atrial fibrillation/flutter | 27/148 (18.2%) | 26/95 (27.4%) | 0.112 |
| Hypertension | 105/148 (70.9%) | 68/95 (71.6%) | 1 |
| Coronary artery disease | 88/148 (59.5%) | 27/95 (28.4%) | <0.001 |
| Myocardial infarction | 37/148 (25%) | 14/95 (14.7%) | 0.075 |
| Heart failure | 24/148 (16.2%) | 19/95 (20%) | 0.493 |
| Peripheral artery disease | 22/148 (14.9%) | 8/95 (8.4%) | 0.164 |
| COPD | 21/148 (14.2%) | 17/95 (17.9%) | 0.472 |
| Diabetes, Type 1 | 0/148 (0%) | 2/95 (2.1%) | 0.152 |
| Diabetes, Type 2 | 42/148 (28.4%) | 13/95 (13.7%) | 0.008 |
| Any Diabetes | 42/148 (28.4%) | 15/95 (15.8%) | 0.03 |
| CVA/TIA | 20/148 (13.5%) | 5/95 (5.3%) | 0.05 |
| Chronic kidney disease | 15/148 (10.1%) | 7/95 (7.4%) | 0.503 |
| Hemodialysis | 2/148 (1.4%) | 3/95 (3.2%) | 0.382 |
| Angioplasty, peripheral and/or coronary | 12/148 (8.1%) | 4/95 (4.2%) | 0.295 |
| Stent, peripheral and/or coronary | 43/148 (29.1%) | 14/95 (14.7%) | 0.013 |
| CABG | 35/148 (23.6%) | 3/95 (3.2%) | <0.001 |
| Percutaneous coronary intervention | 79/148 (53.4%) | 3/95 (3.2%) | <0.001 |
| Medications | | | |
| ACE-I/ARB | 77/147 (52.4%) | 50/94 (53.2%) | 1 |
| Beta blocker | 95/147 (64.6%) | 61/95 (64.2%) | 1 |
| Aldosterone antagonist | 7/147 (4.8%) | 5/95 (5.3%) | 1 |
| Loop diuretics | 28/147 (19%) | 20/95 (21.1%) | 0.743 |
| Nitrates | 27/146 (18.5%) | 13/95 (13.7%) | 0.378 |
| CCB | 41/148 (27.7%) | 24/95 (25.3%) | 0.767 |

TABLE 14-continued

Diagnostic Clinical Variables for Diagnostic Panel FM02/410,
Example 3 (Received Coronary Cath Only) (Validation Set)

| Clinical Characteristics | Subjects with Coronary Stenosis ≥70% (N = 148) | Subjects w/o Coronary Stenosis ≥70% (N = 95) | p-value |
|---|---|---|---|
| Statin | 113/147 (76.9%) | 59/95 (62.1%) | 0.02 |
| Aspirin | 123/148 (83.1%) | 58/95 (61.1%) | <0.001 |
| Warfarin | 24/147 (16.3%) | 23/95 (24.2%) | 0.138 |
| Clopidogrel | 45/147 (30.6%) | 10/95 (10.5%) | <0.001 |
| Echocardiographic results | | | |
| LVEF (%) | 54.6 (15.1) | 56.2 (15.7) | 0.541 |
| RSVP (mmHg) | 41.2 (12.4) | 41.7 (12.9) | 0.856 |
| Stress test results | | | |
| Ischemia on Scan | 28/38 (73.7%) | 9/11 (81.8%) | 0.708 |
| Ischemia on ECG | 13/27 (48.1%) | 6/11 (54.5%) | 1 |
| Angiography results | | | |
| >=70% coronary stenosis in >=2 vessels | 84/148 (56.8%) | 0/95 (0%) | <0.001 |
| >=70% coronary stenosis in >=3 vessels | 43/148 (29.1%) | 0/95 (0%) | <0.001 |
| Lab Measures | | | |
| Sodium | 139.3 (3.2) | 139.9 (3.1) | 0.209 |
| Blood urea nitrogen (mg/dL) | 18 (15, 22.2) | 18 (14.5, 23) | 0.478 |
| Creatinine (mg/dL) | 1.1 (0.9, 1.3) | 1.1 (0.9, 1.2) | 0.371 |
| eGFR (median, CKDEPI) | 100.4 (75.6, 111.1) | 98.5 (81, 110.7) | 0.791 |
| Total cholesterol (mg/dL) | 153.8 (45.9) | 164.9 (43.2) | 0.143 |
| LDL cholesterol (mg/dL) | 87.8 (40.2) | 90.2 (30.3) | 0.692 |
| Glycohemoglobin (%) | 6 (5.7, 6.4) | 6.2 (5.8, 7) | 0.316 |
| Glucose (mg/dL) | 101 (95, 118.5) | 103 (89, 123.5) | 0.986 |
| HGB (mg/dL) | 13.2 (1.7) | 13.2 (1.5) | 0.69 |

Additional differences in Example 3 (as compared for Example 1 and 2) are the clinical variables and proteins which were utilized in the panel (FM02/410). Following the described methods, from the training cohort (N=566), independent predictors of CAD ≥70% in any one vessel included six biomarkers (adiponectin, apolipoprotein C-1, matrix metalloproteinase 9, midkine, myogloblin, and pulmonary surfactant protein D) and three clinical variables (history of coronary artery bypass graft surgery [CABG], history of percutaneous coronary intervention [e.g. balloon angioplasty with or without stent placement], and sex). This combination of biomarkers and clinical variables is represented by panel FM02/410 as shown in Table 25 and FIG. 28.

Table 15 below shows the operating characteristics of the FM02/410 CAD algorithm across various scores. For sensitivity and specificity, the 95% confidence interval is listed in parentheses. At the optimal score cut-point, we found 84.5% sensitivity, 77.9% specificity, PPV of 85.6% and NPV of 76.3% for severe CAD.

TABLE 15

Performance of Diagnostic Panel FM02/410, Example
3 (Received Coronary Cath Only) (Validation Set)

| Cutoff | Sensitivity | Specificity | PPV | NPV |
|---|---|---|---|---|
| 8.5 | 0 (0, 0) | 1 (1, 1) | — | 0.391 |
| 8 | 0.007 (−0.006, 0.02) | 1 (1, 1) | 1 | 0.393 |
| 7.5 | 0.027 (0.001, 0.053) | 1 (1, 1) | 1 | 0.397 |
| 7 | 0.068 (0.027, 0.108) | 0.989 (0.969, 1.01) | 0.909 | 0.405 |
| 6.5 | 0.095 (0.047, 0.142) | 0.989 (0.969, 1.01) | 0.933 | 0.412 |
| 6 | 0.122 (0.069, 0.174) | 0.989 (0.969, 1.01) | 0.947 | 0.42 |
| 5.5 | 0.122 (0.069, 0.174) | 0.979 (0.95, 1.008) | 0.9 | 0.417 |
| 5 | 0.122 (0.069, 0.174) | 0.979 (0.95, 1.008) | 0.9 | 0.417 |
| 4.5 | 0.149 (0.091, 0.206) | 0.979 (0.95, 1.008) | 0.917 | 0.425 |
| 4 | 0.203 (0.138, 0.267) | 0.979 (0.95, 1.008) | 0.938 | 0.441 |
| 2.5 | 0.324 (0.249, 0.4) | 0.979 (0.95, 1.008) | 0.96 | 0.482 |
| 3 | 0.453 (0.373, 0.533) | 0.968 (0.933, 1.004) | 0.957 | 0.532 |
| 2.5 | 0.541 (0.46, 0.621) | 0.947 (0.902, 0.992) | 0.941 | 0.57 |
| 2 | 0.622 (0.543, 0.7) | 0.947 (0.902, 0.992) | 0.948 | 0.616 |
| 1.5 | 0.649 (0.572, 0.726) | 0.937 (0.888, 0.986) | 0.941 | 0.631 |
| 1 | 0.696 (0.622, 0.77) | 0.926 (0.874, 0.979) | 0.936 | 0.662 |
| 0.5 | 0.77 (0.702, 0.838) | 0.842 (0.769, 0.915) | 0.884 | 0.702 |
| 0 | 0.851 (0.794, 0.909) | 0.758 (0.672, 0.844) | 0.846 | 0.766 |
| −0.5 | 0.926 (0.883, 0.968) | 0.537 (0.437, 0.637) | 0.757 | 0.823 |
| −1 | 0.966 (0.937, 0.995) | 0.326 (0.232, 0.421) | 0.691 | 0.861 |
| −1.5 | 0.993 (0.98, 1.006) | 0.147 (0.076, 0.219) | 0.645 | 0.933 |
| −2 | 1 (1, 1) | 0.032 (−0.004, 0.067) | 0.617 | 1 |
| −2.5 | 1 (1, 1) | 0 (0, 0) | 0.609 | — |

Table 16 shows the scoring model using a three-level scoring system, and illustrates the performance of the model when the raw diagnostic value is partitioned into a three-level score, each optimized for different operating characteristics and diagnostic confidence, with a higher score indicating an increased risk for the presence of CAD. In a three-level score, a score of 1 indicates a negative or low likelihood of CAD diagnosis, a score of 3 indicates a positive or high likelihood of CAD diagnosis, and a score of 2 indicates a diagnosis of moderate likelihood of CAD diagnosis. The cutoff for score level 1 was optimized for NPV of 0.8 in the training set, and the cutoff for score level of 3 was optimized for a PPV of 0.95 in the training set.

TABLE 16

Performance of 3-Level Score for Diagnostic Panel FM02/410 (Received Coronary Cath Only) (Validation Set)

| Score | # Patients | Optimized For | | Observed in Validation Set | |
|---|---|---|---|---|---|
| | | PPV | NPV | PPV | NPV |
| 3 | 110 | 0.95 | — | 0.936 | — |
| 2 | 71 | NA | NA | 0.479 | 0.521 |
| 1 | 62 | — | 0.8 | — | 0.823 |

Example 4: A Biomarker Scoring System to Predict 3 Day Post Sample Draw to One Year (3-365 Day) Risk of Composite Cardiovascular Death, Myocardial Infarct or Stroke (FM160/02)

This example demonstrates a non-invasive method employing a biomarker scoring system that offers, among other things, high accuracy in providing a prognosis of one year risk of composite cardiovascular death, myocardial infarct, or stroke. This example utilized the same described methods as Example 1 (study design and subjects, data acquisition, follow up, biomarker testing, statistics and results (Tables 2B, 4B, 17, 18, 19 and 20 and FIG. 30).

The patients selected for analysis consisted of the chronologically initial 927 patients who received only a coronary angiogram. Patients may have also received a peripheral angiogram concomitantly were excluded.

The 927 patients selected for analysis were randomly split into a training set (70%, or N=649; Tables 2B and 4B), and a holdout validation set (30%, or N=278; Tables 17 and 18). The training set had one subject who died on the day following the cath procedure (i.e., prior to Day 3), so this patient was removed from the training set, resulting in a population of N=648. Baseline clinical variables between those with and without MACE was compared (Tables 4B and 18); dichotomous variables were compared using two-sided Fishers exact test, while continuous variables were compared using two-sided two-sample T test. The biomarkers compared were tested with the Wilcoxon Rank Sum test, as their concentrations were not normally distributed. For any marker result that was unmeasurable, we utilized a standard approach of imputing concentrations 50% below the limit of detection.

Table 17 below shows biomarker concentrations and their prognostic association that differ between those in the validation set (N=278) with a major adverse cardiac event (MACE) from 3-365 days of the blood draw and those who did not. The numbers in this table were calculated using the composite endpoint of one-year MACE with CV death, MI, or major stroke; these proteins produce similar results with the composite endpoint of one-year MACE with all-cause death, MI and/or major stroke.

TABLE 17

Prognostic Biomarkers for Prognostic Panel FM160/02, Example 4 (3-365 Days Post-Cath, Received Coronary Cath; Peripheral Cath Optional) (Validation Set)

| Biomarker | Concentration in Subjects with One-Year MACE (N = 36) | Concentration in Subjects without One-Year MACE (N = 242) | p-value |
|---|---|---|---|
| Adiponectin (ug/mL) | 4.55 (3.475, 6.325) | 3.8 (2.4, 6.275) | 0.072 |
| Alpha-1-Antitrypsin (AAT) (mg/mL) | 2.1 (1.9, 2.425) | 1.7 (1.5, 2.075) | <0.001 |
| Alpha-2-Macroglobulin (A2Macro) (mg/mL) | 2.05 (1.575, 2.525) | 1.8 (1.5, 2.2) | 0.036 |
| Angiopoietin-1 (ANG-1) (ng/mL) | 6.4 (5, 10.2) | 6.9 (4.9, 10) | 0.797 |
| Angiotensin-Converting Enzyme (ACE) (ng/mL) | 79.5 (67.8, 101.5) | 80.5 (62, 106.8) | 1 |
| Apolipoprotein(a) (Lp(a)) (ug/mL) | 553.5 (191.8, 881) | 197.5 (63.5, 536) | <0.001 |
| Apolipoprotein A-I (Apo A-I) (mg/mL) | 1.65 (1.3, 2.1) | 1.8 (1.5, 2.2) | 0.105 |
| Apolipoprotein A-II (Apo A-II) (ng/mL) | 273.5 (226.8, 367.5) | 318 (262.5, 392) | 0.037 |
| Apolipoprotein B (Apo B) (ug/mL) | 1325 (922.8, 1700) | 1440 (1155, 1848) | 0.159 |
| Apolipoprotein C-I (Apo C-I) (ng/mL) | 313 (248.8, 366.5) | 323.5 (261.5, 382.5) | 0.253 |
| Apolipoprotein C-III (Apo C-III) (ug/mL) | 194 (151.2, 263.2) | 214.5 (163.8, 266) | 0.695 |
| Apolipoprotein H (Apo H) (ug/mL) | 356 (290.8, 428.5) | 331 (274.2, 397.8) | 0.155 |
| Beta-2-Microglobulin (B2M) (ug/mL) | 2.55 (1.975, 3.65) | 1.7 (1.3, 2.2) | <0.001 |
| Brain-Derived Neurotrophic Factor (BDNF) (ng/mL) | 1.75 (0.98, 3.625) | 2.4 (1.125, 4.675) | 0.237 |
| C-Reactive Protein (CRP) (ug/mL) | 8.55 (3.6, 25) | 3.6 (1.4, 9.375) | <0.001 |
| Carbonic anhydrase 9 (CA-9) (ng/mL) | 0.21 (0.135, 0.29) | 0.13 (0.076, 0.21) | 0.001 |
| Carcinoembryonic antigen-related cell adhesion molecule 1 (CEACAM1) (ng/mL) | 24 (22, 32.2) | 24 (20, 28) | 0.158 |

TABLE 17-continued

Prognostic Biomarkers for Prognostic Panel FM160/02, Example 4 (3-365 Days Post-Cath, Received Coronary Cath; Peripheral Cath Optional) (Validation Set)

| Biomarker | Concentration in Subjects with One-Year MACE (N = 36) | Concentration in Subjects without One-Year MACE (N = 242) | p-value |
|---|---|---|---|
| CD5 Antigen-like (CD5L) (ng/mL) | 4515 (3208, 5472) | 3735 (2760, 4925) | 0.06 |
| Decorin (ng/mL) | 2.7 (2.375, 3.7) | 2.3 (1.9, 3.2) | 0.041 |
| E-Selectin (ng/mL) | 5.6 (3.1, 7.8) | 5.4 (3.9, 6.7) | 0.934 |
| EN-RAGE (ng/mL) | 28.5 (16.2, 59.5) | 28.5 (17.2, 52.8) | 0.859 |
| Eotaxin-1 (pg/mL) | 91.5 (42.5, 136.5) | 97 (42.5, 148) | 0.397 |
| Factor VII (ng/mL) | 453.5 (337.8, 584) | 474.5 (357.8, 592.8) | 0.726 |
| Ferritin (FRTN) (ng/mL) | 124 (50.8, 248.5) | 143 (75.2, 262) | 0.434 |
| Fetuin-A (ug/mL) | 688.5 (493.8, 771.2) | 693.5 (574.2, 832.5) | 0.356 |
| Fibrinogen (mg/mL) | 4.85 (3.9, 6.825) | 4.5 (3.5, 5.475) | 0.009 |
| Follicle-Stimulating Hormone (FSH) (mIU/mL) | 11 (5.3, 38.8) | 7 (4.2, 25.5) | 0.074 |
| Growth Hormone (GH) (ng/mL) | 0.315 (0.07, 1.1) | 0.37 (0.15, 1.2) | 0.476 |
| Haptoglobin (mg/mL) | 1.15 (0.648, 3.025) | 1.1 (0.482, 1.8) | 0.125 |
| Immunoglobulin A (IgA) (mg/mL) | 2.7 (1.8, 3.775) | 2.25 (1.6, 3.175) | 0.199 |
| Immunoglobulin M (IgM) (mg/mL) | 1.1 (0.695, 1.725) | 1.4 (0.922, 2) | 0.084 |
| Insulin (uIU/mL) | 1.3 (0.608, 2.35) | 0.635 (0.11, 1.875) | 0.01 |
| Intercellular Adhesion Molecule 1 (ICAM-1) (ng/mL) | 116 (98.5, 174.8) | 101.5 (83, 126) | 0.002 |
| Interferon gamma Induced Protein 10 (IP-10) (pg/mL) | 369.5 (281.8, 482.5) | 286 (219, 400) | 0.02 |
| Interleukin-1 receptor antagonist (IL-1ra) (pg/mL) | 129.5 (94.5, 172.2) | 114 (82.2, 146) | 0.073 |
| Interleukin-6 receptor (IL-6r) (ng/mL) | 24 (17.8, 33) | 24 (19, 30) | 0.693 |
| Interleukin-8 (IL-8) (pg/mL) | 7 (6.2, 9.9) | 6.5 (4, 9.2) | 0.022 |
| Interleukin-12 Subunit p40 (IL-12p40) (ng/mL) | 0.65 (0.552, 0.882) | 0.57 (0.45, 0.708) | 0.016 |
| Interleukin-15 (IL-15) (ng/mL) | 0.625 (0.48, 0.745) | 0.56 (0.452, 0.67) | 0.119 |
| Interleukin-18 (IL-18) (pg/mL) | 236 (180, 326.8) | 191.5 (141.2, 255.2) | 0.012 |
| Interleukin-18-binding protein (IL-18bp) (ng/mL) | 14.5 (11.8, 17.2) | 9 (6.8, 12) | <0.001 |
| Interleukin-23 (IL-23) (ng/mL) | 2.75 (2.075, 3.225) | 2.6 (2, 3.175) | 0.502 |
| Kidney Injury Molecule-1 (KIM-1) (ng/mL) | 0.064 (0.042, 0.18) | 0.034 (0.014, 0.061) | <0.001 |
| Leptin (ng/mL) | 11 (5.9, 26.5) | 7.9 (4.3, 17) | 0.135 |
| Luteinizing Hormone (LH) (mIU/mL) | 9.4 (4.4, 16.2) | 4.8 (3.3, 9) | 0.002 |
| Macrophage Colony-Stimulating Factor 1 (M-CSF) (ng/mL) | 0.72 (0.428, 1.425) | 0.42 (0.16, 0.62) | <0.001 |
| Macrophage Inflammatory Protein-1 beta (MIP-1 beta) (pg/mL) | 278.5 (236.5, 380.2) | 264.5 (202.5, 359.8) | 0.197 |
| Matrix Metalloproteinase-2 (MMP-2) (ng/mL) | 1500 (1270, 1612) | 1285 (1050, 1608) | 0.032 |
| Matrix Metalloproteinase-3 (MMP-3) (ng/mL) | 8 (5.5, 12.2) | 6.4 (4.5, 9.3) | 0.048 |
| Matrix Metalloproteinase-7 (MMP-7) (ng/mL) | 0.48 (0.27, 0.735) | 0.32 (0.22, 0.5) | 0.003 |
| Matrix Metalloproteinase-9 (MMP-9) (ng/mL) | 127.5 (85.5, 170.8) | 125.5 (91, 187.2) | 0.834 |
| Matrix Metalloproteinase-9, total (MMP-9, total) (ng/mL) | 596.5 (413, 845.8) | 594.5 (434.5, 858) | 0.886 |
| Midkine (ng/mL) | 20 (15, 27.2) | 13 (9.5, 20) | <0.001 |
| Monocyte Chemotactic Protein 1 (MCP-1) (pg/mL) | 107.5 (75.5, 159) | 107.5 (75.2, 151) | 0.813 |
| Monocyte Chemotactic Protein 2 (MCP-2) (pg/mL) | 25 (16.8, 29.5) | 24 (18, 30.8) | 0.766 |
| Monocyte Chemotactic Protein 4 (MCP-4) (pg/mL) | 2075 (1640, 3288) | 2240 (1532, 3215) | 0.906 |
| Monokine Induced by Gamma Interferon (MIG) (pg/mL) | 1595 (1128, 2642) | 856.5 (531, 1498) | <0.001 |
| Myeloid Progenitor Inhibitory Factor 1 (MPIF-1) (ng/mL) | 1.65 (1.175, 2.1) | 1.2 (1, 1.6) | 0.003 |
| Myoglobin (ng/mL) | 42.5 (30, 65.2) | 31.5 (22, 44) | 0.002 |
| N-terminal prohormone of brain natriuretic peptide (NT proBNP) (pg/mL) | 4665 (1822, 15980) | 1275 (520.2, 3805) | <0.001 |

TABLE 17-continued

Prognostic Biomarkers for Prognostic Panel FM160/02, Example 4 (3-365 Days Post-Cath, Received Coronary Cath; Peripheral Cath Optional) (Validation Set)

| Biomarker | Concentration in Subjects with One-Year MACE (N = 36) | Concentration in Subjects without One-Year MACE (N = 242) | p-value |
| --- | --- | --- | --- |
| Osteopontin (ng/mL) | 45 (33.8, 72.2) | 27 (19, 39) | <0.001 |
| Pancreatic Polypeptide (PPP) (pg/mL) | 137 (83.5, 227.8) | 80 (49, 149.5) | <0.001 |
| Plasminogen Activator Inhibitor 1 (PAI-1) (ng/mL) | 45 (24, 68.2) | 45 (27.2, 71.8) | 0.945 |
| Platelet endothelial cell adhesion molecule (PECAM-1) (ng/mL) | 53.5 (45.8, 69) | 54 (46, 67) | 0.67 |
| Prolactin (PRL) (ng/mL) | 7.7 (5.7, 11.2) | 7.6 (5.2, 13) | 0.835 |
| Pulmonary and Activation-Regulated Chemokine (PARC) (ng/mL) | 145.5 (116.8, 199) | 94.5 (72, 127.8) | <0.001 |
| Pulmonary surfactant-associated protein D (SP-D) (ng/mL) | 6.2 (4.2, 10.4) | 5 (3.4, 8.4) | 0.072 |
| Resistin (ng/mL) | 3.2 (1.9, 4.9) | 2.5 (1.8, 3.475) | 0.069 |
| Serotransferrin (Transferrin) (mg/dl) | 251.5 (222.5, 289) | 267.5 (227.8, 314.8) | 0.211 |
| Serum Amyloid P-Component (SAP) (ug/mL) | 13 (10.7, 17) | 13 (9.9, 17) | 0.639 |
| Stem Cell Factor (SCF) (pg/mL) | 421.5 (318.8, 599.2) | 361.5 (280.2, 454.5) | 0.016 |
| T-Cell-Specific Protein RANTES (RANTES) (ng/mL) | 8.2 (5.4, 12.8) | 8.9 (3.9, 16.8) | 0.969 |
| Tamm-Horsfall Urinary Glycoprotein (THP) (ug/mL) | 0.023 (0.017, 0.031) | 0.032 (0.022, 0.043) | <0.001 |
| Thrombomodulin (TM) (ng/mL) | 4.8 (3.75, 6.275) | 3.8 (3.1, 4.6) | <0.001 |
| Thrombospondin-1 (ng/mL) | 4450 (2520, 7698) | 4530 (2215, 7390) | 0.895 |
| Thyroid-Stimulating Hormone (TSH) (uIU/mL) | 1.3 (0.76, 1.825) | 1.2 (0.752, 1.9) | 0.677 |
| Thyroxine-Binding Globulin (TBG) (ug/mL) | 40.5 (33.8, 46.2) | 37 (31, 44) | 0.124 |
| Tissue Inhibitor of Metalloproteinases 1 (TIMP-1) (ng/mL) | 92.5 (80, 114.5) | 70 (58, 89) | <0.001 |
| Transthyretin (TTR) (mg/dl) | 22 (17.8, 29.5) | 26 (22, 31) | 0.05 |
| Troponin (pg/ml) | 21.4 (9.2, 85) | 7.7 (3.5, 32.5) | 0.003 |
| Tumor necrosis factor receptor 2 (TNFR2) (ng/mL) | 9.5 (7.9, 15.2) | 6.3 (4.6, 8.4) | <0.001 |
| Vascular Cell Adhesion Molecule-1 (VCAM-1) (ng/mL) | 686.5 (590.5, 815.5) | 541 (439, 705.5) | <0.001 |
| Vascular Endothelial Growth Factor (VEGF) (pg/mL) | 107.5 (77, 174.5) | 96 (65.2, 132) | 0.105 |
| Vitamin D-Binding Protein (VDBP) (ug/mL) | 226.5 (179.5, 287.8) | 250.5 (187.2, 317) | 0.358 |
| Vitamin K-Dependent Protein S (VKDPS) (ug/mL) | 13.5 (11.8, 16.2) | 14 (11, 17) | 0.914 |
| Vitronectin (ug/mL) | 500 (389.5, 635) | 445.5 (335.5, 563) | 0.038 |
| von Willebrand Factor (vWF) (ug/mL) | 179 (142, 262.8) | 127 (95.2, 171.8) | <0.001 |

Table 18 below shows baseline clinical variables and their prognostic association that differ between those in the validation set (N=278) with a major adverse cardiac event (MACE) from 3-365 days of the blood draw and those who did not. The numbers in this table were calculated using the composite endpoint of one-year MACE with CV death, MI, or major stroke; these proteins produce similar results with the composite endpoint of one-year MACE with all-cause death, MI and/or major stroke.

TABLE 18

Prognostic Clinical Variables for Prognostic Panel FM160/02 Example 4, (3-365 Days Post-Cath, Received Coronary Cath; Peripheral Cath Optional) (Validation Set)

| Clinical Characteristics | Subjects with One-Year MACE (N = 36) | Subjects without One-Year MACE (N = 242) | p-value |
|---|---|---|---|
| Demographics | | | |
| Age (years) | 71.6 (12.2) | 66.3 (11.5) | 0.018 |
| Male sex | 26/36 (72.2%) | 173/242 (71.5%) | 1 |
| Caucasian | 33/36 (91.7%) | 229/242 (94.6%) | 0.445 |
| Vital Signs | | | |
| Heart rate (beat/min) | 70.1 (12) | 68.6 (14.2) | 0.5 |
| Systolic BP (mmHg) | 131 (26.1) | 135.7 (21.6) | 0.311 |
| Diastolic BP (mmHg) | 68.3 (10.3) | 72.7 (11.5) | 0.025 |
| Medical History | | | |
| Smoking | 1/36 (2.8%) | 40/239 (16.7%) | 0.024 |
| Atrial fibrillation/flutter | 8/36 (22.2%) | 50/242 (20.7%) | 0.827 |
| Hypertension | 32/36 (88.9%) | 168/242 (69.4%) | 0.016 |
| Coronary artery disease | 25/36 (69.4%) | 110/242 (45.5%) | 0.008 |
| Myocardial infarction | 12/36 (33.3%) | 50/242 (20.7%) | 0.131 |
| Heart failure | 13/36 (36.1%) | 42/242 (17.4%) | 0.013 |
| Peripheral artery disease | 16/36 (44.4%) | 31/242 (12.8%) | <0.001 |
| COPD | 5/36 (13.9%) | 38/242 (15.7%) | 1 |
| Diabetes, Type 1 | 0/36 (0%) | 3/242 (1.2%) | 1 |
| Diabetes, Type 2 | 18/36 (50%) | 50/242 (20.7%) | <0.001 |
| Any Diabetes | 18/36 (50%) | 52/242 (21.5%) | <0.001 |
| CVA/TIA | 6/36 (16.7%) | 23/242 (9.5%) | 0.237 |
| Chronic kidney disease | 8/36 (22.2%) | 26/242 (10.7%) | 0.059 |
| Hemodialysis | 0/36 (0%) | 6/242 (2.5%) | 1 |
| Angioplasty, peripheral and/or coronary | 7/36 (19.4%) | 16/242 (6.6%) | 0.018 |
| Stent, peripheral and/or coronary | 14/36 (38.9%) | 51/242 (21.1%) | 0.033 |
| CABG | 15/36 (41.7%) | 34/242 (14%) | <0.001 |
| Percutaneous coronary intervention | 10/36 (27.8%) | 80/242 (33.1%) | 0.573 |
| Medications | | | |
| ACE-I/ARB | 22/36 (61.1%) | 123/240 (51.2%) | 0.288 |
| Beta blocker | 27/36 (75%) | 157/241 (65.1%) | 0.264 |
| Aldosterone antagonist | 5/36 (13.9%) | 8/241 (3.3%) | 0.017 |
| Loop diuretics | 14/36 (38.9%) | 43/241 (17.8%) | 0.007 |
| Nitrates | 15/36 (41.7%) | 39/240 (16.2%) | 0.001 |
| CCB | 14/36 (38.9%) | 59/242 (24.4%) | 0.071 |
| Statin | 28/36 (77.8%) | 170/241 (70.5%) | 0.433 |
| Aspirin | 26/36 (72.2%) | 182/242 (75.2%) | 0.684 |
| Warfarin | 7/36 (19.4%) | 43/241 (17.8%) | 0.817 |
| Clopidogrel | 12/36 (33.3%) | 53/241 (22%) | 0.143 |
| Echocardiographic results | | | |
| LVEF (%) | 50.4 (17.7) | 56.7 (14.5) | 0.082 |
| RSVP (mmHg) | 42.4 (10.8) | 41.8 (12.4) | 0.849 |
| Stress test results | | | |
| Ischemia on Scan | 7/9 (77.8%) | 41/52 (78.8%) | 1 |
| Ischemia on ECG | 0/4 (0%) | 25/43 (58.1%) | 0.041 |
| Angiography results | | | |
| >=70% coronary stenosis in >=2 vessels | 17/36 (47.2%) | 87/242 (36%) | 0.201 |
| >=70% coronary stenosis in >=3 vessels | 11/36 (30.6%) | 46/242 (19%) | 0.123 |
| Lab Measures | | | |
| Sodium | 138.3 (2.9) | 139.4 (3.4) | 0.073 |
| Blood urea nitrogen (mg/dL) | 22 (17, 30) | 18 (15, 23) | 0.023 |
| Creatinine (mg/dL) | 1.3 (1.1, 1.5) | 1.1 (0.9, 1.3) | <0.001 |
| eGFR (median, CKDEPI) | 70.9 (49.3, 92.7) | 100.7 (78, 111) | <0.001 |
| Total cholesterol (mg/dL) | 136.2 (42.7) | 161.1 (44.1) | 0.011 |
| LDL cholesterol (mg/dL) | 75.5 (33.5) | 91.8 (37) | 0.033 |
| Glycohemoglobin (%) | 6.5 (6.1, 6.8) | 6.1 (5.7, 6.6) | 0.247 |
| Glucose (mg/dL) | 110 (101, 147) | 102 (92, 118.2) | 0.022 |
| HGB (mg/dL) | 12.3 (1.7) | 13.3 (1.6) | 0.005 |

Table 19 below shows the operating characteristics of the FM160/02 MACE prognostic algorithm across various scores. For sensitivity and specificity, the 95% confidence interval is listed in parentheses. At the optimal score cutpoint, we found 63.9% sensitivity, 77.3% specificity, PPV of 29.5% and NPV of 93.5% for composite endpoint of one-year MACE with CV death, MI, or major stroke.

TABLE 19

Performance of Prognostic Panel FM160/02, Example 4 (3-365 Days Post-Cath, Received Coronary Cath; Peripheral Cath Optional) (Validation Set)

| Cutoff | Sensitivity | Specificity | PPV | NPV |
|---|---|---|---|---|
| 1 | 0 (0, 0) | 1 (1, 1) | — | 0.871 |
| 0.5 | 0 (0, 0) | 0.988 (0.974, 1.002) | 0 | 0.869 |
| 0 | 0.111 (0.008, 0.214) | 0.967 (0.944, 0.989) | 0.333 | 0.88 |
| −0.5 | 0.278 (0.131, 0.424) | 0.942 (0.913, 0.972) | 0.417 | 0.898 |
| −1 | 0.389 (0.23, 0.548) | 0.905 (0.868, 0.942) | 0.378 | 0.909 |
| −1.5 | 0.528 (0.365, 0.691) | 0.86 (0.816, 0.903) | 0.358 | 0.924 |
| −2 | 0.667 (0.513, 0.821) | 0.748 (0.693, 0.803) | 0.282 | 0.938 |
| −2.5 | 0.889 (0.786, 0.992) | 0.624 (0.563, 0.685) | 0.26 | 0.974 |
| −3 | 0.917 (0.826, 1.007) | 0.475 (0.412, 0.538) | 0.206 | 0.975 |
| −3.5 | 0.944 (0.87, 1.019) | 0.277 (0.22, 0.333) | 0.163 | 0.971 |
| −4 | 1 (1, 1) | 0.128 (0.086, 0.17) | 0.146 | 1 |
| −4.5 | 1 (1, 1) | 0.058 (0.028, 0.087) | 0.136 | 1 |
| −5 | 1 (1, 1) | 0.004 (−0.004, 0.012) | 0.13 | 1 |
| −5.5 | 1 (1, 1) | 0 (0, 0) | 0.129 | — |

Table 20 below shows the scoring model using a three-level scoring system, and illustrates the performance of the model when the raw prognostic value is partitioned into a three-level score, each optimized for different operating characteristics and prognostic confidence, with a higher score indicating an increased risk for composite MACE. In a three-level score, a score of 1 indicates a low risk or negative prognosis, a score of 3 indicates a high risk or positive prognosis, and a score of 2 indicates a prognosis of moderate risk. The cutoff for score level 1 was optimized for NPV of 0.97 in the training set, and the cutoff for score level of 3 was optimized for a PPV of 0.45 in the training set.

TABLE 20

Performance of 3-Level Score for Prognostic Panel FM160/02, Example 4 (3-365 Days Post-Cath, Received Coronary Cath; Peripheral Cath Optional) (Validation Set)

| | | Optimized For | | Observed in Validation Set | |
|---|---|---|---|---|---|
| Score | # Patients | PPV | NPV | PPV | NPV |
| 3 | 33 | 0.45 | — | 0.394 | — |
| 2 | 127 | NA | NA | 0.157 | 0.843 |
| 1 | 118 | — | 0.97 | — | 0.975 |

Example 5: A Biomarker Scoring System to Predict One Year (0 Day-365 Day) Risk of Composite Cardiovascular Death, Myocardial Infarct or Stroke (FM96/04)

This example demonstrates a non-invasive method employing a biomarker scoring system that offers, among other things, high accuracy in providing a prognosis of one year risk (0-365 day) of MACE composite of cardiovascular death, myocardial infarct, or stroke. This example utilized the same methods described in Example 1 (study design, subjects, data acquisition, follow up, biomarker testing, statistics and results (Tables 2A, 4A, 21, 22, 23, and 24 and FIG. 31).

The patients selected for analysis consisted of the chronologically initial 928 patients who received a coronary angiogram. Patients may have also received a peripheral angiogram concomitantly.

The 928 patients selected for analysis were randomly split into a training set (70%, or N=649, Table 2A) and a holdout validation set (30%, or N=279, Table 21).

Baseline characteristics between those with and without MACE were compared; dichotomous variables were compared using two-sided Fishers exact test, while continuous variables were compared using two-sided two-sample T test. The biomarkers compared were tested with the Wilcoxon Rank Sum test, as their concentrations were not normally distributed. For any marker result that was unmeasurable, we utilized a standard approach of imputing concentrations 50% below the limit of detection.

Table 21 below shows biomarker concentrations and their prognostic association that differ between those in the validation set (N=278) with a major adverse cardiac event (MACE) from 0-365 days and those who did not. The numbers in this table were calculated using the composite endpoint of one-year MACE with CV death, MI, or major stroke; these proteins produce similar results with the composite endpoint of one-year MACE with all-cause death, MI and/or major stroke.

TABLE 21

Prognostic Biomarkers for Prognostic Panel FM96/04, Example 5 (0-365 Days Post-Cath, Received Coronary Cath; Peripheral Cath Optional) (Validation Set)

| Biomarker | Concentration in Subjects with One-Year MACE (N = 39) | Concentration in Subjects without One-Year MACE (N = 239) | p-value |
|---|---|---|---|
| Adiponectin (ug/mL) | 4.5 (3.4, 6.3) | 3.8 (2.4, 6.3) | 0.17 |
| Alpha-1-Antitrypsin (AAT) (mg/mL) | 2.1 (1.75, 2.45) | 1.7 (1.5, 2.05) | <0.001 |
| Alpha-2-Macroglobulin (A2Macro) (mg/mL) | 2 (1.5, 2.5) | 1.8 (1.5, 2.2) | 0.132 |
| Angiopoietin-1 (ANG-1) (ng/mL) | 7.1 (5, 11) | 6.8 (4.9, 9.8) | 0.798 |
| Angiotensin-Converting Enzyme (ACE) (ng/mL) | 79 (66.5, 100) | 81 (62, 108) | 0.849 |

TABLE 21-continued

Prognostic Biomarkers for Prognostic Panel FM96/04, Example 5 (0-365 Days Post-Cath, Received Coronary Cath; Peripheral Cath Optional) (Validation Set)

| Biomarker | Concentration in Subjects with One-Year MACE (N = 39) | Concentration in Subjects without One-Year MACE (N = 239) | p-value |
|---|---|---|---|
| Apolipoprotein(a) (Lp(a)) (ug/mL) | 586 (204.5, 924) | 190 (62.5, 534) | <0.001 |
| Apolipoprotein A-I (Apo A-I) (mg/mL) | 1.7 (1.3, 2.1) | 1.8 (1.5, 2.2) | 0.186 |
| Apolipoprotein A-II (Apo A-II) (ng/mL) | 290 (233, 364) | 318 (262, 393.5) | 0.045 |
| Apolipoprotein B (Apo B) (ug/mL) | 1430 (985, 1790) | 1430 (1140, 1835) | 0.463 |
| Apolipoprotein C-I (Apo C-I) (ng/mL) | 313 (256, 361.5) | 325 (260.5, 383) | 0.253 |
| Apolipoprotein C-III (Apo C-III) (ug/mL) | 197 (156, 249) | 215 (162, 267.5) | 0.717 |
| Apolipoprotein H (Apo H) (ug/mL) | 351 (289.5, 429) | 331 (274, 397.5) | 0.138 |
| Beta-2-Microglobulin (B2M) (ug/mL) | 2.4 (1.75, 3.5) | 1.7 (1.3, 2.25) | <0.001 |
| Brain-Derived Neurotrophic Factor (BDNF) (ng/mL) | 2 (1.05, 4) | 2.4 (1.1, 4.6) | 0.548 |
| C-Reactive Protein (CRP) (ug/mL) | 8.2 (3.1, 25) | 3.6 (1.4, 9.25) | 0.001 |
| Carbonic anhydrase 9 (CA-9) (ng/mL) | 0.24 (0.145, 0.315) | 0.12 (0.076, 0.21) | <0.001 |
| Carcinoembryonic antigen-related cell adhesion molecule 1 (CEACAM1) (ng/mL) | 24 (22, 34) | 24 (20, 28) | 0.119 |
| CD5 Antigen-like (CD5L) (ng/mL) | 4560 (3280, 5515) | 3720 (2740, 4900) | 0.021 |
| Decorin (ng/mL) | 2.7 (2.4, 3.7) | 2.3 (1.9, 3.2) | 0.013 |
| E-Selectin (ng/mL) | 5.7 (3.2, 7.5) | 5.4 (3.9, 6.7) | 0.949 |
| EN-RAGE (ng/mL) | 38 (18.5, 69.5) | 28 (17, 51) | 0.415 |
| Eotaxin-1 (pg/mL) | 93 (42.5, 138) | 97 (42.5, 148) | 0.56 |
| Factor VII (ng/mL) | 433 (348, 579.5) | 475 (358.5, 593) | 0.499 |
| Ferritin (FRTN) (ng/mL) | 131 (54.5, 255) | 143 (74, 255.5) | 0.67 |
| Fetuin-A (ug/mL) | 689 (515.5, 825.5) | 693 (573, 825.5) | 0.599 |
| Fibrinogen (mg/mL) | 4.7 (4, 6.8) | 4.5 (3.5, 5.45) | 0.007 |
| Follicle-Stimulating Hormone (FSH) (mIU/mL) | 9.8 (4.3, 35.5) | 7.2 (4.3, 26.5) | 0.281 |
| Growth Hormone (GH) (ng/mL) | 0.38 (0.115, 1.1) | 0.37 (0.15, 1.2) | 0.756 |
| Haptoglobin (mg/mL) | 1.1 (0.57, 2.95) | 1.1 (0.485, 1.85) | 0.27 |
| Immunoglobulin A (IgA) (mg/mL) | 2.7 (1.8, 3.65) | 2.3 (1.6, 3.2) | 0.26 |
| Immunoglobulin M (IgM) (mg/mL) | 1.3 (0.78, 1.8) | 1.3 (0.92, 2) | 0.237 |
| Insulin (uIU/mL) | 1.3 (0.405, 2.3) | 0.64 (0.11, 1.9) | 0.03 |
| Intercellular Adhesion Molecule 1 (ICAM-1) (ng/mL) | 115 (95.5, 172.5) | 102 (83, 126) | 0.005 |
| Interferon gamma Induced Protein 10 (IP-10) (pg/mL) | 364 (264, 465) | 286 (219, 400) | 0.036 |
| Interleukin-1 receptor antagonist (IL-1ra) (pg/mL) | 129 (98.5, 170) | 113 (82, 146.5) | 0.059 |
| Interleukin-6 receptor (IL-6r) (ng/mL) | 24 (18.5, 33) | 24 (19, 30) | 0.657 |
| Interleukin-8 (IL-8) (pg/mL) | 7.1 (6.3, 10.3) | 6.4 (4, 9.1) | 0.012 |
| Interleukin-12 Subunit p40 (IL-12p40) (ng/mL) | 0.64 (0.545, 0.845) | 0.57 (0.45, 0.705) | 0.013 |
| Interleukin-15 (IL-15) (ng/mL) | 0.62 (0.49, 0.73) | 0.56 (0.45, 0.67) | 0.088 |
| Interleukin-18 (IL-18) (pg/mL) | 239 (178, 339) | 191 (141.5, 251.5) | 0.007 |
| Interleukin-18-binding protein (IL-18bp) (ng/mL) | 14 (9.9, 17) | 9 (6.8, 12) | <0.001 |
| Interleukin-23 (IL-23) (ng/mL) | 2.8 (2.2, 3.25) | 2.6 (2, 3.15) | 0.351 |
| Kidney Injury Molecule-1 (KIM-1) (ng/mL) | 0.063 (0.038, 0.16) | 0.035 (0.014, 0.062) | <0.001 |
| Leptin (ng/mL) | 9.6 (5.7, 24.5) | 8 (4.3, 17.5) | 0.255 |
| Luteinizing Hormone (LH) (mIU/mL) | 8.3 (3.7, 16) | 4.9 (3.3, 9) | 0.013 |
| Macrophage Colony-Stimulating Factor 1 (M-CSF) (ng/mL) | 0.72 (0.425, 1.25) | 0.42 (0.16, 0.615) | <0.001 |
| Macrophage Inflammatory Protein-1 beta (MIP-1 beta) (pg/mL) | 278 (234, 388.5) | 264 (200.5, 358.5) | 0.167 |

TABLE 21-continued

Prognostic Biomarkers for Prognostic Panel FM96/04, Example 5 (0-365 Days Post-Cath, Received Coronary Cath; Peripheral Cath Optional) (Validation Set)

| Biomarker | Concentration in Subjects with One-Year MACE (N = 39) | Concentration in Subjects without One-Year MACE (N = 239) | p-value |
|---|---|---|---|
| Matrix Metalloproteinase-2 (MMP-2) (ng/mL) | 1480 (1260, 1615) | 1290 (1050, 1605) | 0.05 |
| Matrix Metalloproteinase-3 (MMP-3) (ng/mL) | 7.7 (5.4, 12) | 6.4 (4.5, 9.3) | 0.066 |
| Matrix Metalloproteinase-7 (MMP-7) (ng/mL) | 0.44 (0.26, 0.73) | 0.33 (0.22, 0.505) | 0.009 |
| Matrix Metalloproteinase-9 (MMP-9) (ng/mL) | 133 (89, 187) | 125 (90.5, 184) | 0.674 |
| Matrix Metalloproteinase-9, total (MMP-9, total) (ng/mL) | 638 (426, 874) | 590 (431.5, 851.5) | 0.697 |
| Midkine (ng/mL) | 19 (13, 26) | 13 (9.6, 20) | <0.001 |
| Monocyte Chemotactic Protein 1 (MCP-1) (pg/mL) | 111 (73, 159) | 107 (75.5, 151) | 0.854 |
| Monocyte Chemotactic Protein 2 (MCP-2) (pg/mL) | 25 (16, 30) | 24 (18.5, 30.5) | 0.663 |
| Monocyte Chemotactic Protein 4 (MCP-4) (pg/mL) | 2060 (1640, 3395) | 2270 (1535, 3210) | 0.869 |
| Monokine Induced by Gamma Interferon (MIG) (pg/mL) | 1540 (1003, 2545) | 857 (534, 1510) | <0.001 |
| Myeloid Progenitor Inhibitory Factor 1 (MPIF-1) (ng/mL) | 1.6 (1.1, 2.1) | 1.2 (1, 1.6) | 0.007 |
| Myoglobin (ng/mL) | 39 (30, 63) | 32 (22, 44) | 0.006 |
| N-terminal prohormone of brain natriuretic peptide (NT proBNP) (pg/mL) | 4400 (1685, 15980) | 1270 (521.5, 3835) | <0.001 |
| Osteopontin (ng/mL) | 43 (29, 70) | 27 (19, 39) | <0.001 |
| Pancreatic Polypeptide (PPP) (pg/mL) | 119 (82, 221.5) | 80 (49, 151) | 0.002 |
| Plasminogen Activator Inhibitor 1 (PAI-1) (ng/mL) | 50 (26.5, 68.5) | 44 (27, 71.5) | 0.6 |
| Platelet endothelial cell adhesion molecule (PECAM-1) (ng/mL) | 54 (46.5, 67.5) | 54 (46, 67.5) | 0.62 |
| Prolactin (PRL) (ng/mL) | 8 (5.7, 11.5) | 7.6 (5.2, 13) | 0.692 |
| Pulmonary and Activation-Regulated Chemokine (PARC) (ng/mL) | 135 (112.5, 197) | 96 (72, 128.5) | <0.001 |
| Pulmonary surfactant-associated protein D (SP-D) (ng/mL) | 6.2 (4.1, 10.4) | 5 (3.4, 8.4) | 0.079 |
| Resistin (ng/mL) | 3.1 (1.9, 4.75) | 2.5 (1.8, 3.45) | 0.054 |
| Serotransferrin (Transferrin) (mg/dl) | 249 (225, 288.5) | 268 (226.5, 315.5) | 0.119 |
| Serum Amyloid P-Component (SAP) (ug/mL) | 13 (10.5, 17) | 13 (9.8, 17) | 0.793 |
| Stem Cell Factor (SCF) (pg/mL) | 417 (316.5, 595.5) | 362 (280, 456.5) | 0.028 |
| T-Cell-Specific Protein RANTES (RANTES) (ng/mL) | 8.3 (5.2, 13.5) | 8.6 (3.8, 16.5) | 0.878 |
| Tamm-Horsfall Urinary Glycoprotein (THP) (ug/mL) | 0.026 (0.018, 0.031) | 0.032 (0.022, 0.042) | 0.002 |
| Thrombomodulin (TM) (ng/mL) | 4.7 (3.6, 6.05) | 3.8 (3.1, 4.6) | <0.001 |
| Thrombospondin-1 (ng/mL) | 4630 (2765, 8155) | 4440 (2200, 7300) | 0.533 |
| Thyroid-Stimulating Hormone (TSH) (uIU/mL) | 1.3 (0.76, 2.05) | 1.2 (0.755, 1.9) | 0.526 |
| Thyroxine-Binding Globulin (TBG) (ug/mL) | 40 (33.5, 46.5) | 37 (31, 44) | 0.115 |
| Tissue Inhibitor of Metalloproteinases 1 (TIMP-1) (ng/mL) | 92 (78, 114.5) | 70 (58, 89) | <0.001 |
| Transthyretin (TTR) (mg/dl) | 23 (18, 30.5) | 26 (21.5, 31) | 0.095 |
| Troponin (pg/ml) | 22.1 (8.8, 167.4) | 7.3 (3.5, 30.8) | <0.001 |
| Tumor necrosis factor receptor 2 (TNFR2) (ng/mL) | 9.2 (7, 15) | 6.3 (4.6, 8.7) | <0.001 |
| Vascular Cell Adhesion Molecule-1 (VCAM-1) (ng/mL) | 676 (576, 807) | 541 (438.5, 707) | <0.001 |
| Vascular Endothelial Growth Factor (VEGF) (pg/mL) | 106 (74, 170) | 95 (65.5, 132) | 0.117 |
| Vitamin D-Binding Protein (VDBP) (ug/mL) | 236 (185, 281) | 250 (185.5, 317) | 0.457 |
| Vitamin K-Dependent Protein S (VKDPS) (ug/mL) | 14 (12, 17) | 14 (11, 17) | 0.827 |

TABLE 21-continued

Prognostic Biomarkers for Prognostic Panel FM96/04, Example 5 (0-365 Days Post-Cath, Received Coronary Cath; Peripheral Cath Optional) (Validation Set)

| Biomarker | Concentration in Subjects with One-Year MACE (N = 39) | Concentration in Subjects without One-Year MACE (N = 239) | p-value |
|---|---|---|---|
| Vitronectin (ug/mL) | 503 (398.5, 629) | 442 (333.5, 558.5) | 0.017 |
| von Willebrand Factor (vWF) (ug/mL) | 176 (137, 259.5) | 127 (94.5, 171.5) | <0.001 |

Table 22 below shows baseline clinical variables and their prognostic association that differ between those in the validation set (N=278) with a major adverse cardiac event (MACE) from 0-365 days and those who did not. The numbers in this table were calculated using the composite endpoint of one-year MACE with CV death, MI, or major stroke; these proteins produce similar results with the composite endpoint of one-year MACE with all-cause death, MI and/or major stroke.

TABLE 22

Prognostic Clinical Variables for Prognostic Panel FM96/04, Example 5 (0-365 Days Post-Cath, Received Coronary Cath; Peripheral Cath Optional) (Validation Set)

| Clinical Characteristics | Subjects with One-Year MACE (N = 39) | Subjects without One-Year MACE (N = 239) | p-value |
|---|---|---|---|
| Demographics | | | |
| Age (years) | 70.6 (12.4) | 66.4 (11.5) | 0.054 |
| Male sex | 29/39 (74.4%) | 170/239 (71.1%) | 0.848 |
| Caucasian | 36/39 (92.3%) | 226/239 (94.6%) | 0.477 |
| Vital Signs | | | |
| Heart rate (beat/min) | 69.6 (11.9) | 68.6 (14.2) | 0.658 |
| Systolic BP (mmHg) | 131.1 (25.1) | 135.7 (21.7) | 0.28 |
| Diastolic BP (mmHg) | 68.7 (10) | 72.7 (11.6) | 0.028 |
| Medical History | | | |
| Smoking | 2/39 (5.1%) | 39/236 (16.5%) | 0.087 |
| Atrial fibrillation/flutter | 8/39 (20.5%) | 50/239 (20.9%) | 1 |
| Hypertension | 33/39 (84.6%) | 167/239 (69.9%) | 0.082 |
| Coronary artery disease | 25/39 (64.1%) | 110/239 (46%) | 0.039 |
| Myocardial infarction | 12/39 (30.8%) | 50/239 (20.9%) | 0.212 |
| Heart failure | 13/39 (33.3%) | 42/239 (17.6%) | 0.03 |
| Peripheral artery disease | 16/39 (41%) | 31/239 (13%) | <0.001 |
| COPD | 5/39 (12.8%) | 38/239 (15.9%) | 0.812 |
| Diabetes, Type 1 | 0/39 (0%) | 3/239 (1.3%) | 1 |
| Diabetes, Type 2 | 18/39 (46.2%) | 50/239 (20.9%) | 0.002 |
| Any Diabetes | 18/39 (46.2%) | 52/239 (21.8%) | 0.002 |
| CVA/TIA | 6/39 (15.4%) | 23/239 (9.6%) | 0.265 |
| Chronic kidney disease | 8/39 (20.5%) | 26/239 (10.9%) | 0.111 |
| Hemodialysis | 0/39 (0%) | 6/239 (2.5%) | 1 |
| Angioplasty | 7/39 (17.9%) | 16/239 (6.7%) | 0.027 |
| Angioplasty, peripheral and/or coronary | 15/39 (38.5%) | 50/239 (20.9%) | 0.024 |
| Stent, peripheral and/or coronary | 15/39 (38.5%) | 34/239 (14.2%) | <0.001 |
| Percutaneous coronary intervention | 11/39 (28.2%) | 79/239 (33.1%) | 0.586 |
| Medications | | | |
| ACE-I/ARB | 23/39 (59%) | 122/237 (51.5%) | 0.489 |
| Beta blocker | 28/39 (71.8%) | 156/238 (65.5%) | 0.583 |
| Aldosterone antagonist | 5/39 (12.8%) | 8/238 (3.4%) | 0.023 |
| Loop diuretics | 14/39 (35.9%) | 43/238 (18.1%) | 0.017 |
| Nitrates | 16/39 (41%) | 38/237 (16%) | <0.001 |
| CCB | 14/39 (35.9%) | 59/239 (24.7%) | 0.169 |
| Statin | 30/39 (76.9%) | 168/238 (70.6%) | 0.566 |
| Aspirin | 28/39 (71.8%) | 180/239 (75.3%) | 0.691 |
| Warfarin | 7/39 (17.9%) | 43/238 (18.1%) | 1 |
| Clopidogrel | 13/39 (33.3%) | 52/238 (21.8%) | 0.152 |

TABLE 22-continued

Prognostic Clinical Variables for Prognostic Panel FM96/04, Example 5 (0-365 Days Post-Cath, Received Coronary Cath; Peripheral Cath Optional) (Validation Set)

| Clinical Characteristics | Subjects with One-Year MACE (N = 39) | Subjects without One-Year MACE (N = 239) | p-value |
|---|---|---|---|
| Echocardiographic results | | | |
| LVEF (%) | 50.9 (17.5) | 56.7 (14.6) | 0.095 |
| RSVP (mmHg) | 42.4 (10.8) | 41.8 (12.4) | 0.849 |
| Stress test results | | | |
| Ischemia on Scan | 8/10 (80%) | 40/51 (78.4%) | 1 |
| Ischemia on ECG | 1/5 (20%) | 24/42 (57.1%) | 0.171 |
| Angiography results | | | |
| >=70% coronary stenosis in >=2 vessels | 19/39 (48.7%) | 85/239 (35.6%) | 0.153 |
| >=70% coronary stenosis in >=3 vessels | 12/39 (30.8%) | 45/239 (18.8%) | 0.091 |
| Lab Measures | | | |
| Sodium | 138.2 (3.3) | 139.4 (3.4) | 0.055 |
| Blood urea nitrogen (mg/dL) | 21 (16.2, 30) | 18 (15, 23) | 0.039 |
| Creatinine (mg/dL) | 1.3 (1.2, 1.5) | 1.1 (0.9, 1.3) | <0.001 |
| eGFR (median, CKDEPI) | 73.1 (49.9, 97) | 100.5 (77.8, 111) | <0.001 |
| Total cholesterol (mg/dL) | 136.4 (42.2) | 161.4 (44.1) | 0.008 |
| LDL cholesterol (mg/dL) | 75.8 (32.8) | 91.9 (37.2) | 0.027 |
| Glycohemoglobin (%) | 6.5 (6.1, 6.8) | 6.1 (5.7, 6.6) | 0.247 |
| Glucose (mg/dL) | 109.5 (99.8, 147.5) | 102 (92, 118) | 0.018 |
| HGB (mg/dL) | 12.6 (1.8) | 13.3 (1.6) | 0.028 |

Table 23 below shows the operating characteristics of the FM96/04 MACE prognostic algorithm across various scores. For sensitivity and specificity, the 95% confidence interval is listed in parentheses. At the optimal score cut-point, we found 66.7% sensitivity, 76.6% specificity, PPV of 31.7% and NPV of 93.4% for composite endpoint of one-year (0-365) MACE with CV death, MI, or major stroke.

TABLE 23

Performance of Prognostic Panel FM96/04, Example 5 (0-365 Days Post-Cath, Received Coronary Cath; Peripheral Cath Optional) (Validation Set)

| Cutoff | Sensitivity | Specificity | PPV | NPV |
|---|---|---|---|---|
| 1 | 0 (0, 0) | 1 (1, 1) | — | 0.86 |
| 0.5 | 0 (0, 0) | 0.992 (0.98, 1.003) | 0 | 0.859 |
| 0 | 0.077 (−0.007, 0.161) | 0.967 (0.944, 0.989) | 0.273 | 0.865 |
| −0.5 | 0.256 (0.119, 0.393) | 0.929 (0.896, 0.961) | 0.37 | 0.884 |
| −1 | 0.359 (0.208, 0.51) | 0.9 (0.861, 0.938) | 0.368 | 0.896 |
| −1.5 | 0.487 (0.33, 0.644) | 0.82 (0.771, 0.869) | 0.306 | 0.907 |
| −2 | 0.718 (0.577, 0.859) | 0.678 (0.619, 0.737) | 0.267 | 0.936 |
| −2.5 | 0.897 (0.802, 0.993) | 0.51 (0.447, 0.574) | 0.23 | 0.968 |
| −3 | 0.974 (0.925, 1.024) | 0.326 (0.267, 0.386) | 0.191 | 0.987 |
| −3.5 | 1 (1, 1) | 0.151 (0.105, 0.196) | 0.161 | 1 |
| −4 | 1 (1, 1) | 0.059 (0.029, 0.088) | 0.148 | 1 |
| −4.5 | 1 (1, 1) | 0.004 (−0.004, 0.012) | 0.141 | 1 |
| −5 | 1 (1, 1) | 0 (0, 0) | 0.14 | — |

Table 24 below shows the scoring model using a three-level scoring system, and illustrates the performance of the model when the raw prognostic value is partitioned into a three-level score, each optimized for different operating characteristics and prognostic confidence, with a higher score indicating an increased risk for composite MACE. In a three-level score, a score of 1 indicates a low risk or negative prognosis, a score of 3 indicates a high risk or positive prognosis, and a score of 2 indicates a prognosis of moderate risk. The cutoff for score level 1 was optimized for NPV of 0.97 in the training set, and the cutoff for score level of 3 was optimized for a PPV of 0.4 in the training set.

TABLE 24

Performance of 3-Level Score for Prognostic Panel FM96/04, Example 5 (0-365 Days Post-Cath, Received Coronary Cath; Peripheral Cath Optional) (Validation Set)

| | | Optimized For | | Observed in Validation Set | |
|---|---|---|---|---|---|
| Score | # Patients | PPV | NPV | PPV | NPV |
| 3 | 38 | 0.4 | — | 0.368 | — |
| 2 | 168 | NA | NA | 0.143 | 0.857 |
| 1 | 71 | — | 0.97 | — | 0.986 |

Example 6: Further Demonstration of Methods Employing Clinical and Biomarker Analysis for the Diagnosis Cardiovascular Diseases Table 25 is a chart of the different panels comprising protein biomarkers and optionally clinical variables with corresponding AUCs for the given outcome. These reflect aforementioned Examples 1 through 5, as well as additional panels generated using the methods and analysis provided herein.

TABLE 25

Performance of Different Panels for Various Outcomes Comprising Protein Biomarkers and Optionally Clinical Variables with Corresponding AUCs and Figures

| Analysis # | Test Outcome/ Positive Endpoint | Biomarkers & Clinical Variables | Cross Validated Mean AUCs | Validation Set AUCs | Figure Reference |
|---|---|---|---|---|---|
| Diagnostic | | | | | |
| FM139/685 Example 1 | Diagnosis of 70% or > obstruction in any major epicardial vessels | Adiponectin, Apolipoprotein C-I, Kidney Injury Molecule-1 (KIM-1), Midkine, History of percutaneous coronary intervention (e.g., balloon angioplasty with or without stent placement), Sex | 0.83 | 0.87 | 1, 2, 3, 4 |
| FM144/696 | Diagnosis of 70% or > obstruction in any major epicardial vessels | Adiponectin, Apolipoprotein C-1, Kidney Injury Molecule-1 (KIM-1), Midkine, History of percutaneous coronary intervention (e.g., balloon angioplasty with or without stent placement), Sex, Age | 0.83 | 0.87 | 5 |
| FM145/701 | Diagnosis of 70% or > obstruction in any major epicardial vessels | Adiponectin, Apolipoprotein C-I, Kidney Injury Molecule-1 (KIM-1), Midkine, Sex, Age | 0.71 | 0.72 | 6 |
| FM146/690 | Diagnosis of 70% or > obstruction in any major epicardial vessels | Adiponectin, Apolipoprotein C-I, Kidney Injury Molecule-1 (KIM-1), Midkine | 0.69 | 0.69 | 7 |
| FM152/757 | Diagnosis of 70% or > obstruction in any major epicardial vessels | Adiponectin, Kidney Injury Molecule-1 (KIM-1), Midkine, History of Diabetes Mellitus Type 2, Sex, Age | 0.72 | 0.73 | 8 |
| FM117a/657 | Diagnosis of 70% or > obstruction in any major epicardial vessels | Midkine, History of percutaneous coronary intervention (e.g., balloon angioplasty with or without stent placement), Sex | 0.80 | 0.84 | 9 |
| FM139CLa/658 | Diagnosis of 70% or > obstruction in any major epicardial vessels | Adiponectin, History of percutaneous coronary intervention (e.g., balloon angioplasty with or without stent placement), Sex | 0.76 | 0.80 | 10 |
| FM139CLb/750 | Diagnosis of 70% or > obstruction in any major epicardial vessels | Apolipoprotein C-I, History of percutaneous coronary intervention (e.g., balloon angioplasty with or without stent placement), Sex | 0.78 | 0.84 | 11 |
| FM139CLc/751 | Diagnosis of 70% or > obstruction in any major epicardial vessels | Kidney Injury Molecule-1 (KIM-1), History of percutaneous coronary intervention (e.g., balloon angioplasty with or without stent placement), Sex | 0.80 | 0.83 | 12 |
| FM117b/663 | Diagnosis of 70% or > obstruction in any major epicardial vessels | Adiponectin, Midkine, History of percutaneous coronary intervention (e.g., balloon angioplasty with or without stent placement), Sex | 0.82 | 0.85 | 13 |

TABLE 25-continued

Performance of Different Panels for Various Outcomes Comprising Protein Biomarkers and Optionally Clinical Variables with Corresponding AUCs and Figures

| Analysis # | Test Outcome/ Positive Endpoint | Biomarkers & Clinical Variables | Cross Validated Mean AUCs | Validation Set AUCs | Figure Reference |
|---|---|---|---|---|---|
| FM139CLd/752 | Diagnosis of 70% or > obstruction in any major epicardial vessels | Apolipoprotein C-I, Midkine, History of percutaneous coronary intervention (e.g., balloon angioplasty with or without stent placement), Sex | 0.81 | 0.86 | 14 |
| FM139CLe/753 | Diagnosis of 70% or > obstruction in any major epicardial vessels | Kidney Injury Molecule-1 (KIM-1), Midkine, History of percutaneous coronary intervention (e.g., balloon angioplasty with or without stent placement), Sex | 0.81 | 0.85 | 15 |
| FM139CLf/754 | Diagnosis of 70% or > obstruction in any major epicardial vessels | Adiponectin, Apolipoprotein C-I, Midkine, History of percutaneous coronary intervention (e.g., balloon angioplasty with or without stent placement), Sex | 0.82 | 0.86 | 16 |
| FM139CLg/755 | Diagnosis of 70% or > obstruction in any major epicardial vessels | Adiponectin, Kidney Injury Molecule-1 (KIM-1), Midkine, History of percutaneous coronary intervention (e.g., balloon angioplasty with or without stent placement), Sex | 0.83 | 0.86 | 17 |
| FM46/572 Example 2 | Diagnosis of 70% or > obstruction in any major epicardial vessels | Adiponectin, Decorin, Midkine, History of Myocardial Infarct (MI), History of percutaneous coronary intervention (e.g., balloon angioplasty with or without stent placement), Sex | 0.84 | 0.84 | 18, 19, 20 |
| FM46Fd/586 | Diagnosis of 70% or > obstruction in any major epicardial vessels | Adiponectin, Midkine, History of Myocardial Infarct (MI), History of percutaneous coronary intervention (e.g., balloon angioplasty with or without stent placement), Sex | 0.84 | 0.84 | 21 |
| FM46Fe/587 | Diagnosis of 70% or > obstruction in any major epicardial vessels | Decorin, Midkine, History of Myocardial Infarct (MI), History of percutaneous coronary intervention (e.g., balloon angioplasty with or without stent placement), Sex | 0.83 | 0.83 | 22 |
| FM46Ff/588 | Diagnosis of 70% or > obstruction in any major epicardial vessels | Adiponectin, Decorin, History of Myocardial Infarct (MI), History of percutaneous coronary intervention (e.g., balloon angioplasty with or without stent placement), Sex | 0.81 | 0.80 | 23 |

TABLE 25-continued

Performance of Different Panels for Various Outcomes Comprising Protein Biomarkers and Optionally Clinical Variables with Corresponding AUCs and Figures

| Analysis # | Test Outcome/ Positive Endpoint | Biomarkers & Clinical Variables | Cross Validated Mean AUCs | Validation Set AUCs | Figure Reference |
|---|---|---|---|---|---|
| FM186/796 | Diagnosis of 70% or > obstruction in any major epicardial vessels | Adiponectin, Interleukin-8, Kidney Injury Molecule-1 (KIM-1), Stem Cell Factor, History of percutaneous coronary intervention (e.g., balloon angioplasty with or without stent placement), Sex, Age | 0.83 | 0.84 | 24 |
| FM189/798 | Diagnosis of 70% or > obstruction in any major epicardial vessels | Adiponectin, Interleukin-8, Kidney Injury Molecule-1 (KIM-1), Stem Cell Factor, History of percutaneous coronary intervention (e.g., balloon angioplasty with or without stent placement), Sex | 0.82 | 0.83 | 25 |
| FM187/792 | Diagnosis of 70% or > obstruction in any major epicardial vessels | Adiponectin, Apolipoprotein C-1, Interleukin-8, Kidney Injury Molecule-1 (KIM-1), Stem Cell Factor, History of percutaneous coronary intervention (e.g., balloon angioplasty with or without stent placement), Sex, Age | 0.83 | 0.85 | 26 |
| FM188/794 | Diagnosis of 70% or > obstruction in any major epicardial vessels | Adiponectin, Apolipoprotein C-1, Interleukin-8, Kidney Injury Molecule-1 (KIM-1), Stem Cell Factor, History of percutaneous coronary intervention (e.g., balloon angioplasty with or without stent placement), Sex | 0.83 | 0.85 | 27 |
| FM02/410 Example 3 | Diagnosis of 70% or > obstruction in any major epicardial vessels | Adiponectin, Apolipoprotein C-1, Matrix Metalloproteinase 9, Midkine, Myoglobin, Pulmonary Surfactant Associated Protein D, History of Coronary Artery Bypass Graft Surgery (CABG), History of percutaneous coronary intervention (e.g., balloon angioplasty with or without stent placement), Sex | 0.88 | 0.89 | 28 |
| FM01/390 | Diagnosis of 70% or > obstruction in any major epicardial vessels | Adiponectin, Midkine, Pulmonary Surfactant Associated Protein D, Troponin, History of Coronary Artery Bypass Graft Surgery (CABG), History of Hemodialysis, History of Myocardial Infarct, Sex | 0.90 | 0.87 | 29 |

TABLE 25-continued

Performance of Different Panels for Various Outcomes Comprising Protein Biomarkers and Optionally Clinical Variables with Corresponding AUCs and Figures

| Analysis # | Test Outcome/ Positive Endpoint | Biomarkers & Clinical Variables | Cross Validated Mean AUCs | Validation Set AUCs | Figure Reference |
|---|---|---|---|---|---|
| Prognostic | | | | | |
| FM160/02 Example 4 | 1 yr (3 day-365 day) Prognosis of composite cardiovascular death (CVD), myocardial infarct (MI), or Stroke | Kidney Injury Molecule-1 (KIM-1), N terminal prohormone of brain natriuretic protein (NT-proBNP), Osteopontin, Tissue Inhibitor of Metalloproteinases -1 (TIMP-1) | 0.82 | 0.79 | 30 |
| FM96/04 Example 5 | 1 year (0 day-365 day) Prognosis of composite cardiovascular death (CVD), myocardial infarct (MI), Stroke | N terminal prohormone of brain natriuretic protein (NT-proBNP), Osteopontin, Tissue Inhibitor of Metalloproteinases -1 (TIMP-1) | 0.77 | 0.77 | 31 |
| FM190/33 | 1 yr (3 day-365 day) Prognosis of composite cardiovascular death (CVD), myocardial infarct (MI), or Stroke | N terminal prohormone of brain natriuretic protein (NT-proBNP), Osteopontin, Tissue Inhibitor of Metalloproteinases -1 (TIMP-1) | 0.80 | 0.78 | 32 |
| FM98/03 | 1 year (0 day-365 day) Prognosis of composite cardiovascular death (CVD), myocardial infarct (MI), or Stroke | N terminal prohormone of brain natriuretic protein (NT-proBNP), Osteopontin | 0.76 | 0.75 | 33 |
| FM209/02 | 1 yr (3 day-365 day) Prognosis of composite All-cause death (ACD), myocardial infarct (MI), or Stroke | Kidney Injury Molecule-1 (KIM-1), N terminal prohormone of brain natriuretic protein (NT-proBNP), Osteopontin, Tissue Inhibitor of Metalloproteinases-1 (TIMP-1) | 0.80 | 0.79 | 34 |
| FM111/05 | 1 year (0 day-365 day) Prognosis of composite All-cause death (ACD), myocardial infarct (MI), or Stroke | N terminal prohormone of brain natriuretic protein (NT-proBNP), Osteopontin, Tissue Inhibitor of Metalloproteinases-1 (TIMP-1) | 0.78 | 0.77 | 35 |
| FM210/03 | 1 yr (3 day-365 day) Prognosis of composite All-cause death (ACD), myocardial infarct (MI), or Stroke | N terminal prohormone of brain natriuretic protein (NT-proBNP), Osteopontin, Tissue Inhibitor of Metalloproteinases-1 (TIMP-1) | 0.79 | 0.78 | 36 |
| FM110/04 | 1 year (0 day-365 day) Prognosis of composite All-cause death (ACD), myocardial infarct (MI), or Stroke | N terminal prohormone of brain natriuretic protein (NT-proBNP), Osteopontin | 0.78 | 0.75 | 37 |
| FM211/03 | 1 year (3 day-365 day) Prognosis of composite cardiovascular death (CVD) or myocardial infarct (MI) | Apolipoprotein A-II, N terminal prohormone of brain natriuretic protein (NT-proBNP), Osteopontin | 0.79 | 0.79 | 38 |

TABLE 25-continued

Performance of Different Panels for Various Outcomes Comprising Protein Biomarkers and Optionally Clinical Variables with Corresponding AUCs and Figures

| Analysis # | Test Outcome/ Positive Endpoint | Biomarkers & Clinical Variables | Cross Validated Mean AUCs | Validation Set AUCs | Figure Reference |
|---|---|---|---|---|---|
| FM77/26 | 1 year (0 day-365 day) Prognosis of composite cardiovascular death (CVD) or myocardial infarct (MI) | Apolipoprotein A-II, Midkine, N terminal prohormone of brain natriuretic protein (NT-proBNP), Osteopontin | 0.78 | 0.77 | 39 |
| FM212/02 | 1 year (3 day-365 day) Prognosis of composite cardiovascular death (CVD) or myocardial infarct (MI) | Apolipoprotein A-II, Midkine, N terminal prohormone of brain natriuretic protein (NT-proBNP), Osteopontin | 0.79 | 0.79 | 40 |
| FM201/MI002 | 1 year (3 day-365 day) myocardial infarct (MI) | N terminal prohormone of brain natriuretic protein (NT-proBNP), Osteopontin | 0.78 | 0.76 | 41 |
| FM204/MI003 | 1 year (3 day-365 day) myocardial infarct (MI) | N terminal prohormone of brain natriuretic protein (NT-proBNP), Osteopontin, Vascular Cell Adhesion Molecule (VCAM) | 0.78 | 0.76 | 42 |
| FM202/MI005 | 1 year (3 day-365 day) myocardial infarct (MI) | Kidney Injury Molecule-1 (KIM-1), N terminal prohormone of brain natriuretic protein (NT-proBNP), Vascular Cell Adhesion Molecule (VCAM) | 0.80 | 0.75 | 43 |
| FM205/MI007 | 1 year (3 day-365 day) myocardial infarct (MI) | Kidney Injury Molecule-1 (KIM-1), N terminal prohormone of brain natriuretic protein (NT-proBNP), Osteopontin | 0.78 | 0.75 | 44 |
| FM63/64 | 1 year (0 day-365 day) myocardial infarct (MI) | N terminal prohormone of brain natriuretic protein (NT-proBNP), Osteopontin | 0.78 | 0.73 | 45 |
| FM52/244 | 1 year (0 day-365 day) Cardiovascular death (CVD) | Apolipoprotein A-II, Osteopontin | 0.85 | 0.80 | 46 |
| FM194/CVD001 | 1 year (3 day-365 day) Cardiovascular death (CVD) | Apolipoprotein A-II, Osteopontin | 0.85 | 0.80 | 47 |
| FM193/R08 | 1 year (3 day-365 day) Cardiovascular death (CVD) | Apolipoprotein A-II, Osteopontin, History of Diabetes Mellitus Type 2 | 0.86 | 0.80 | 48 |
| FM53/237 | 1 year (0 day-365 day) Cardiovascular death (CVD) | Apolipoprotein A-II, Midkine, Osteopontin | 0.85 | 0.81 | 49 |
| FM195/CVD002 | 1 year (3 day-365 day) Cardiovascular death (CVD) | Apolipoprotein A-II, Midkine, Osteopontin | 0.84 | 0.81 | 50 |
| FM207/R04 | 1 year (3 day-365 day) Cardiovascular death (CVD) | Apolipoprotein A-II, N terminal prohormone of brain natriuretic protein (NT-proBNP), Osteopontin, Tissue Inhibitor of Metalloproteinases -1 (TIMP-1) | 0.84 | 0.83 | 51 |

TABLE 25-continued

Performance of Different Panels for Various Outcomes Comprising Protein Biomarkers and Optionally Clinical Variables with Corresponding AUCs and Figures

| Analysis # | Test Outcome/ Positive Endpoint | Biomarkers & Clinical Variables | Cross Validated Mean AUCs | Validation Set AUCs | Figure Reference |
| --- | --- | --- | --- | --- | --- |
| FM208/R05 | 1 year (3 day-365 day) Cardiovascular death (CVD) | N terminal prohormone of brain natriuretic protein (NT-proBNP), Osteopontin, Tissue Inhibitor of Metalloproteinases -1 (TIMP-1) | 0.82 | 0.82 | 52 |

What is claimed is:

1. A method for treating a patient at risk of cardiovascular disease or having chest pain or discomfort in the shoulder, arm, back, neck or jaw, comprising:
   (i) determining whether the patient suffers from obstructive coronary artery disease by: obtaining or having obtained a biological sample from the patient; performing or having performed a biomarker assay on the biological sample for kidney injury molecule-1, adiponectin, and either or both of troponin and midkine; and calculating a score based on the biomarker levels; and
   (ii) identifying the patient as having a score indicative of obstructive coronary artery disease, then administering at least one cardiac treatment selected from a cardiovascular disease pharmacologic agent, cardiac catheterization, percutaneous coronary intervention, and coronary artery bypass graft.

2. The method of claim 1, comprising performing or having performed a biomarker assay on the biological sample for kidney injury molecule-1, adiponectin, and troponin.

3. The method of claim 1, comprising performing or having performed a biomarker assay on the biological sample for kidney injury molecule-1, adiponectin, and midkine.

4. The method of claim 1, comprising performing or having performed a biomarker assay on the biological sample for kidney injury molecule-1, adiponectin, troponin, and midkine.

5. The method of claim 1, wherein the score identifies the patient as having at least 70% obstruction in a major epicardial vessel.

6. The method of claim 1, wherein the score is based on the biomarker levels and one or more clinical variables.

7. The method of claim 6, wherein the one or more clinical variables comprises two or more of the patient's sex, the patient's age, and the patient's history of percutaneous coronary intervention.

8. The method of claim 7, wherein the score identifies the patient as having at least 70% obstruction in a major epicardial vessel.

9. The method of claim 1, wherein the at least one cardiac treatment comprises administration of the cardiovascular disease pharmacologic agent.

10. The method of claim 9, wherein the cardiovascular disease pharmacologic agent is a nitrate.

11. The method of claim 9, wherein the cardiovascular disease pharmacologic agent is a beta blocker.

12. The method of claim 9, wherein the cardiovascular disease pharmacologic agent comprises an ACE inhibitor.

13. The method of claim 9, wherein the cardiovascular disease pharmacologic agent comprises an antiplatelet agent.

14. The method of claim 9, wherein the cardiovascular disease pharmacologic agent comprises a lipid-lowering agent.

15. The method of claim 1, wherein the at least one cardiac treatment comprises cardiac catheterization.

16. The method of claim 1, wherein the at least one cardiac treatment comprises percutaneous coronary intervention.

17. The method of claim 1, wherein the at least one cardiac treatment comprises coronary artery bypass graft.

18. The method of claim 1, wherein the score is a diagnostic score.

19. The method of claim 8, wherein the score is a diagnostic score.

20. The method of claim 7, wherein the one or more clinical variables comprises all three of the patient's sex, the patient's age, and the patient's history of percutaneous coronary intervention.

* * * * *